(12) United States Patent
Siegwart et al.

(10) Patent No.: US 11,858,884 B2
(45) Date of Patent: *Jan. 2, 2024

(54) COMPOSITIONS AND METHODS FOR MODULATING GENE OR GENE PRODUCT IN CELLS

(71) Applicant: The Board of Regents of The University of Texas System, Austin, TX (US)

(72) Inventors: Daniel J. Siegwart, Dallas, TX (US); Kejin Zhou, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/566,666

(22) Filed: Dec. 30, 2021

(65) Prior Publication Data

US 2022/0257792 A1    Aug. 18, 2022

Related U.S. Application Data

(63) Continuation of application No. 15/265,064, filed on Sep. 14, 2016, now Pat. No. 11,247,968.

(60) Provisional application No. 62/218,412, filed on Sep. 14, 2015.

(51) Int. Cl.
| | | |
|---|---|---|
| C07C 321/14 | (2006.01) | |
| A61K 9/51 | (2006.01) | |
| A61K 31/7105 | (2006.01) | |
| A61K 31/7125 | (2006.01) | |
| A61K 47/59 | (2017.01) | |
| A61K 47/60 | (2017.01) | |
| A61K 47/69 | (2017.01) | |
| A61K 48/00 | (2006.01) | |
| C07C 323/52 | (2006.01) | |
| C07D 295/15 | (2006.01) | |
| A61K 47/20 | (2006.01) | |
| A61K 47/22 | (2006.01) | |

(52) U.S. Cl.
CPC ........... *C07C 321/14* (2013.01); *A61K 9/513* (2013.01); *A61K 9/5146* (2013.01); *A61K 31/7105* (2013.01); *A61K 31/7125* (2013.01); *A61K 47/20* (2013.01); *A61K 47/22* (2013.01); *A61K 47/59* (2017.08); *A61K 47/60* (2017.08); *A61K 47/6931* (2017.08); *A61K 48/0041* (2013.01); *C07C 323/52* (2013.01); *C07D 295/15* (2013.01)

(58) Field of Classification Search
CPC ... C07C 321/14; C07C 323/52; C07D 295/15; A61K 9/513; A61K 9/5146; A61K 31/7105; A61K 31/7125; A61K 47/59; A61K 47/60; A61K 47/6931; A61K 48/0041

See application file for complete search history.

(56) References Cited

U.S. PATENT DOCUMENTS

| | | | |
|---|---|---|---|
| 4,558,120 A | * | 12/1985 | Tomalia ................... C09D 7/43 564/468 |
| 7,314,956 B2 | | 1/2008 | Li et al. |
| 8,017,804 B2 | | 9/2011 | Keil et al. |
| 8,450,298 B2 | | 5/2013 | Mahon et al. |
| 11,247,968 B2 | * | 2/2022 | Siegwart ............ A61K 31/7125 |
| 2004/0236015 A1 | | 11/2004 | Kozlowski et al. |
| 2007/0298006 A1 | | 12/2007 | Tomalia et al. |
| 2008/0242626 A1 | | 10/2008 | Zugates et al. |
| 2008/0294089 A1 | | 11/2008 | Hardy |
| 2009/0221684 A1 | | 9/2009 | Grinstaff et al. |
| 2010/0178267 A1 | | 7/2010 | Puerta et al. |
| 2011/0009641 A1 | | 1/2011 | Anderson et al. |
| 2016/0220681 A1 | | 8/2016 | Siegwart et al. |
| 2017/0354672 A1 | * | 12/2017 | Siegwart .................. A61P 25/08 |
| 2021/0023120 A1 | * | 1/2021 | Siegwart ............ A61K 31/7088 |
| 2021/0121411 A1 | * | 4/2021 | Siegwart ................ C12N 15/88 |

FOREIGN PATENT DOCUMENTS

| | | | |
|---|---|---|---|
| CN | 101591428 | 12/2009 | |
| CN | 103999853 | 8/2014 | |
| JP | 2014-103108 | 6/2014 | |
| JP | 2014-529328 | 11/2014 | |
| JP | 2019-515016 | 6/2019 | |
| WO | WO 2006-138380 | 12/2006 | |
| WO | WO-2010056403 A1 * | 5/2010 | ......... A61K 31/7088 |

(Continued)

OTHER PUBLICATIONS

He D, Wagner E. Defined polymeric materials for gene delivery. Macromol Biosci. May 2015;15(5):600-12. doi: 10.1002/mabi.201400524. Epub Feb. 5, 2015. PMID: 25655078. (Year: 2015).*

(Continued)

*Primary Examiner* — Abigail Vanhorn
(74) *Attorney, Agent, or Firm* — Parker Highlander PLLC

(57) ABSTRACT

Disclosed herein are methods for modulating an amount or activity of a gene or a gene product in a cell. The methods herein may comprise contacting a cell with a therapeutic agent assembled with a lipid composition, which lipid composition may comprise a dendrimer or dendron which may comprise one or more degradable diacyl group, in which may result in modulating the amount or activity of the gene or the gene product in the cell. The therapeutic agent modulating a gene or gene product in a cell may be sufficient to treat a disease or disorder in a subject. Further disclosed herein are pharmaceutical compositions, kits, and lipid compositions for modulating an amount or activity of a gene or a gene product in a cell.

44 Claims, 52 Drawing Sheets
(3 of 52 Drawing Sheet(s) Filed in Color)
Specification includes a Sequence Listing.

(56) References Cited

FOREIGN PATENT DOCUMENTS

| WO | WO 2012-090223 | 7/2012 |
|---|---|---|
| WO | WO 2012-170952 | 12/2012 |
| WO | WO 2014-026283 | 2/2014 |
| WO | WO 2016-094342 | 6/2016 |
| WO | WO 2017-048789 | 3/2017 |
| WO | WO 2017-201091 | 11/2017 |

OTHER PUBLICATIONS

Akinc et al., "A combinatorial library of lipid-like materials for delivery of RNAi therapeutics," Nat. Biotechnol., 26:561-569, 2008.
Bosman et al., "About dendrimers: Structure, physical propertie, and applications," Chem. Rev., 99:1665-1688, 1999.
Boyerinas et al., "The role of let-7 in cell differentiation and cancer," Endocr.-Relat. Cancer, 17:F19-F36, 2010.
Carlmark et al., "New methodologies in the construction of dendritic materials," Chem. Soc. Rev., 38:352-362, 2009.
Chatani et al., "Facile and efficient synthesis of dendrimers and one-pot preparation of dendritic-linear polymer conjugates via a single chemistry: utilization of kinetically selective thiol-michael addition reactions," Macromolecules, 47:4894-4900, 2014.
Duncan and Izzo, "Dendrimer biocompatibility and toxicity," Adv. Drug Deliv. Rev., 57:2215-2237, 2005.
Extended European Search Report issued in European Application No. 16847196.6, dated Feb. 19, 2019.
Extended European Search Report issued in European Application No. 21183801.6, dated Jan. 11, 2022.
Franc and Kakkar, ""Click" methodologies: efficient, simple and greener routes to design dendrimers," Chem. Soc. Rev., 39:1536-1544, 2010.
Gillies and Fréchet, "Designing macromolecules for therapeutic applications: Polyester dendrimer-poly(ethylene oxide) "bow-tie" hybrids with tunable molecular weight and architecture," J. Am. Chem. Soc., 124:14137-14146, 2002.
Grayson and Fréchet, "Convergent dendrons and dendrimers: From synthesis to applications," Chem. Rev., 101:3819-3868, 2001.
Hao et al., "Rapid Synthesis of a Lipocationic Polyester Library via Ring-Opening Polymerization of Functional Valerolactones for Efficacious siRNA Delivery," Journal of the American Chemical Society, 137(29):9206-9209, 2015.
Hoyle et al., "Thiol-click chemistry: a multifaceted toolbox for small molecule and polymer synthesis," Chem. Soc. Rev., 39:1355-1387, 2010.
Jayaraman et al., "Maximizing the potency of siRNA lipid nanoparticles for hepatic gene silencing in vivo," Angew. Chem. Int. Ed., 51:8529-8533, 2012.
Kang et al., "Tat-conjugated PAMAM dendrimers as delivery agents for antisense and siRNA oligonucleotides," Pharm. Res., 22:2099-2106, 2005.
Khan et al., "Ionizable amphiphilic dendrimer-based nanomaterials with alkyl-chain-substituted amines for tunable siRNA delivery to the liver endothelium in vivo," Angew. Chem. Int. Ed., 53:14397-14401, 2014.
Killops et al., "Robust, efficient, and orthogonal synthesis of dendrimers via thiol-ene "click" chemistry," J. Am. Chem. Soc., 130:5062-5064, 2008.
Lee et al., "Designing dendrimers for biological applications," Nat. Biotechnol., 23:1517-1526, 2005.
Leung et al., "Lipid nanoparticles containing SiRNA synthesized by microfluidic mixing exhibit an electron-dense nanostrucutre core," J. Phys. Chem. C Nanomater Interaces, 116:18440-18450, 2012.
Li et al., "A biomimetric lipid library for gene delivery through thiol-yne click chemistry," Biomaterials, 33(32):8160-8166, 2012.
Love et al., "Lipid-like materials for low-dose, in vitro gene silencing," Proc Natl Acad Sci U S A, 107(5):1864-1869, 2010.

Ma et al., "Facile synthesis of polyester dendrimers from sequential click coupling of asymmetrical monomers," J. Am. Chem. Soc., 131(41):14795-14803, 2009.
Murat and Grest, "Molecular dynamics study of dendrimer molecules in solvents of varying quality," Macromolecules, 29:1278-1285, 1996.
Office Action issued in Chinese Application No. 201680065889.9, dated Feb. 28, 2022, and English translation thereof.
Office Action issued in Chinese Application No. 201680065889.9, dated Jul. 23, 2021, and English translation thereof.
Office Action issued in Chinese Application No. 201680065889.9, dated Sep. 25, 2020, and English translation thereof.
Office Action issued in European Application No. 16847193.6, dated Feb. 10, 2020.
Office Action issued in Japanese Application No. 2018-513463, dated Sep. 7, 2020.
Office Action issued in Japanese Application No. 2018-513463, dated Feb. 10, 2022.
Office Action issued in Japanese Application No. 2018-513463, dated Jul. 8, 2021, and English translation thereof.
Office Action issued in U.S. Appl. No. 15/265,064, dated Aug. 3, 2020.
Office Action issued in U.S. Appl. No. 15/265,064, dated Dec. 26, 2019.
Office Action issued in U.S. Appl. No. 15/265,064, dated Feb. 9, 2018.
Office Action issued in U.S. Appl. No. 15/265,064, dated May 3, 2017.
Office Action issued in U.S. Appl. No. 15/265,064, dated May 14, 2019.
Office Action issued in U.S. Appl. No. 15/265,064, dated Sep. 21, 2018.
Office Action issued in U.S. Appl. No. 15/265,064, dated Sep. 22, 2017.
PCT International Search Report and Written Opinion issued in International Application No. PCT/US2016/051648, dated Feb. 7, 2017.
PCT Invitation to Pay Additional Fees issued in International Application No. PCT/US2016/051648, dated Nov. 14, 2016.
Percec et al., "Self-assembly of Janus dendrimers into uniform dendrimersomes and other complex architectures," Science, 328:1009-1014, 2010.
Regnaud, "Design and synthesis of dendrimers by combination of 'click' chemistry and A3-coupling," Thesis, McGill University, pp. 1-67, 2013.
Schaffert et al., "Solid-phased synthesis of sequence-defined T-, i-, and U-shape polymers for pDNA and siRNA delivery," Angew. Chem. Int. Ed., 50:8986-8989, 2011.
Semple et al., "Rational design of cationic lipids for siRNA delivery," Nat. Biotechnol., 28:172-176, 2010.
Siegwart et al., "Combinatorial synthesis of chemically diverse core-shell nanoparticles for intracellular delivery," Proc. Natl. Acad. Sci. U.S.A., 108:12996-13001, 2011.
Stiriba et al., "Dendritic polymers in biomedical applications: From potential to clinical use in diagnostics and therapy," Angew. Chem. Int. Ed., 41:1329-1334, 2002.
Taratula et al., "Surface engineered targeted PPI dendrimer for efficient intracellular and intratumoral siRNA delivery," J. Control. Release, 140:284-293, 2009.
Whitehead et al., "Degradable lipid nanoparticles with predictable in vivo siRNA delivery activity," Nat. Commun., 5:4277, 2014.
Wu et al., "Dendrimers in medicine: Therapeutic concepts and pharmaceutical challenges," Bioconjugate Chem., 26(7):1198-1211, 2005.
Wu et al., "Efficiency and fidelity in a click-chemistry route to triazole dendrimers by the copper(I)-catalyzed ligation of azides and alkynes," Angew. Chem. Int. Ed., 43:3928-3932, 2004.
Xu et al., "Fluorescent water-soluble perylenedimide-cored cationic dendrimers: synthesis, optical properties, and cell uptake," Chem. Commun., 49:3646-3648, 2013.
Yu et al., "An amphiphilic dendrimer for effective delivery of small interfering RNA and gene silencing in vitro and in vivo," Angewandte Chem. Int. Ed., 51:8478-8484, 2012.

(56) References Cited

OTHER PUBLICATIONS

Zhou et al., "Modular degradable dendrimers enable small RNAs to extend survival in an aggressive liver cancer model," *PNAS*, 113(3):520-525, 2016.

Zhou et al., "PAMAM dendrimers for effficient siRNA delivery and potent gene silencing," *Chem. Commun.*, (22):2362-2364, 2006.

Alabi et al., "Multiparametric approach for the evaluation of lipid nanoparticle for siRNA delivery," *Proc Natl Acad Sci USA*, 110(32):12881-12886, 2013.

Ball et al., "Lipidoid Nanoparticles for siRNA Delivery to the Intestinal Epithelium: In Vitro Investigations in a Caco-2 Model," *PLoS One*, 10(7):e0133154, 2015.

\* cited by examiner

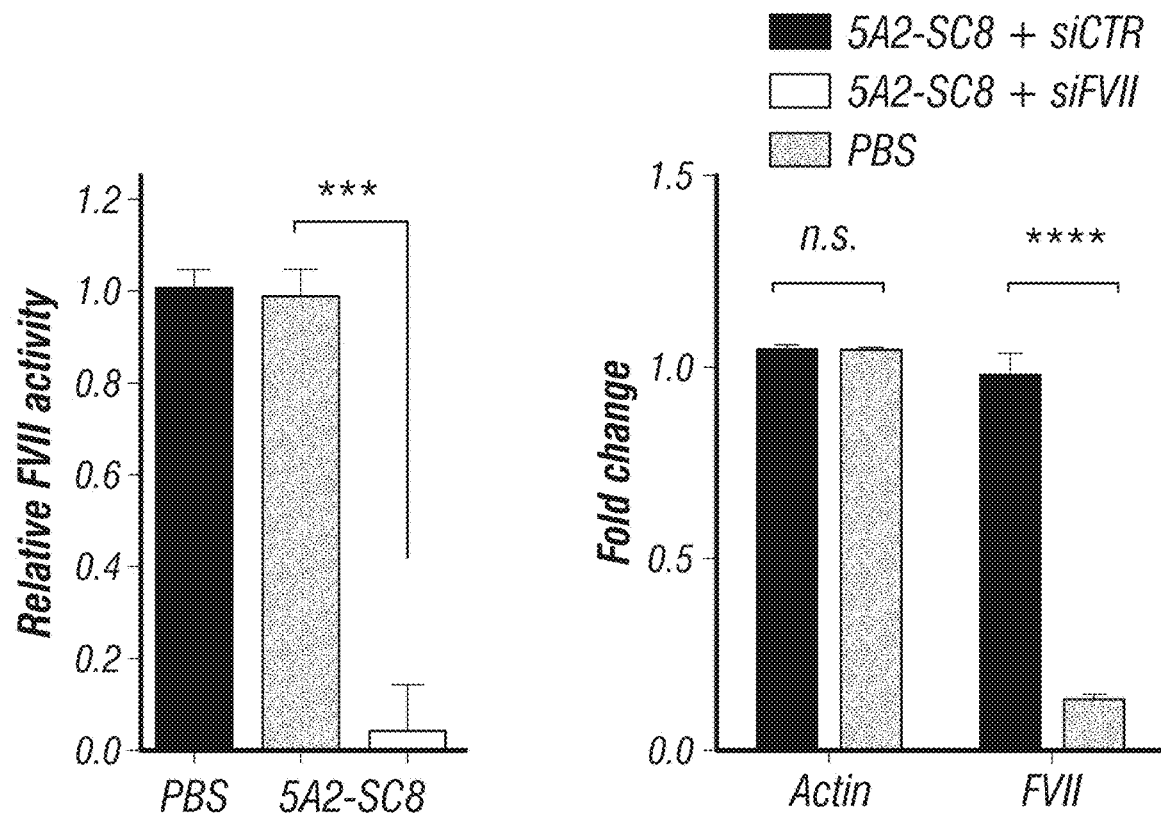
FIG. 16A
FIG. 16B
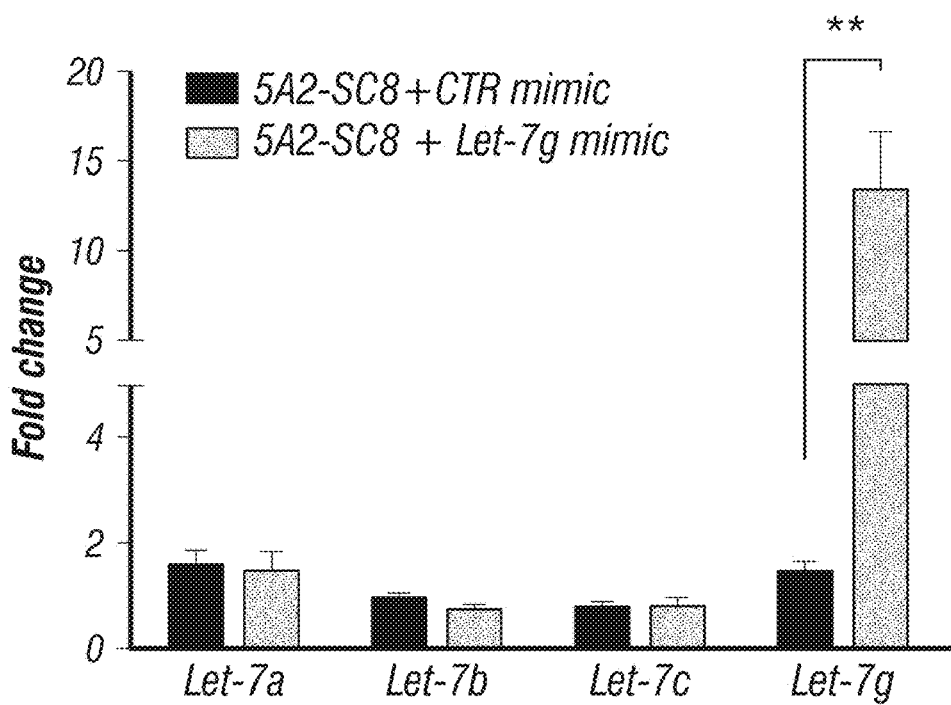
FIG. 16C

- ● 5A2-SC8 + CTR mimic
- □ 5A2-SC8 + Let-7g mimic
- ▲ WT control

COMPOSITIONS AND METHODS FOR MODULATING GENE OR GENE PRODUCT IN CELLS

The present application is a continuation of U.S. application Ser. No. 15/265,064, filed Sep. 14, 2016, now U.S. Pat. No. 11,247,968, which claims benefit of U.S. Provisional Application No. 62/218,412, filed Sep. 14, 2015.

BACKGROUND OF THE INVENTION

1. Field of the Invention

The present invention relates generally to the fields of dendrimers. In particular, it relates to dendrimer nanoparticle compositions comprising a nucleic acid. More particularly, it relates to dendrimer nanoparticle compositions for the delivery of the nucleic acid. More particularly, it relates to dendrimer nanoparticle compositions for the delivery of drugs and other excipients.

2. Description of Related Art

Since the discovery of RNAi or other nucleic acid agents and the recognition of their therapeutic potential, there has been a continuous search for effective delivery carriers (Whitehead et al., 2009; Kanasty et al., 2013; Akinc et al., 2008; Davis et al., 2010; Love et al., 2010; Siegwart et al., 2011; Jayaraman et al., 2012). Progress has been made with regard to delivery efficacy of small RNAs to healthy livers, but the clinically required combination of high potency to tumors and low normal cell hepatotoxicity is not currently met by existing delivery vehicles. Unfortunately, all five Phase III human clinical trials of small molecule drugs for hepatocellular carcinoma (HCC) treatment failed within the past four years in part because debilitating, late-stage liver dysfunction amplifies drug toxicity (Roberts, L. R., 2008; Scudellari, M., 2014). MicroRNAs (miRNAs) represent a promising alternative strategy because they can function as tumor suppressors by concurrently targeting multiple pathways involved in cell differentiation, proliferation, and survival, but these therapeutic agents require carriers to be effective (Ventura and Jacks, 2009; Kasinski and Slack, 2011; Ling et al., 2013; Cheng et al., 2015). A balance of potency versus toxicity of the drug carrier is a useful criteria particularly in the context of liver cancer where the carrier's own toxicity can abate the therapeutic effectiveness of the small RNA therapies.

To achieve this balance of low toxicity and high potency, the influence of chemical structure by expanding the structural diversity and molecular size of delivery carriers is useful in achieving a therapeutically effective balance. Dendrimers are monodisperse macromolecules composed of multiple perfectly branched monomers that emanate radially from a central core. The dendrimers therefore have the same high degree of molecular uniformity as small molecules and the broad theoretical space for chemical tuning as polydisperse polymers (Bosman et al., 1999; Fréchet and Tomalia, 2002; Gillies and Frechet, 2002; Grayson and Fréchet, 2001). These intrinsic characteristics enable dendrimers to have unique properties (Murat and Grest, 1996; Percec et al., 2010; Duncan and Izzo, 2005) for various biomedical applications (Stiriba et al., 2002; Lee et al., 2005; Wu et al., 2015). In gene delivery, most studies have used the limited number of commercial dendrimers for further chemical modification. (Kang et al., 2005; Taratula et al., 2009; Khan et al., 2014). The expansion of dendrimer applications therefore depends on the ability to easily tune the size, chemistry, topology, and ultimately, dendrimer physical properties through chemical synthesis. As such, the development of new dendrimers which can act as carriers of nucleic acids and other drugs is clinically useful.

SUMMARY OF THE INVENTION

In some aspects, the present disclosure provides dendrimers of the formula:

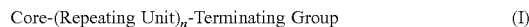

Core-(Repeating Unit)$_n$-Terminating Group     (I)

wherein the core is linked to the repeating unit by removing one or more hydrogen atoms from the core and replacing the atom with the repeating unit and wherein: the core has the formula:

(II)

wherein:
  $X_1$ is amino or alkylamino$_{(C \leq 12)}$, dialkylamino$_{(C \leq 12)}$, heterocycloalkyl$_{(C \leq 12)}$, heteroaryl$_{(C \leq 12)}$, or a substituted version thereof;
  $R_1$ is amino, hydroxy, or mercapto, or alkylamino$_{(C \leq 12)}$, dialkylamino$_{(C \leq 12)}$, or a substituted version of either of these groups; and
  a is 1, 2, 3, 4, 5, or 6; or
the core has the formula:

(III)

wherein:
  $X_2$ is $N(R_5)_y$;
    $R_5$ is hydrogen, alkyl$_{(C \leq 18)}$, or substituted alkyl$_{(C \leq 18)}$; and
    y is 0, 1, or 2, provided that the sum of y and z is 3;
  $R_2$ is amino, hydroxy, or mercapto, or alkylamino$_{(C \leq 12)}$, dialkylamino$_{(C \leq 12)}$, or a substituted version of either of these groups;
  b is 1, 2, 3, 4, 5, or 6; and
  z is 1, 2, 3; provided that the sum of z and y is 3; or
the core has the formula:

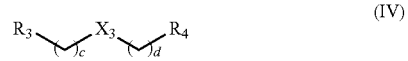

(IV)

wherein:
  $X_3$ is —NR$_6$—, wherein R$_6$ is hydrogen, alkyl$_{(C \leq 8)}$, or substituted alkyl$_{(C \leq 8)}$, —O—, or alkylaminodiyl$_{(C \leq 8)}$, alkoxydiyl$_{(C \leq 8)}$, arenediyl$_{(C \leq 8)}$, heteroarenediyl$_{(C \leq 8)}$, heterocycloalkanediyl$_{(C \leq 8)}$, or a substituted version of any of these groups;
  $R_3$ and $R_4$ are each independently amino, hydroxy, or mercapto, or alkylamino$_{(C \leq 12)}$, dialkylamino$_{(C \leq 12)}$, or a substituted version of either of these groups; or a group of the formula: —(CH$_2$CH$_2$N)$_e$ (R$_c$)R$_d$;

wherein:
  e is 1, 2, or 3;
  $R_c$ and $R_d$ are each independently hydrogen, alkyl$_{(C \leq 6)}$, or substituted alkyl$_{(C \leq 6)}$;
  c and d are each independently 1, 2, 3, 4, 5, or 6; or
the core is alkylamine$_{(C \leq 18)}$, dialkylamine$_{(C \leq 36)}$, heterocycloalkane$_{(C \leq 12)}$, or a substituted version of any of these groups;
wherein the repeating unit comprises a degradable diacyl and a linker;
the degradable diacyl group has the formula:

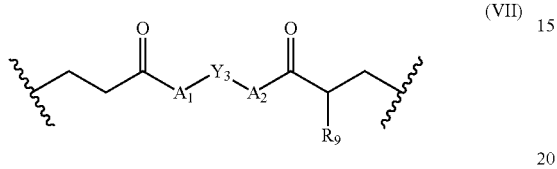
(VII)

wherein:
  $A_1$ and $A_2$ are each independently —O— or —NR$_a$—, wherein:
    $R_a$ is hydrogen, alkyl$_{(C \leq 6)}$, or substituted alkyl$_{(C \leq 6)}$;
  $Y_3$ is alkanediyl$_{(C \leq 12)}$, alkenediyl$_{(C \leq 12)}$, arenediyl$_{(C \leq 12)}$, or a substituted version of any of these groups; or a group of the formula:

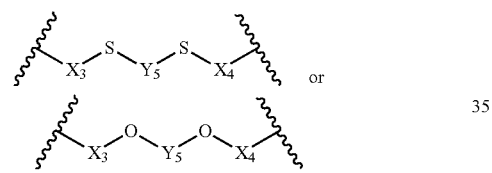

wherein:
  $X_3$ and $X_4$ are alkanediyl$_{(C \leq 12)}$, alkenediyl$_{(C \leq 12)}$, arenediyl$_{(C \leq 12)}$, or a substituted version of any of these groups;
  $Y_5$ is a covalent bond, alkanediyl$_{(C \leq 12)}$, alkenediyl$_{(C \leq 12)}$, arenediyl$_{(C \leq 12)}$, or a substituted version of any of these groups; and
  $R_9$ is alkyl$_{(C \leq 8)}$ or substituted alkyl$_{(C \leq 8)}$;
the linker group has the formula:

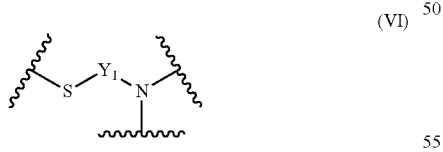
(VI)

wherein:
  $Y_1$ is alkanediyl$_{(C \leq 12)}$, alkenediyl$_{(C \leq 12)}$, arenediyl$_{(C \leq 12)}$, or a substituted version of any of these groups; and
wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and
the terminating group has the formula:

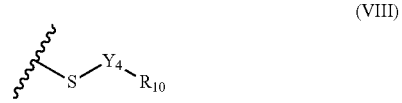
(VIII)

wherein:
  $Y_4$ is alkanediyl$_{(C \leq 18)}$ or an alkanediyl$_{(C \leq 18)}$ wherein one or more of the hydrogen atoms on the alkanediyl$_{(C \leq 18)}$ has been replaced with —OH, —F, —Cl, —Br, —I, —SH, —OCH$_3$, —OCH$_2$CH$_3$, —SCH$_3$, or —OC(O)CH$_3$;
  $R_{10}$ is hydrogen, carboxy, hydroxy, or aryl$_{(C \leq 12)}$, alkylamino$_{(C \leq 12)}$, dialkylamino$_{(C \leq 12)}$, N-heterocycloalkyl$_{(C \leq 12)}$, —C(O)N(R$_{11}$)-alkanediyl$_{(C \leq 6)}$-heterocycloalkyl$_{(C \leq 12)}$, —C(O)-alkyl-amino$_{(C \leq 12)}$, —C(O)-dialkylamino$_{(C \leq 12)}$, —C(O)—N-heterocycloalkyl$_{(C \leq 12)}$, wherein:
    $R_{11}$ is hydrogen, alkyl$_{(C \leq 6)}$, or substituted alkyl$_{(C \leq 6)}$;
wherein the final degradable diacyl in the chain is attached to a terminating group;
n is 0, 1, 2, 3, 4, 5, or 6;
or a pharmaceutically acceptable salt thereof. In some embodiments, the structure of the dendrimer is further defined:
the core has the formula:

(II)

wherein:
  $X_1$ is amino or alkylamino$_{(C \leq 12)}$, dialkylamino$_{(C \leq 12)}$, heterocycloalkyl$_{(C \leq 12)}$, heteroaryl$_{(C \leq 12)}$, or a substituted version thereof;
  $R_1$ is amino, hydroxy, or mercapto, or alkylamino$_{(C \leq 12)}$, dialkylamino$_{(C \leq 12)}$, or a substituted version of either of these groups; and
  a is 1, 2, 3, 4, 5, or 6; and
wherein the repeating unit comprises a degradable diacyl and a linker;
the degradable diacyl group has the formula:

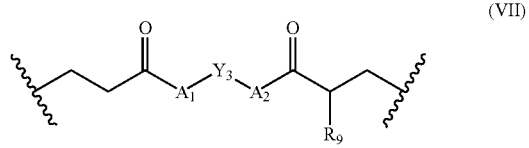
(VII)

wherein:
  $A_1$ and $A_2$ are each independently —O— or —NR$_a$—, wherein:
    $R_a$ is hydrogen, alkyl$_{(C \leq 6)}$, or substituted alkyl$_{(C \leq 6)}$;
  $Y_3$ is alkanediyl$_{(C \leq 12)}$, alkenediyl$_{(C \leq 12)}$, arenediyl$_{(C \leq 12)}$, or a substituted version of any of these groups; or a group of the formula:

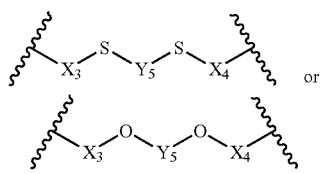

wherein:
X$_3$ and X$_4$ are alkanediyl$_{(C \leq 12)}$, alkenediyl$_{(C \leq 12)}$, arenediyl$_{(C \leq 12)}$, or a substituted version of any of these groups;
Y$_5$ is a covalent bond, alkanediyl$_{(C \leq 12)}$, alkenediyl$_{(C \leq 12)}$, arenediyl$_{(C \leq 12)}$, or a substituted version of any of these groups; and
R$_9$ is alkyl$_{(C \leq 8)}$ or substituted alkyl$_{(C \leq 8)}$;
the linker group has the formula:

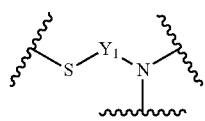
(VI)

wherein:
Y$_1$ is alkanediyl$_{(C \leq 12)}$, alkenediyl$_{(C \leq 12)}$, arenediyl$_{(C \leq 12)}$, or a substituted version of any of these groups; and
wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and
the terminating group, wherein the terminating group has the formula:

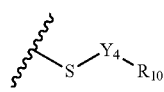
(VIII)

wherein:
Y$_4$ is alkanediyl$_{(C \leq 18)}$ or an alkanediyl$_{(C \leq 18)}$ wherein one or more of the hydrogen atoms on the alkanediyl$_{(C \leq 18)}$ has been replaced with —OH, —F, —Cl, —Br, —I, —SH, —OCH$_3$, —OCH$_2$CH$_3$, —SCH$_3$, or —OC(O)CH$_3$;
R$_{10}$ is hydrogen, carboxy, hydroxy, or aryl$_{(C \leq 12)}$, alkylamino$_{(C \leq 12)}$, dialkylamino$_{(C \leq 12)}$, N-heterocycloalkyl$_{(C \leq 12)}$, —C(O)N(R$_{11}$)-alkanediyl$_{(C \leq 6)}$-heterocycloalkyl$_{(C \leq 12)}$, —C(O)-alkyl-amino$_{(C \leq 12)}$, —C(O)-dialkylamino$_{(C \leq 12)}$, —C(O)—N-heterocycloalkyl$_{(C \leq 12)}$, wherein:
R$_{11}$ is hydrogen, alkyl$_{(C \leq 6)}$, or substituted alkyl$_{(C \leq 6)}$;
wherein the final degradable diacyl in the chain is attached to a terminating group;
n is 0, 1, 2, 3, 4, 5, or 6;

or a pharmaceutically acceptable salt thereof. In some embodiments, the dendrimer has the formula:

Core-(Repeating Unit)$_n$-Terminating Group (I)

wherein the core is linked to the repeating unit by removing one or more hydrogen atoms from the core and replacing the atom with the repeating unit and wherein:
the core has the formula:

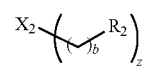
(III)

wherein:
X$_2$ is N(R$_5$)$_y$;
R$_5$ is hydrogen or alkyl$_{(C \leq 8)}$, or substituted alkyl$_{(C \leq 18)}$; and
y is 0, 1, or 2, provided that the sum of y and z is 3;
R$_2$ is amino, hydroxy, or mercapto, or alkylamino$_{(C \leq 12)}$, dialkylamino$_{(C \leq 12)}$, or a substituted version of either of these groups;
b is 1, 2, 3, 4, 5, or 6; and
z is 1, 2, 3; provided that the sum of z and y is 3;
wherein the repeating unit comprises a degradable diacyl and a linker;
the degradable diacyl group has the formula:

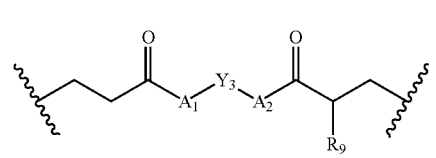
(VII)

wherein:
A$_1$ and A$_2$ are each independently —O— or —NR$_a$—, wherein:
R$_a$ is hydrogen, alkyl$_{(C \leq 6)}$, or substituted alkyl$_{(C \leq 6)}$;
Y$_3$ is alkanediyl$_{(C \leq 12)}$, alkenediyl$_{(C \leq 12)}$, arenediyl$_{(C \leq 12)}$, or a substituted version of any of these groups; or a group of the formula:

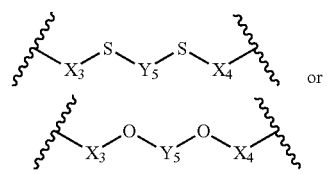

wherein:
X$_3$ and X$_4$ are alkanediyl$_{(C \leq 12)}$, alkenediyl$_{(C \leq 12)}$, arenediyl$_{(C \leq 12)}$, or a substituted version of any of these groups;
Y$_5$ is a covalent bond, alkanediyl$_{(C \leq 12)}$, alkenediyl$_{(C \leq 12)}$, arenediyl$_{(C \leq 12)}$, or a substituted version of any of these groups; and
R$_9$ is alkyl$_{(C \leq 8)}$ or substituted alkyl$_{(C \leq 8)}$;

the linker group has the formula:

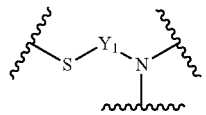
(VI)

wherein:
- $Y_1$ is alkanediyl$_{(C≤12)}$, alkenediyl$_{(C≤12)}$, arenediyl$_{(C≤12)}$, or a substituted version of any of these groups; and
- wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and
- the terminating group, wherein the terminating group has the formula:

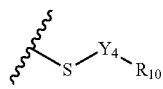
(VIII)

wherein:
- $Y_4$ is alkanediyl$_{(C≤18)}$ or an alkanediyl$_{(C≤18)}$ wherein one or more of the hydrogen atoms on the alkanediyl$_{(C≤18)}$ has been replaced with —OH, —F, —Cl, —Br, —I, —SH, —OCH$_3$, —OCH$_2$CH$_3$, —SCH$_3$, or —OC(O)CH$_3$;
- $R_{10}$ is hydrogen, carboxy, hydroxy, or aryl$_{(C≤12)}$, alkylamino$_{(C≤12)}$, dialkylamino$_{(C≤12)}$, N-heterocycloalkyl$_{(C≤12)}$, —C(O)N(R$_{11}$)-alkanediyl$_{(C≤6)}$-heterocycloalkyl$_{(C≤12)}$, —C(O)-alkyl-amino$_{(C≤12)}$, —C(O)-dialkylamino$_{(C≤12)}$, —C(O)—N-heterocycloalkyl$_{(C≤12)}$, wherein:
- wherein the final degradable diacyl in the chain is attached to a terminating group;
- n is 0, 1, 2, 3, 4, 5, or 6;
- or a pharmaceutically acceptable salt thereof. In other embodiments, the dendrimer has the formula:

Core-(Repeating Unit)$_n$-Terminating Group (I)

wherein the core is linked to the repeating unit by removing one or more hydrogen atoms from the core and replacing the atom with the repeating unit and wherein: the core has the formula:

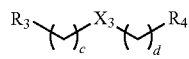
(IV)

wherein:
- $X_3$ is —NR$_6$—, wherein R$_6$ is hydrogen, alkyl$_{(C≤8)}$ or substituted alkyl$_{(C≤8)}$, —O—, or alkylaminodiyl$_{(C≤8)}$, alkoxydiyl$_{(C≤8)}$, arenediyl$_{(C≤8)}$, heteroarenediyl$_{(C≤8)}$, heterocycloalkanediyl$_{(C≤8)}$, or a substituted version of any of these groups;
- $R_3$ and $R_4$ are each independently amino, hydroxy, or mercapto, or alkylamino$_{(C≤12)}$, dialkylamino$_{(C≤12)}$, or a substituted version of either of these groups; or a group of the formula: —(CH$_2$CH$_2$N)$_e$(R$_c$)R$_d$;

wherein:
- e is 1, 2, or 3;
- $R_c$ and $R_d$ are each independently hydrogen, alkyl$_{(C≤6)}$, or substituted alkyl$_{(C≤6)}$;
- c and d are each independently 1, 2, 3, 4, 5, or 6; and wherein the repeating unit comprises a degradable diacyl and a linker;
the degradable diacyl group has the formula:

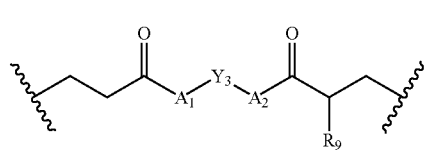
(VII)

wherein:
- $A_1$ and $A_2$ are each independently —O— or —NR$_a$—, wherein:
- $R_a$ is hydrogen, alkyl$_{(C≤6)}$, or substituted alkyl$_{(C≤6)}$;
- $Y_3$ is alkanediyl$_{(C≤12)}$, alkenediyl$_{(C≤12)}$, arenediyl$_{(C≤12)}$, or a substituted version of any of these groups; or a group of the formula:

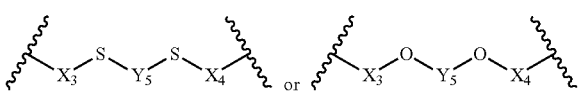

wherein:
- $X_3$ and $X_4$ are alkanediyl$_{(C≤12)}$, alkenediyl$_{(C≤12)}$, arenediyl$_{(C≤12)}$, or a substituted version of any of these groups;
- $Y_5$ is a covalent bond, alkanediyl$_{(C≤12)}$, alkenediyl$_{(C≤12)}$, arenediyl$_{(C≤12)}$, or a substituted version of any of these groups; and
- $R_9$ is alkyl$_{(C≤8)}$ or substituted alkyl$_{(C≤8)}$;

the linker group has the formula:

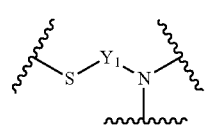
(VI)

wherein:
- $Y_1$ is alkanediyl$_{(C≤12)}$, alkenediyl$_{(C≤12)}$, arenediyl$_{(C≤12)}$, or a substituted version of any of these groups; and
- wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and the terminating group, wherein the terminating group has the formula:

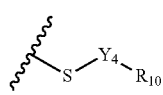

(VIII)

wherein:
Y$_4$ is alkanediyl$_{(C \leq 18)}$ or an alkanediyl$_{(C \leq 18)}$ wherein one or more of the hydrogen atoms on the alkanediyl$_{(C \leq 18)}$ has been replaced with —OH, —F, —Cl, —Br, —I, —SH, —OCH$_3$, —OCH$_2$CH$_3$, —SCH$_3$, or —OC(O)CH$_3$;

R$_{10}$ is hydrogen, carboxy, hydroxy, or aryl$_{(C \leq 12)}$, alkylamino$_{(C \leq 12)}$, dialkylamino$_{(C \leq 12)}$, N-heterocycloalkyl$_{(C \leq 12)}$, —C(O)N(R$_{11}$)-alkanediyl$_{(C \leq 6)}$-heterocycloalkyl$_{(C \leq 12)}$, —C(O)-alkyl-amino$_{(C \leq 12)}$, —C(O)-dialkylamino$_{(C \leq 12)}$, —C(O)—N-heterocycloalkyl$_{(C \leq 12)}$, wherein:
R$_{11}$ is hydrogen, alkyl$_{(C \leq 6)}$, or substituted alkyl$_{(C \leq 6)}$;

wherein the final degradable diacyl in the chain is attached to a terminating group;
n is 0, 1, 2, 3, 4, 5, or 6;
or a pharmaceutically acceptable salt thereof. In other embodiments, the dendrimer has the formula:

Core-(Repeating Unit)$_n$-Terminating Group (I)

wherein the core is linked to the repeating unit by removing one or more hydrogen atoms from the core and replacing the atom with the repeating unit and wherein:
the core is alkylamine$_{(C \leq 18)}$, dialkylamine$_{(C \leq 36)}$, heterocycloalkane$_{(C \leq 12)}$, or a substituted version of any of these groups; and
wherein the repeating unit comprises a degradable diacyl and a linker;
the degradable diacyl group has the formula:

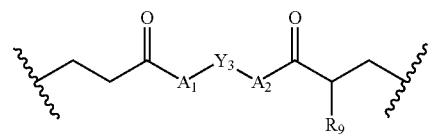

(VII)

wherein:
A$_1$ and A$_2$ are each independently —O— or —NR$_a$—, wherein:
R$_a$ is hydrogen, alkyl$_{(C \leq 6)}$, or substituted alkyl$_{(C \leq 6)}$;
Y$_3$ is alkanediyl$_{(C \leq 12)}$, alkenediyl$_{(C \leq 12)}$, arenediyl$_{(C \leq 12)}$, or a substituted version of any of these groups; or a group of the formula:

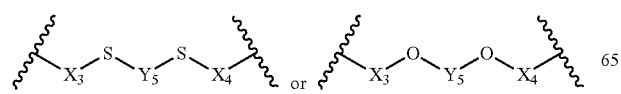

wherein:
X$_3$ and X$_4$ are alkanediyl$_{(C \leq 12)}$, alkenediyl$_{(C \leq 12)}$, arenediyl$_{(C \leq 12)}$, or a substituted version of any of these groups;
Y$_5$ is a covalent bond, alkanediyl$_{(C \leq 12)}$, alkenediyl$_{(C \leq 12)}$, arenediyl$_{(C \leq 12)}$, or a substituted version of any of these groups; and
R$_9$ is alkyl$_{(C \leq 8)}$ or substituted alkyl$_{(C \leq 8)}$;
the linker group has the formula:

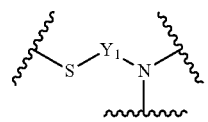

(VI)

wherein:
Y$_1$ is alkanediyl$_{(C \leq 12)}$, alkenediyl$_{(C \leq 12)}$, arenediyl$_{(C \leq 12)}$, or a substituted version of any of these groups; and
wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and
the terminating group, wherein the terminating group has the formula:

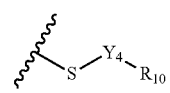

(VIII)

wherein:
Y$_4$ is alkanediyl$_{(C \leq 18)}$ or an alkanediyl$_{(C \leq 18)}$ wherein one or more of the hydrogen atoms on the alkanediyl$_{(C \leq 18)}$ has been replaced with —OH, —F, —Cl, —Br, —I, —SH, —OCH$_3$, —OCH$_2$CH$_3$, —SCH$_3$, or —OC(O)CH$_3$;

R$_{10}$ is hydrogen, carboxy, hydroxy, or aryl$_{(C \leq 12)}$, alkylamino$_{(C \leq 12)}$, dialkylamino$_{(C \leq 12)}$, N-heterocycloalkyl$_{(C \leq 12)}$, —C(O)N(R$_{11}$)-alkanediyl$_{(C \leq 6)}$-heterocycloalkyl$_{(C \leq 12)}$, —C(O)-alkyl-amino$_{(C \leq 12)}$, —C(O)-dialkylamino$_{(C \leq 12)}$, —C(O)—N-heterocycloalkyl$_{(C \leq 12)}$, wherein:
R$_{11}$ is hydrogen, alkyl$_{(C \leq 6)}$, or substituted alkyl$_{(C \leq 6)}$;

wherein the final degradable diacyl in the chain is attached to a terminating group;
n is 0, 1, 2, 3, 4, 5, or 6;
or a pharmaceutically acceptable salt thereof. In some embodiments, the terminating group is further defined by the formula:

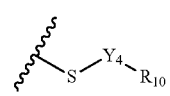

(VIII)

wherein:
Y$_4$ is alkanediyl$_{(C \leq 18)}$ or an alkanediyl$_{(C \leq 18)}$ wherein one or more of the hydrogen atoms has been replaced with —OH, —F, —Cl, —Br, —I, —SH, —OCH$_3$, —OCH$_2$CH$_3$, —SCH$_3$, or —OC(O)CH$_3$; and
R$_{10}$ is hydrogen.

In other embodiments, the terminating group is further defined by the formula:

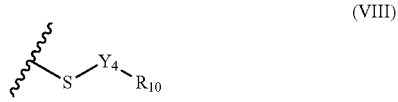

(VIII)

wherein:
Y$_4$ is alkanediyl$_{(C \leq 18)}$; and R$_{10}$ is hydrogen.

In some embodiments, Y$_4$ is alkanediyl$_{(C \leq 18)}$. In other embodiments, the terminating group is further defined by the formula:

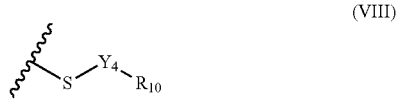

(VIII)

wherein:
Y$_4$ is alkanediyl$_{(C \leq 18)}$ or an alkanediyl$_{(C \leq 18)}$ wherein one or more of the hydrogen atoms has been replaced with —OH, —F, —Cl, —Br, —I, —SH, —OCH$_3$, —OCH$_2$CH$_3$, —SCH$_3$, or —OC(O)CH$_3$;
R$_{10}$ is alkylamino$_{(C \leq 12)}$, dialkylamino$_{(C \leq 12)}$, N-heterocycloalkyl$_{(C \leq 12)}$.

In some embodiments, the terminating group is further defined by the formula:

(VIII)

wherein:
Y$_4$ is alkanediyl$_{(C \leq 18)}$ or an alkanediyl$_{(C \leq 18)}$ wherein one or more of the hydrogen atoms has been replaced with —OH, —F, —Cl, —Br, —I, —SH, —OCH$_3$, —OCH$_2$CH$_3$, —SCH$_3$, or —OC(O)CH$_3$;
R$_{10}$ is hydroxy.

In some embodiments, the core is further defined by the formula:

(II)

wherein:
X$_1$ is alkylamino$_{(C \leq 12)}$, dialkylamino$_{(C \leq 12)}$, heterocycloalkyl$_{(C \leq 12)}$, heteroaryl$_{(C \leq 12)}$, or a substituted version thereof;
R$_1$ is amino, hydroxy, or mercapto, or alkylamino$_{(C \leq 12)}$, dialkylamino$_{(C \leq 12)}$, or a substituted version of either of these groups; and
a is 1, 2, 3, 4, 5, or 6;

In some embodiments, X$_1$ is alkylamino$_{(C \leq 12)}$ or substituted alkylamino$_{(C \leq 12)}$. In some embodiments, X$_1$ is ethylamino. In other embodiments, X$_1$ is dialkylamino$_{(C \leq 12)}$ or substituted dialkylamino$_{(C \leq 12)}$. In some embodiments, X$_1$ is dimethylamino. In other embodiments, X$_1$ is heterocycloalkyl$_{(C \leq 12)}$ or substituted heterocycloalkyl$_{(C \leq 12)}$. In some embodiments, X$_1$ is 4-piperidinyl, N-piperidinyl, N-morpholinyl, N-pyrrolidinyl, 2-pyrrolidinyl, N-piperazinyl, or N-4-methylpiperadizinyl. In other embodiments, X$_1$ is heteroaryl$_{(C \leq 12)}$ or substituted heteroaryl$_{(C \leq 12)}$. In some embodiments, X$_1$ is 2-pyridinyl or N-imidazolyl. In some embodiments, R$_1$ is hydroxy. In other embodiments, R$_1$ is amino. In other embodiments, R$_1$ is alkylamino$_{(C \leq 12)}$ or substituted alkylamino$_{(C \leq 12)}$. In some embodiments, R$_1$ is alkylamino$_{(C \leq 12)}$. In some embodiments, R$_1$ is methylamino or ethylamino. In some embodiments, a is 1, 2, 3, or 4. In some embodiments, a is 2 or 3. In some embodiments, a is 2. In other embodiments, a is 3. In some embodiments, the core is further defined as a compound of the formula:

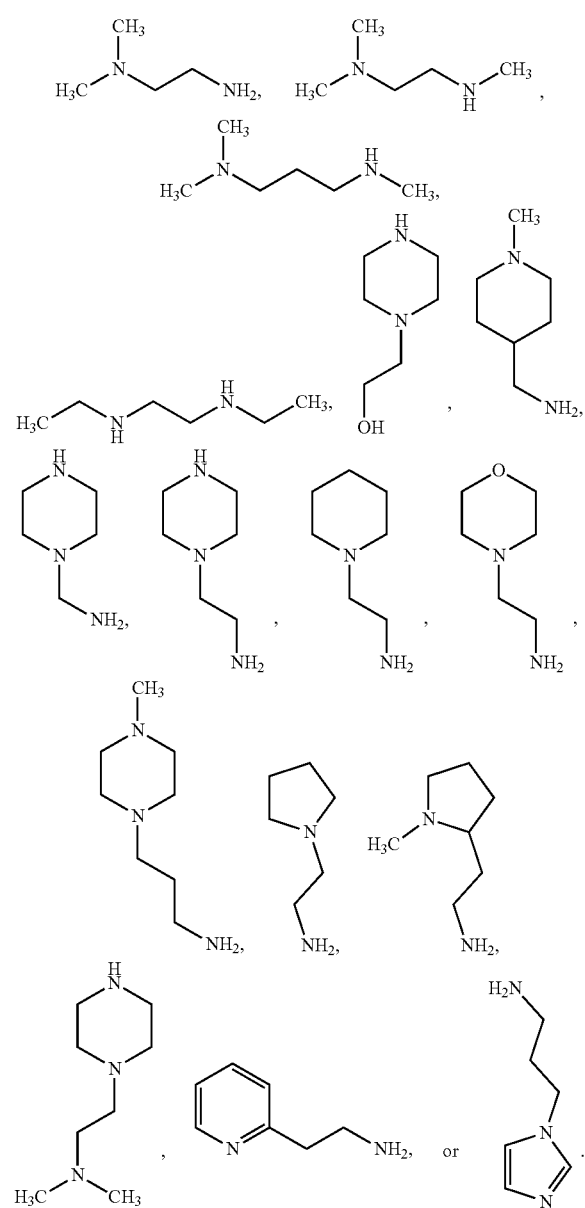

In some embodiments, the core is further defined as:

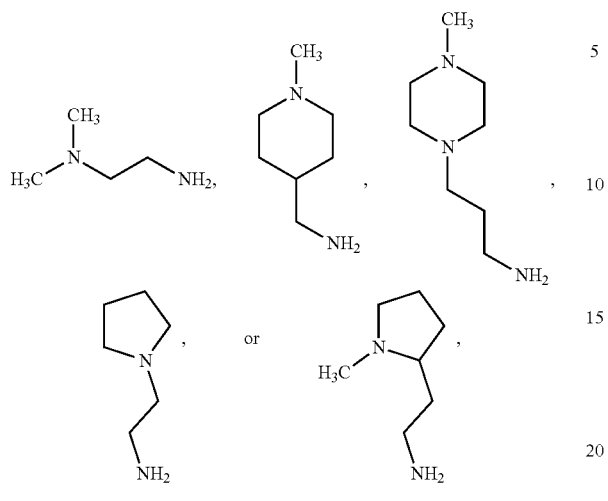

In other embodiments, the core is further defined by the formula:

(III)

wherein:

X$_2$ is N(R$_5$)$_y$;

R$_5$ is hydrogen or alkyl$_{(C\leq8)}$, or substituted alkyl$_{(C\leq18)}$; and y is 0, 1, or 2, provided that the sum of y and z is 3;

R$_2$ is amino, hydroxy, or mercapto, or alkylamino$_{(C\leq12)}$, dialkylamino$_{(C\leq12)}$, or a substituted version of either of these groups;

b is 1, 2, 3, 4, 5, or 6; and z is 1, 2, 3; provided that the sum of z and y is 3.

In some embodiments, X$_2$ is N. In other embodiments, X$_2$ is NR$_5$, wherein R$_5$ is hydrogen or alkyl$_{(C\leq8)}$. In some embodiments, R$_5$ is hydrogen. In other embodiments, R$_5$ is methyl. In some embodiments, z is 3. In other embodiments, z is 2. In some embodiments, R$_2$ is hydroxy. In other embodiments, R$_2$ is amino. In other embodiments, R$_2$ is alkylamino$_{(C\leq12)}$ or substituted alkylamino$_{(C\leq12)}$. In some embodiments, R$_2$ is alkylamino$_{(C\leq12)}$. In some embodiments, R$_2$ is methylamino. In other embodiments, R$_2$ is dialkylamino$_{(C\leq12)}$ or substituted dialkylamino$_{(C\leq12)}$. In some embodiments, R$_2$ is dialkylamino$_{(C\leq12)}$. In some embodiments, R$_2$ is dimethylamino. In some embodiments, b is 1, 2, 3, or 4. In some embodiments, b is 2 or 3. In some embodiments, b is 2. In other embodiments, b is 3. In some embodiments, the core is further defined as:

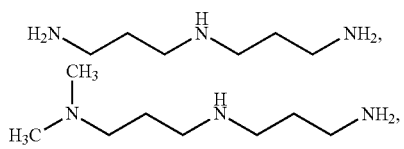

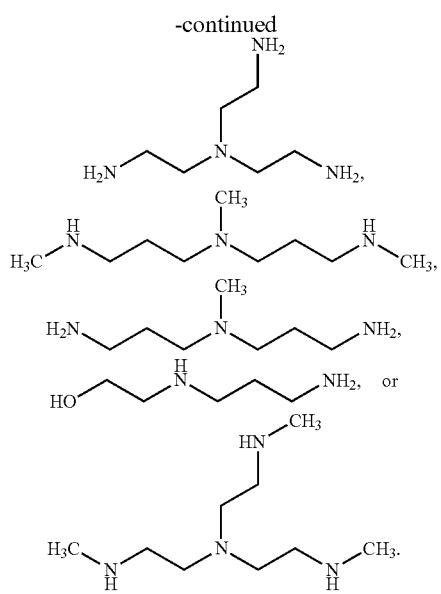

In some embodiments, the core is further defined as:

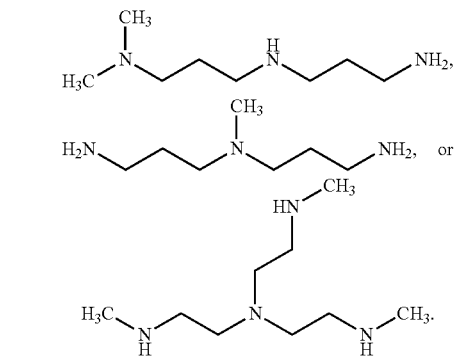

In other embodiments, the core is further defined as:

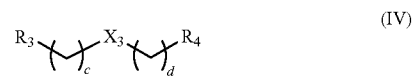

(IV)

wherein:

X$_3$ is —NR$_6$—, wherein R$_6$ is hydrogen, alkyl$_{(C\leq8)}$, or substituted alkyl$_{(C\leq8)}$, —O—, or alkylaminodiyl$_{(C\leq8)}$, alkoxydiyl$_{(C\leq8)}$, arenediyl$_{(C\leq8)}$, heteroarenediyl$_{(C\leq8)}$, heterocycloalkanediyl$_{(C\leq8)}$, or a substituted version of any of these groups;

R$_3$ and R$_4$ are each independently amino, hydroxy, or mercapto, or alkylamino$_{(C\leq12)}$, dialkylamino$_{(C\leq12)}$, or a substituted version of either of these groups; or a group of the formula: —(CH$_2$CH$_2$N)$_e$(R$_c$)R$_d$;

wherein:

e is 1, 2, or 3;

R$_c$ and R$_d$ are each independently hydrogen, alkyl$_{(C\leq6)}$, or substituted alkyl$_{(C\leq6)}$;

c and d are each independently 1, 2, 3, 4, 5, or 6.

In some embodiments, X$_3$ is —O—. In other embodiments, X$_3$ is —NR$_6$—, wherein R$_6$ is hydrogen, alkyl$_{(C\leq8)}$, or substituted alkyl$_{(C\leq8)}$. In some embodiments, X$_3$ is —NH— or —NCH$_3$—. In other embodiments, X$_3$ is alkylaminodiyl$_{(C≤8)}$ or substituted alkylaminodiyl$_{(C≤8)}$. In some embodiments, X$_3$ is —NHCH$_2$CH$_2$NH— or —NHCH$_2$CH$_2$NHCH$_2$CH$_2$NH—. In other embodiments, X$_3$ is alkoxydiyl$_{(C≤8)}$ or substituted alkoxydiyl$_{(C≤8)}$. In some embodiments, X$_3$ is —OCH$_2$CH$_2$O—. In other embodiments, X$_3$ is arenediyl$_{(C≤8)}$ or substituted arenediyl$_{(C≤8)}$. In some embodiments, X$_3$ is benzenediyl. In other embodiments, X$_3$ is heterocycloalkanediyl$_{(C≤8)}$ or substituted heterocycloalkanediyl$_{(C≤8)}$. In some embodiments, X$_3$ is N,N'-piperazindiyl.

In some embodiments, R$_3$ is amino. In other embodiments, R$_3$ is hydroxy. In other embodiments, R$_3$ is alkylamino$_{(C≤12)}$ or substituted alkylamino$_{(C≤12)}$. In some embodiments, R$_3$ is alkylamino$_{(C≤12)}$. In some embodiments, R$_3$ is methylamino. In other embodiments, R$_3$ is dialkylamino$_{(C≤12)}$ or substituted dialkylamino$_{(C≤12)}$. In some embodiments, R$_3$ is dialkylamino$_{(C≤12)}$. In some embodiments, R$_3$ is dimethylamino.

In some embodiments, R$_4$ is amino. In other embodiments, R$_4$ is hydroxy. In other embodiments, R$_4$ is alkylamino$_{(C≤12)}$ or substituted alkylamino$_{(C≤12)}$. In some embodiments, R$_4$ is alkylamino$_{(C≤12)}$. In some embodiments, R$_4$ is methylamino. In other embodiments, R$_4$ is dialkylamino$_{(C≤12)}$ or substituted dialkylamino$_{(C≤12)}$. In some embodiments, R$_4$ is dialkylamino$_{(C≤12)}$. In some embodiments, R$_4$ is dimethylamino. In other embodiments, R$_4$ is —(CH$_2$CH$_2$N)$_e$(R$_c$)R$_d$: wherein: e is 1, 2, or 3; and R$_c$ and R$_d$ are each independently hydrogen, alkyl$_{(C≤6)}$, or substituted alkyl$_{(C≤6)}$. In some embodiments, e is 1 or 2. In some embodiments, e is 1. In some embodiments, R$_c$ is hydrogen. In some embodiments, R$_d$ is hydrogen.

In some embodiments, c is 1, 2, 3, or 4. In some embodiments, c is 2 or 3. In some embodiments, c is 2. In other embodiments, c is 3. In some embodiments, d is 1, 2, 3, or 4. In some embodiments, d is 2 or 3. In some embodiments, d is 2. In other embodiments, d is 3. In some embodiments, the core is further defined as:

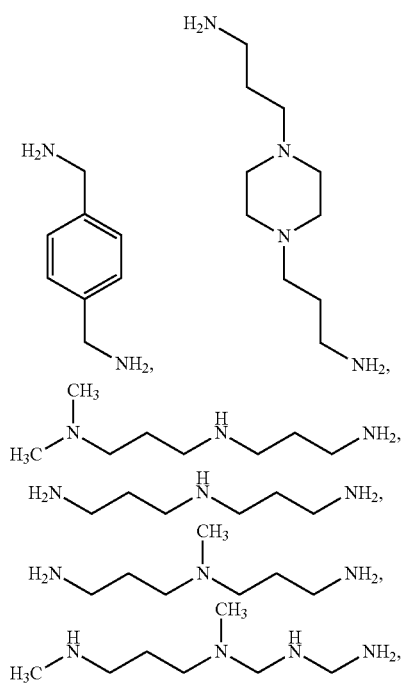

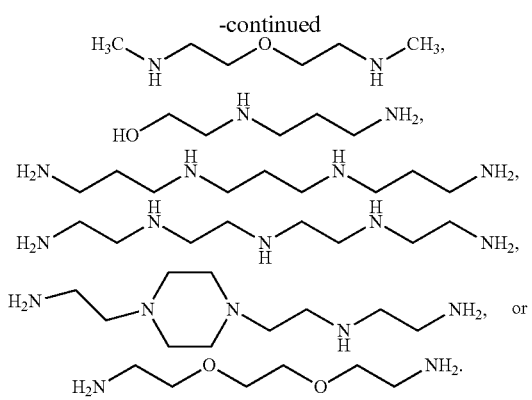

In some embodiments, the core is further defined as:

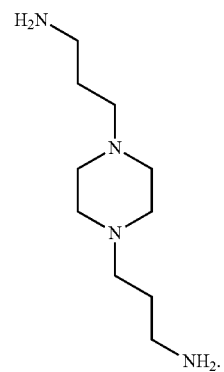

In other embodiments, the core is alkylamine$_{(C≤18)}$, dialkylamine$_{(C≤36)}$, heterocycloalkane$_{(C≤12)}$, or a substituted version of any of these groups. In some embodiments, the core is an alkylamine$_{(C≤18)}$ or substituted alkylamine$_{(C≤18)}$. In some embodiments, the core is octylamine, decylamine, dodecylamine, tetradecylamine, hexadecylamine, and octadecylamine. In other embodiments, the core is an dialkylamine$_{(C≤36)}$ or substituted dialkylamine$_{(C≤36)}$. In some embodiments, the core is N-methyl, N-dodecylamine, dioctylamine, or didecylamine. In other embodiments, the core is heterocycloalkane$_{(C≤12)}$ or substituted heterocycloalkane$_{(C≤12)}$. In some embodiments, the core is 4-N-methylpiperazinyl. In some embodiments, Y$_1$ is alkanediyl$_{(C≤8)}$ or substituted alkanediyl$_{(C≤8)}$. In some embodiments, Y$_1$ is alkanediyl$_{(C≤8)}$. In some embodiments, Y$_1$ is —CH$_2$CH$_2$—. In some embodiments, Y$_3$ is alkanediyl$_{(C≤8)}$ or substituted alkanediyl$_{(C≤8)}$. In some embodiments, Y$_3$ is alkanediyl$_{(C≤8)}$. In some embodiments, Y$_3$ is —CH$_2$CH$_2$—. In other embodiments, Y$_3$ is:

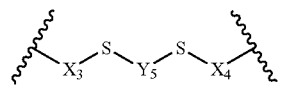

wherein:
X$_3$ and X$_4$ are alkanediyl$_{(C≤12)}$, alkenediyl$_{(C≤12)}$, arenediyl$_{(C≤12)}$, or a substituted version of any of these groups;
Y$_5$ is a covalent bond, alkanediyl$_{(C≤12)}$, alkenediyl$_{(C≤12)}$, arenediyl$_{(C≤12)}$, or a substituted version of any of these groups.

In some embodiments, $X_3$ is alkanediyl$_{(C≤12)}$ or substituted alkanediyl$_{(C≤12)}$. In some embodiments, $X_3$ is —CH$_2$CH$_2$—. In some embodiments, $X_4$ is alkanediyl$_{(C≤12)}$ or substituted alkanediyl$_{(C≤12)}$. In some embodiments, $X_4$ is —CH$_2$CH$_2$—. In some embodiments, $Y_5$ is a covalent bond. In some embodiments, $Y_3$ is:

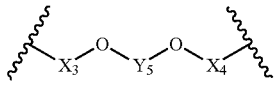

wherein:
$X_3$ and $X_4$ are alkanediyl$_{(C≤12)}$, alkenediyl$_{(C≤12)}$, arenediyl$_{(C≤12)}$, or a substituted version of any of these groups;
$Y_5$ is a covalent bond, alkanediyl$_{(C≤12)}$, alkenediyl$_{(C≤12)}$, arenediyl$_{(C≤12)}$, or a substituted version of any of these groups.

In some embodiments, $X_3$ is alkanediyl$_{(C≤12)}$ or substituted alkanediyl$_{(C≤12)}$. In some embodiments, $X_3$ is —CH$_2$CH$_2$—. In some embodiments, $X_4$ is alkanediyl$_{(C≤12)}$ or substituted alkanediyl$_{(C≤12)}$. In some embodiments, $X_4$ is —CH$_2$CH$_2$—. In some embodiments, $Y_5$ is a covalent bond. In some embodiments, $Y_5$ is —CH$_2$— or —C(CH$_3$)$_2$—. In some embodiments, $A_1$ is —O—. In other embodiments, $A_1$ is —NR$_a$—. In some embodiments, $R_a$ is hydrogen. In some embodiments, $A_2$ is —O—. In other embodiments, $A_2$ is —NR$_a$—. In some embodiments, $R_a$ is hydrogen. In some embodiments, $R_9$ is alkyl$_{(C≤8)}$. In some embodiments, $R_9$ is methyl. In some embodiments, n is 0, 1, 2, 3 or 4. In some embodiments, n is 0, 1, 2, or 3. In some embodiments, n is 0. In other embodiments, n is 1. In other embodiments, n is 2. In other embodiments, n is 3.

In yet another aspect, the present disclosure provides compositions comprising:
(a) a dendrimer described herein; and
(b) a nucleic acid.

In some embodiments, the nucleic acid is a short interfering RNA (e.g. small interfering RNA) (siRNA), a microRNA (miRNA), a pri-miRNA, a messenger RNA (mRNA), a cluster regularly interspaced short palindromic repeats (CRISPR) related nucleic acid, a single guide RNA (sgRNA), a CRISPR-RNA (crRNA), a trans-activating crRNA (tracrRNA), a plasmid DNA (pDNA), a transfer RNA (tRNA), an antisense oligonucleotide (ASO), a guide RNA, a double stranded DNA (dsDNA), a single stranded DNA (ssDNA), a single stranded RNA (ssRNA), and a double stranded RNA (dsRNA). In some embodiments, the nucleic acid is a siRNA, a tRNA, or a nucleic acid which may be used in a CRISPR process. The nucleic acid may be a siRNA. In other embodiments, the nucleic acid which may be used in a CRISPR process such as a cluster regularly interspaced short palindromic repeats (CRISPR) related nucleic acid, a single guide RNA (sgRNA), a CRISPR-RNA (crRNA), or a trans-activating crRNA (tracrRNA). In some embodiments, the nucleic acid is a siRNA against Factor VII comprising the sequence:
5'-GGAucAucucAAGucuuAc[dT][dT]-3' (SEQ ID NO: 1); or
3'-GuAAGAcuuGAGAuGAucc[dT][dT]-5' (SEQ ID NO: 2).

In other embodiments, the nucleic acid is a miRNA. In other embodiments, the nucleic acid is a mRNA. In other embodiments, the nucleic acid is a tRNA. In other embodiments, the nucleic acid is a guide RNA. In some embodiments, the guide RNA is used in CRISPR processes. In other embodiments, the nucleic acid is a pDNA.

In some embodiments, the dendrimer and the nucleic acid are present in a weight ratio from about 100:1 to about 1:5. In some embodiments, the weight ratio of dendrimer to nucleic acid is from about 50:1 to about 2:1. In some embodiments, the weight ratio of dendrimer to nucleic acid is 25:1. In other embodiments, the weight ratio of dendrimer to nucleic acid is 7:1. In some embodiments, the composition further comprises one or more helper lipids. In some embodiments, the helper lipid is selected from a steroid, a steroid derivative, a PEG lipid, or a phospholipid. In some embodiments, the helper lipid is a steroid or steroid derivative. In some embodiments, the steroid is cholesterol. In some embodiments, the steroid or steroid derivative and the dendrimer are present in a molar ratio from about 10:1 to about 1:20. In some embodiments, the molar ratio of the steroid or steroid derivative and dendrimer is from about 1:1 to about 1:10. In some embodiments, the molar ratio of the steroid or steroid derivative and dendrimer is about 38:50. In some embodiments, the molar ratio of the steroid or steroid derivative and dendrimer is about 1:5.

In other embodiments, the helper lipid is a PEG lipid. In some embodiments, the PEG lipid is a PEGylated diacylglycerol such as a compound of the formula:

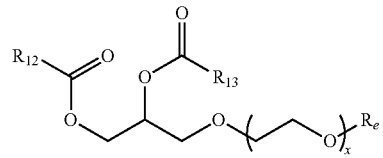

wherein:
$R_{12}$ and $R_{13}$ are each independently alkyl$_{(C≤24)}$, alkenyl$_{(C≤24)}$, or a substituted version of either of these groups;
$R_e$ is hydrogen, alkyl$_{(C≤8)}$, or substituted alkyl$_{(C≤8)}$; and
x is 1-250.

In some embodiments, the PEG lipid is dimyristoyl-sn-glycerol or a compound of the formula:

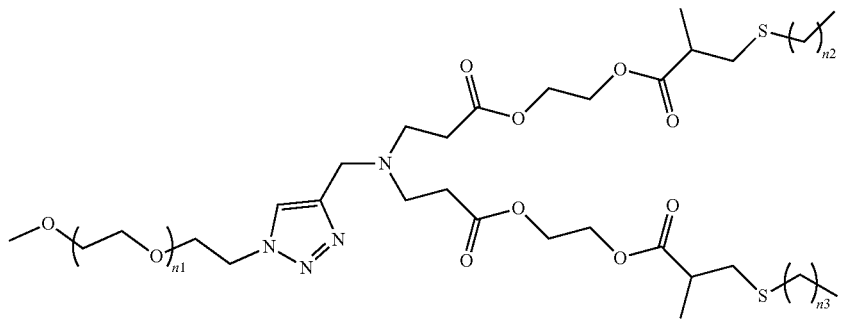

wherein:
  $n_1$ is 5-250; and
  $n_2$ and $n_3$ are each independently 2-25.

In some embodiments, the PEG lipid and the dendrimer are present in a molar ratio from about 1:1 to about 1:250. In some embodiments, the molar ratio of the PEG lipid and the dendrimer is from about 1:10 to about 1:125. In some embodiments, the molar ratio of the PEG lipid and the dendrimer is from about 1:20 to about 1:50.

In other embodiments, the helper lipid is a phospholipid. In some embodiments, the phospholipid is 1,2-distearoyl-sn-glycero-3-phosphocholine (DSPC). In other embodiments, the phospholipid is 1,2-dioleoyl-sn-glycero-3-phosphoethanolamine (DOPE). In some embodiments, the phospholipid and the dendrimer are present in a molar ratio from about 10:1 to about 1:20. In some embodiments, the molar ratio of the phospholipid and dendrimer is from about 1:1 to about 1:10. In some embodiments, the molar ratio of the phospholipid and dendrimer is about 4:5. In some embodiments, the molar ratio of the phospholipid and dendrimer is about 1:5. In some embodiments, the composition consists essentially of the dendrimer, the nucleic acid, and one or more helper lipids.

In still yet another aspect, the present disclosure provides pharmaceutical composition comprising:
  (a) a composition or dendrimer described herein; and
  (b) a pharmaceutically acceptable carrier.

In some embodiments, the pharmaceutical acceptable carrier is a solvent or solution. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for intravenous or intraarterial injection. In some embodiments, the pharmaceutical composition is formulated as a unit dose.

In yet another aspect, the present disclosure provides methods of modulating the expression of a gene comprising delivering a nucleic acid to a cell, the methods comprising contacting the cell with a composition or a pharmaceutical composition described herein under conditions sufficient to cause uptake of the nucleic acid into the cell. In some embodiments, the cell is contacted in vitro. In other embodiments, the cell is contacted in vivo. In other embodiments, the cell is contacted ex vivo. In some embodiments, the modulation of the gene expression is sufficient to treat a disease or disorder. In some embodiments, the disease or disorder is cancer. In some embodiments, the disease or disorder is liver cancer. In some embodiments, the disease or disorder is hepatocellular carcinoma.

In still yet another aspect, the present disclosure provides methods of treating a disease or disorder in a patient comprising administering to the patient in need thereof a pharmaceutically effective amount of a composition or a pharmaceutical composition described herein. In some embodiments, the disease or disorder is cancer. In some embodiments, the disease or disorder is liver cancer. In some embodiments, the disease or disorder is hepatocellular carcinoma. In some embodiments, the methods further comprise administering one or more additional cancer therapies to the patient. In some embodiments, the cancer therapy is a chemotherapeutic compound, surgery, radiation therapy, or immunotherapy. In some embodiments, the compositions or pharmaceutical compositions are administered to the patient once. In other embodiments, the compositions or pharmaceutical compositions are administered to the patient two or more times. In some embodiments, the patient is a mammal such as a human.

In still yet another aspects, the present disclosure provides dendrimers of the formula:

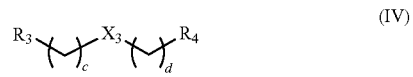

Core-(Repeating Unit)$_n$-Terminating Group (I)

wherein the core is linked to the repeating unit by removing one or more hydrogen atoms from the core and replacing the atom with the repeating unit and wherein: the core has the formula:

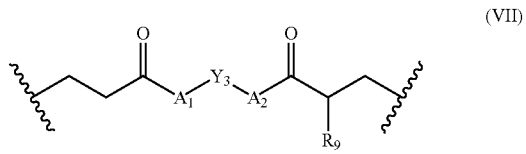

(IV)

wherein:
  $X_3$ is —$NR_6$—, wherein $R_6$ is hydrogen, alkyl$_{(C\leq 8)}$, or substituted alkyl$_{(C\leq 8)}$, —O—, or alkylaminodiyl$_{(C\leq 8)}$, alkoxydiyl$_{(C\leq 8)}$, arenediyl$_{(C\leq 8)}$, heteroarenediyl$_{(C\leq 8)}$, heterocycloalkenediyl$_{(C\leq 8)}$, or a substituted version of any of these groups;
  $R_3$ and $R_4$ are each independently amino, hydroxy, or mercapto, or alkylamino$_{(C\leq 12)}$, dialkylamino$_{(C\leq 12)}$, or a substituted version of either of these groups;
  c and d are each independently 1, 2, 3, 4, 5, or 6; or
wherein the repeating unit comprises a degradable diacyl and a linker;
  the degradable diacyl group has the formula:

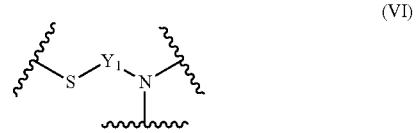

(VII)

wherein:
  $A_1$ and $A_2$ are each independently —O— or —$NR_a$—, wherein:
    $R_a$ is hydrogen, alkyl$_{(C\leq 6)}$, or substituted alkyl$_{(C\leq 6)}$;
  $Y_3$ is alkanediyl$_{(C\leq 12)}$, alkenediyl$_{(C\leq 12)}$, arenediyl$_{(C\leq 12)}$, or a substituted version of any of these groups; and
  $R_9$ is alkyl$_{(C\leq 8)}$ or substituted alkyl$_{(C\leq 8)}$;
the linker group has the formula:

(VI)

wherein:
Y₁ is alkanediyl$_{(C \leq 12)}$, alkenediyl$_{(C \leq 12)}$, arenediyl$_{(C \leq 12)}$, or a substituted version of any of these groups; and wherein when the repeating unit comprises a linker group, then the linker group is attached to a degradable diacyl group on both the nitrogen and the sulfur atoms of the linker group, wherein the first group in the repeating unit is a degradable diacyl group, wherein for each linker group, the next group comprises two degradable diacyl groups attached to the nitrogen atom of the linker group; and wherein n is the number of linker groups present in the repeating unit; and the terminating group has the formula:

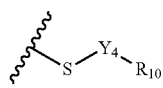

(VIII)

wherein:
Y₄ is alkanediyl$_{(C \leq 18)}$; and
R₁₀ is hydrogen;
wherein the final degradable diacyl in the chain is attached to a terminating group;
n is 0, 1, 2, 3, 4, 5, or 6;
or a pharmaceutically acceptable salt thereof.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 1A) Small RNAs are too large and anionic to enter cells on their own. To efficiently utilize the RNAi machinery, delivery carriers must chaperone small RNAs through numerous extracellular and intracellular barriers. A modular design which would enable fine tuning of functional group identity and placement within dendrimer architectures was envisioned. (FIG. 1B) The library was established via sequential orthogonal reactions. First, amines with a series of initial branching centers (IBCs) reacted quantitatively and selectively with the less sterically hindered acrylate groups of AEMA containing two degradable ester groups. The products then underwent DMPP-catalyzed reaction with various thiols. (FIG. 1C) To identify degradable dendrimers with optimized topological structures to mediate small RNAs to overcome the multiple extracellular and intracellular delivery barriers, the library is divided into four zones: core binding—periphery stabilization (zone I), core binding—periphery binding (zone II), core stabilization—periphery stabilization (zone III), and core stabilization—periphery binding (zone IV). (FIG. 1D) Dendrimers are independently modulated with chemically diverse amines and thiols for cores and peripheries. Selected amines are divided into two categories: ionizable amines for RNA binding that will generate one to six branched species are labeled 1A-6A and hydrophobic amines for NP stabilization are labeled 1H-2H. These amines are expected to increase potency with higher dendrimer generation. Hydrophobic alkyl amines for NP stabilization are labeled SC1-SC19 based on the hydrocarbon length. Alcohol and carboxylic acid terminated thiols (SO1-SO9) and amine-functionalized thiols (SN1-SN11) are included in the library design to increase chemical diversity. G2-G4 higher generation dendrimers with multiple branches were also synthesized using generation expansion reactions (see FIG. 10B and FIG. 11).

(FIG. 6A) The different amines C with various initial branching centers (IBCs) reacted with 2-(acryloyloxy)ethyl methacrylate (AEMA) at exact 1:1 feed equivalence in the presence of 5 mol % of butylated hydroxyltoluene (BHT) at 50° C. for 24 hours. Conversion yield of all 42 reactions is nearly quantitative by $^1$H NMR. (FIG. 6B) Each of 42 C-L-G1s reacted with each of 36 thiols (P) in 66 μL DMSO with 5% DMPP at small scale (~20 mg on average). The thiol concentration is 750 mM and the concentration of 1An&1Hn, 2An&2Hn, 3An, 4An, 5An, and 6An is 750 mM, 275 mM, 250 mM, 187.5 mM, 150 mM and 125 mM, respectively. Without addition of any thiol compounds, all 42 C-L-G1s remained stable at 60° C. for 48 hours. Each reaction of all 42 with SC4, SN8, and SO9 has nearly quantitative conversion (measured by $^1$H NMR).

(FIG. 7B) A heat map of luciferase silencing in HeLa-Luc cells after treatment with dendrimer nanoparticles (33 nM siLuc, n=3) illustrates zone activity relationships. Luciferase activity and cell viability were measured to identify dendrimers that balance high delivery potency with low toxicity (see additional data in FIG. 8). (FIG. 7C) Analysis of nanoparticle groups that enabled more than 50% silencing identified dendrimers with optimized topological structures to overcome the intracellular delivery barriers. The daughter zone was further analyzed if its hit rate was higher than that of its parental zone under a series of criteria. The hit rate of the parental zone is marked in orange, and higher or lower hit rate of its daughter group is marked in green or blue, respectively. ~6% of whole library enabled >50% gene silencing. The core binding—periphery stabilization zone I had a 10% hit rate. Within zone I, the subzone with SC branches yielded 15%, while subzone with SO branches had only a 1% hit rate. In the subzone with SC branches, dendrimers with three to six branches, SC5-8 branches, or SC9-12 branches had a much higher chance to efficiently mediate siRNA delivery.

FIG. 8 shows cell viability after addition of 1,512 first-generation degradable dendrimer (G1DD) NPs containing siLuc (33 nM siRNA, value is average of n=3). G1DDs were formulated into nanoparticles containing the firefly luciferase-targeting siRNA (siLuc) with weight ratio of 12.5:1 (G1DD:siRNA) and the helper lipids cholesterol, 1,2-distearoyl-sn-glycero-3-phosphocholine (DSPC) and lipid PEG2000 with molar ratio of 50:38:10:2 (G1DD:cholesterol:DSPC:lipid PEG). Cell viability was measured with ONE-Glo+Tox luciferase reporter and cell viability assay (Promega) by following its protocol. Cell viability was obtained by normalizing to untreated cells. Untreated control (n=6). Experimental samples (n=3).

(FIG. 9A) The heat map of luciferase activity reduction in HeLa cell stably expressing firefly luciferases after treatment of G1DD nanoparticles with 33 nM siRNA is divided into zones and regions to describe the breakdown of the dendritic analysis process (see part FIG. 9B). Cell viability and luciferase activity was measured with ONE-Glo+Tox Luciferase reporter and cell viability assay (Promega) by following its protocol. Luciferase reduction was obtained by normalizing luciferase activity to the luciferase activity and viability of untreated cells. Untreated control (n=6). Experimental samples (n=3). (FIG. 9B) Utilization of a dendrimer-inspired tree analysis process to identify degradable dendrimers with optimized structures to mediate siRNA to overcome the intracellular delivery barriers by analyzing their hit rate with luciferase activity reduction more than 50%. The daughter zone is further analyzed if its hit rate is higher than that of its parental zone under a series of standards. Hit rate of parental zone is with the black bar graph, and higher or low hit rate of its daughter group is with the blue or red font. ~6% of whole library induced >50% gene silencing. The corebinding-periphery-stabilization zone (zone I) has 10% hit rate. In zone I, subzone with SC branches has 15% while subzone with SO branches 1%. In subzone with SC branches, dendrimers with three, four, five, or six branches SC5-8 branches or SC9-12 branches have much higher chance efficiently to mediate siRNA to overcome the intracellular delivery barriers.

(FIG. 10A) 26 first-generation degradable dendrimers with diversified structures were evaluated for Factor VII knockdown in mice at a siRNA dosage of 1 mg/kg (n=3). PBS control (n=3). Data are shown as mean±s.d. (FIG. 10B) Rational design of degradable dendrimers with multiple branches was accomplished by (I) choosing polyamines with multiple IBCs and (II) increasing branching via generation expansion. Natural polyamines spermidine 5A5 and spermine 6A4 were utilized. 1A2 (one IBC), 2A2 & 2A11 (two IBCs), 3A3 & 3A5 (three IBCs), and 4A1 & 4A3 (four IBCs) were chosen to synthesize degradable dendrimers with multiple branches via generation expansion (see also FIG. 11). (FIG. 10C) 24 rationally designed degradable dendrimers via strategies I and II were evaluated for Factor VII knockdown in mice at a siRNA dosage of 1 mg/kg (n=3). PBS control (n=3). Data are shown as mean±s.d. Rationally designed dendrimers were active at a high hit rate.

(FIG. 12C) Wild type mice (p26) were injected i.v. with some NPs at 4 mg siCTR/kg (100 mg dendrimer/kg or 28 mg control C12-200/kg) (n=3). Body weight change varied among the formulations according to the dendrimer identity, but all NPs were largely nontoxic in normal, WT mice. (FIG. 12D) Body weight change of transgenic mice bearing aggressive MYC-driven tumors (p32) after injection with 3 mg siCTR/kg (75 mg/kg 5A2-SC8 and 6A3-SC12 or 21 mg/kg C12-200) (n=5). (FIG. 12E) Kaplan-Meier survival curve of transgenic mice injected at days 32, 36, 40, and 44 with 5A2-SC8 and 6A3-SC12 nanoparticles at 3 mg siCTR/kg dosage (75 mg dendrimer/kg) (n=5). In tumor-bearing mice (a vulnerable host), toxicity of the carrier was exaggerated, and only 5A2-SC8 was able to be well tolerated and not affect survival. Data are shown as mean±s.d. Statistical analysis performed with (e) Mantel-Cox test; n.s. P>0.05; *P<0.05.

(FIG. 13A) Schematic showing the LAP-tTa; TRE-MYC transgenic mouse model. TRE-MYC is turned ON or OFF by the liver-specific LAP promoter when present with the LAP-tTA transgene in the absence or presence of doxycycline (Dox). (FIG. 13B) Without any treatment, liver tumors are visible around p20-26, then the liver is full of small tumors by p32, and finally tumors grow large and the liver size increases dramatically at p42 to p60.

(FIG. 14A) Gross anatomy and fluorescence imaging of transgenic mice bearing aggressive liver tumors at the age of 41 days. Fluorescence imaging shows that 5A2-SC8 nanoparticles formulated with Cy5.5-labeled siRNA mediate massive siRNA accumulation in the whole cancerous liver, with minor accumulation in the spleen and kidneys 24 hours after i.v. injection of 1 mg Cy5.5-siRNA/kg. To further confirm whether 5A2-SC8 NPs can deliver siRNA in vivo into tumor cells, tumor tissues of the liver were collected, embedded in OTC and sectioned for H&E staining and confocal imaging 24 hours after i.v. injection. (FIG. 14B) H&E staining confirms that the livers contain tumors. The same slides of tumor tissues were scanned using confocal imaging and were captured under three channels: DAPI for nuclei (blue), FITC for phalloidin-stained actin (green), and Cy5.5 for siRNA (red). (FIG. 14C) Confocal imaging of the same region shows that 5A2-SC8 can efficiently deliver siRNA into tumor cells inside of the liver.

FIGS. 16A-16H show modular degradable dendrimers can deliver a therapeutic Let-7g miRNA mimic to a clinically relevant and aggressive, MYC-driven genetic tumor model, resulting in a significant survival benefit. (FIG. 16A) 5A2-SC8 NPs enable silencing of FVII protein in transgenic mice bearing MYC-driven liver tumors, as measured in the blood and (FIG. 16B) in harvested liver tissues (single injection, 1 mg/kg, p26 mice, 48 hours post-injection) (siCTR on left and siFVII on right). (FIG. 16C) 5A2-SC8 NPs enable delivery of Let-7g to liver tissues of transgenic mice bearing MYC-driven liver tumors (single injection, 1 mg/kg, p26 mice, 48 hours post-injection). Let-7g expression was significantly increased, while other Let-7 family members were unaffected (siCTR on left and siFVII on right). (FIG. 16D) Transgenic mice bearing MYC-driven liver tumors were given weekly i.v. injections of 1 mg/kg Let-7g, starting on day 26 (which is after initiation of tumor development) until day 61. Mice receiving Let-7g had visibly smaller abdomens. (FIG. 16E) Abdominal circumference was smaller for treated mice compared to controls. (FIG. 16F) Representative images of livers from Let-7g mimic and control mimic injected mice show reduced tumor burden. (FIG. 16G) Weekly delivery of miRNA mimics inside of 5A2-SC8 NPs did not affect normal weight gain, while delivery of miRNA mimics inside of C12-200 LNPs caused weight loss and death. n=5. (FIG. 16H) Delivery of Let-7g weekly from 26 to 61 days extended survival. All control mice receiving no treatment (n=9) and mice receiving 5A2-SC8 NPs (n=5) containing a control untargeted mimic died around 60 days after birth. C12-200 LNP injected mice died prematurely (n=7). #C12-200+CTR mimic experiments were halted because all mice receiving the C12-200+Let-7g mimic injections had died (n=7). Delivery of Let-7g inside of 5A2-SC8 NPs provided a pronounced survival benefit. Data are shown as mean±s.d. Statistical analysis performed with (a,b,c,e) two-tailed Student's t-test, or (h) Mantel-Cox test; n.s. P>0.05; *P<0.05; P<0.01; *P<0.001; ****P<0.0001.

FIG. 18B shows the comparison of different composition formulation with DSPC lipids vs. DOPE lipids with PEG-DHD in delivering siLuc to HeLa-Luc.

DESCRIPTION OF ILLUSTRATIVE EMBODIMENTS

Figure 1A:
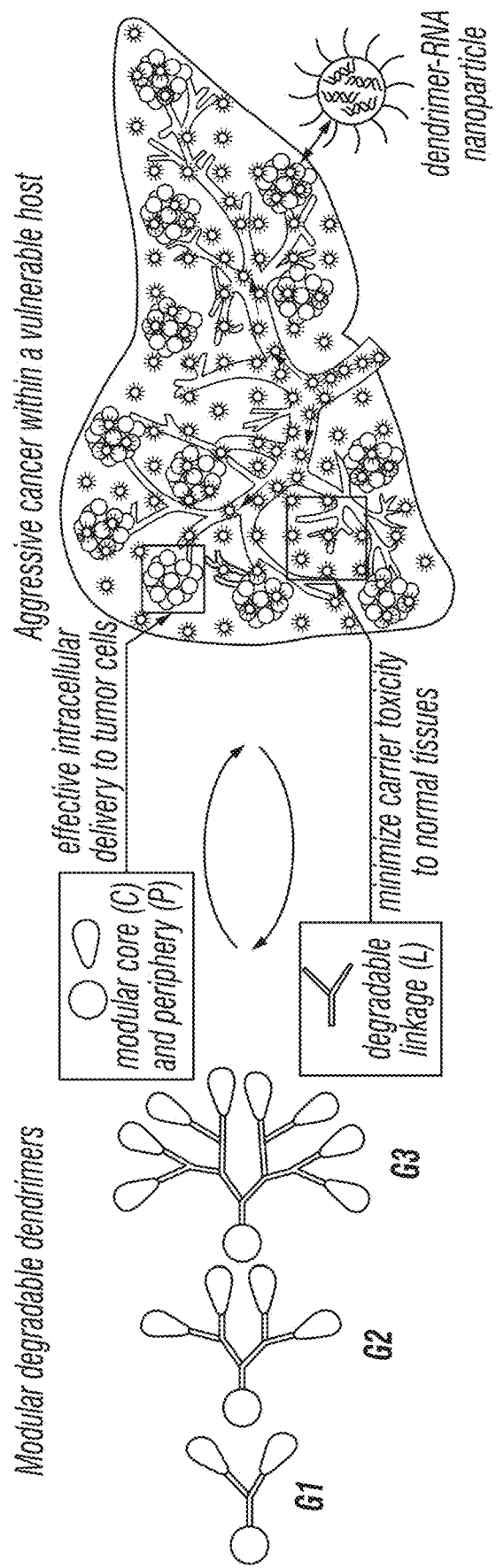
FIGS. 1A-1D show a combination of high potency to tumor cells and low toxicity to normal cells is required for small RNA therapies within vulnerable liver cancers. A modular strategy for diversifying the chemical functionality and size of biocompatible, ester-based dendrimers allowed discovery of dendrimers that balance low toxicity and high in vivo small RNA delivery potency. Orthogonal reactions accelerated the synthesis of 1,512 G1 modular degradable dendrimers, thereby increasing the number, size, and chemical diversity of molecular structures. Inclusion of degradable ester bonds at each step promoted low toxicity.

In some aspects, the present disclosure provides lipocationic dendrimers which may be used as carriers of nucleic acids. In some embodiments, the dendrimers contain one or more groups which undergoes degradation under physiological conditions. In some embodiments, the dendrimers are formulated into compositions comprising the dendrimers and one or more nucleic acids. These compositions may also further comprise one or more helper lipids such as cholesterol and/or a phospholipid. Finally, in some aspects, the present disclosure also provides methods of treating one or more diseases which may be treated with a nucleic acid therapeutic using the dendrimer compositions.

A. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof, "mercapto" means —SH; and "thio" means =S; "sulfonyl" means —S(O)₂—; "hydroxysulfonyl" means —S(O)₂OH; "sulfonamide" means —S(O)₂NH₂; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⸺" represents a single bond or a double bond. Thus, for example, the formula

includes

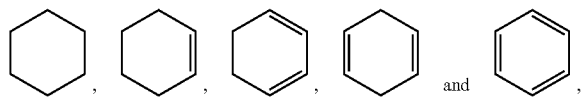

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "▫▫▫▫" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

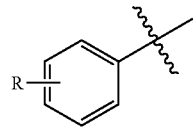

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

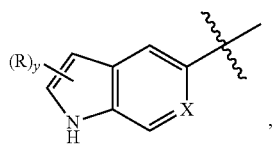

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$," or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$(i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$(isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CHCH═CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH═CH—, —CH═C(CH$_3$)CH$_2$—, —CH═CHCH$_2$—, and —CH$_2$CH═CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH═CHF, —CH═CHCl and —CH═CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

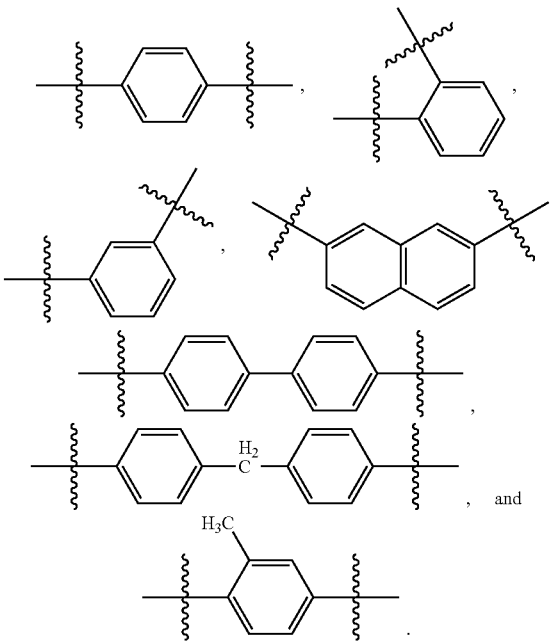

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from are nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

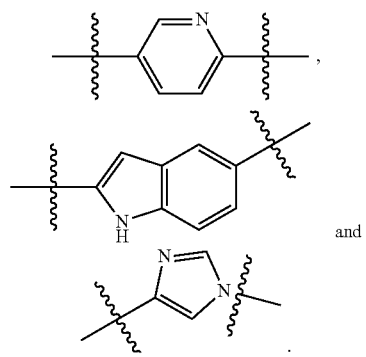

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

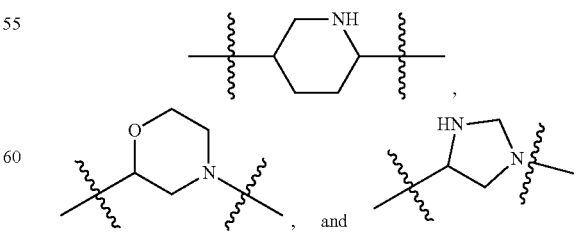

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "alkylaminodiyl" refers to the divalent group —NH-alkanediyl-, —NH-alkanediyl-NH—, or -alkanediyl-NH-alkanediyl-. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc. Within the context of the dendrimer, the repeating unit may also be described as the branching unit, interior layers, or generations. Similarly, the terminating group may also be described as the surface group.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. DENDRIMERS AND DENDRITIC STRUCTURES

In some aspects of the present disclosure, dendrimers containing lipophilic and cationic components are provided. Dendrimers are a polymer exhibiting regular dendritic branching, formed by the sequential or generational addition of branched layers to or from a core and are characterized by a core, at least one interior branched layer, and a surface branched layer. (See Petar R. Dvornic and Donald A. Tomalia in Chem. in Britain, 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to described compounds described herein which have a dendron like appearance (e.g. molecules which radiate from a single focal point).

While dendrimers are polymers, dendrimers are preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bio-attachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction.

Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some aspects, the dendrimers of the present disclosure are assembled using the differential reactivity of the acrylate and methacrylate groups with amines and thiols. The dendrimers that may be used herein include secondary or tertiary amines and thioethers formed by the reaction of an acrylate group with a primary or secondary amine and a methacrylate with a mercapto group. Additionally, the repeating units of the dendrimers described herein may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine (—NH$_2$) or a carboxylic acid (—CO$_2$H). In still other embodiments, the terminating group is an aliphatic or aromatic group containing one or more hydrogen bond donors such as a hydroxide group, an amide group, or an ester.

The dendrimers provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The dendrimers of the present disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Dendrimers may occur as racemates and racemic mixtures, single enantiomers, diastereomeric mixtures and individual diastereomers. In some embodiments, a single diastereomer is obtained. The chiral centers of the dendrimers of the present disclosure can have the S or the R configuration. Furthermore, it is contemplated that one or more of the dendrimers may be present as constitutional isomers. In some embodiments, the compounds have the same formula but different connectivity to the nitrogen atoms of the core. Without wishing to be bound by any theory, it is believed that such dendrimers exist because the starting monomers react first with the primary amines and then statistically with any secondary amines present. Thus, the constitutional isomers may present the fully reacted primary amines and then a mixture of reacted secondary amines.

Chemical formulas used to represent dendrimers of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The dendrimers of the present disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the dendrimers of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

It should be recognized that the particular anion or cation forming a part of any salt form of a dendrimer provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. HELPER LIPIDS

In some aspects of the present disclosure, one or more helper lipids are mixed with the polymers of the instant disclosure to create a composition. In some embodiments, the polymers are mixed with 1, 2, 3, 4, or 5 different types of helper lipids. It is contemplated that the polymers can be mixed with multiple different lipids of a single type. In some embodiments, the lipid could be a steroid or a steroid derivative. In other embodiments, the lipid is a PEG lipid. In other embodiments, the lipid is a phospholipid. In other embodiments, the dendrimer composition comprises a steroid or a steroid derivative, a PEG lipid, and a phospholipid.

1. Steroids and Steroid Derivatives

In some aspects of the present disclosure, the polymers are mixed with one or more steroid or a steroid derivative to create a dendrimer composition. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula below:

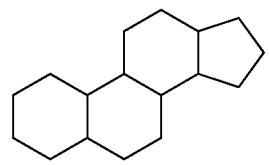

In some embodiments, a steroid derivative comprises the ring structure above with one or more non-alkyl substitutions. In some embodiments, the steroid or steroid derivative is a sterol wherein the formula is further defined as:

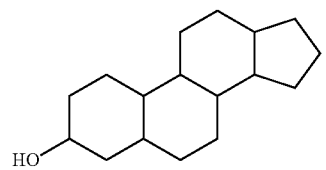

In some embodiments of the present disclosure, the steroid or steroid derivative is a cholestane or cholestane derivative. In a cholestane, the ring structure is further defined by the formula:

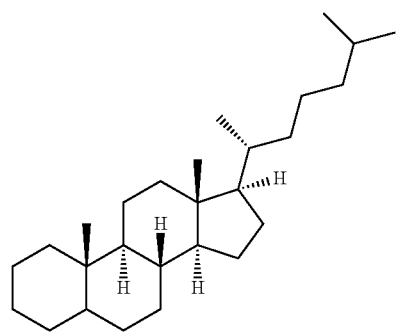

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestere and a sterol or a derivative thereof.

In some embodiments, the compositions may further comprise a molar ratio of the steroid to the dendrimer from about 1:10 to about 1:20. In some embodiments, the molar ratio is from about 1:20, 1:18, 1:16, 1:14, 1:12, 1:10, 1:8, 1:6, 1:4, 1:2, 1:1, 2:1, 4:1, 6:1, 8:1, to about 10:1 or any range derivable therein. In some embodiments, the molar ratio is about 38:50 or about 1:5.

2. PEG or PEGylated Lipid

In some aspects of the present disclosure, the polymers are mixed with one or more PEGylated lipids (or PEG lipid) to create a dendrimer composition. In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present invention are taught by U.S. Pat. No. 5,820,873, WO 2010/141069, or U.S. Pat. No. 8,450,298, which is incorporated herein by reference.

In another aspect, the PEG lipid has the formula:

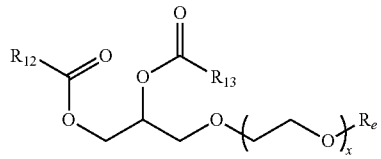

wherein: $R_{12}$ and $R_{13}$ are each independently alkyl$_{(C \leq 24)}$, alkenyl$_{(C \leq 24)}$, or a substituted version of either of these groups; $R_e$ is hydrogen, alkyl$_{(C \leq 8)}$, or substituted alkyl$_{(C \leq 8)}$; and x is 1-250. In some embodiments, $R_e$ is alkyl$_{(C \leq 8)}$ such as methyl. $R_{12}$ and $R_{13}$ are each independently alkyl$_{(C \leq 4-20)}$. In some embodiments, x is 5-250. In one embodiment, x is 5-125 or x is 100-250. In some embodiments, the PEG lipid is 1,2-dimyristoyl-sn-glycerol, methoxypolyethylene glycol.

In another aspect, the PEG lipid has the formula:

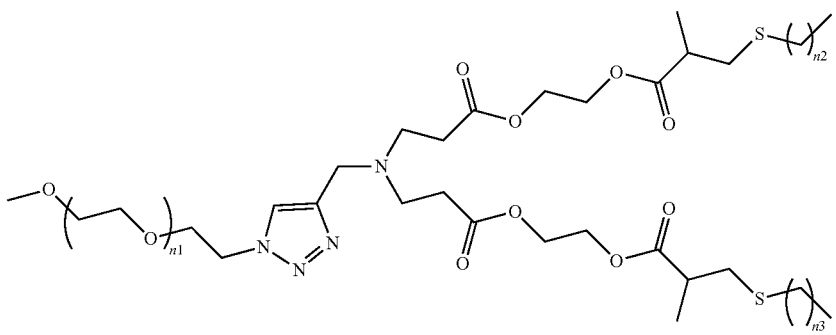

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments, the compositions may further comprise a molar ratio of the PEG lipid to the dendrimer from about 1:1 to about 1:250. In some embodiments, the molar ratio is from about 1:1, 1:10, 1:20, 1:30, 1:40, 1:50, 1:60, 1:70, 1:80, 1:90, 1:100, 1:110, 1:120, 1:125, 1:150, 1:175, 1:200, 1:225, to about 1:250 or any range derivable therein. In some embodiments, the molar ratio is about 1:25 or about 3:100.

3. Phospholipid

In some aspects of the present disclosure, the polymers are mixed with one or more phospholipids to create a dendrimer composition. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine.

In some embodiments, the compositions may further comprise a molar ratio of the phospholipid to the dendrimer from about 1:10 to about 1:20. In some embodiments, the molar ratio is from about 1:20, 1:18, 1:16, 1:14, 1:12, 1:10, 1:8, 1:6, 1:4, 1:2, 1:1, 2:1, 4:1, 6:1, 8:1, to about 10:1 or any range derivable therein. In some embodiments, the molar ratio is about 38:50 or about 1:5.

D. NUCLEIC ACIDS AND NUCLEIC ACID BASED THERAPEUTIC AGENTS

1. Nucleic Acids

In some aspects of the present disclosure, the dendrimer compositions comprise one or more nucleic acids. In some embodiments, the dendrimer composition comprises one or more nucleic acids present in a weight ratio to the dendrimer from about 5:1 to about 1:100. In some embodiments, the weight ratio of nucleic acid to dendrimer is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any range derivable therein. In some embodiments, the weight ratio is about 1:25 or about 1:7. In addition, it should be clear that the present disclosure is not limited to the specific nucleic acids disclosed herein. The present invention is not limited in scope to any particular source, sequence, or type of nucleic acid, however, as one of ordinary skill in the art could readily identify related homologs in various other sources of the nucleic acid including nucleic acids from non-human species (e.g., mouse, rat, rabbit, dog, monkey, gibbon, chimp, ape, baboon, cow, pig, horse, sheep, cat and other species). It is contemplated that the nucleic acid used in the present disclosure can comprises a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In another embodiment, the nucleic acid is a complementary sequence to a naturally occurring sequence, or complementary to 75%, 80%, 85%, 90%, 95% and 100%.

In some aspects, the nucleic acid is a sequence which silences, is complimentary to, or replaces another sequence present in vivo. Sequences of 17 bases in length should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or longer are contemplated as well.

The nucleic acid used herein may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the nucleic acid comprises one or more antisense segments which inhibits expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to form a siRNA or to generate specific constructs. For example, where an intron is desired in the ultimate construct, a genomic clone will need to be used. The cDNA, siRNA, or a synthesized polynucleotide may provide more convenient restriction sites for the remaining portion of the construct and, therefore, would be used for the rest of the sequence. Other embodiments include dsRNA or ssRNA, which may be used to target genomic sequences or coding/non-coding transcripts.

In other embodiments, the dendrimer compositions may comprise a nucleic acid which comprises one or more expression vectors are used in a gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

2. siRNA

As mentioned above, the present invention contemplates the use of one or more inhibitory nucleic acid for reducing expression and/or activation of a gene or gene product. Examples of an inhibitory nucleic acid include but are not limited to molecules targeted to an nucleic acid sequence, such as an siRNA (small interfering RNA), short hairpin RNA (shRNA), double-stranded RNA, an antisense oligonucleotide, a ribozyme and molecules targeted to a gene or gene product such as an aptamer.

An inhibitory nucleic acid may inhibit the transcription of a gene or prevent the translation of the gene transcript in a cell. An inhibitory nucleic acid may be from 16 to 1000 nucleotides long, and in certain embodiments from 18 to 100 nucleotides long.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Since the discovery of RNAi by Fire and colleagues in 1998, the biochemical mechanisms have been rapidly characterized. Double stranded RNA (dsRNA) is cleaved by Dicer, which is an RNAase III family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). miRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

In designing a nucleic acid capable of generating an RNAi effect, there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or even 100% identity between the sequence of the siRNA and a portion of a EphA nucleotide sequence. Sequences less than about 80% identical to the target gene are substantially less effective. Thus, the greater identity between the siRNA and the gene to be inhibited, the less likely expression of unrelated genes will be affected.

In addition, the size of the siRNA is an important consideration. In some embodiments, the present disclosure relates to siRNA molecules that include at least about 19-25 nucleotides, and are able to modulate gene expression. In the context of the present disclosure, the siRNA is particularly less than 500, 200, 100, 50, 25, or 20 nucleotides in length. In some embodiments, the siRNA is from about 25 nucleotides to about 35 nucleotides or from about 19 nucleotides to about 25 nucleotides in length.

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present invention, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges derivable thereof. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, CA), Ambion® (Austin, TX), and Qiagen® (Valencia, CA).

An inhibitory nucleic acid that can be applied in the compositions and methods of the present invention may be any nucleic acid sequence that has been found by any source to be a validated downregulator of the gene or gene product.

In some embodiments, the invention features an isolated siRNA molecule of at least 19 nucleotides, having at least one strand that is substantially complementary to at least ten but no more than thirty consecutive nucleotides of a nucleic acid that encodes a gene, and that reduces the expression of a gene or gene product. In one embodiments of the present disclosure, the siRNA molecule has at least one strand that is substantially complementary to at least ten but no more than thirty consecutive nucleotides of the mRNA that encodes a gene or a gene product.

In one embodiments, the siRNA molecule is at least 75, 80, 85, or 90% homologous, particularly at least 95%, 99%, or 100% similar or identical, or any percentages in between the foregoing (e.g., the invention contemplates 75% and greater, 80% and greater, 85% and greater, and so on, and said ranges are intended to include all whole numbers in between), to at least 10 contiguous nucleotides of any of the nucleic acid sequences encoding a target therapeutic protein.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In one embodiment, siRNA is capable of decreasing the expression of a particular genetic product by at least 10%, at least 20%, at least 30%, or at least 40%, at least 50%, at least 60%, or at least 70%, at least 75%, at least 80%, at least 90%, at least 95% or more or any ranges in between the foregoing.

3. CRISPR/CAS

CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced eubacteria genomes and 90% of sequenced archaea. CRISPRs are often associated with cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

Repeats were first described in 1987 for the bacterium *Escherichia coli*. In 2000, similar clustered repeats were identified in additional bacteria and archaea and were termed Short Regularly Spaced Repeats (SRSR). SRSR were renamed CRISPR in 2002. A set of genes, some encoding putative nuclease or helicase proteins, were found to be associated with CRISPR repeats (the cas, or CRISPR-associated genes).

In 2005, three independent researchers showed that CRISPR spacers showed homology to several phage DNA and extrachromosomal DNA such as plasmids. This was an indication that the CRISPR/cas system could have a role in adaptive immunity in bacteria. Koonin and colleagues proposed that spacers serve as a template for RNA molecules, analogously to eukaryotic cells that use a system called RNA interference.

In 2007 Barrangou, Horvath (food industry scientists at Danisco) and others showed that they could alter the resistance of *Streptococcus thermophilus* to phage attack with spacer DNA. Doudna and Charpentier had independently been exploring CRISPR-associated proteins to learn how bacteria deploy spacers in their immune defenses. They jointly studied a simpler CRISPR system that relies on a protein called Cas9. They found that bacteria respond to an invading phage by transcribing spacers and palindromic DNA into a long RNA molecule that the cell then uses tracrRNA and Cas9 to cut it into pieces called crRNAs.

CRISPR was first shown to work as a genome engineering/editing tool in human cell culture by 2012 It has since been used in a wide range of organisms including bakers yeast (*S. cerevisiae*), zebra fish, nematodes (*C. elegans*), plants, mice, and several other organisms. Additionally CRISPR has been modified to make programmable transcription factors that allow scientists to target and activate or silence specific genes. Libraries of tens of thousands of guide RNAs are now available.

The first evidence that CRISPR can reverse disease symptoms in living animals was demonstrated in March 2014, when MIT researchers cured mice of a rare liver disorder. Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype Ecoli) proteins (called CasA-E in *E. coli*) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in *E. coli* requires Cascade and Cas3, but not Cas1 and Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes.

See also U.S. Patent Publication 2014/0068797, which is incorporated by reference in its entirety.

i. Cas9

Cas9 is a nuclease, an enzyme specialized for cutting DNA, with two active cutting sites, one for each strand of the double helix. It has been demonstrated that one could disable one or both sites while preserving Cas9's ability to home located its target DNA. Jinek combined tracrRNA and spacer RNA into a "single-guide RNA" molecule that, mixed with Cas9, could find and cut the correct DNA targets. Jinek et al. proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of *Francisella novicida* uses a unique, small, CRISPR/Cas-associated RNA (scaRNA) to repress an endogenous transcript encoding a bacterial lipoprotein that is critical for *F. novicida* to dampen host response and promote virulence.

ii. gRNA or sgRNA

As an RNA guided protein, Cas9 requires a short RNA to direct the recognition of DNA targets (Mali et al., 2013a). Though Cas9 preferentially interrogates DNA sequences containing a PAM sequence NGG it can bind here without a protospacer target. However, the Cas9-gRNA complex requires a close match to the gRNA to create a double strand break (Cho et al., 2013; Hsu et al., 2013). CRISPR sequences in bacteria are expressed in multiple RNAs and then processed to create guide strands for RNA (Bikard et al., 2013). Because Eukaryotic systems lack some of the proteins required to process CRISPR RNAs the synthetic construct gRNA was created to combine the essential pieces of RNA for Cas9 targeting into a single RNA expressed with the RNA polymerase type III promoter U6 (Mali et al., 2013a, b). Synthetic gRNAs are slightly over 100 bp at the minimum length and contain a portion which is targets the 20 protospacer nucleotides immediately preceding the PAM sequence NGG; gRNAs do not contain a PAM sequence.

4. Modified Nucleobases

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In some embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R. is, independently, H, an amino protecting group or substituted or unsubstituted C$_1$-C$_{10}$ alkyl.

In some embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In some embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399, 845); 4'-C(CH$_3$)(CH$_3$)—O-2' and analogs thereof, (see, e.g., WO 2009/006478); 4'-CH$_2$—N(OCH$_3$)-2' and analogs thereof (see, e.g., WO2008/150729); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' and analogs thereof (see, PCT International Application WO 2008/154401).

In some embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Methoxy(ethyleneoxy) (4'-CH(CH$_2$OMe)-O-2') BNA (also referred to as constrained MOE or cMOE).

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 5561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794, 499, 7,034,133, 6,525,191, 6,670,461, and 7,399,845; WO 2004/106356, WO 1994/14226, WO 2005/021570, and WO 2007/134181; U.S. Patent Publication Nos. US 2004/0171570, US 2007/0287831, and US 2008/0039618; U.S.

Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-CH$_2$—O-2') bicyclic nucleosides have been incorporated into antisense oligonucleotides that showed antisense activity (Frieden et al., Nucleic Acids Research, 2003, 21, 6365-6372).

In some embodiments, substituted sugar moieties comprise one or more non-bridging sugar substituent and one or more bridging sugar substituent (e.g., 5'-substituted and 4'-2' bridged sugars; PCT International Application WO 2007/134181, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfer, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US 2005/0130923) and/or the 5' position. By way of additional example, carbocyclic bicyclic nucleosides having a 4'-2' bridge have been described (see, e.g., Freier et al., Nucleic Acids Research, 1997, 25(22), 4429-4443 and Albaek et al., J. Org. Chem., 2006, 71, 7731-7740).

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. Bioorg. & Med. Chem. (2002) 10:841-854), and fluoro HNA (F-HNA).

In some embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ is other than H. In some embodiments, at least one of $q_1$, $q_2$, $q_3$, $q_4$, $q_5$, $q_6$ and $q_7$ is methyl. In some embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854).

Combinations of modifications are also provided without limitation, such as 2'-F-5'-methyl substituted nucleosides (see PCT International Application WO 2008/101157 for other disclosed 5',2'-bis substituted nucleosides) and replacement of the ribosyl ring oxygen atom with S and further substitution at the 2'-position (see U.S. Patent Publication US 2005/0130923) or alternatively 5'-substitution of a bicyclic nucleic acid (see PCT International Application WO 2007/134181 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., 2007).

In some embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In some embodiments, oligonucleotides comprise one or more RNA-like nucleosides. In some embodiments, oligonucleotides comprise one or more DNA-like nucleotides.

In some embodiments, nucleosides of the present invention comprise one or more unmodified nucleobases. In certain embodiments, nucleosides of the present invention comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., 1991; and those disclosed by Sanghvi, Y. S., 1993.

Representative United States Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In some embodiments, the present invention provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., 1989), cholic acid (Manoharan et al., 1994), a thioether, e.g., hexyl-5-tritylthiol (Manoharan et al., 1992; Manoharan et al., 1993), a thiocholesterol (Oberhauser et al., 1992), an aliphatic chain, e.g., dodecandiol or undecyl residues (Saison-Behmoaras et al., 1991; Kabanov et al., 1990; Svinarchuk et al., 1993), a phospholipid, e.g., di-hexadecyl-rac-glycerol or triethylammonium 1,2-di-O-hexadecyl-rac-glycero-3-H-phosphonate (Manoharan et al., 1995; Shea et al., 1990), a polyamine or a polyethylene glycol chain (Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

E. KITS

The present disclosure also provides kits. Any of the components disclosed herein may be combined in the form of a kit. In some embodiments, the kits comprise a dendrimer or a composition as described above or in the claims.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the nucleic acid delivery components are combined in a single container. In other embodiments, some or all of the dendrimer delivery components with the instant polymers are provided in separate containers.

The kits of the present invention also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Materials and Instrumentation

1. Materials for Chemical Synthesis

All amines, thiols, and otherwise unspecified chemicals were purchased from Sigma-Aldrich. 1,2-distearoyl-sn-glycero-3-phosphocholine (DSPC) was purchased from Avanti Lipids. Lipid PEG2000 was chemically synthesized, as described below. C12-200 was synthesized following the reported procedure (Love et al., 2010). All organic solvents were purchased from Fisher Scientific and purified with a solvent purification system (Innovative Technology).

2. Nucleic Acids and Other Materials for In Vitro and In Vivo Experiments

All siRNAs were purchased from Sigma-Aldrich. Let-7g miRNA mimic and its control mimic were purchased from Ambion by Life Technologies. Dulbecco's Modified Eagle Media (DMEM) and fetal bovine serum (FBS) were purchased from Sigma-Aldrich. OptiMEM, DAPI, and Alexa Fluor 488 phalloidin were purchased from Life Technologies. ONE-Glo+Tox was purchased from Promega. Biophen FVII was purchased from Aniara Corporation.

The sequence for the sense and antisense strands of siRNAs were as follows:

siLuc siRNA against Luciferase). dT are DNA bases. All others are RNA bases.

```
sense:
                                      (SEQ ID NO: 3)
5'-GAUUAUGUCCGGUUAUGUA[dT][dT]-3' antisense:
                                      (SEQ ID NO: 4)
3'-UACAUAACCGGACAUAAUC[dT][dT]-5'
``` siFVII (siRNA against FVII). 2'-Fluoro modified nucleotides are lower case.

```
sense:
                                      (SEQ ID NO: 1)
5'-GGAucAucucAAGucuuAc[dT][dT]-3' antisense:
                                      (SEQ ID NO: 2)
3'-GuAAGAcuuGAGAuGAucc[dT][dT]-5'
``` siCTR (siRNA as control)

```
sense:
                                      (SEQ ID NO: 5)
5'-GCGCGAUAGCGCGAAUAUA[dT][dT]-3' antisense:
                                      (SEQ ID NO: 6)
3'-UAUAUUCGCGCUAUCGCGC[dT][dT]-5'
```

Sigma-Aldrich MISSION siRNA Universal Negative Control #1 (catalog number: SIC001) was used as a non-targeted siRNA in control experiments. 2' OMe modified control siRNAs (Sigma-Aldrich, proprietary modifications) were used in in vivo studies to reduce immune stimulation.

Cy5.5-labeled siRNA (siRNA for imaging)

```
sense:
                                      (SEQ ID NO: 3)
5'-Cy5.5-GAUUAUGUCCGGUUAUGUA[dT][dT]-3' antisense:
                                      (SEQ ID NO: 4)
3'-UACAUAACCGGACAUAAUC[dT][dT]-5'
```

Let-7g miRNA mimic

Ambion (Life Technologies) mirVana miRNA mimic (catalog number: 4464070, product ID: MC11758, name: has-let-7g). Exact sequence and modifications not disclosed by Ambion. Mimics mature human Let-7g.

Negative Control (CTR) miRNA Mimic

Ambion (Life Technologies) mirVana miRNA Mimic, Negative Control #1 (catalog number: 4464061). Exact sequence and modifications not disclosed by Ambion.

3. Robotic Automation

Nanoparticle (NP) formulations and in vitro screening were performed on a Tecan Freedom EVO 200 fluid handling robot equipped with an 8-channel liquid handling arm (LiHa), multi-channel arm with 96-channel head (MCA), robotic manipulator arm (RoMa), and an integrated InfiniTe F/M200 Pro microplate reader (Tecan). Two integrated custom heating and stirring chemical reaction stations (V&P Scientific 710E-3HM Series Tumble Stirrers) provided reaction and mixing support. All operations were programmed in EVOware Standard software (Tecan).

4. Synthetic Characterization $^1$H and $^{13}$C NMR were performed on a Varian 500 MHz spectrometer. MS was performed on a Voyager DE-Pro MALDI TOF. Flash chromatography was performed on a Teledyne Isco CombiFlash Rf-200i chromatography system equipped with UV-vis and evaporative light scattering detectors (ELSD). Particle sizes and zeta potentials were measured by Dynamic Light Scattering (DLS) using a Malvern Zetasizer Nano ZS (He—Ne laser, λ=632 nm).

5. Nanoparticle Formulation for In Vivo Studies

Formulated dendrimer nanoparticles for in vivo studies were prepared using a microfluidic mixing instrument with herringbone rapid mixing features (Precision Nanosystems NanoAssemblr). Ethanol solutions of dendrimers, DSPC, cholesterol, and lipid PEG2000 were rapidly combined with acidic solutions of siRNA as described below. The typical ratio of aqueous:EtOH was 3:1 (volume) and the typical flow rate was 12 mL/minute.

6. Automated, In Vitro Delivery Screening of Modular Degradable Dendrimers

Nanoparticle (NP) formulations and in vitro screening were performed on a Tecan Freedom EVO 200 fluid handling robot equipped with an 8-channel liquid handling arm (LiHa), multi-channel arm with 96-channel head (MCA), robotic manipulator arm (RoMa), and an integrated InfiniTe F/M200 Pro microplate reader (Tecan).

HeLa cells stably expressing firefly luciferase (HeLa-Luc) were derived from HeLa cells (ATCC) by stable transfection of the luciferase gene using lentiviral infection followed by clonal selection. HeLa-Luc cells were seeded (10,000 cells/well) into each well of an opaque white 96-well plate (Corning) and allowed to attach overnight in phenol red-free DMEM supplemented with 5% FBS. The media was replaced with fresh, FBS-containing media on the second day before starting the transfection.

G1DD-siLuc nanoparticles were formulated with the aid of an automated, fluid-handling robot to accelerate the discovery process. All operations were programmed in EVOware Standard software. First, dendrimer reaction solutions were diluted from the original reaction concentration to 12.5 mM in ethanol. Next, the dendrimer solutions were diluted a second time from 12.5 mM to 1 mM in ethanol using the LiHa arm. Then, 89.2 μL of a lipid mixture in ethanol was added into a 96-well clear plate. The lipid mixture was composed of DSPC (0.0690 mM), cholesterol (0.2622 mM), and lipid PEG2000 (0.0138 mM) in ethanol. Subsequently, 30.8 μL of each dendrimer (1 mM) was added to the lipid mixture in the 96-well plate via the LiHa, followed by rapid mixing (15 times; 75 μL mixing volume; 250 μL/second speed). The LiHa added and mixed 8 tips at once. To a second clear 96-well plate, 50 μL of siLuc (20 ng/μL) in citrate buffer (pH=4.3) was added via the LiHa. 30 μL of the ethanol mixture (dendrimer, DSPC, cholesterol, lipid PEG2000) was then added to the 50 μL siLuc solution, followed by rapid mixing (15 times; 75 μL mixing volume; 250 μL/second speed) to form the dendrimer nanoparticles.

Next, 120 µL of sterile PBS (1x) was added and mixed using the LiHa to dilute the NPs and increase the pH. Subsequently, the plates were re-formatted to allow for facile transfer to growing cells. Finally, 20 µL of the NP solutions was added to culturing cells using sterile disposable tips via the MCA96 head to avoid contamination. The cells ultimately received 100 ng siLuc (33 nM). The mol ratio of dendrimer to siLuc was 100:1 during this screening phase. The final composition of the formulation was G1DD:cholesterol:DSPC:lipid PEG2000: =50:38:10:2 (by mole). Cells were incubated for 24 h at 37° C., 5% $CO_2$ and then firefly luciferase activity and viability was analyzed using One Glo+Tox assay kits (Promega).

7. Dendrimer-Small RNA Formulations for In Vivo Studies

Formulated dendrimer nanoparticles for in vivo studies were prepared using a microfluidic mixing instrument with herringbone rapid mixing features (Precision Nanosystems NanoAssemblr). Ethanol solutions of dendrimer, DSPC, cholesterol, and lipid PEG2000 (molar ratio of 50:38:10:2) were rapidly combined with acidic solutions of small RNA to give the final weight ratio of 25:1 (dendrimer:small RNA). The typical ratio of aqueous:EtOH was 3:1 (volume) and the typical flow rate was 12 mL/minute. C12-200 LNPs were prepared according to the reported procedure (Love et al., 2010). Ethanol solutions of C12-200, DSPC, cholesterol, and lipid PEG2000 (molar ratio of 50:38.5:10:1.5) were rapidly combined with acidic solutions of small RNA to give the final weight ratio of 7:1 (C12-200:small RNA). All formulated NPs were purified by dialysis in sterile PBS with 3.5 kD cut-off and the size was measured by Dynamic Light Scattering (DLS) prior to in vivo studies. When applicable, the encapsulation of small RNAs was measured with Ribogreen binding assay (Invitrogen) by taking the small amount of solution and following its protocol.

8. Animal Studies

All experiments were approved by the Institutional Animal Care and Use Committees of The University of Texas Southwestern Medical Center and were consistent with local, state and federal regulations as applicable. Female C57BL/6 mice were purchased from Harlan Laboratories (Indianapolis, IN). Transgenic mice bearing MYC-driven liver tumors were generated by crossing the TRE-MYC strain with LAP-tTA strain. Mice bearing the LAP-tTA and TRE-MYC genotype were maintained on 1 mg/mL of dox, and MYC was induced by withdrawing dox. Power analysis was performed to anticipate required number of animals to achieve statistical significance.

9. In Vivo Factor VII Silencing in Mice

For in vivo delivery screening, female C57BL/6 mice received tail vein i.v. injections of PBS (negative control, n=3) or dendrimer NPs containing non-targeting siRNA (siCTR, negative control, n=3) or dendrimer NPs containing anti-Factor VII siRNA (siFVII, n=3) diluted in PBS (200 µL or less in total volume). After 48 h, body-weight gain/loss was measured and mice were anaesthetized by isofluorane inhalation for blood sample collection by retro-orbital eye bleed. Serum was isolated with serum separation tubes (Becton Dickinson) and Factor VII protein levels were analyzed by a chromogenic assay (Biophen FVII, Aniara Corporation). A standard curve was constructed using samples from PBS-injected mice and relative Factor VII expression was determined by comparing treated groups to an untreated PBS control.

For the therapeutic study, FVII knockdown in transgenic mice were verified with the above blood assay and by qPCR using harvested liver tissues. To evaluate statistical significance, two-tailed Student's t-tests with the 95% confidence level were conducted.

10. Biodistribution

Female C57BL/6 mice or transgenic mice bearing liver tumors received tail vein i.v. injections with dendrimer NPs containing Cy5.5-siRNA at 1 mg/kg of siRNA in 200 µL. At 24 h post injection, mice were euthanized and organs were removed. The biodistribution was assessed by imaging whole organs with an IVIS Lumina System (Caliper Life Sciences) with the Cy5.5 filter setting.

For confocal imaging, the tissue was cryo-sectioned (7 µm) and fixed using 4% paraformaldehyde at room temperature for 10 min. The slides were washed three times with PBS and blocked for 30 min in PBS with 1% albumin. Sections were then incubated for 30 min with Alexa Fluor 488 Phalloidin (1:200 dilution, Life Technologies) in PBS with 1% albumin. Slides were washed three times with 0.1% Tween 20 and mounted using ProLong Gold Antifade (Life Technologies). Sections were imaged using an LSM 700 point scanning confocal microscope (Zeiss) equipped with a 25× objective.

11. In Vivo Toxicity Evaluation and Let-7g Therapeutic Studies

Wild-type mice or transgenic mice bearing liver tumors were randomly divided into different groups. Mice received tail vein i.v. injections of dendrimer NPs containing siCTR. Their body weight was monitored daily. For transgenic mice bearing liver tumors, multiple tail vain injections were performed to simulate repeated dosing.

For Let-7g therapeutic studies, transgenic mice bearing liver tumors received weekly tail vein i.v. injections of dendrimer NPs with Let-7g mimic or CTR mimic at a dosage of 1 mg/kg in 200 µL PBS from the age of 26 to 61 days. Processing order randomization was used. No blinding was done. Their body weight, abdomen size, and survival were carefully monitored. To evaluate statistical significance, two-tailed T tests with the 95% confidence level or Mantel-Cox tests were conducted.

Example 2: Synthesis and Characterization of PEG Lipids and Dendrimers

1. Synthesis of Library Containing 1,512 First-Generation Degradable Dendrimers (G1DDs)

G1DDs were synthesized through two sequential orthogonal reactions. At first, amines with different initial branching centers (IBCs) were separately reacted with the acrylate group of 2-(acryloyloxy)ethyl methacrylate (AEMA) with the mole ratio of amine to AEMA equaling the IBC numbers (e.g. 2A amines: two equivalents of AEMA were added; 6A amines: six equivalents of AEMA were added). Reactions were conducted with the addition of 5 mol % butylated hydroxyltoluene (BHT) for 24 hours at 50° C. Next, each first-step adduct was reacted separately with each thiol at the mole ratio of thiol to adduct equaling the amine IBC numbers (e.g. 2A amine first-step adduct: two equivalents of each thiol was added; 6A amine first-step adduct: six equivalents of each thiol was added). Reactions were conducted with the addition of 5 mol % dimethylphenylphosphine (DMPP) catalyst for 48 hours at 60° C. The 1,512 member library synthesis was accelerated by conducting reactions in glass vials and aluminum reaction blocks. Custom heating and stirring chemical reaction stations (V&P Scientific 710E-3HM Series Tumble Stirrers) were employed.

Initial in vitro delivery screening experiments were conducted with crude G1DDs. Follow-up studies to verify activity were performed using purified dendrimers.

All in vivo animal experiments were performed with purified G1DDs. Purified G1DDs were obtained by column flash chromatography on a neutral alumina column using a Teledyne Isco chromatography system with the gradient eluent of hexane and ethyl acetate.

2. Synthesis of Higher Generation Degradable Dendrimers (HGDDs) (1A2-G2-SC8 as an Example)

was prepared directly after 1A2 amine reacted with one equivalent of AEMA in the presence of 5 mol % BHT at 50° C. for 24 hours. 1A2-G1 (4.00 g, 11.7 mmol) was dissolved in 10 mL DMSO. After addition of 2-aminoethanthiol (1.37 g, 17.5 mmol) into the above solution, the reaction was stirred at room temperature for 30 min. Then 300 mL dichloromethane was immediately added into the reaction solution and was washed with cold brine water (50 mL×3) to remove extra 2-aminoethanthiol. The organic phase was dried with magnesium sulfate and condensed via rotary

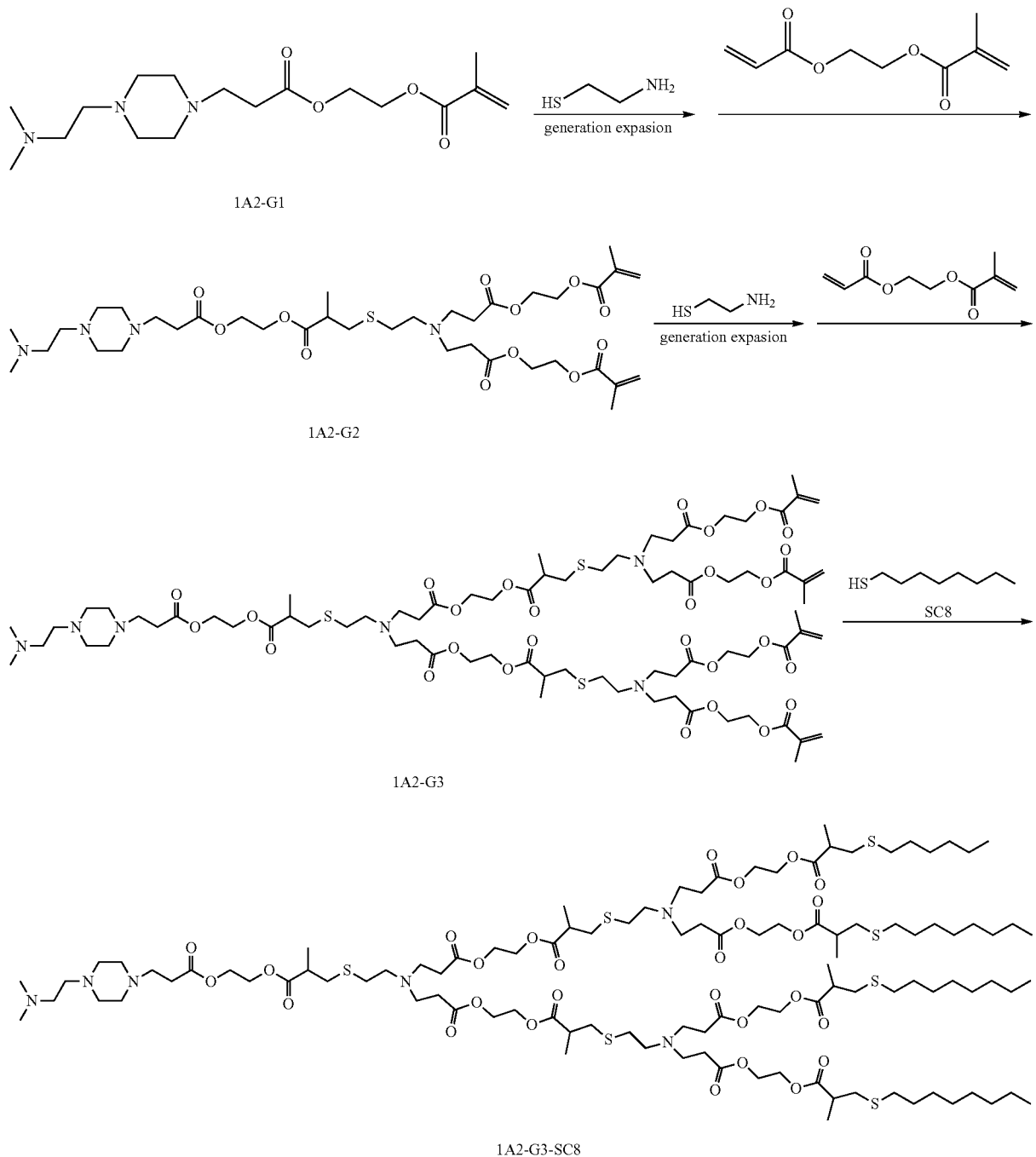

Higher generation degradable dendrimers were prepared according to the previous method (Ma et al., 2009). 1A2-G1 evaporation to use directly for next step. AEMA (4.75 g, 25.8 mmol) and BHT (227 mg, 1.08 mmol) were added into the above solution. The reaction was stirred at 50° C. and monitored by $^1$H NMR. After the reaction was complete, the solution was repeatedly washed with 20 mL hexane portions until no EAMA was found through TLC plate analysis. The washed solution was dried in vacuum to yield a viscous liquid 1A3-G2 directly for the next step. 1A3-G2 was reacted by following the above two-step synthetic procedure to give the viscous liquid 1A3-G3 directly for next the step. After 1A2-G3 (0.5 g, 0.3 mmol) was dissolved in 0.5 mL DMSO, 1-octanethiol (216 μL, 1.22 mmol) and dimethylphenylphosphine (DMPP) (8.6 μL, 0.061 mmol) was added. The reaction was stirred at 60° C. for 48 hours and then purified by running a neutral alumina column with the gradient eluent of hexane and ethyl acetate. A light-yellow viscous liquid 1A2-G3-SC8 was obtained.

3. Synthesis of Lipid PEG2000

PEG$_{44}$-OH (80 g, 40 mmol) and pyridine (6.5 mL, 80 mmol) were dissolved in 250 mL anhydrous DCM and cooled at 0° C. Methanesulfonyl chloride (15.5 mL, 200 mmol) in 50 mL DCM was added over 30 min and the mixture was stirred overnight at room temperature. Another 100 mL DCM was added and the organic phase washed with saturated NaHCO$_3$ solution (50 mL×3), and then brine (50 mL×3). The resulting solution was concentrated and the residue was recrystallized in isopropanol and dried to yield a white powder PEG2000-Ms (74 g, 93%).

PEG2000-Ms (35.41 g, 17.7 mmol) was dissolved in 250 mL of DMF. Then, NaN$_3$ (12.4 g, 19.0 mmol) was added into the solution. The reaction was stirred under nitrogen for 2

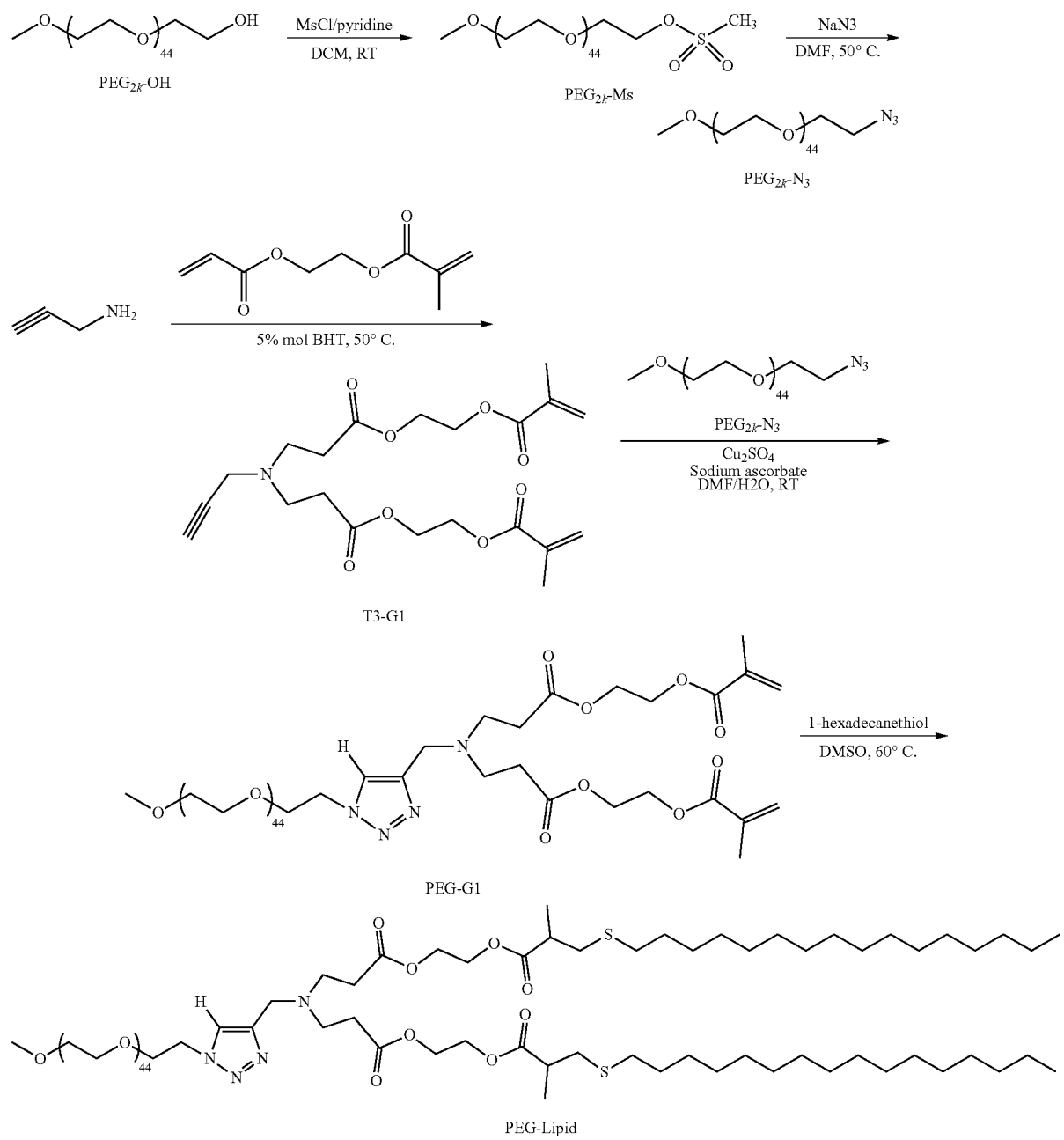

days at 50° C. After removal of DMF, the residual was dissolved in 300 mL DCM and washed with brine (50 mL×3). After removal of solvents, the residual oil was dissolved in 50 mL of methanol and the product was precipitated three times with 300 mL of diethyl ether to give the desired compound (25.55 g, 72%) as a white powder PEG2000-$N_3$.

Propargylamine (0.50 g, 9.1 mmol), BHT (191 mg, 0.91 mmol), and EAMA (2.73 g, 18.2 mmol) were added into a 25 mL reaction vial. The mixture was stirred for 48 hours at 50° C. The reaction was cooled down to give a colorless oil product T3-G1 without purification for use in the next reaction.

4. Characterization of Select Dendrimers $^1$H NMR (400 MHz, CDCl$_3$, δ): 4.34-4.21 (br, 16H, —OCH$_2$CH$_2$O—), 2.82-2.76 (m, 4H, —SCH$_2$CH(CH$_3$)—), 2.73 (t, J=7.1 Hz, 8H, —C(O)CH$_2$CH$_2$N—), 2.70-2.64 (m, 4H, —SCH$_2$CH(CH$_3$)—), 2.58-2.51 (m, 4H, —SCH$_2$CH(CH$_3$)—), 2.51-2.46 (m, 8H, —CH$_2$CH$_2$S—), 2.45-2.40 (m, 18H, (—C(O)CH$_2$CH$_2$)$_2$NCH$_2$CH$_2$CH$_2$N(CH$_2$-)$_2$), 2.35-2.26 (br, 4H, —CH$_2$CH$_2$N(CH$_2$-)$_2$), 1.65-1.58 (br, 4H, —NCH$_2$CH$_2$CH$_2$N—), 1.57-1.49 (m, 8H, —SCH$_2$CH$_2$CH$_2$—), 1.37-1.28 (br, 8H, —SCH$_2$CH$_2$CH$_2$—), 1.28-1.16 (br, 44H, —SCH$_2$CH$_2$(CH$_2$)$_4$CH$_3$, —CHC(CH$_3$)CH$_2$S—), 0.85 (t, J=7.0 Hz, 12H, —(CH$_2$)$_4$CH$_3$). $^{13}$C NMR (400 MHz, CDCl$_3$, δ): 174.90, 172.18, 62.18, 62.05, 49.05, 40.14, 35.37, 32.68, 32.40, 31.76, 29.60, 29.15, 28.83, 22.60, 16.81, 14.08. MS (MALDI-TOF, m/z) Calc. for C$_{78}$H$_{144}$N$_4$O$_{16}$S$_4$: 1520.95, found: 1521.32.

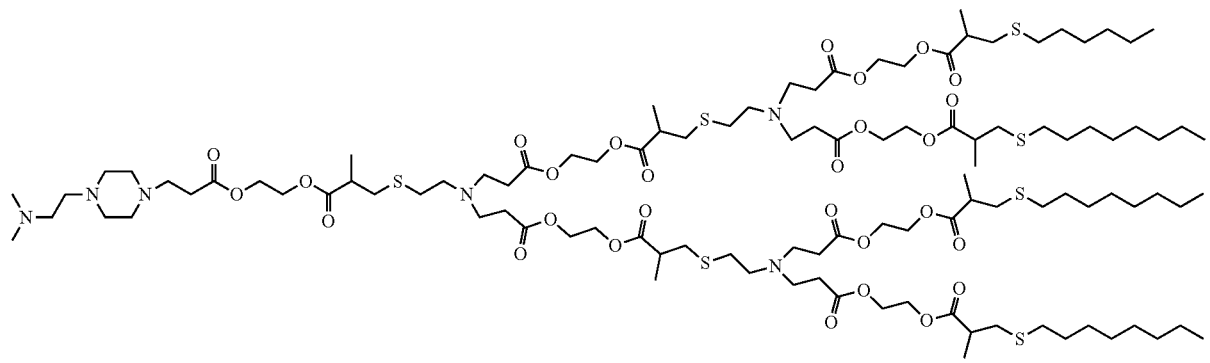

1A2-G3-SC8

$^1$H NMR (400 MHz, CDCl$_3$, δ): 4.38-4.19 (br, 28H, —OCH$_2$CH$_2$O—), 2.90-2.80 (br, 7H, —C(O)CH(CH$_3$)CH$_2$S—), 2.75-2.71 (br, 14H, —NCH$_2$CH$_2$C(O)—), 2.70-2.49 (br, 28H, —C(O)CH(CH$_3$)CH$_2$S—, —SCH$_2$—), 2.49-2.39 (br, 36H, —N(CH$_3$)$_2$, —NCH$_2$CH$_2$N(CH$_2$CH$_2$)$_2$NCH$_2$—, —CH$_2$N(CH$_2$-)$_2$), 1.57-1.48 (m, 8H, —SCH$_2$CH$_2$CH$_2$—), 1.37-1.28 (br, 8H, SCH$_2$CH$_2$CH$_2$—), 1.28-1.16 (br, 53H, —SCH$_2$CH$_2$(CH$_2$)$_4$CH$_3$, —CHC(CH$_3$)CH$_2$S—), 0.85 (t, J=7.1 Hz, 12H, —(CH$_2$)$_4$CH$_3$). $^{13}$C NMR (400 MHz, CDCl$_3$, δ): 174.92, 172.03, 62.22, 62.17, 62.13, 62.07, 49.06, 40.23, 40.14, 35.36, 32.68, 32.56, 31.76, 29.60, 29.14, 28.82, 22.58, 16.85, 16.81, 14.04. MS (MALDI-TOF, m/z) Calc. for C$_{109}$H$_{196}$N$_6$O$_{28}$S$_7$: 2261.21, found: 2262.43.

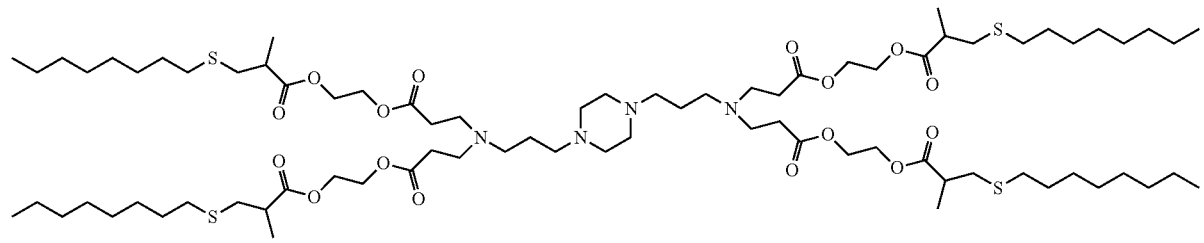

4A1-SC8

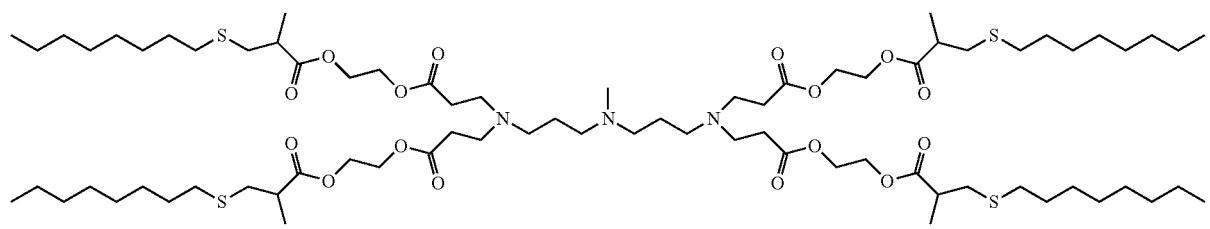

4A3-SC8

¹H NMR (400 MHz, CDCl₃, δ): 4.32-4.21 (br, 16H, —OCH₂CH₂O—), 2.82-2.76 (m, 4H, —SCH₂CH(CH₃)—), 2.73 (t, J=7.0 Hz, 8H, —C(O)CH₂CH₂N—), 2.69-2.62 (m, 4H, —SCH₂CH(CH₃)—), 2.58-2.50 (m, 4H, —SCH₂CH(CH₃)—), 2.50-2.45 (m, 8H, —CH₂CH₂S—), 2.45-2.38 (m, 12H, (—C(O)CH₂CH₂)₂NCH₂—), 2.34-2.24 (br, 4H, —CH₂N(CH₃)CH₂—), 2.24-2.00 (br, 3H, —CH₂N(CH₃)CH₂—) 1.66-1.57 (br, 4H, —NCH₂CH₂CH₂N—), 1.57-1.48 (m, 8H, —SCH₂CH₂CH₂—), 1.37-1.28 (br, 8H, —SCH₂CH₂CH₂—), 1.28-1.16 (br, 45H, —SCH₂CH₂(CH₂)₄CH₃, —CHC(CH₃)CH₂S—), 0.85 (t, J=7.0 Hz, 12H, —(CH₂)₄CH₃). ¹³C NMR (400 MHz, CDCl₃, δ): 174.90, 172.18, 62.18, 62.05, 49.00, 40.13, 35.36, 32.68, 32.35, 31.76, 29.60, 29.15, 28.83, 22.60, 16.81, 14.04. MS (MALDI-TOF, m/z) Calc. for C₇₅H₁₃₉N₃O₁₆S₄: 1465.90, found: 1465.65.

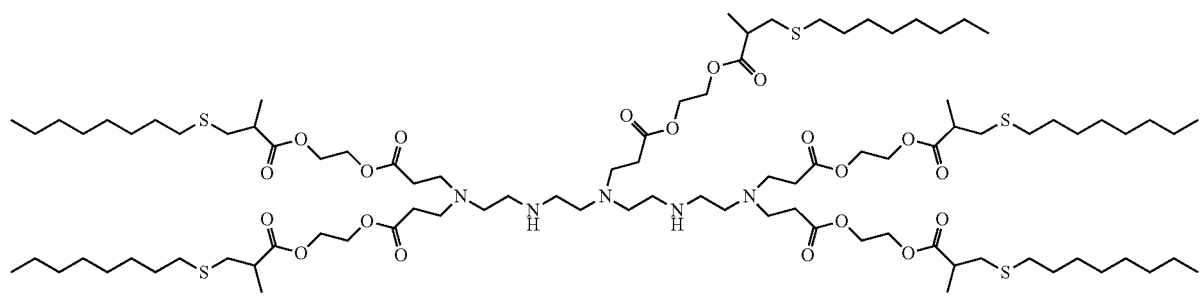

5A2-SC8

¹H NMR (400 MHz, CDCl₃, δ): 4.34-4.20 (br, 20H, —OCH₂CH₂O—), 2.82-2.76 (m, 5H, —SCH₂CH(CH₃)—), 2.75-2.70 (br, 10H, —C(O)CH₂CH₂N—), 2.69-2.62 (m, 5H, —SCH₂CH(CH₃)—), 2.60-2.52 (m, 5H, —SCH₂CH(CH₃)—), 2.52-2.49 (m, 10H, —CH₂CH₂S—), 2.49-2.45 (br, 16H, —NCH₂CH₂N—), 2.45-2.40 (br, 10H, —CH₂N—), 1.57-1.48 (br, 10H, —SCH₂CH₂CH₂—), 1.37-1.28 (br, 10H, —SCH₂CH₂CH₂—), 1.28-1.16 (br, 55H, —SCH₂CH₂(CH₂)₄CH₃, —CHC(CH₃)CH₂S—), 0.87-0.79 (br, 15H, —(CH₂)₄CH₃). ¹³C NMR (400 MHz, CDCl₃, δ): 174.93, 172.13, 62.28, 62.01, 49.04, 40.13, 35.36, 32.68, 32.35, 31.76, 29.60, 29.15, 28.83, 22.59, 16.82, 14.05. MS (MALDI-TOF, m/z) Calc. for C₉₃H₁₇₃N₅O₂₀S₅: 1840.13, found: 1841.37. 5A2-SC8 has also been prepared with 6 arms (structure shown below).

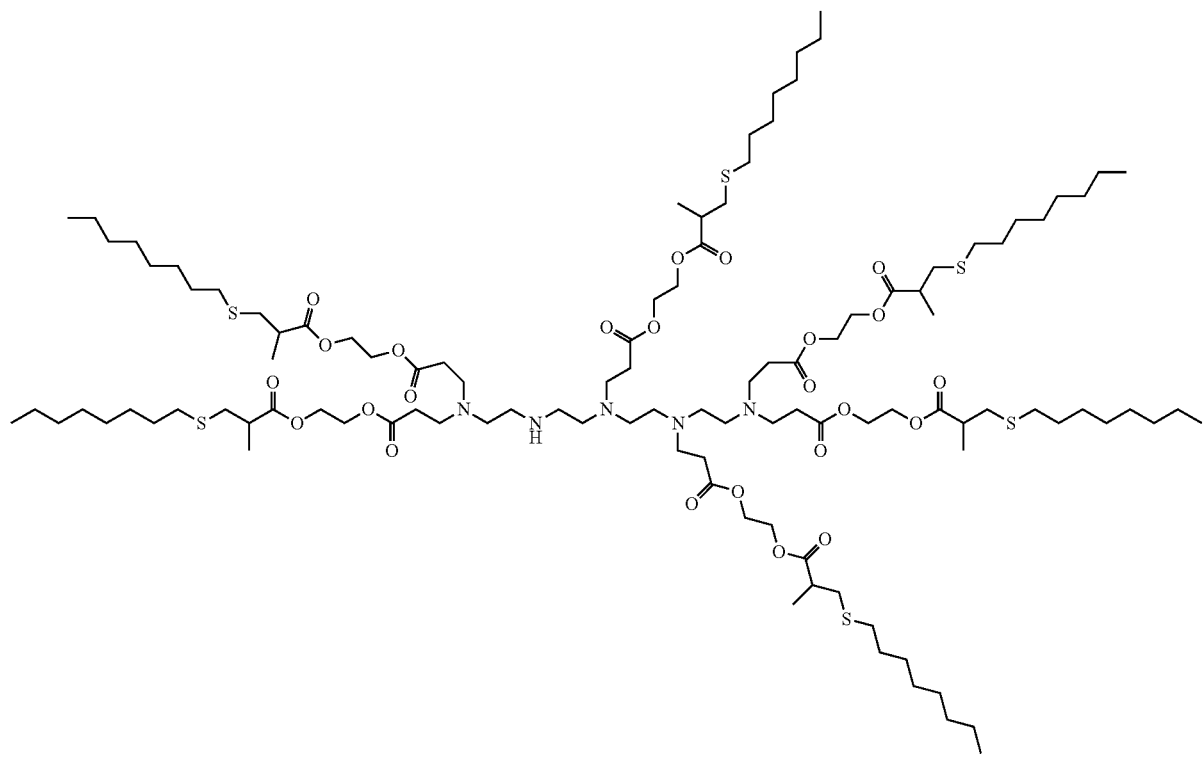
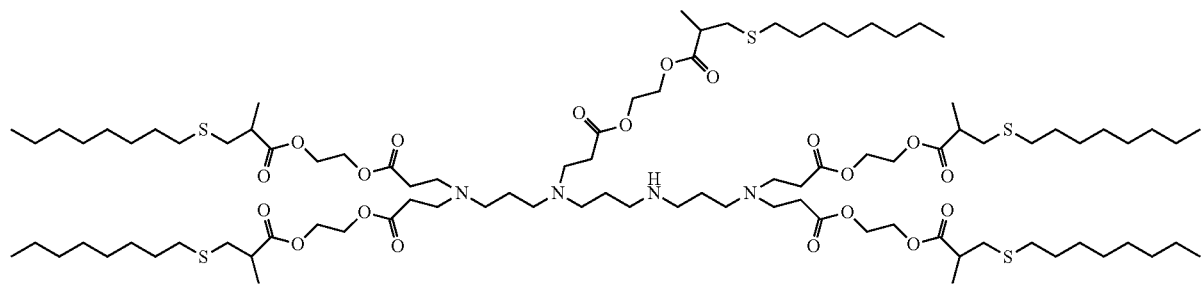
5A3-SC8
¹H NMR (400 MHz, CDCl₃, δ): 4.32-4.21 (br, 20H, —OCH₂CH₂O—), 2.82-2.76 (m, 5H, —SCH₂CH(CH₃)—), 2.76-2.70 (br, 10H, —C(O)CH₂CH₂N—), 2.69-2.62 (m, 5H, —SCH₂CH(CH₃)—), 2.58-2.50 (m, 5H, —SCH₂CH(CH₃)—), 2.50-2.45 (m, 10H, —CH₂CH₂S—), 2.45-2.20 (br, 20H, (—(CH₂)₂NCH₂—, —CH₂NHCH₂—), 1.66-1.57 (br, 6H, —NCH₂CH₂CH₂N—), 1.57-1.48 (br, 10H, —SCH₂CH₂CH₂—), 1.37-1.28 (br, 10H, —SCH₂CH₂CH₂—), 1.28-1.16 (br, 55H, —SCH₂CH₂(CH₂)₄CH₃, —CHC(CH₃)CH₂S—), 0.82-0.75 (br, 15H, —(CH₂)₄CH₃). ¹³C NMR (400 MHz, CDCl₃, δ): 174.98, 172.13, 62.28, 62.01, 49.04, 40.13, 35.36, 32.68, 32.35, 31.76, 29.60, 29.15, 28.83, 22.61, 16.85, 14.14. MS (MALDI-TOF, m/z) Calc. for C₉₄H₁₇₄N₄O₂₀S₅: 1839.13, found: 1838.97.

6A3-SC12

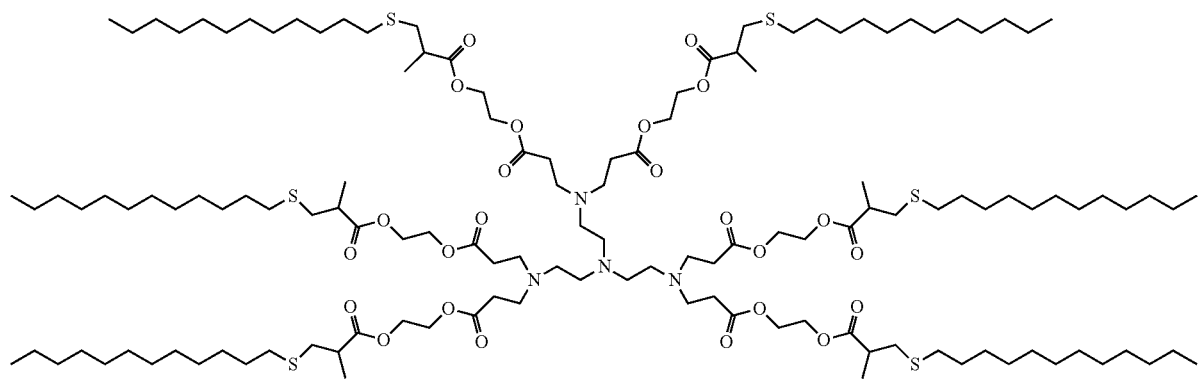

$^1$H NMR (400 MHz, CDCl$_3$, δ): 4.33-4.20 (br, 24H, —OCH$_2$CH$_2$O—), 2.82-2.77 (m, 6H, —SCH$_2$CH(CH$_3$)—), 2.77-2.71 (br, 12H, —C(O)CH$_2$CH$_2$N—), 2.68-2.62 (m, 6H, —SCH$_2$CH(CH$_3$)—), 2.60-2.52 (m, 6H, —SCH$_2$CH (CH$_3$)—), 2.52-2.48 (br, 12H, —CH$_2$CH$_2$S—), 2.48-2.46 (br, 12H, —NCH$_2$CH$_2$N—), 2.45-2.40 (br, 12H, (—CH$_2$)$_2$N—), 1.57-1.47 (br, 12H, —SCH$_2$CH$_2$CH$_2$—), 1.37-1.28 (br, 12H, —SCH$_2$CH$_2$CH$_2$—), 1.28-1.16 (br, 108H, —SCH$_2$CH$_2$(CH$_2$)$_8$CH$_3$, —CHC(CH$_3$)CH$_2$S—), 0.87-0.80 (br, 18H, —(CH$_2$)$_8$CH$_3$). $^{13}$C NMR (400 MHz, CDCl$_3$, δ): 174.87, 172.07, 62.16, 62.04, 49.48, 40.47, 40.11, 35.34, 32.69, 32.42, 31.86, 29.61, 29.58, 29.57, 29.50, 29.29, 29.21, 28.85, 22.62, 16.81, 14.06. MS (MALDI-TOF, m/z) Calc. for C$_{132}$H$_{246}$N$_4$O$_{24}$S$_6$: 2463.65, found: 2464.52.

Example 3: Library Design and Synthesis of First Generation Degradable Dendrimers (G1DDs)

Figure 1B:
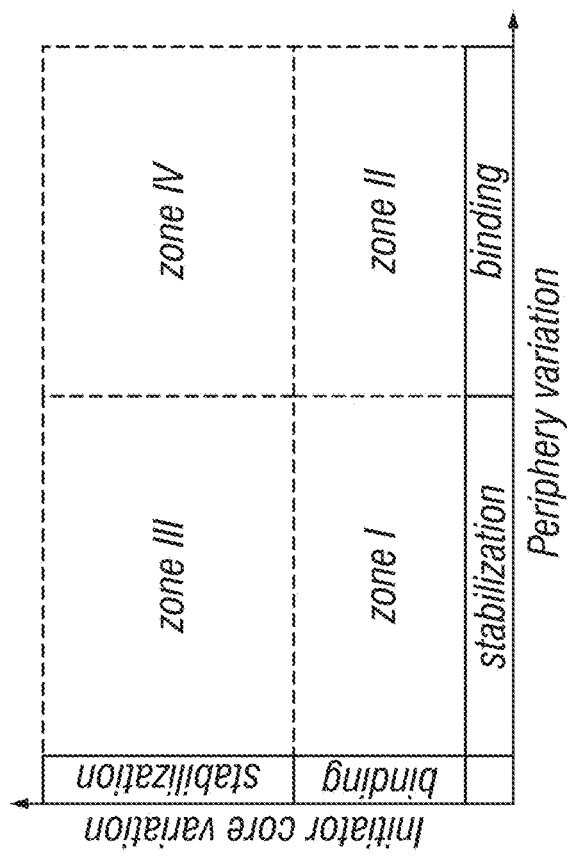

Liver cancer is a challenging host for therapeutic intervention because drug-induced hepatotoxicity can exacerbate the underlying liver disease (Boyerinas et al., 2010). To achieve effective RNAi-mediated therapy, a balance of high potency and low toxicity of the carrier therefore has to be maintained. This requires a versatile strategy to easily tune the delivery carrier in terms of size, chemical structure, and ultimate physical properties (FIG. 1A). In some embodiments, dendrimers were designed that exhibit one or more of the following characteristics: optimal, monodisperse materials for chemical and size manipulation (Wu et al., 2004; Carlmark et al., 2009; Killops et al., 2008; Ma et al., 2009; Franc and Kakkar, 2010). Orthogonal reactions were utilized to sequentially react with 2-(acryloyloxy)ethyl methacrylate (AEMA) to diversify first generation degradable dendrimers (G1DDs) through various parameters: core (C), linkage or repeating unit (L), and periphery or terminating group (P) (FIG. 1B). In some embodiments, esters were chosen as a starting degradable linkage because polyesters are used in FDA-approved products with minimal toxicity. At each growth step, the ester number increases, which provides an opportunity to identify degradable dendrimers with balanced potency and toxicity.

Figure 2:
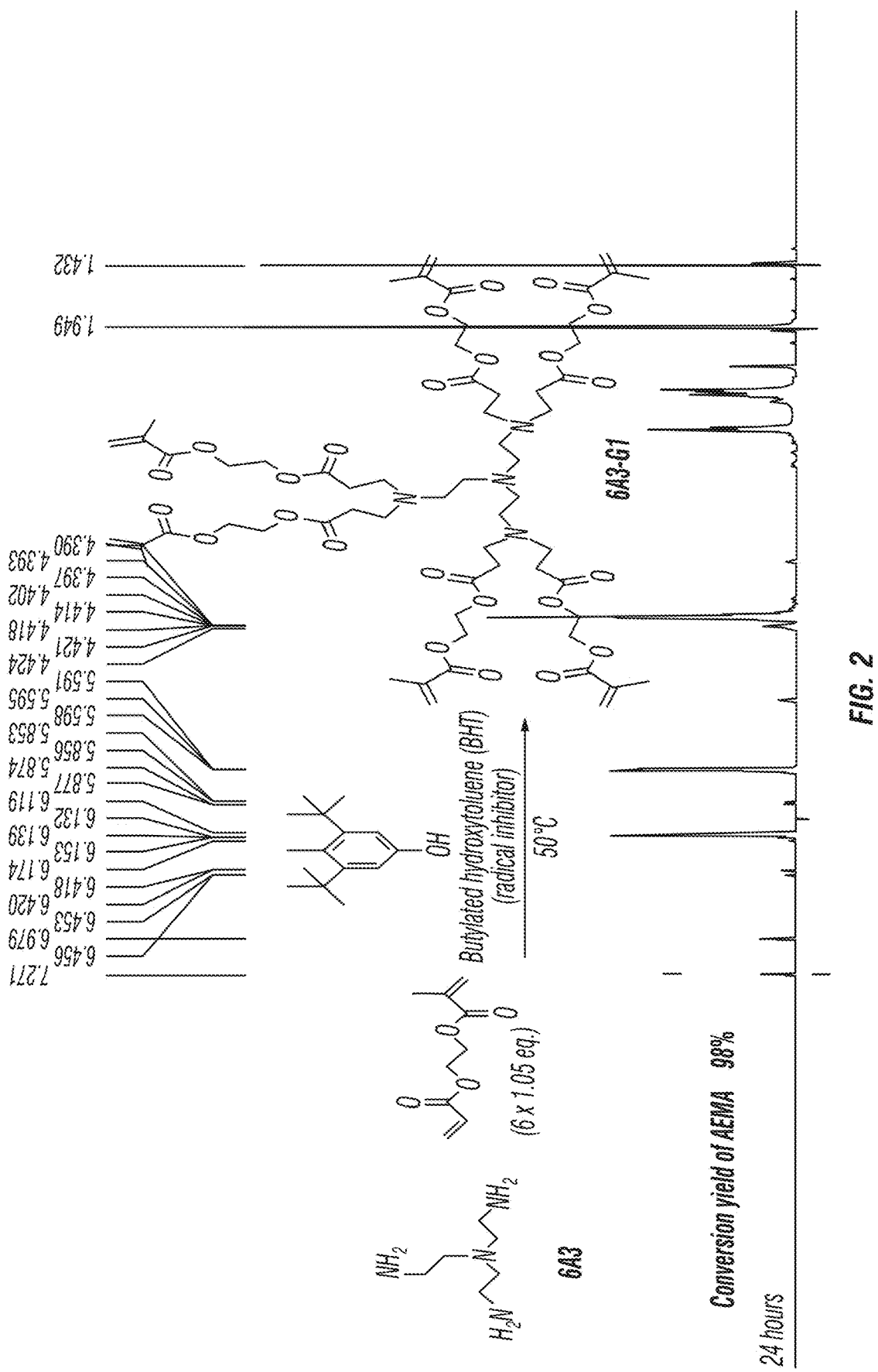
FIG. 2 shows high aza-Michael addition selectivity of tris(2-aminoethyl)amine 6A3 with 2-(acryloyloxy)ethyl methacrylate (AEMA) in the presence of 5 mol % of butylated hydroxyltoluene (BHT) at 50° C. Without addition of tris(2-aminoethyl)amine, AEMA alone is unreacted after 24 hours and its conversion is 0%. After adding tris(2-aminoethyl)amine, AEMA conversion is around 82% after 2 hours and 98% after 24 hours to generate a first-generation dendrimer with six branches, 6A3-G1. Note that excess EAMA (6×0.05 eq.) is added with aim to easily monitor the reaction by $^1$H NMR tracking of EAMA. If EAMA conversion is complete, there should still be 5% signal of $H_a$ and $H_b$ remaining.
Figure 2:
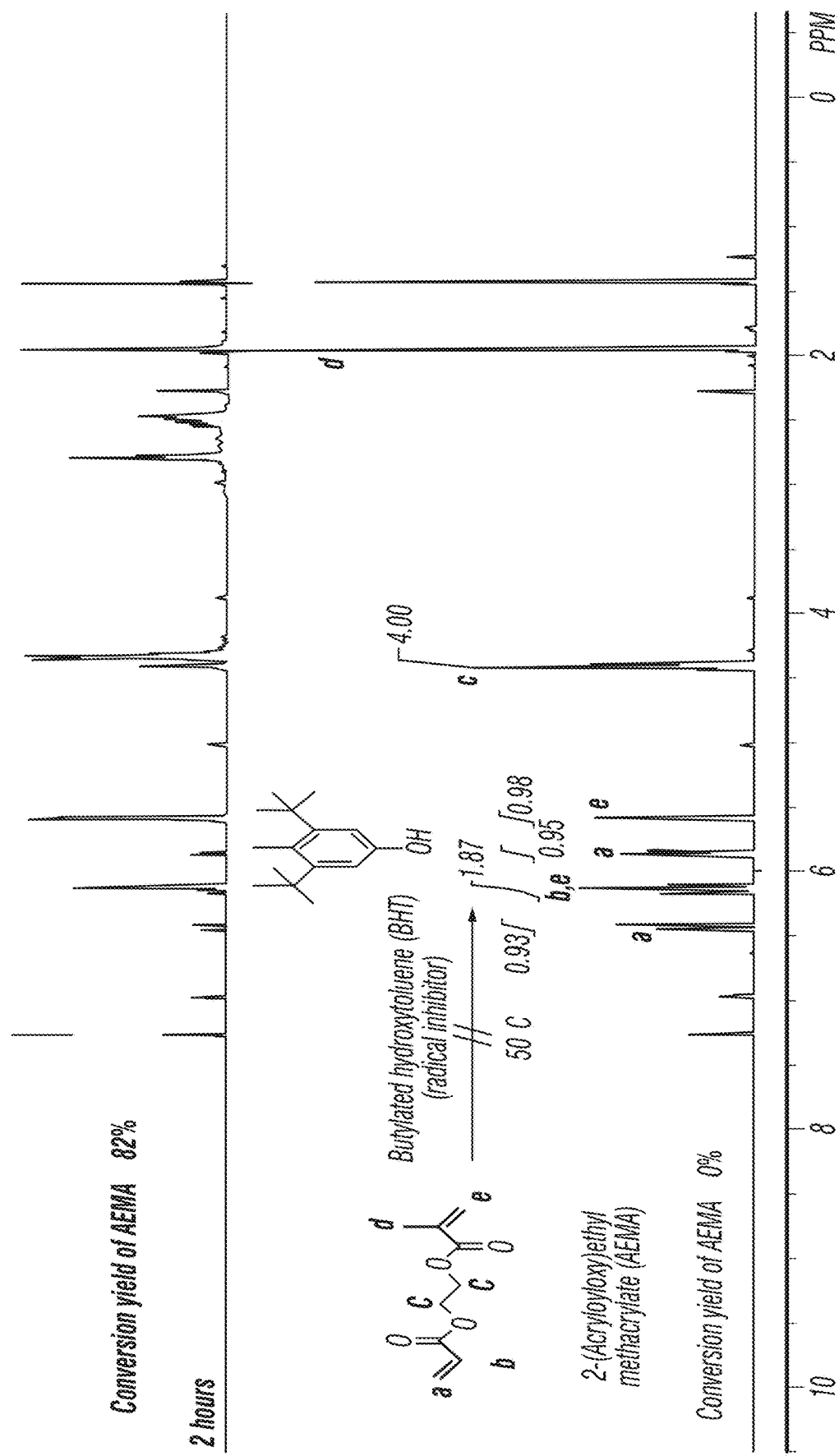
Figure 3:
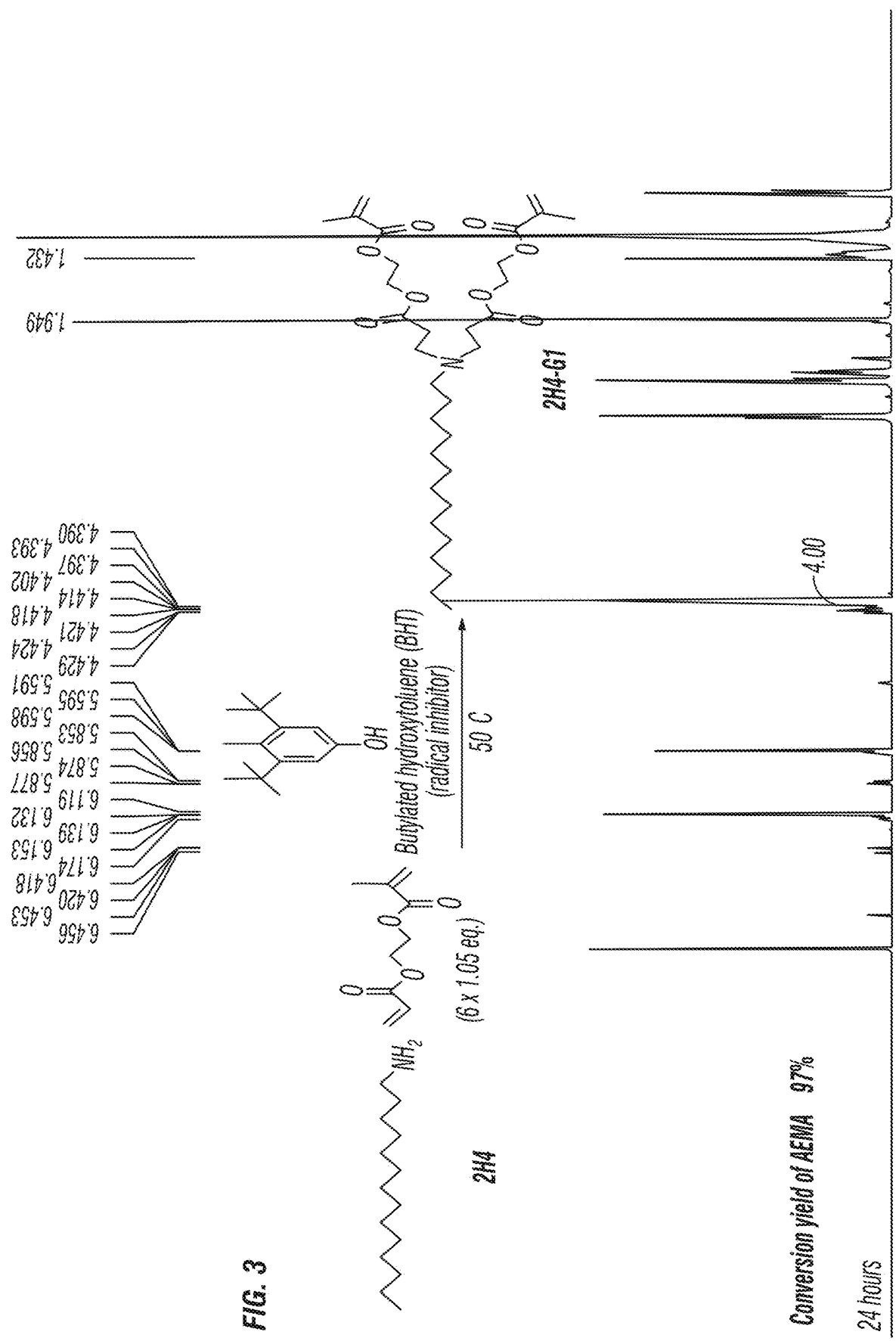
FIG. 3 shows high aza-Michael addition selectivity of long alkyl chain tetradecylamine 2H4 with 2-(acryloyloxy) ethyl methacrylate (AEMA) in the presence of 5 mol % of butylated hydroxyltoluene (BHT) at 50° C. AEMA alone is unreacted after 24 hours and its conversion is 0%. After adding tetradecylamine, AEMA conversion is around 97% after 24 hours to generate a first-generation dendrimer with long alkyl chain core 2H4-G1. Note that excess EAMA (2×0.05 eq.) is added with the purpose to easily monitor the reaction by $^1$H NMR tracking of EAMA. If EAMA conversion is complete, there should still be 5% signal of $H_a$ and $H_b$ remaining.
Figure 3:
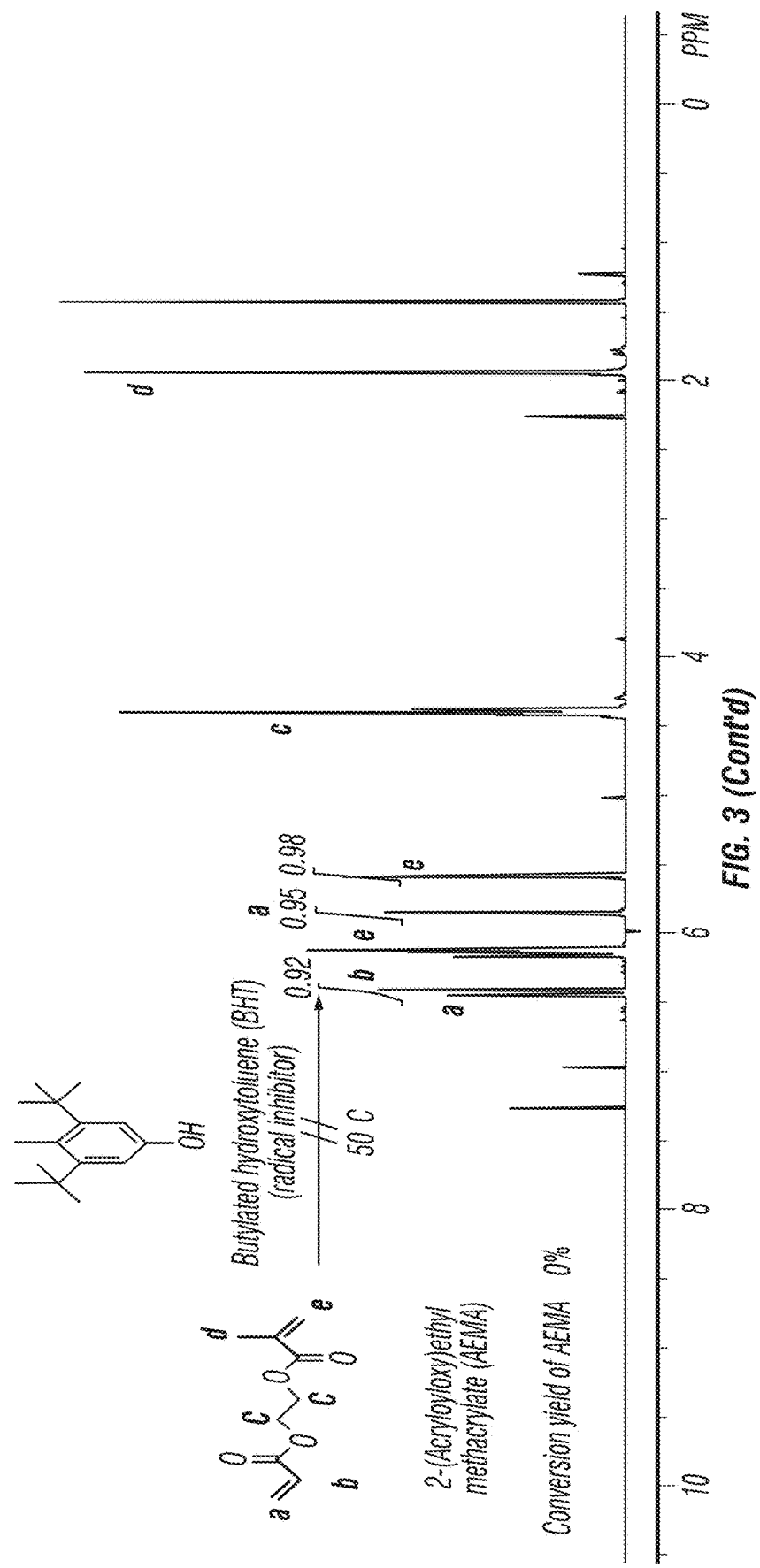
Figure 4:
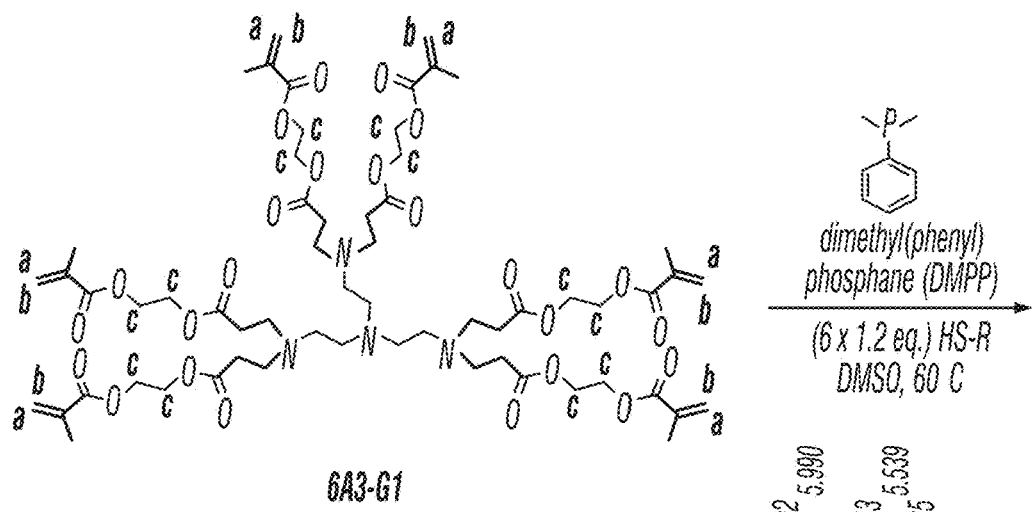
FIG. 4 shows sulfa-Michael addition of 6A3-G1 (125 mM) with 2-(butylamino)ethanethiol (6×1.2 eq.) or 1-tetradecanethiol (6×1.2 eq.) at 60° C. in 400 μL DMSO-D6 for 48 hours. Without addition of thiol compounds, 6A3-G1 remains the same at 60° C. in DMSO-D6 for 48 hours. With addition of (5 mol %) dimethylphenylphosphine (DMPP) as a catalyst, 6A3-G1 reacts with 1-tetradecanethiol at 100% conversion yield at 60° C. in DMSO-D6 within 48 hours while the conversion yield of 6A3-G1 is only 57% without DMPP. The conversion yield of 6A3-G1 with 2-(butylamino)ethanethiol is nearly quantitative with or without the addition of DMPP, probably because the amine group in 2-(butylamino)ethanethiol may act as a catalyst. Note that excess thiol (6×0.2 eq.) is added because 6A3-G1 contains (6×0.05 eq.) EAMA which consumes thiol reactant (6×0.1 eq.) with its two double bonds.
Figure 4:
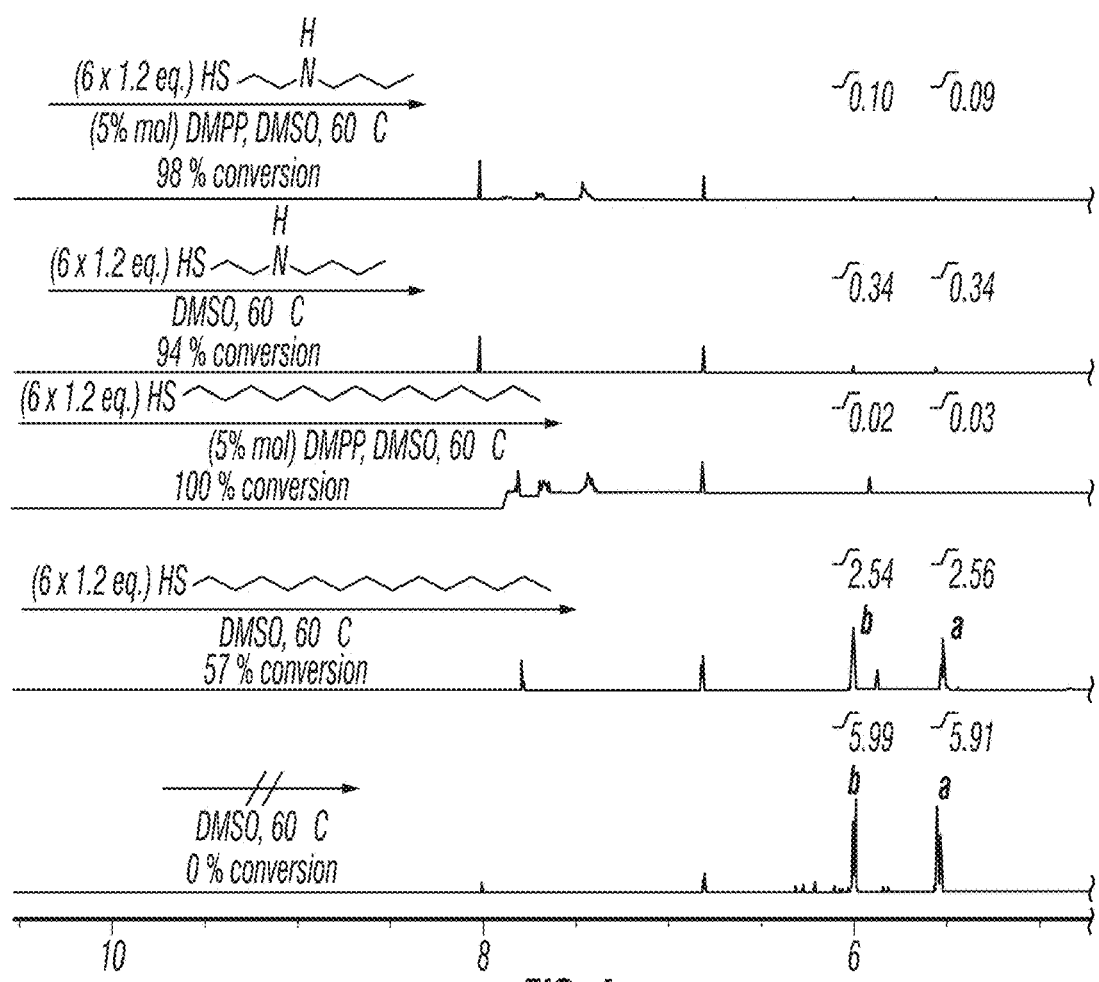
Figure 4:
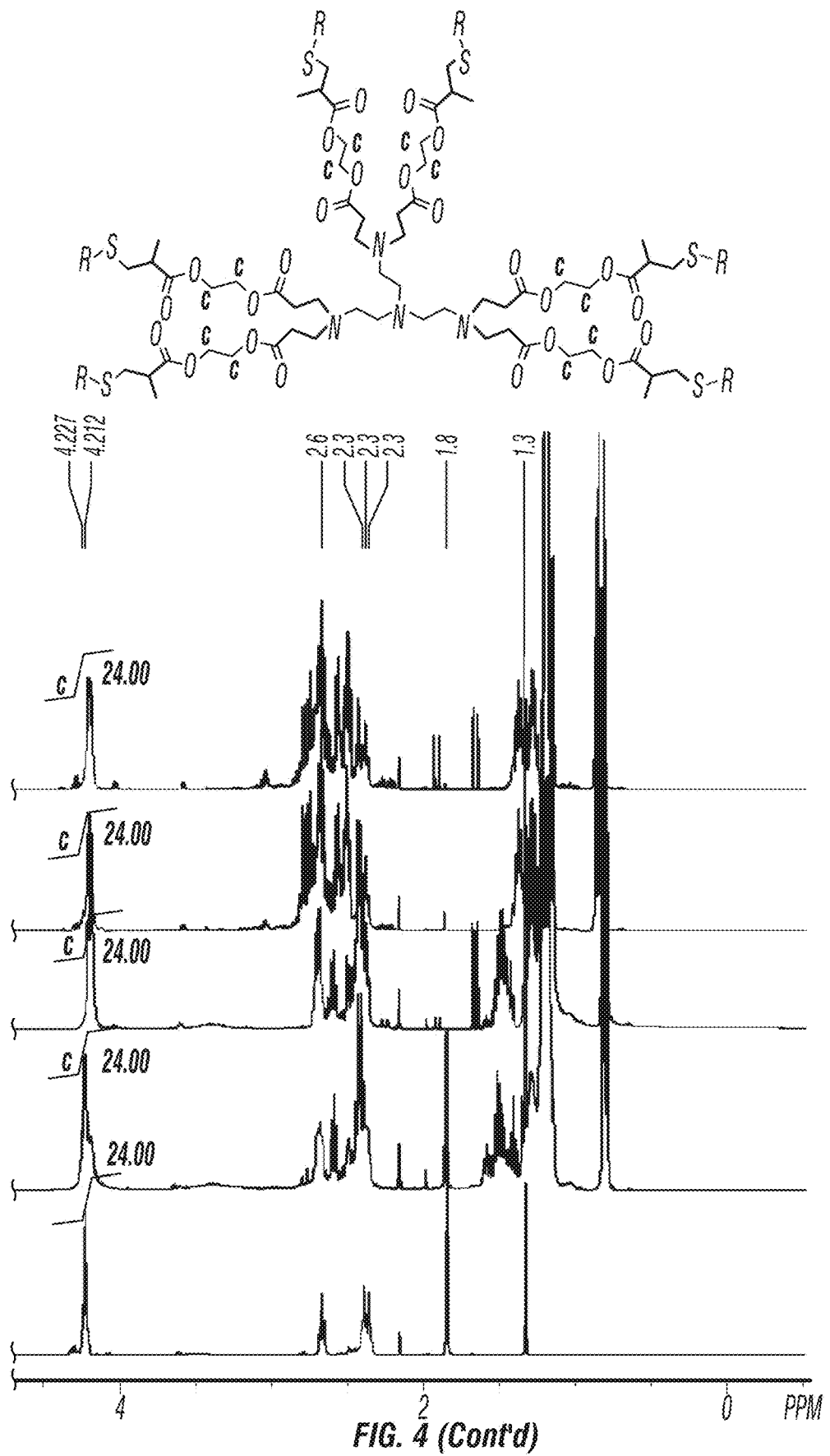
Figure 5:
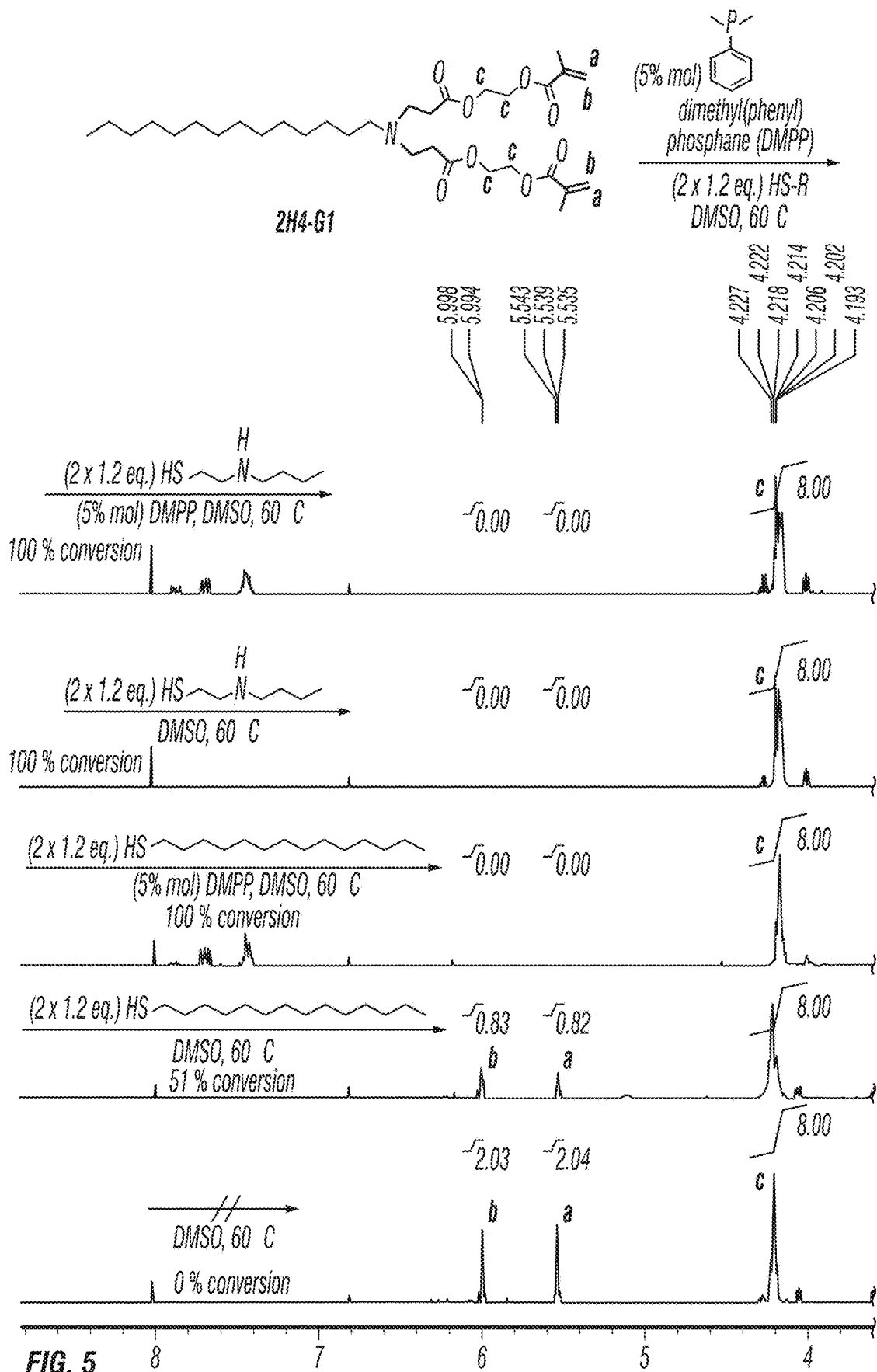
FIG. 5 shows sulfa-Michael addition of 2H4-G1 (125 mM) with 2-(butylamino)ethanethiol (2×1.2 eq.) or 1-tetradecanethiol (2×1.2 eq.) at 60° C. in DMSO-D6 for 48 hours. Without addition of thiol compounds, 2H4-G1 remains the same at 60° C. in DMSO-D6 for 48 hours. With addition of (5 mol %) dimethylphenylphosphine (DMPP) as a catalyst, 2H4-G1 reacts with 1-tetradecanethiol at 100% conversion yield at 60° C. in DMSO-D6 within 48 hours while the conversion yield of 2H4-G1 is only 51% without DMPP. The conversion yield of 2H4-G1 with 2-(butylamino)ethanethiol is quantitative with or without the addition of DMPP probably because the amine group in 2-(butylamino) ethanethiol may act as a catalyst. Note that excess thiol (2×0.2 eq.) is added because 2H4-G1 contains (2×0.05 eq.) EAMA which consumes thiol reactant (2×0.1 eq.) with its two double bonds.
Figure 5:
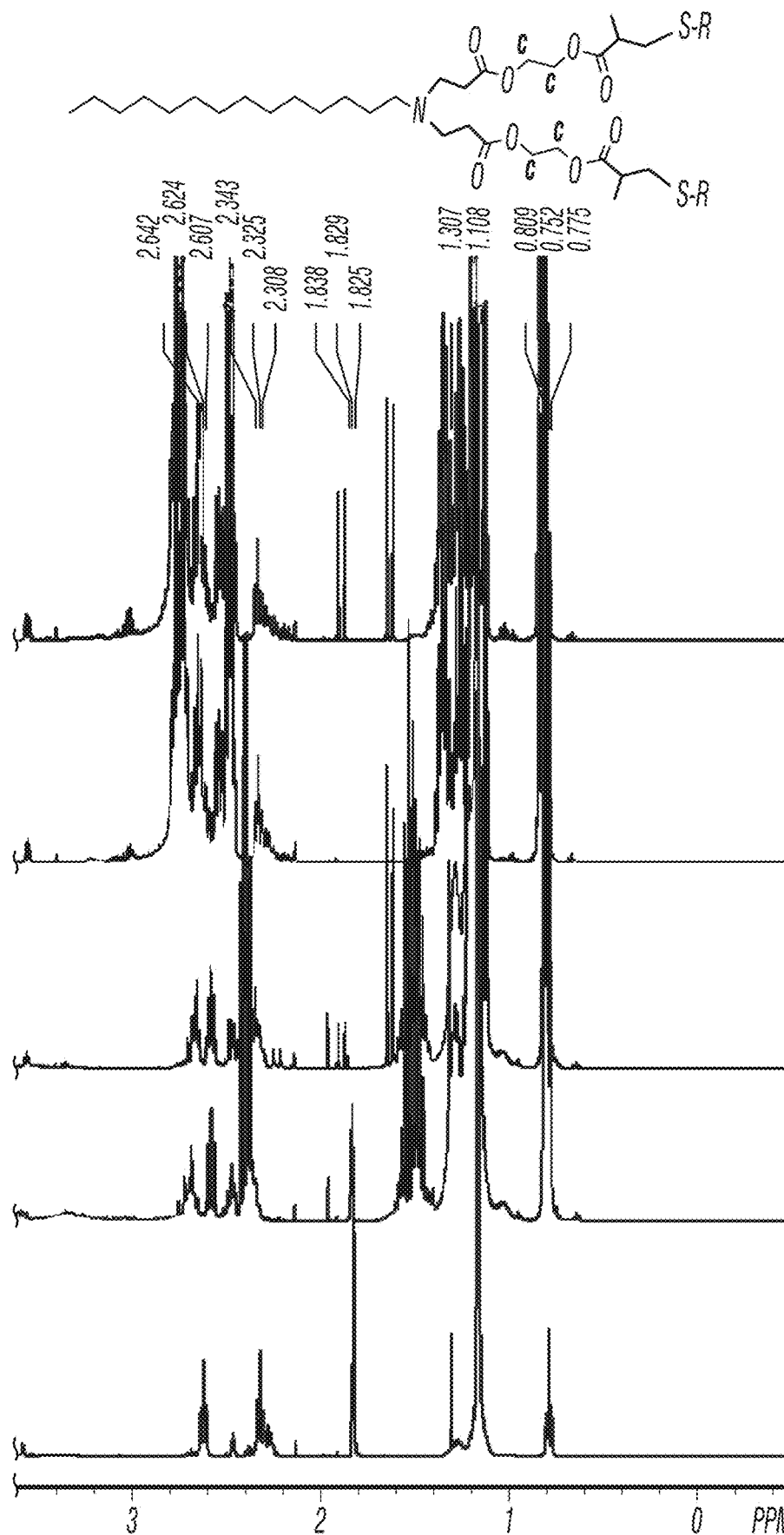

Previous results show that these orthogonal reactions can construct polyester dendrimers with a series of generations (Ma et al., 2009). However, before this strategy was utilized, it was verified that the methods are capable to yield diversified dendrimers using a variety of chemically distinct amine and thiol compounds without purification. To examine the robustness of this chemistry, the most difficult starting materials, tris(2-aminoethyl)amine with six N—H bonds as initial branching centers (IBCs) and tetradecylamine with a 14-carbon-length alkyl chain, were used to test structural limits of the orthogonal Michael addition reactions. Both tris(2-aminoethyl)amine and tetradecylamine quantitatively and selectively reacted with the acrylate functionality in AEMA after 24 hours in the presence of 5 mol % of butylated hydroxyltoluene (BHT) (to inhibit radical formation) at 50° C., while AEMA by itself remains unreacted under these conditions (FIGS. 2 & 3). In the second orthogonal reaction (sulfa-Michael addition), dimethylphenylphosphine was required as a catalyst to achieve the final product in low concentration (the lowest is 125 mM) or small scale (~20 mg on average) conditions as well as to achieve high conversion (100% by $^1$H NMR) so that the material can be used without purification for subsequent testing or generation expansion (FIGS. 4 & 5). Some of the dendrimers were re-synthesized in larger scale and purified by flash chromatography before conducting in vivo studies.

Figure 1C:
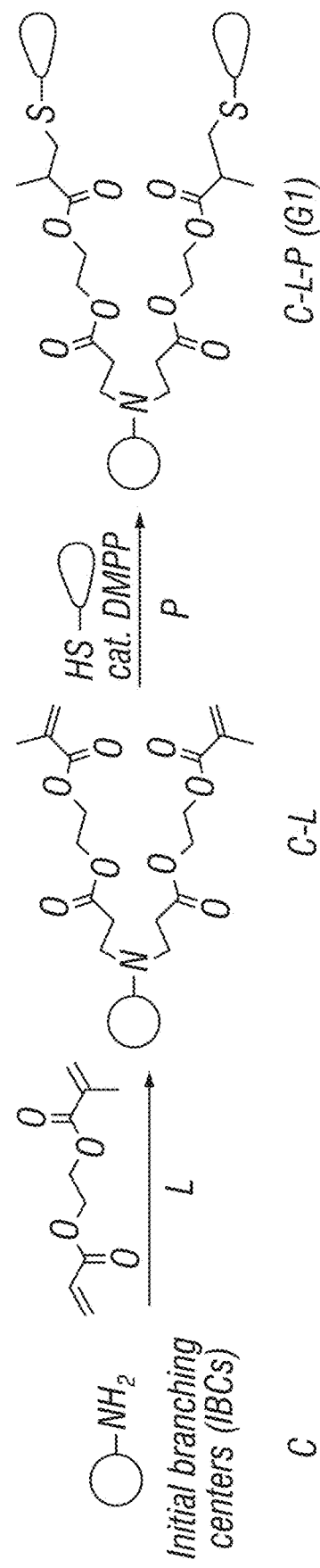
Figure 1D:
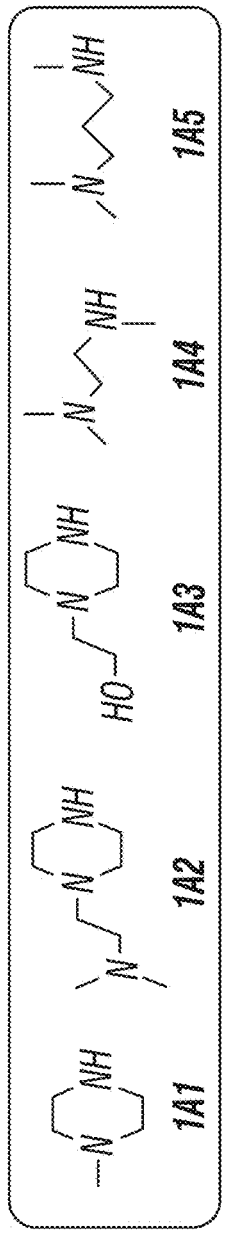
Figure 1D:
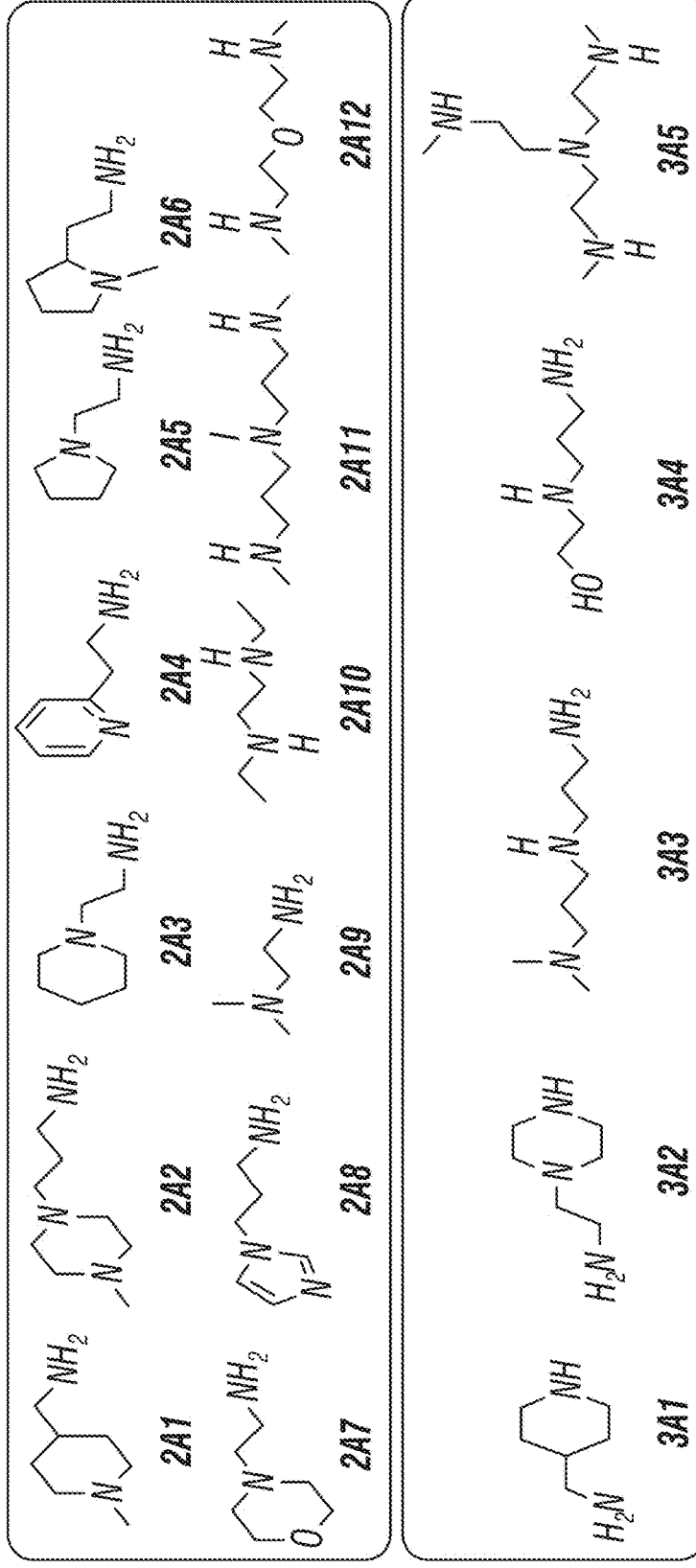
Figure 1D:
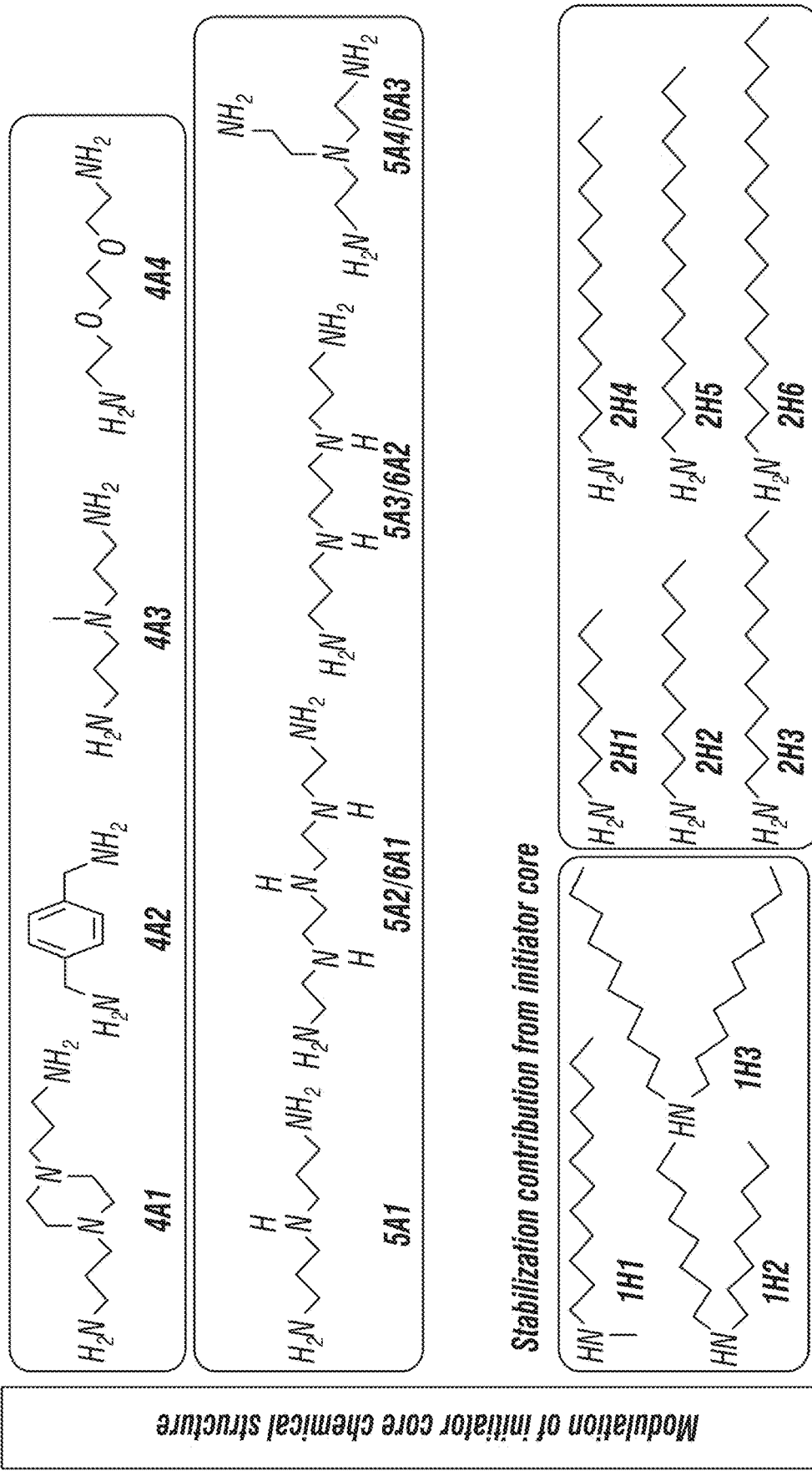
Figure 1D:
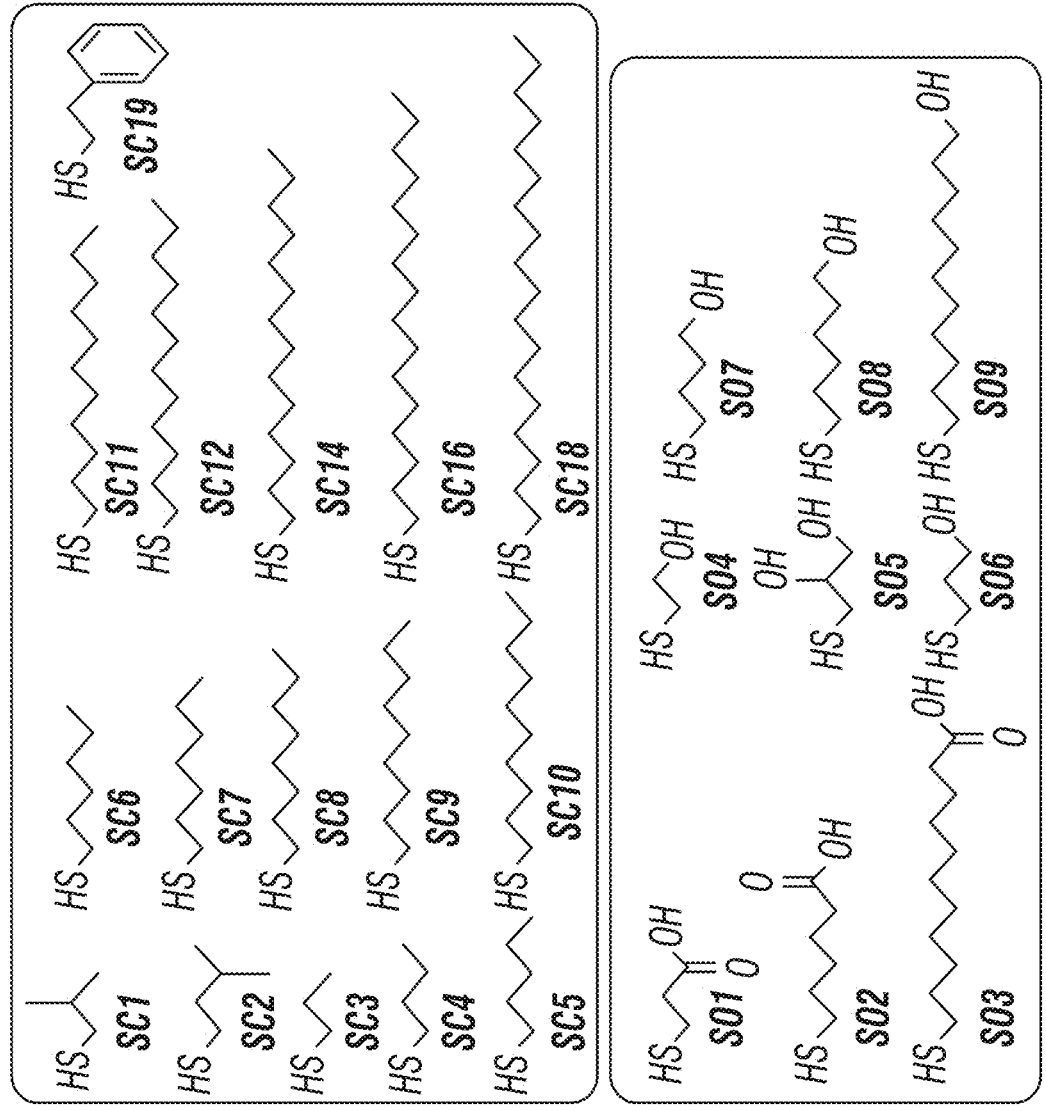
Figure 1D:
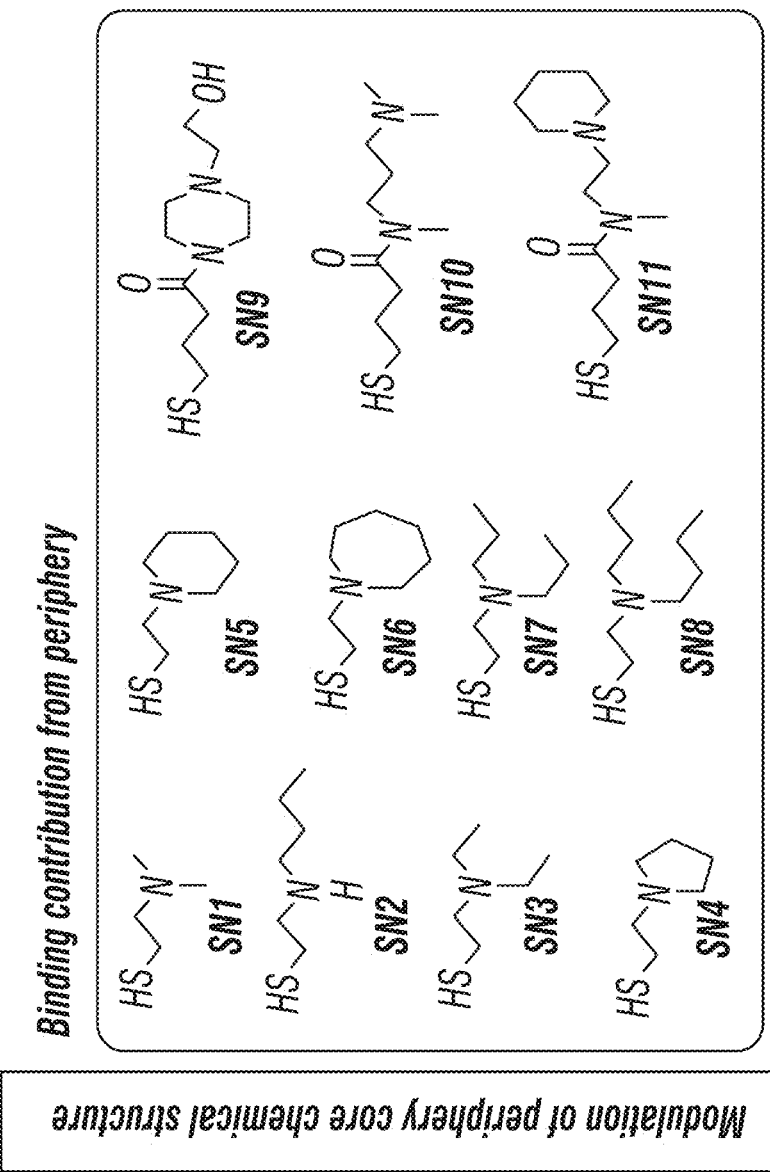
Figure 6A:
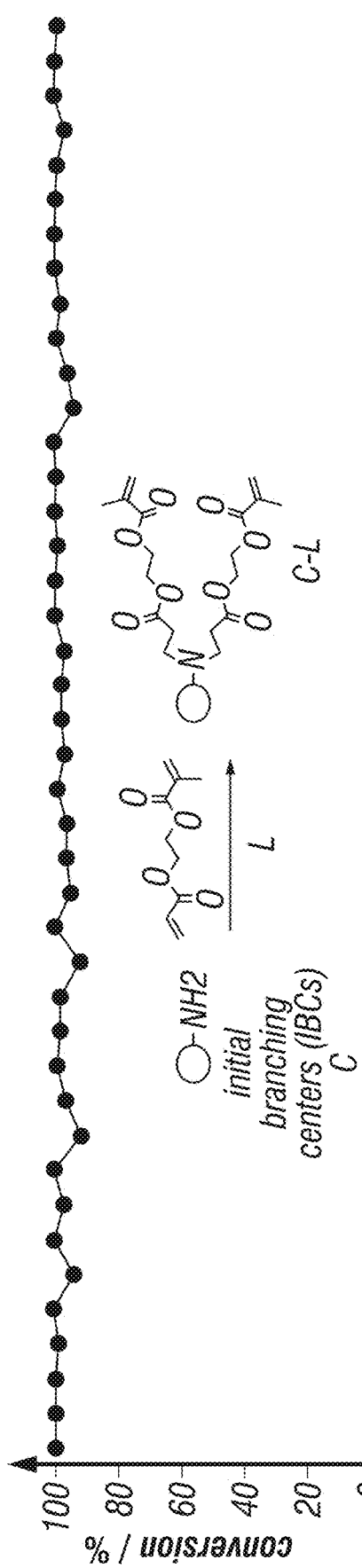
FIGS. 6A & 6B show the library of 1,512 first-generation degradable dendrimers was established with high efficiency.
Figure 6B:
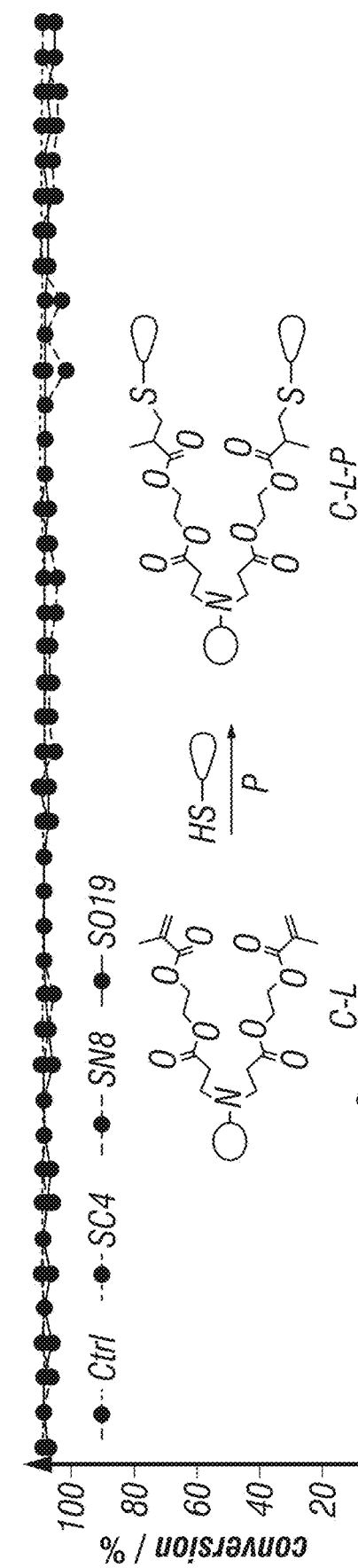

Due to multiple delivery barriers, the potency of small RNA carriers through nanoencapsulation is influenced by various factors, including pK$_a$, topology/structure, and hydrophobicity (Siegwart et al., 2011; Jayaraman et al., 2012; Schaffert et al., 2011; Whitehead et al., 2014). To easily identify degradable dendrimers with high delivery potency, a library of G1DDs was designed with four zones: core binding—periphery stabilization (zone I), core binding—periphery binding (zone II), core stabilization—periphery stabilization (zone III), and core stabilization—periphery binding (zone IV) by chemically diversifying core-forming amines C and periphery-forming thiols P (FIGS. 1C & 1D). In zones I and II, RNA binding was modulated by amines with one (1An) to six (6An) initial branching centers (IBCs). Corresponding dendrimers therefore contained one to six branches. In zones III and IV, stabilization of RNA-dendrimer NPs was mainly changed with different length of alkyl chains (1Hn and 2Hn). In zones II and IV, binding capability of aminothiols (SNn) was mainly modulated with different amines while in zones I and III, stabilization was changed with alkylthiol (SCn) length and carboxyl- and hydroxyl-alkylthiols (SOn). The entire library of compounds was tested for the dendrimers' efficacy (FIG. 6).

Example 4: In Vitro G1DD Screening for siRNA Intracellular Delivery

Figure 8:
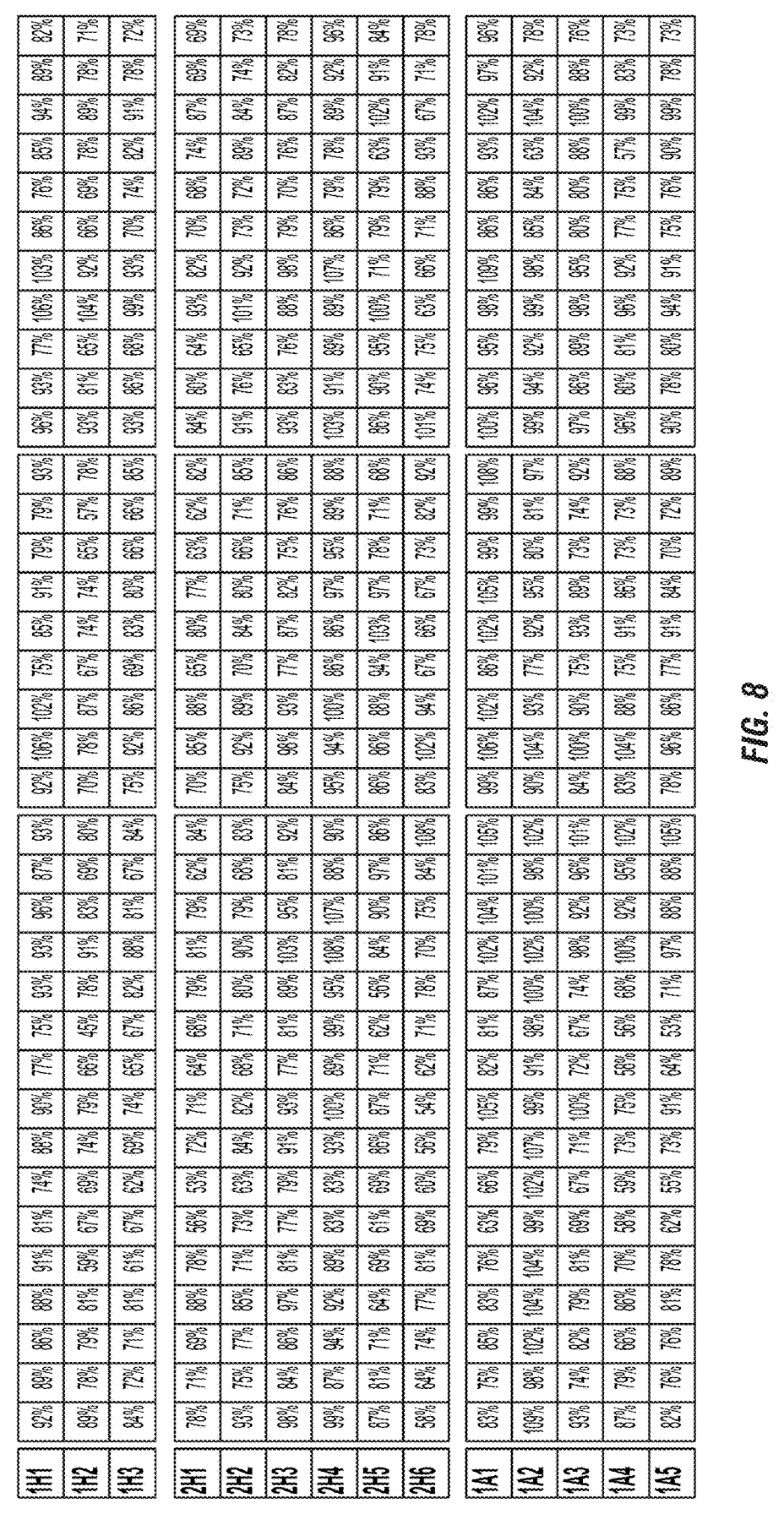
Figure 8:
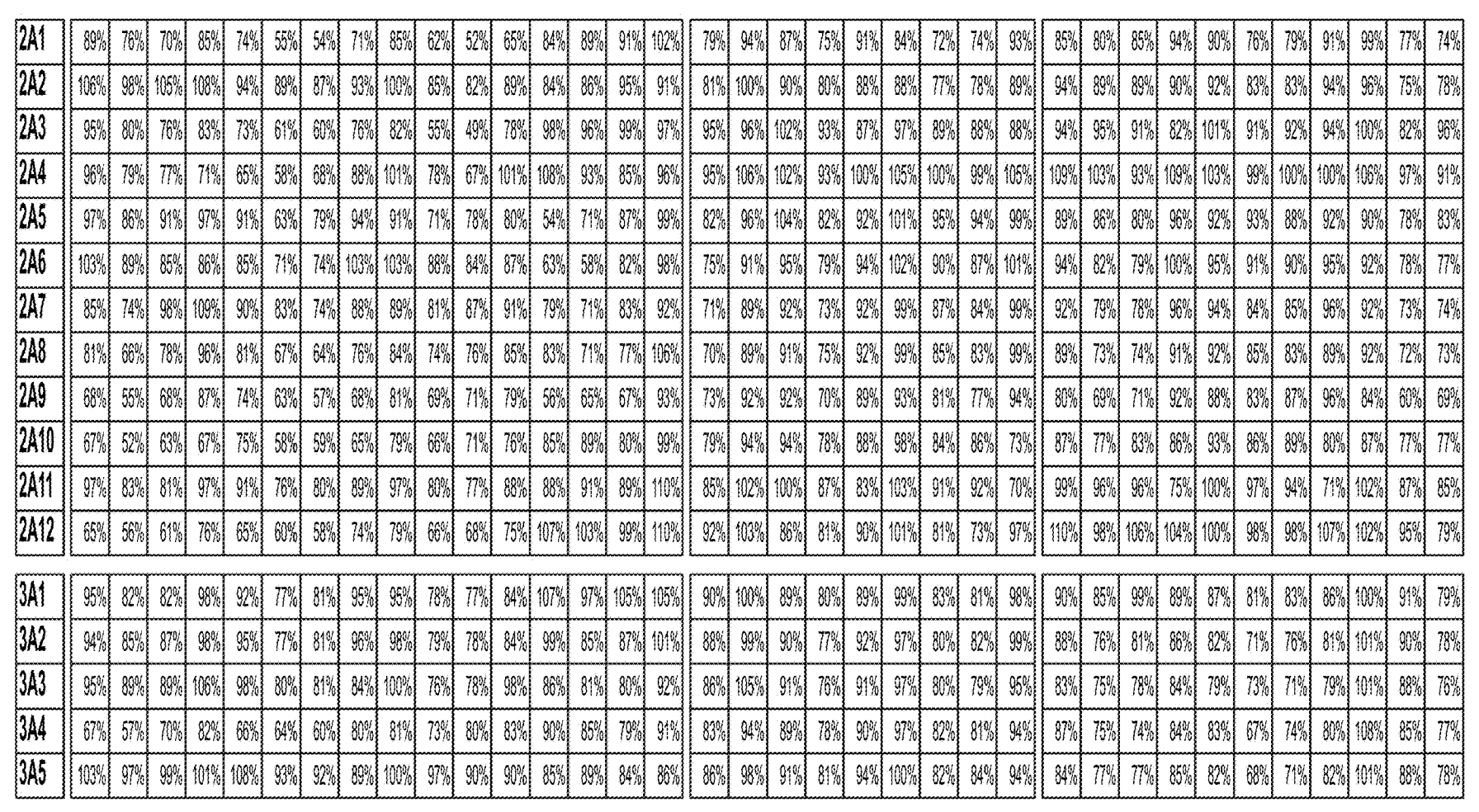
Figure 8:
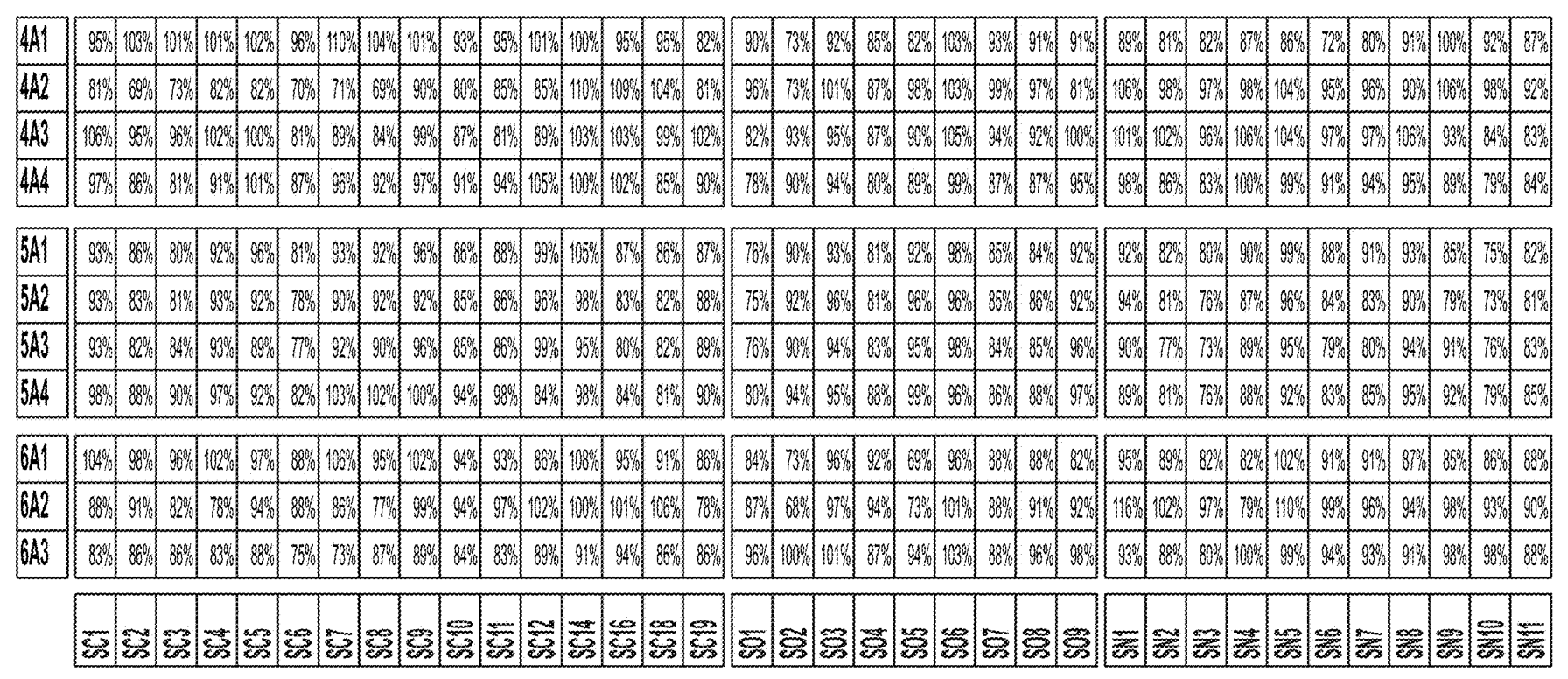
Figure 9A:
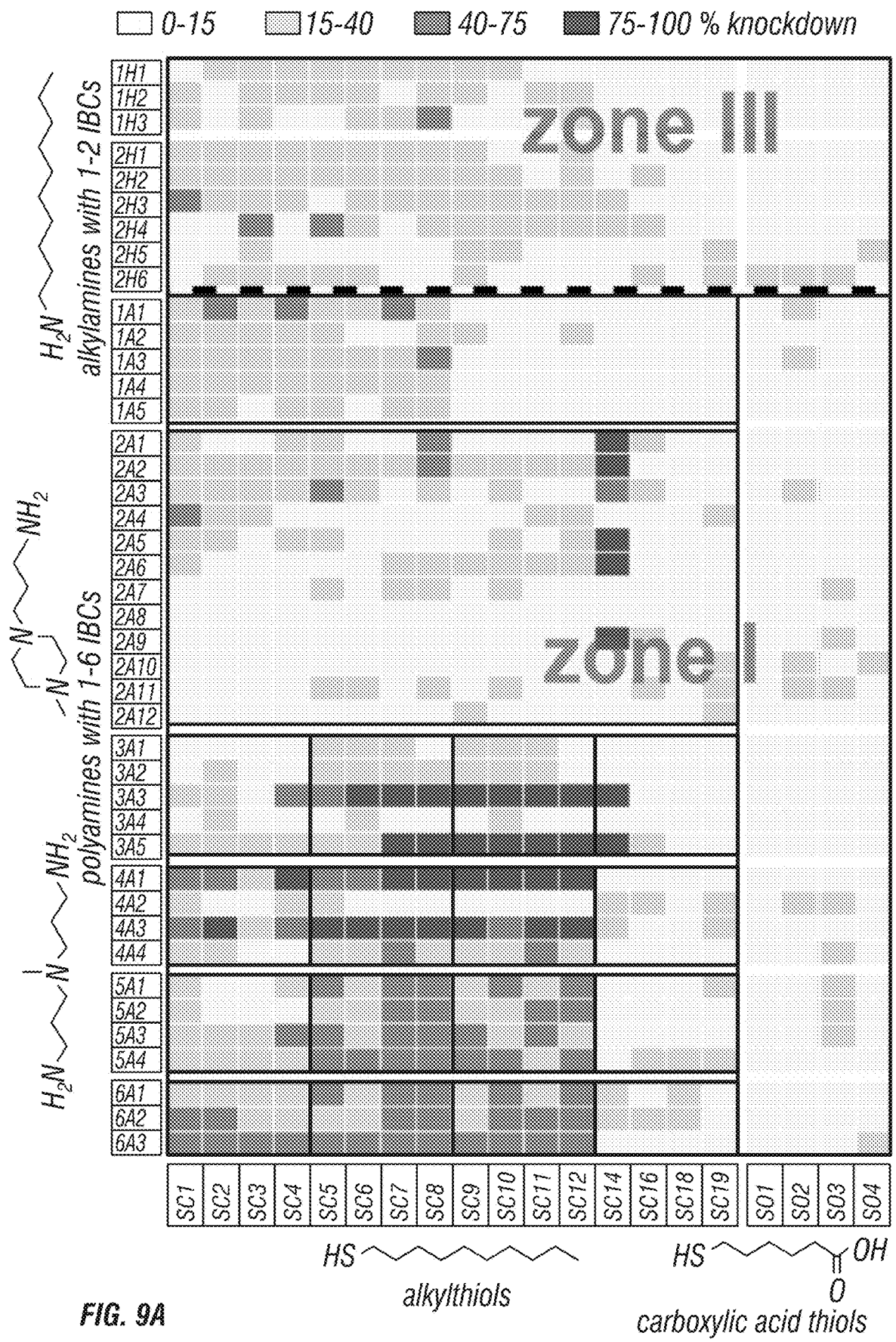
FIGS. 9A & 9B show intracellular siRNA delivery activity of 1,512 first-generation degradable dendrimers (G1DDs). G1DDs were formulated into nanoparticles containing firefly luciferase-targeting siRNA (siLuc) with a weight ratio of 12.5:1 (G1DD:siRNA) and the helper lipids cholesterol, 1,2-distearoyl-sn-glycero-3-phosphocholine (DSPC) and lipid PEG2000 with molar ratio of 50:38:10:2 (G1DD:cholesterol:DSPC:lipid PEG).
Figure 9A:
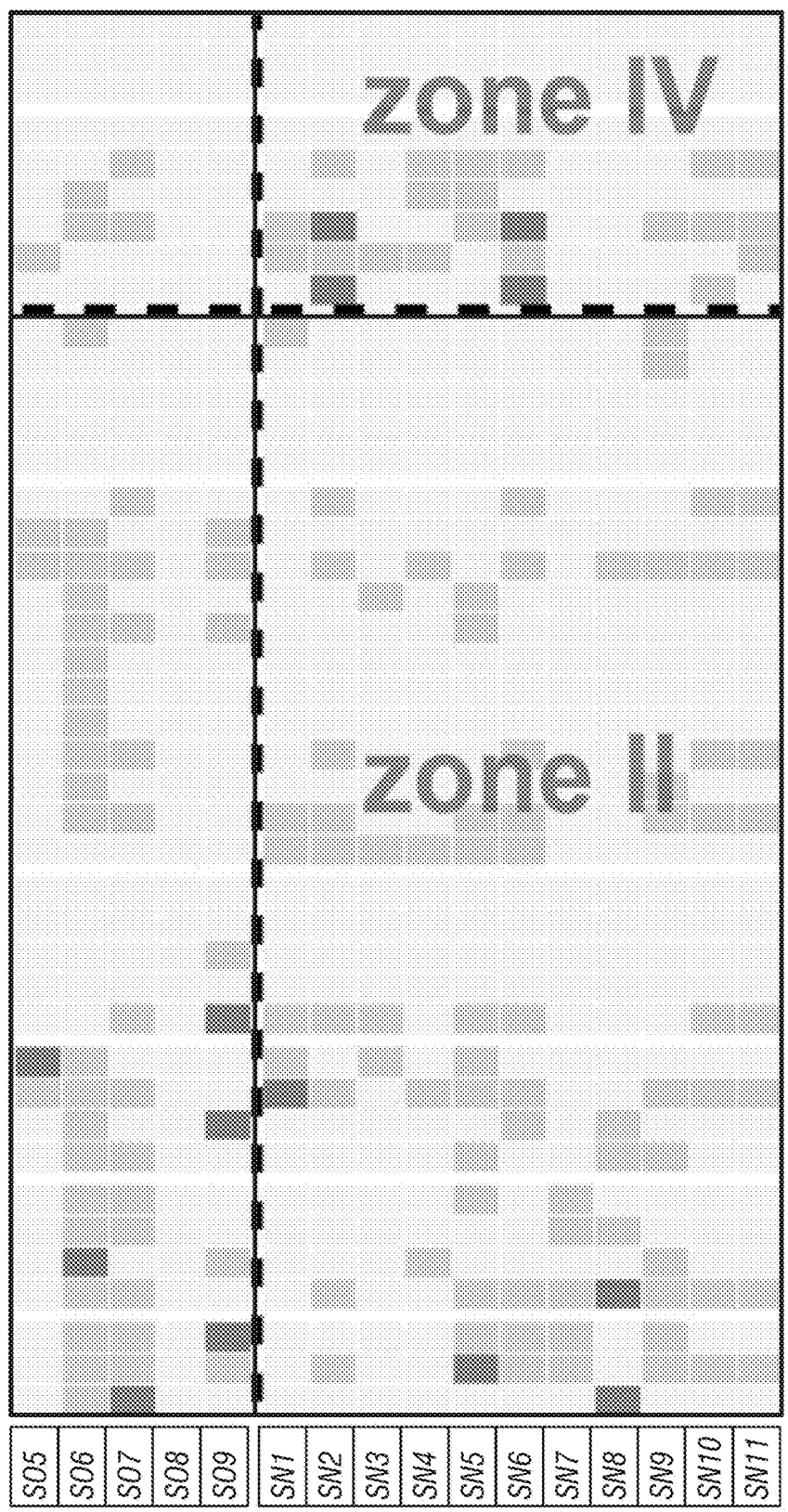

Delivery carriers must overcome a series of extracellular and intracellular barriers to enable small RNAs to be active inside of tumor cells. G1DDs were identified which can mediate siRNA to overcome the intracellular barriers by screening of the 1,512 member G1DD library for the ability to deliver siRNA in vitro to HeLa cells that stably expressed luciferase. G1DDs were formulated into nanoparticles (NPs) containing luciferase-targeting siRNA (siLuc) and the helper lipids cholesterol, 1,2-distearoyl-sn-glycero-3-phosphocholine (DSPC) and lipid PEG2000 (Akinc et al., 2008; Semple et al., 2010). Intracellular delivery potential was assessed by quantifying luciferase reduction and cell viability (FIGS. 7-9).

Figure 7A:
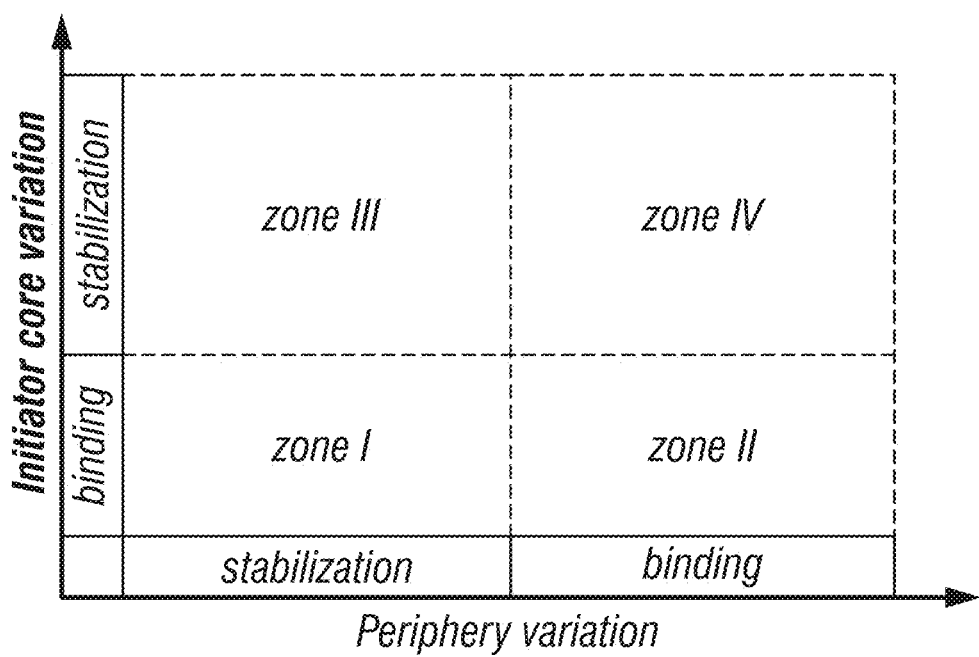
FIGS. 7A-7C show in vitro siRNA delivery screening of 1,512 G1DDs enabled discovery of dendrimers that can overcome intracellular barriers and established structure-activity relationships (FIG. 7A).
Figure 7B:
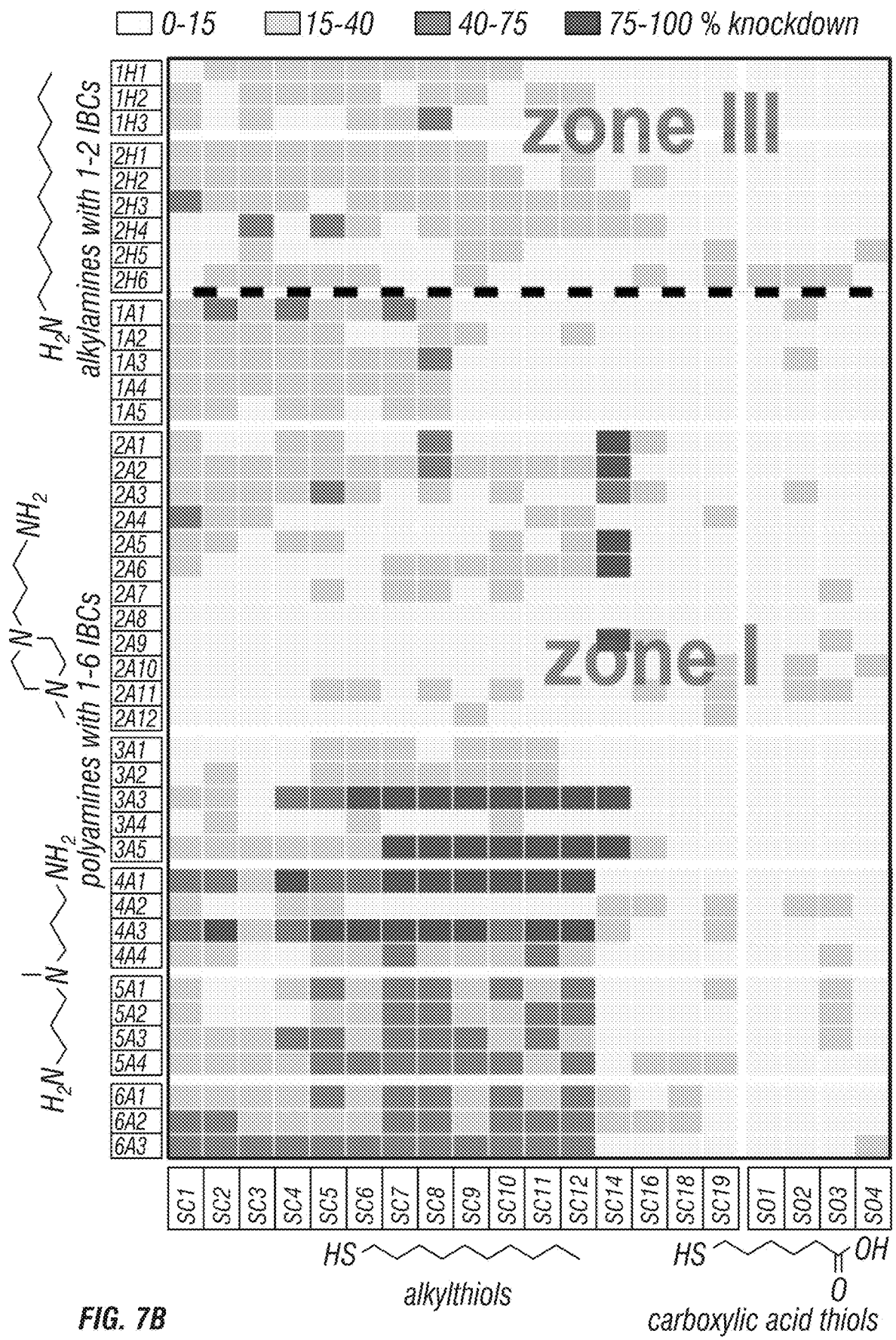
Figure 7B:
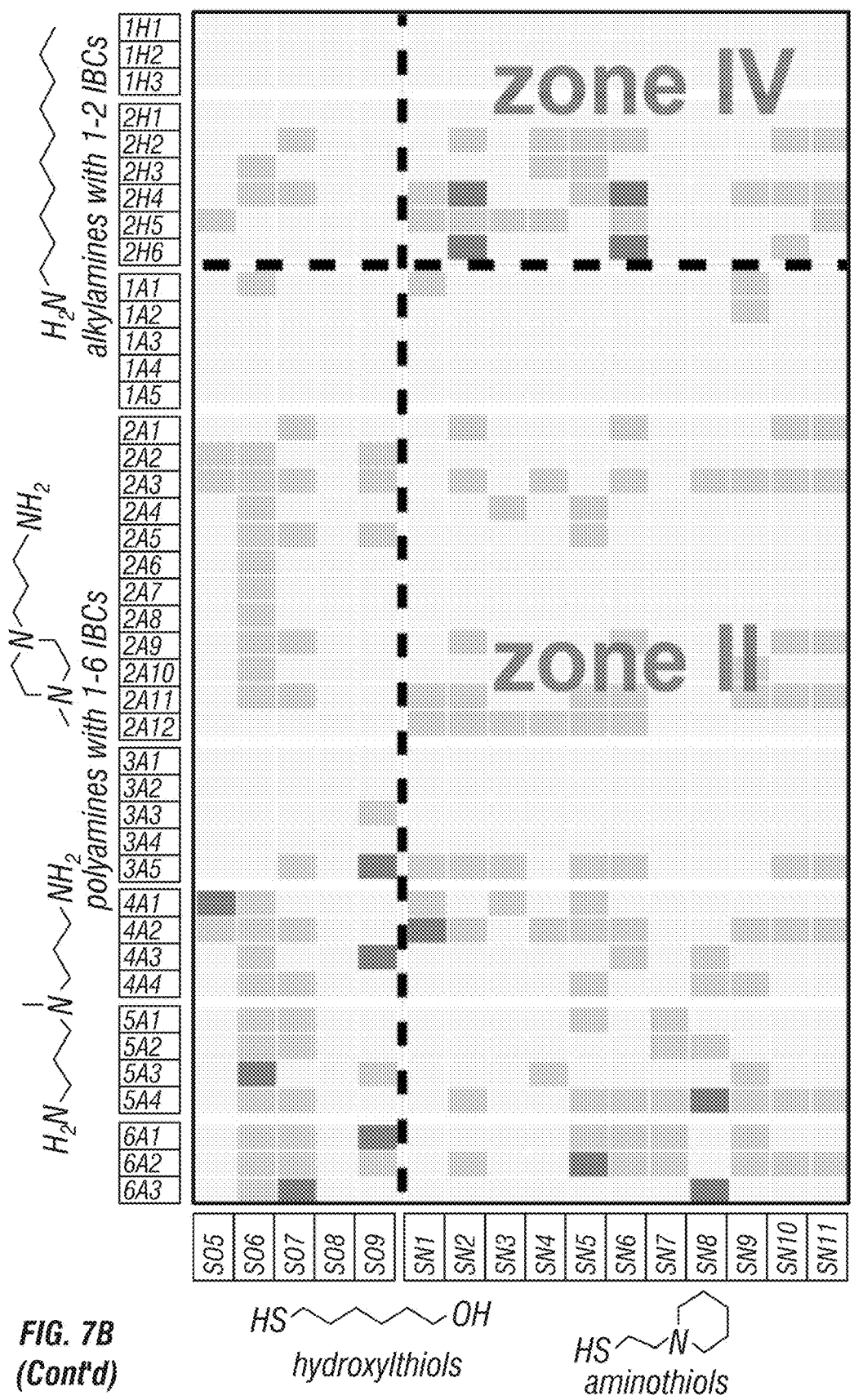
Figure 7C:
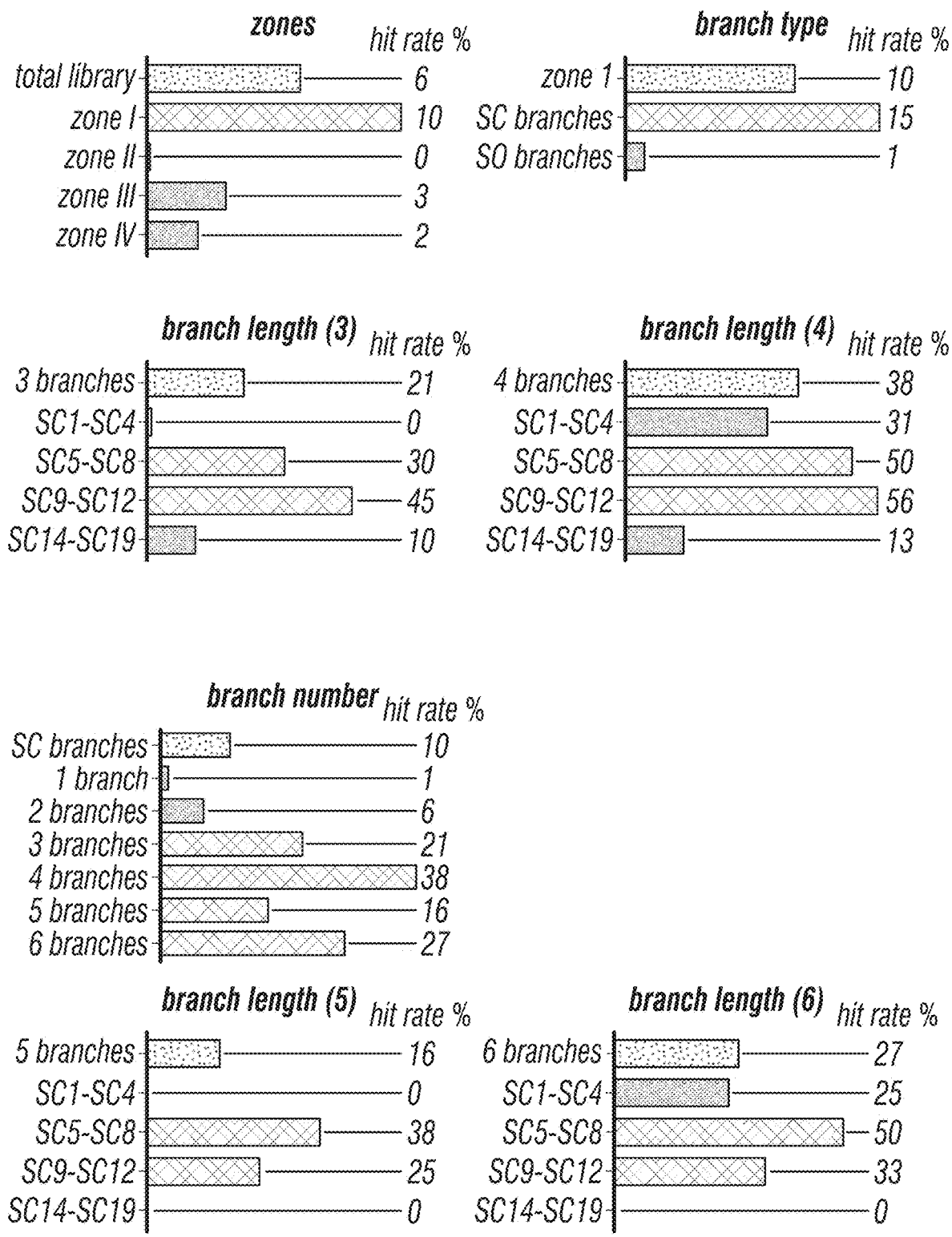
Figure 9B:
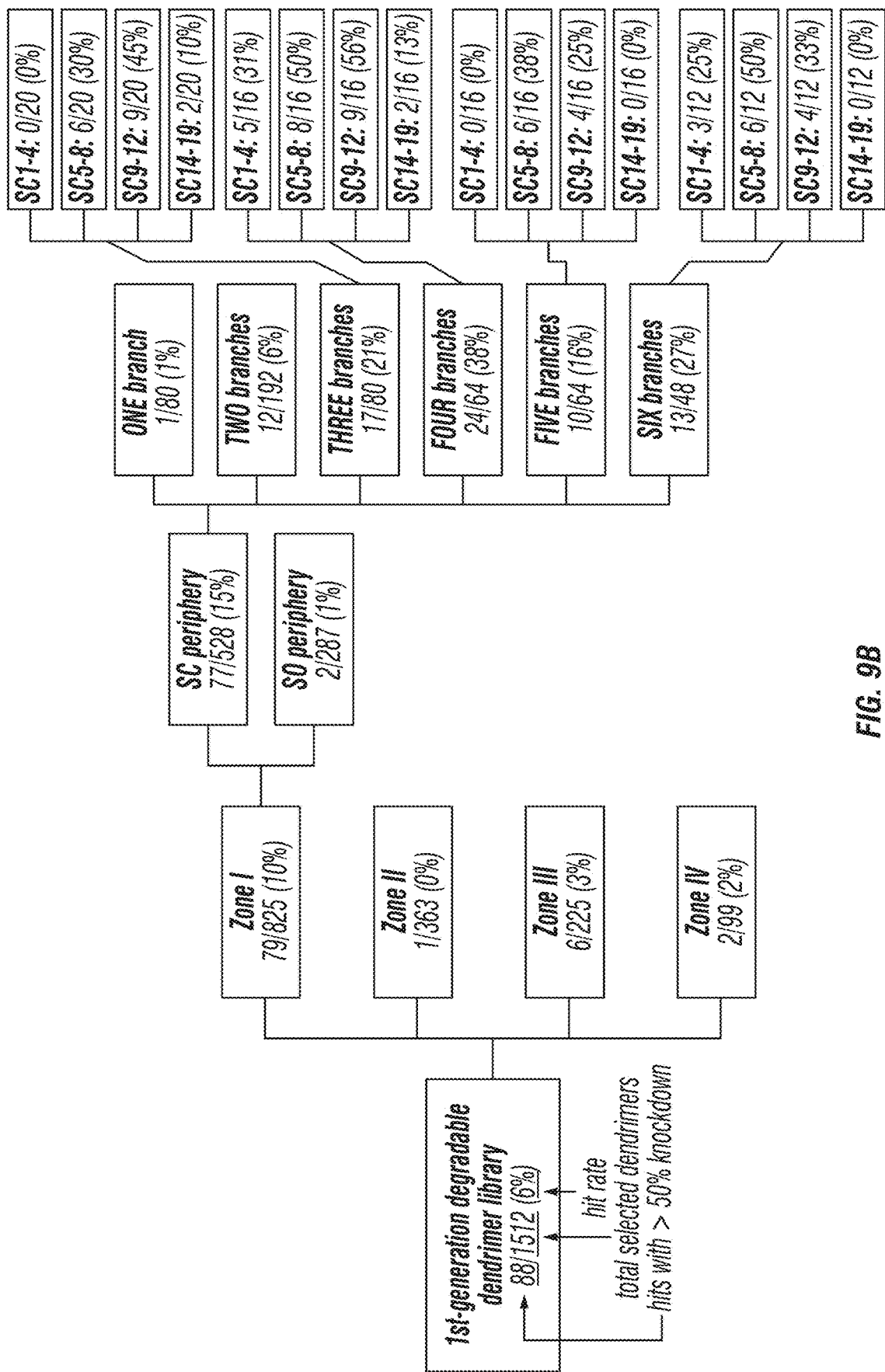

In order to extract SAR from the in vitro data, we utilized a dendrimer-inspired tree analysis process (FIGS. 7B & 9B). Among the 1,512 dendrimers, 88 mediated luciferase silencing of >50% and the hit rate of the whole library was 6%. When the hit rate of all four zones (I-IV) was analyzed, the hit rate of zone I was 10%, while those of zone II, III, and IV were 0%, 2%, and 3%, respectively. This result indicated that these dendrimers with siRNA-binding core and stabilizing periphery (zone I) have much higher intracellular siRNA delivery potential. Within the branching types of zone 1, the hit rates of dendrimers with an SO periphery is as low as 1% while that of the dendrimers with an SC periphery was as high as 15%. Without wishing to be bound by any theory, it is believed that the hydrophobic stabilization from the dendrimer periphery is crucial to efficiently deliver siRNA into cells through nanoencapsulation. This likely results in increased hydrophobic packing that provides additional NP stability (Leung et al., 2012). After branch number and branch lengths of these dendrimers with binding core and SC periphery was further examined, the dendrimers with binding core and three, four, five or six SC5-8 branches or SC9-12 branches have >25% chance to deliver siLuc into HeLa cells with >50% luciferase knockdown. Through in vitro screening of the full G1DD library and the dendritic analysis process, the group of dendrimers which showed increased intracellular siRNA delivery was identified: the groups with binding core/SC periphery and binding core with three to six SC5-8 or SC9-12 branches.

Example 5: Identification of Degradable Dendrimers for Effective In Vivo siRNA Delivery and Design of G2-G4 Dendrimers Having identified dendrimers that can overcome intracellular barriers, next, the dendrimers that can overcome extracellular barriers to efficiently deliver siRNA in vivo were identified. By separating these two processes, chemical functionality that overcomes barriers including blood stability, liver (tumor) localization, cellular uptake, and active siRNA release could be identified. Dendrimers were evaluated for their ability to silence Factor VII in hepatocytes because this blood clotting factor can be readily quantified from a small serum sample (Akinc et al., 2008; Semple et al., 2010). 26 of the hit degradable dendrimers were selected to maximize chemical diversity: 22 possessed an optimized chemical structure based on the dendritic analysis process and an additional 4 (2A2-SC14, 2A6-SC14, 2A9-SC14, and 6A1-SO9) were chosen based on their high intracellular siRNA delivery ability. Dendrimers were formulated with anti-Factor VII siRNA (siFVII) and were injected i.v. into mice at a dosage of 1 mg siFVII/kg. FVII activity was quantified 3 days post injection. Despite high in vitro potency, 2A2-SC14, 2A6-SC14, 2A9-SC14, 6A1-SO9 and most three-branch dendrimers showed only minimal in vivo FVII knockdown (FIG. 3A). The dendrimers that contained a binding core and four, five or six SC8 or SC12 branches showed higher knockdown. Based upon these studies, SC8 branch dendrimers were generally more effective than SC12 branch compounds.

Figures 10A, 10C:
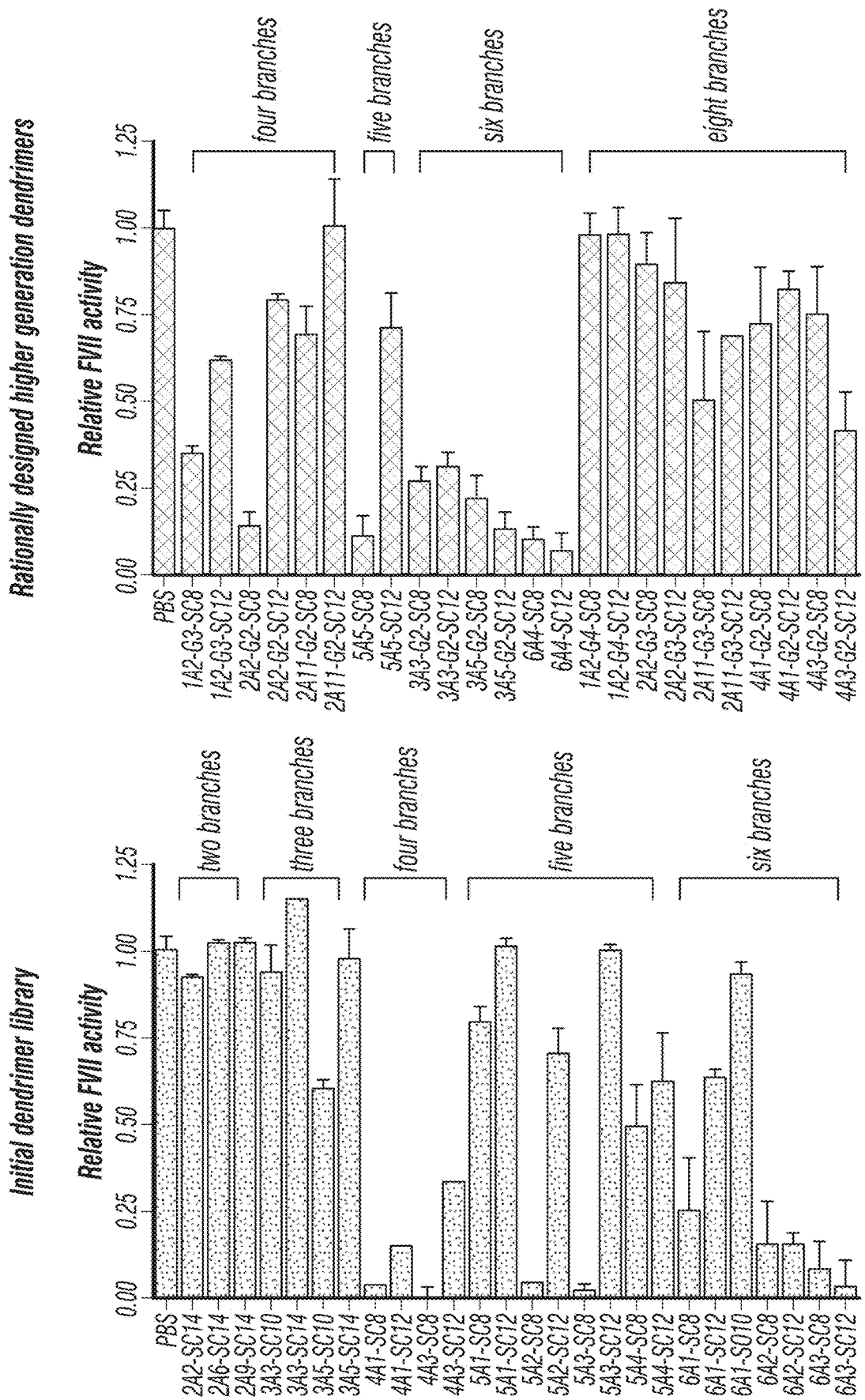
FIGS. 10A-10C show systematic in vivo siRNA delivery screening further identified dendrimers that can also overcome extracellular barriers. Analysis provided SAR to design additional dendrimers with predicted activity.
Figure 10B:
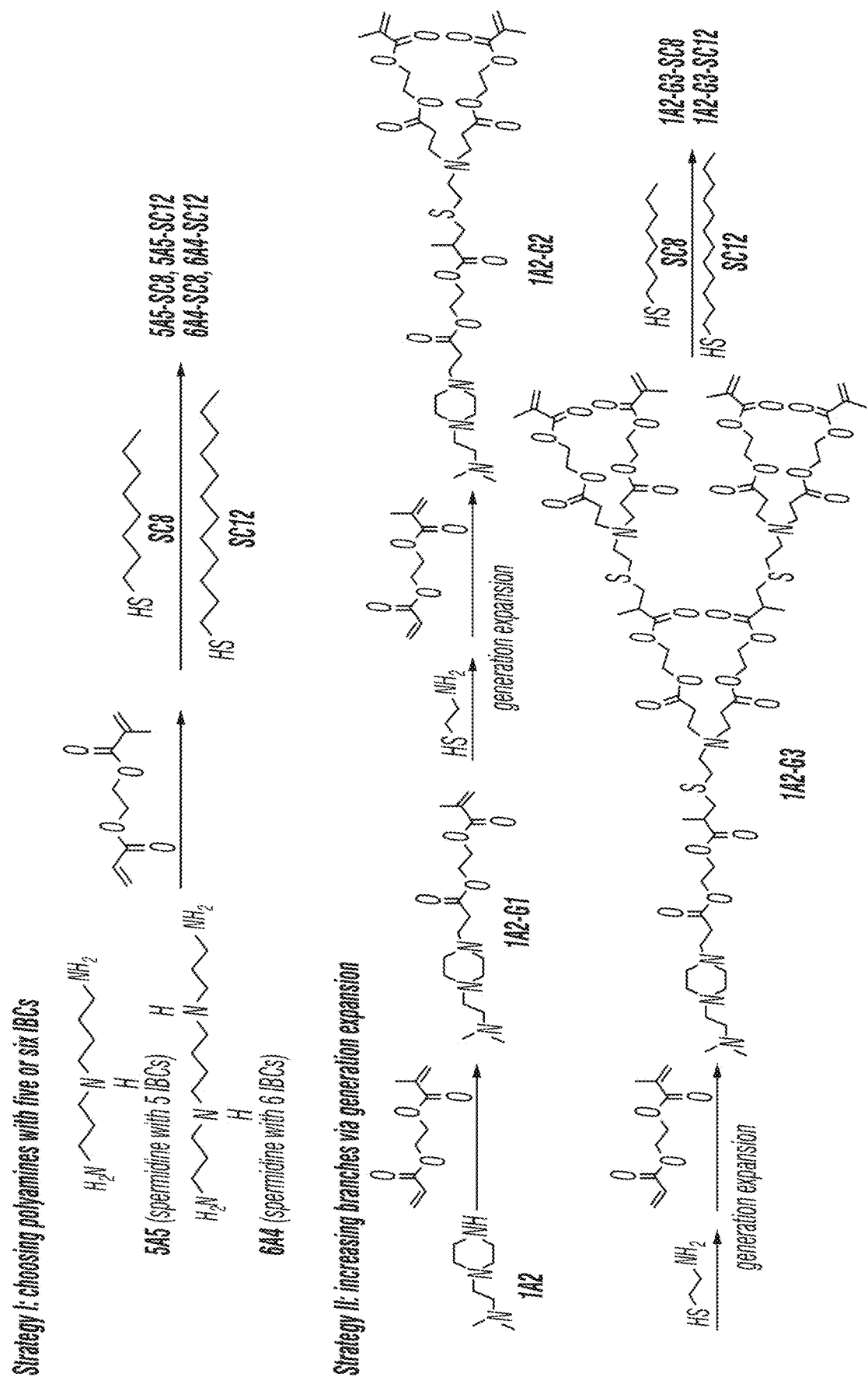
Figure 10B:
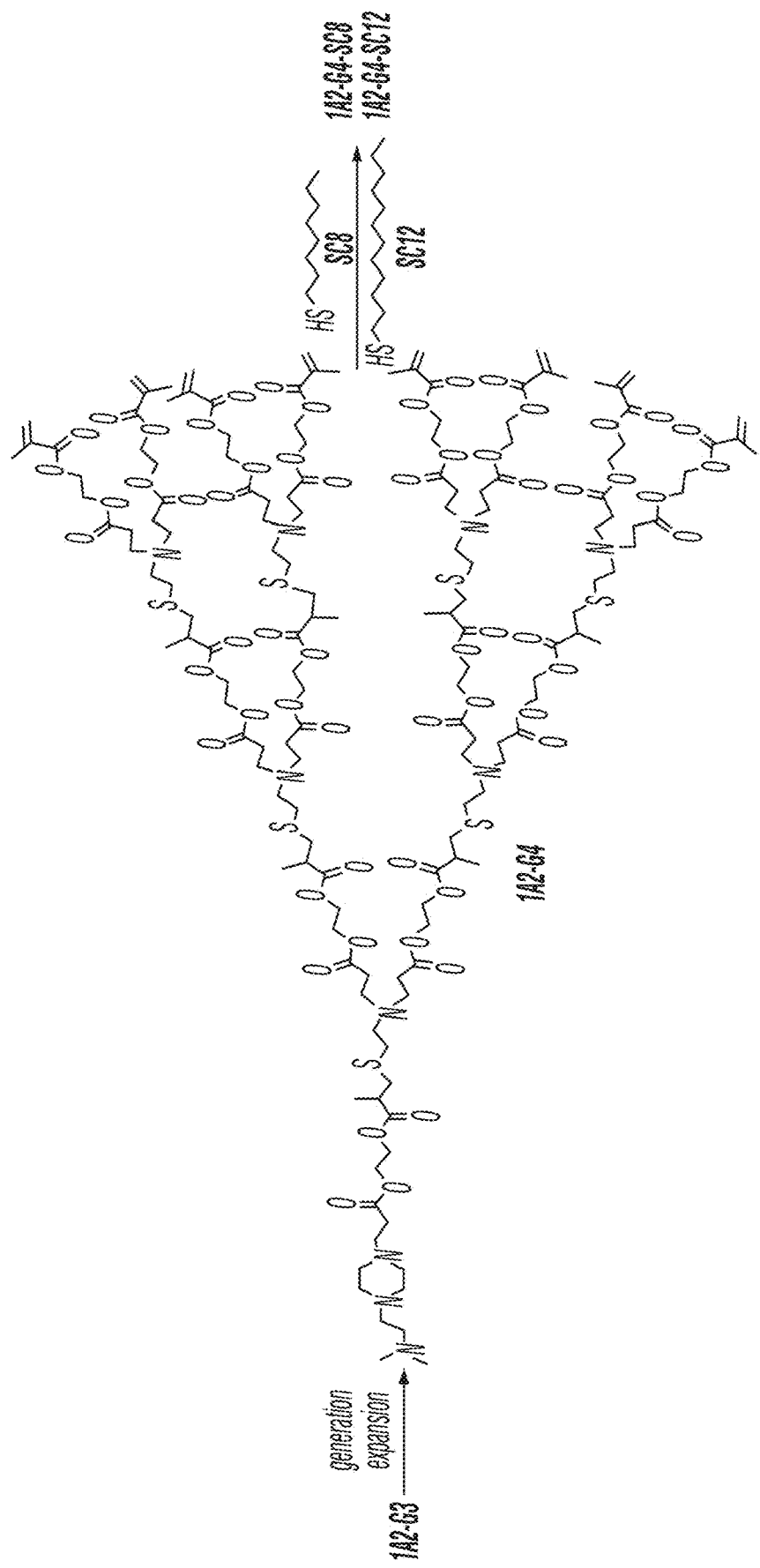
Figure 11:
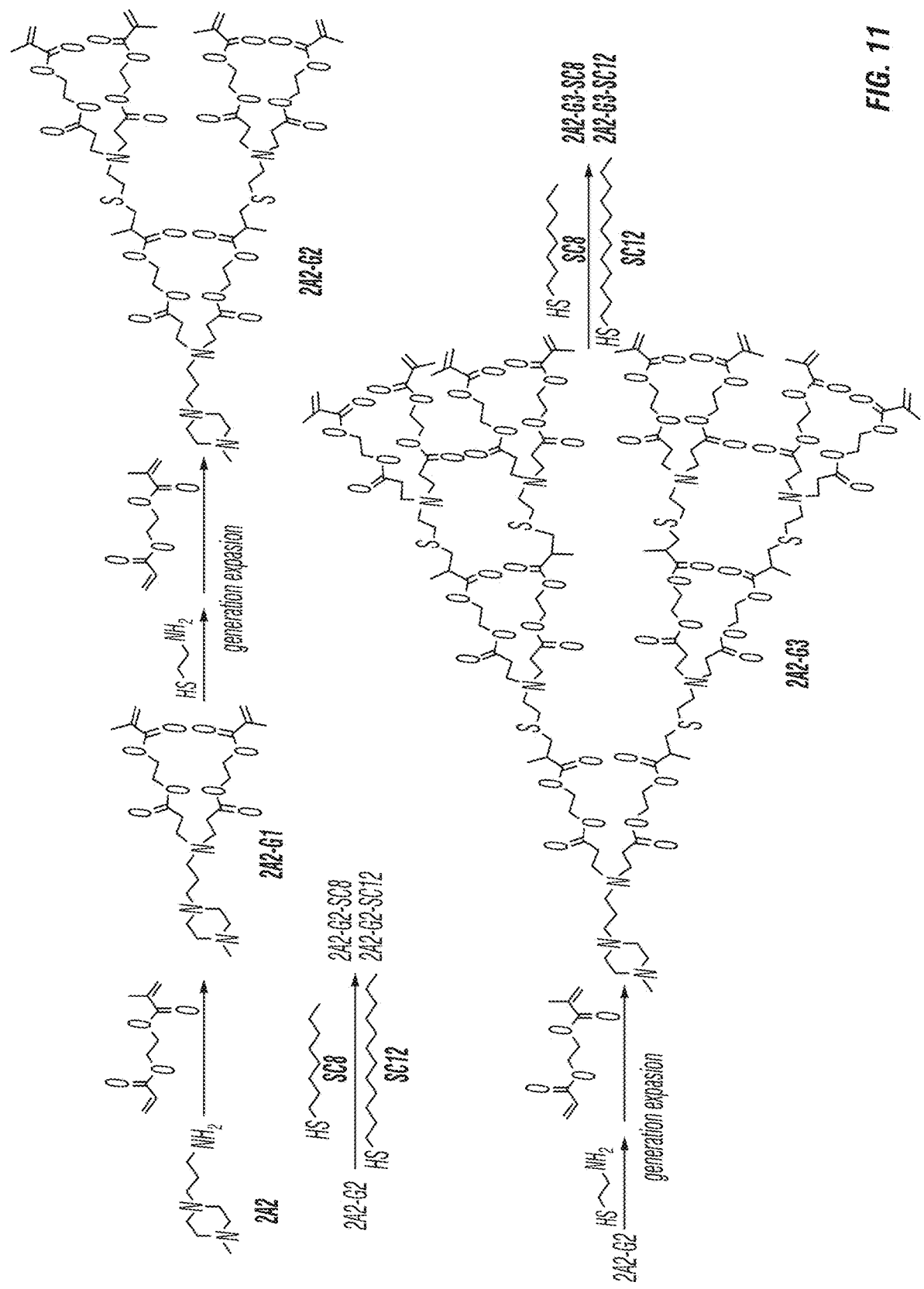
FIG. 11 shows synthetic route of 2A2 & 2A11 (two IBCs), 3A3 & 3A5 (three IBCs), and 4A1 & 4A3 (four IBCs) to prepare degradable dendrimers with multiple branches via the generation expansion strategy.
Figure 11:
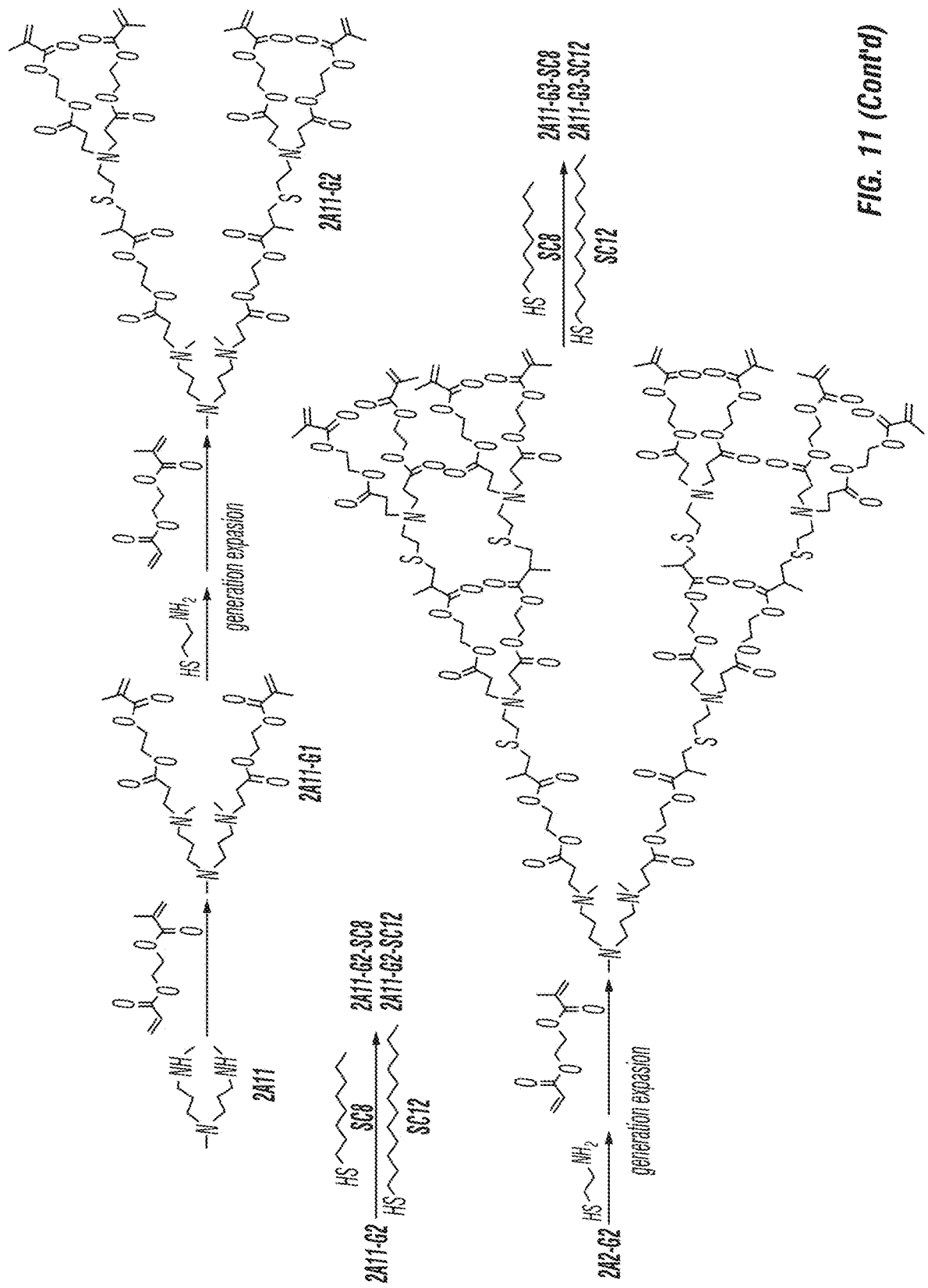
Figure 11:
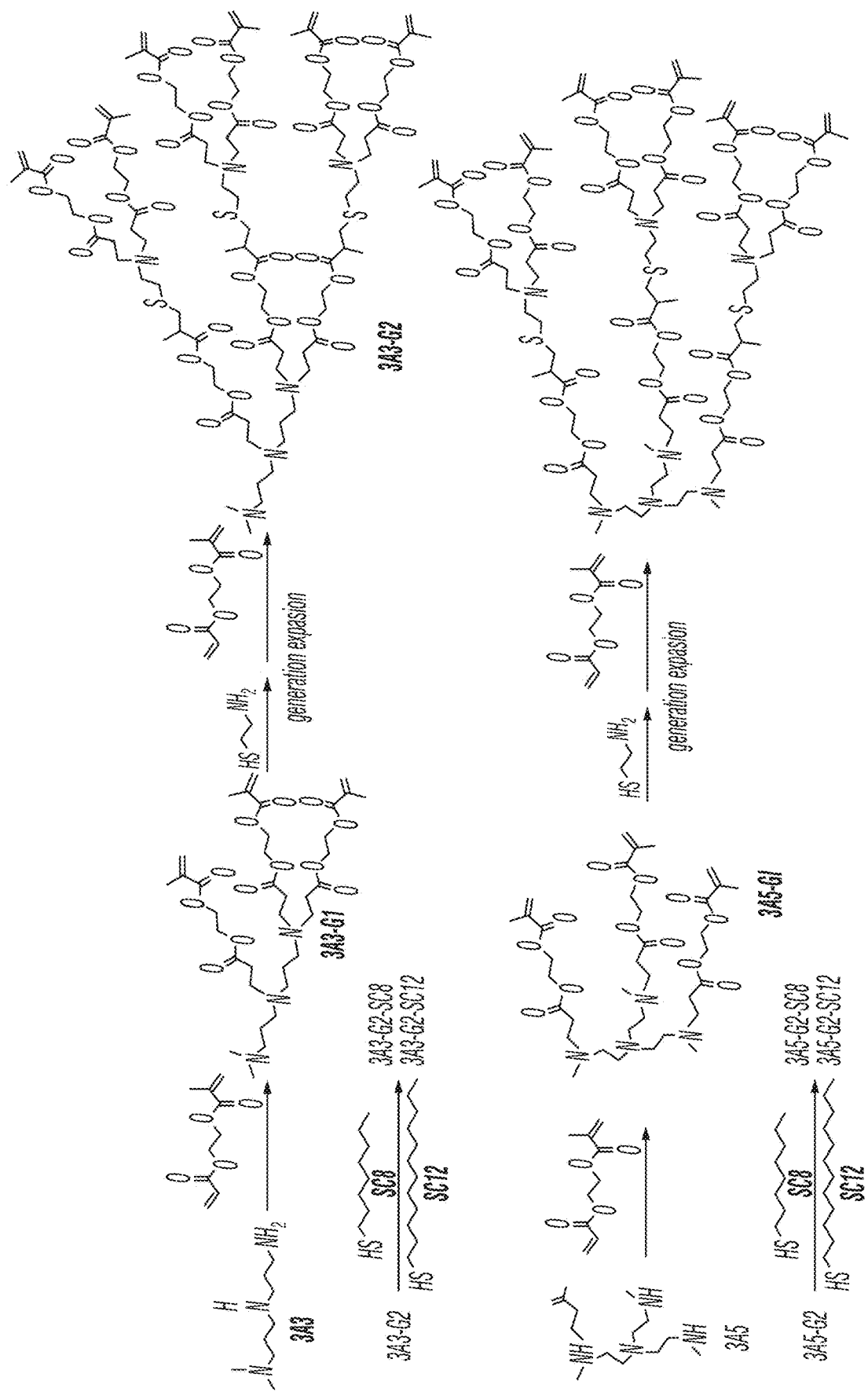
Figure 11:
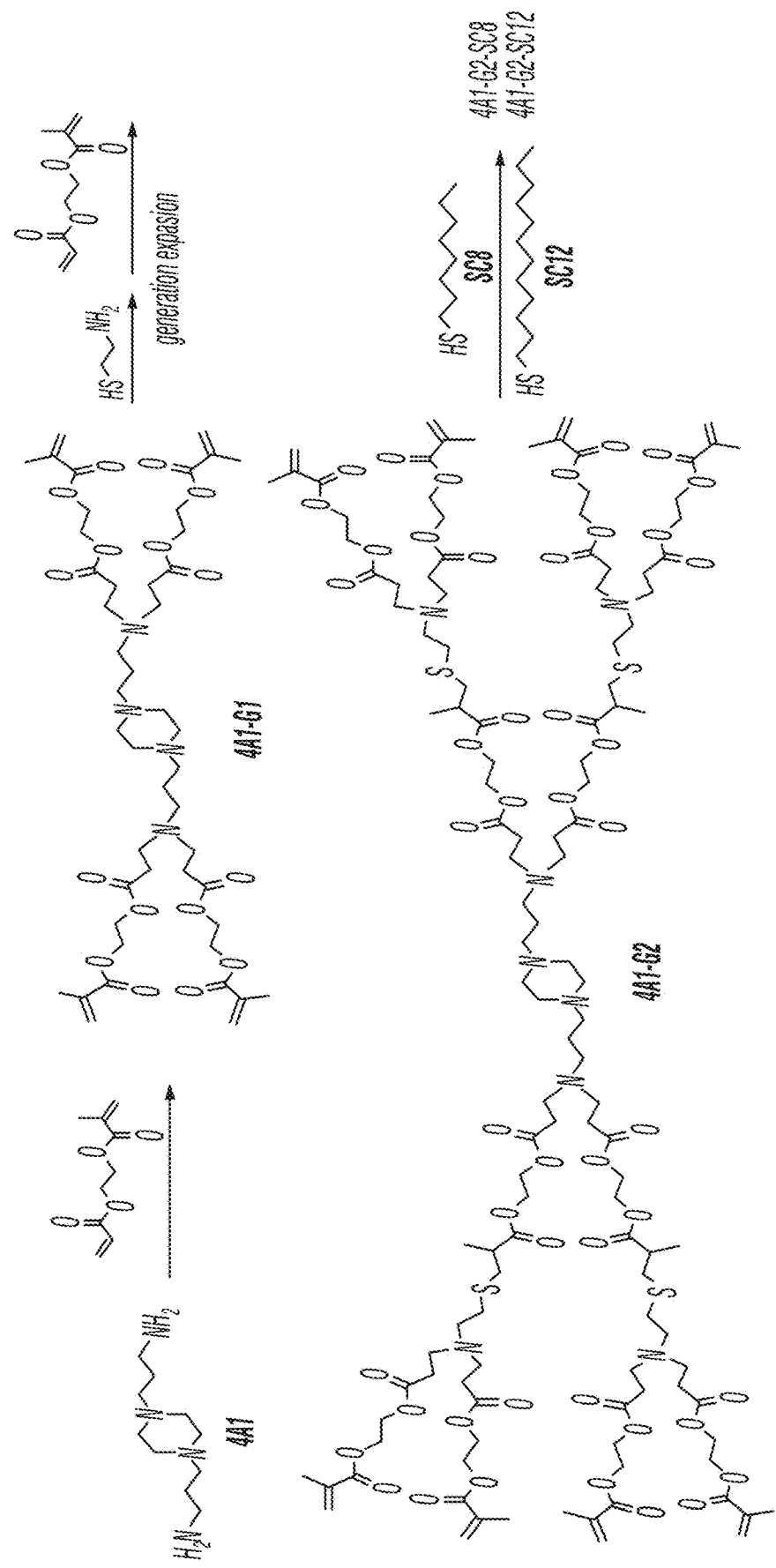
Figure 11:
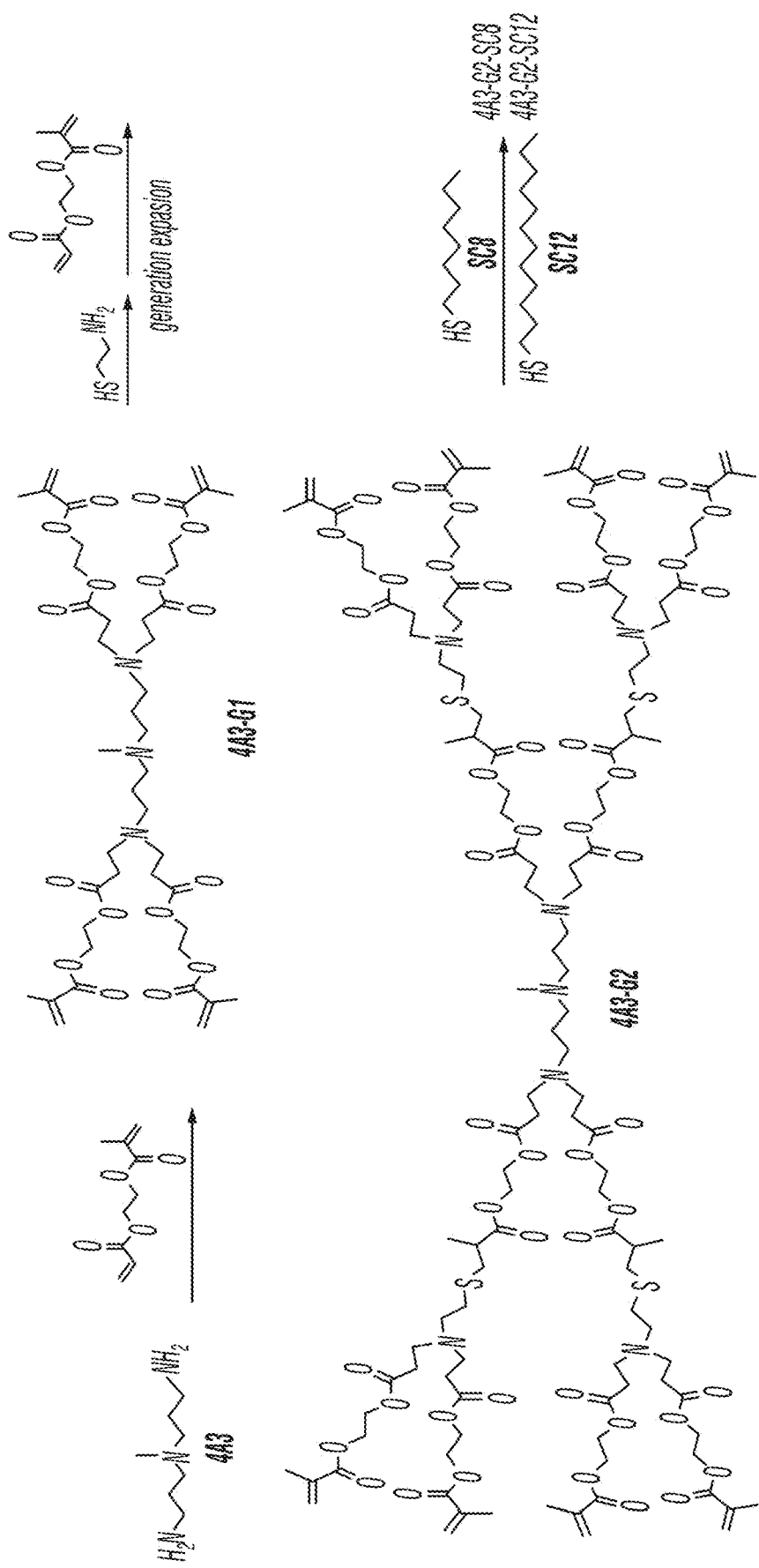

With the in vitro and in vivo high-throughput screening results in hand, we asked whether we could now use that SAR information to rationally design dendrimers with predicted activity to validate our approach. A series of degradable dendrimers were prepared using two strategies: (I) by choosing polyamines with five or six IBCs; and (II) by increasing branches via dendrimer generation expansion (FIG. 10). Two natural amines, spermidine (5 IBCs) and spermine (6 IBCs), were chosen to implement strategy I. As to strategy II, 1A2 (one IBC), 2A2 & 2A11 (two IBCs), 3A3 & 3A5 (three IBCs), and 4A1 & 4A3 (four IBCs) were chosen to yield degradable dendrimers with multiple branches via generation expansion (FIGS. 10C & 11). 24 additional degradable dendrimers were evaluated (FIG. 10C) to further examine in vivo SAR. After generation expansion, higher-generation dendrimers of 1A2 (one IBC), 2A2 (two IBCs), and 3A3 & 3A5 (three IBCs) with four or six SC branches had good in vivo siRNA delivery to hepatocytes, while the dendrimers with eight branches were less active. This process transformed amine cores that were inactive in the in vitro screen, and then rationally design higher generation dendrimers which showed in vivo activity.

Figure 12A:
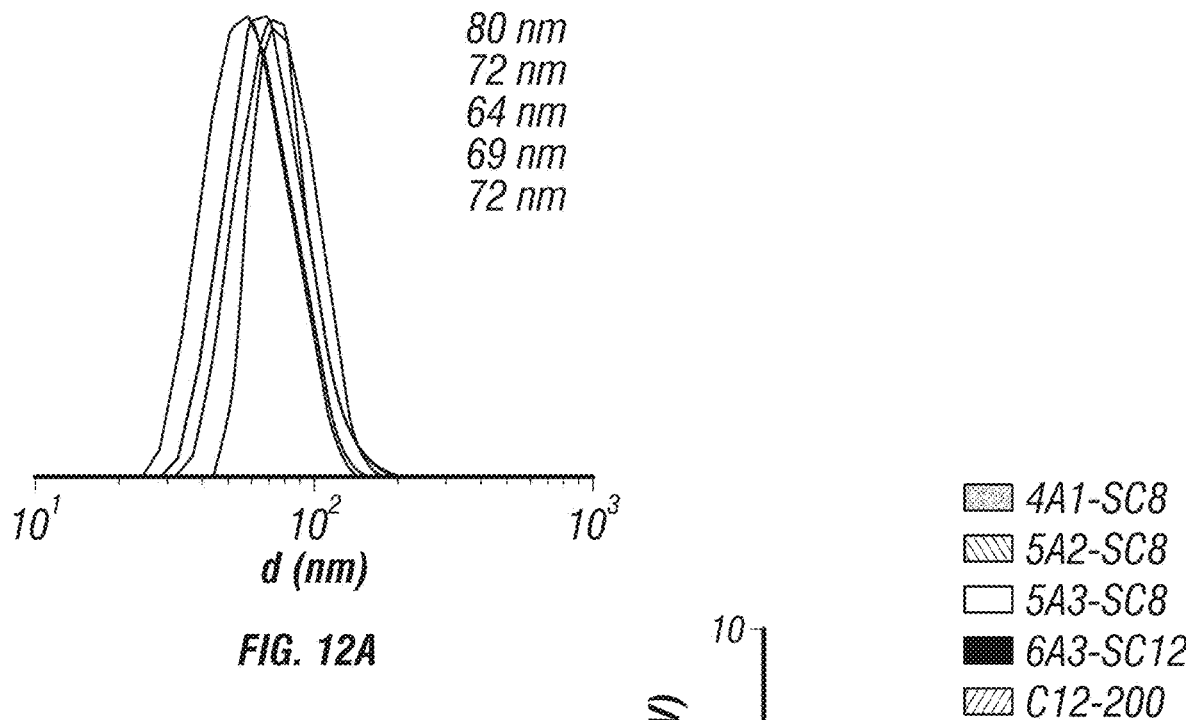
FIGS. 12A-12E show in vivo toxicity evaluation of some of the degradable dendrimers (>95% in vivo FVII knockdown) further identifying dendrimers that could balance high delivery efficacy with low toxicity. Some of the degradable dendrimer NPs possessed (FIG. 12A) similar size and (FIG. 12B) net surface charge after binding control siRNA (siCTR) (nanoparticles are depicted in the graph from left to right based upon the legend for FIG. 12B). C12-200 lipidoid LNPs provided a challenging comparison, as they represent the best example of a non-hydrolyzable system with comparable in vivo efficacy.
Figure 12B:
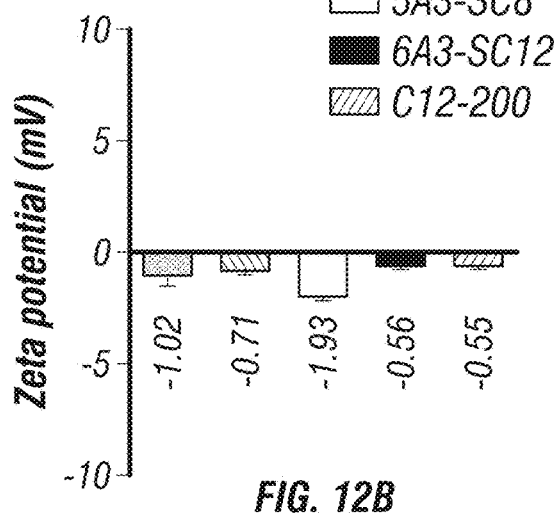
Figure 12C:
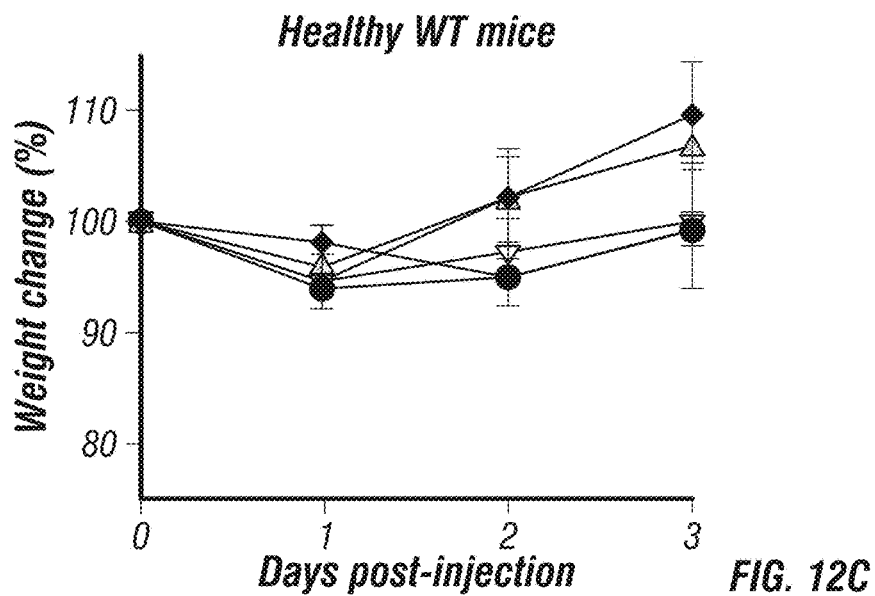

Example 6: In Vivo Toxicity Evaluation of Degradable Dendrimers in Mice Bearing MYC-Driven Liver Tumors To identify degradable dendrimers with the required balance of low toxicity and high potency required for liver cancer treatment, the degradable dendrimers were chose to evaluate their in vivo toxicity. In parallel, we analyzed C12-200 lipidoid LNPs wee chose as the best example of a non-hydrolyzable system previously shown to be potent in mice and non-human primates (Love et al., 2010). Lipidoids, as a class, are benchmark materials at the forefront of clinical research (Kanasty et al., 2013; Love et al., 2010; Sahay et al., 2013). Non-immunogenic control siRNA was used to best evaluate the toxicity of the individual dendrimers themselves. Dendrimer NPs were formulated at a weight ratio of 25:1 (dendrimer:siCTR), higher than necessary to better probe toxicity. C12-200 LNPs were prepared using identical formulation parameters as previously reported (Love et al., 2010). Size and zeta potential of each NP in PBS buffer was characterized. They all possessed similar size, 64-80 nm in diameter, and their surfaces were close to neutral in charge (FIGS. 12A & 12B). Each formulated NP was injected i.v. into wild type mice at a 4 mg siCTR/kg dose (100 mg dendrimer/kg or 28 mg C12-200/kg). Among the many different ways to evaluate in vivo toxicity, body weight loss can be utilized as a simple and informative parameter. In normal mice, there were minimal body weight changes for the selected NPs, including C12-200 control LNPs. However, among candidates, the mice injected with 5A2-SC8 and 6A3-SC12 experienced quicker recovery and gained weight normally after the first day.

Figure 12D:
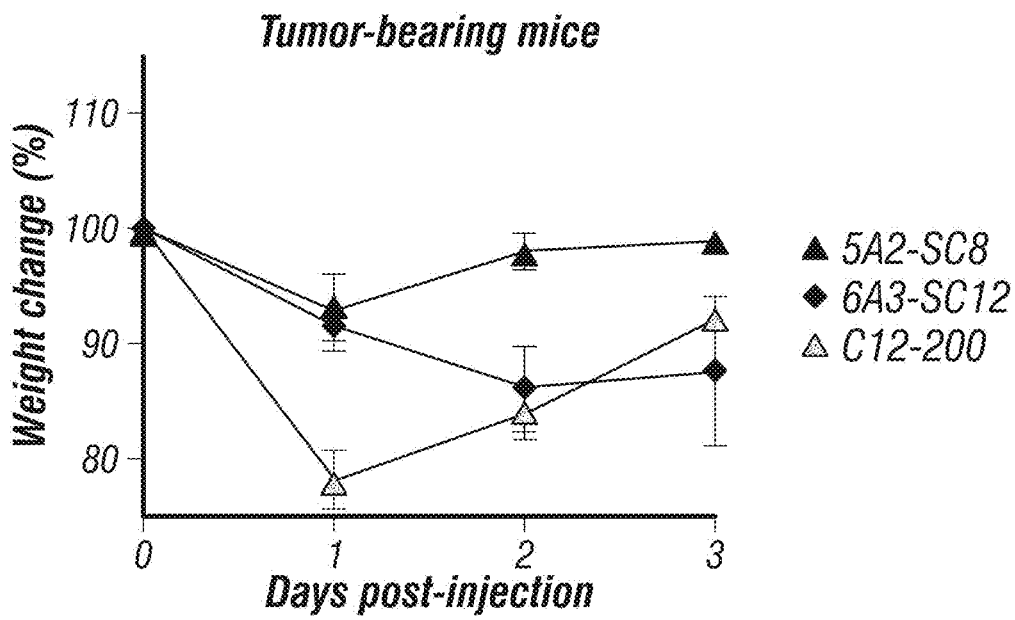
Figure 12E:
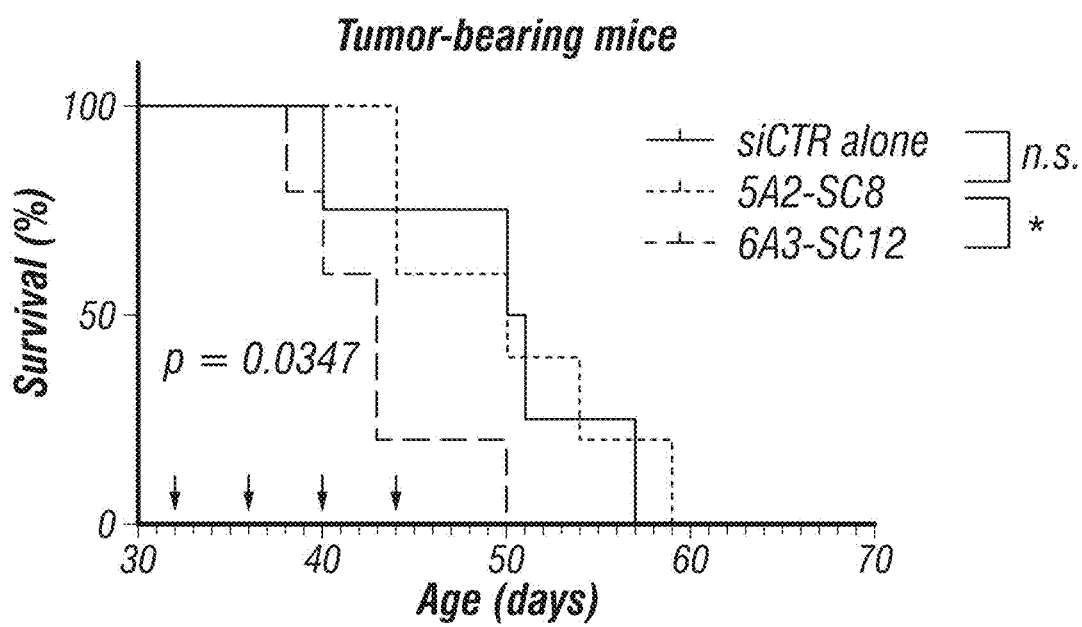
Figure 13A:
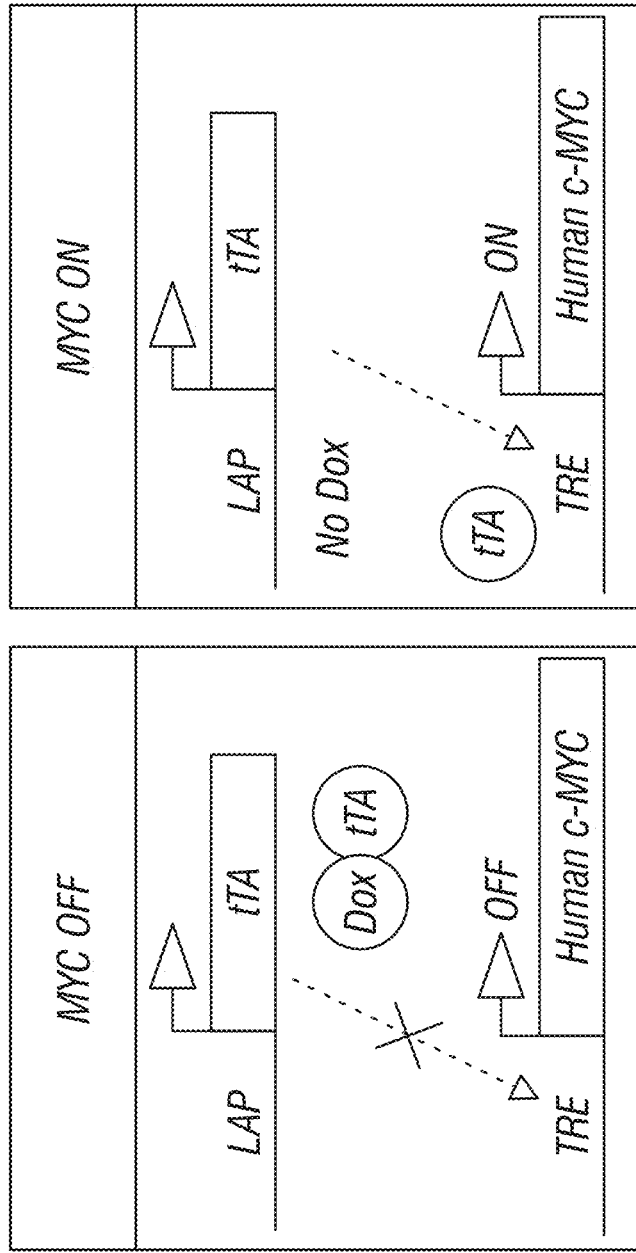
FIGS. 13A & 13B show the aggressive transgenic MYC-driven liver tumor model was chosen to evaluate the toxicity and potency of modular degradable dendrimers to deliver miRNA for suppression of tumor growth (Nguyen et al., 2014).
Figure 13B:
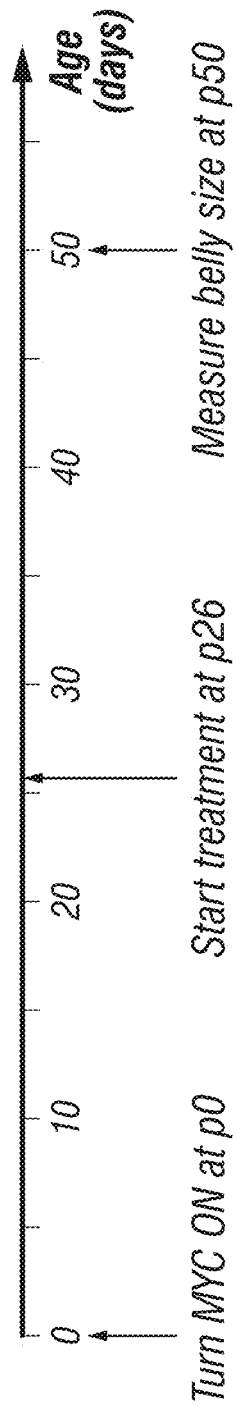

Based on these results, 5A2-SC8 and 6A3-SC12 were chose for further evaluation of their in vivo toxicity in chronically ill transgenic mice bearing aggressive liver tumors with single and multiple injections. A well-established Tet-On MYC inducible transgenic liver cancer model was chosen (FIG. 13A) (Nguyen et al., 2014). Since tumors are more aggressive when MYC is overexpressed at earlier developmental time points, MYC was induced immediately after birth (p0), which resulted in rapidly growing liver tumors. At the age of 32 days (p32), these sick transgenic mice bearing aggressive liver tumors were injected with 5A2-SC8 or 6A3-SC12 NPs at 3 mg siCTR/kg dosage (75 mg dendrimer/kg or 21 mg C12-200/kg). The mice receiving 5A2-SC8 injection lost about 5% body weight on the first day and quickly returned to their starting weight on the second day while those mice receiving 6A3-SC12 injection still lost 10% body weight by the third day and could not recover (FIG. 12D). After multiple injections, these mice died seven days earlier compared to mice that received no treatment because of the toxicity of 6A3-SC12 carrier (FIG. 12E). In contrast to the result in WT mice, injection of C12-200 LNPs to mice bearing aggressive tumors lost >20% weight after one day, despite receiving ~3 times less lipid than 5A2-SC8 injected mice (FIG. 12D). These data showed that small changes in chemical structure can produce large changes in toxicity. It also showed that tumor-bearing mice are more sensitive to intervention than healthy mice. Based on these results, 5A2-SC8 emerged as a degradable dendrimer possessing a balance of low toxicity (tolerance in tumor-bearing mice up to 75 mg/kg) and effective in vivo FVII knockdown (>95% at 1 mg siFVII/kg). In addition to being less toxic than benchmark compounds, 5A2-SC8 NPs are more efficacious because these dendrimers reduce clinical concern for dose limiting toxicity and enable a wider therapeutic window.

Example 7: Potent Suppression of Liver Tumor Growth Through Systemic Administration of a Let-7g miRNA Mimic In order to evaluate the ability of degradable dendrimer NPs to deliver a therapeutic miRNA mimic without causing additional toxicity, the aggressive, MYC transgenic liver cancer model induced at p0 was again used (Nguyen et al., 2014). These mice developed rapidly growing cancers resembling pediatric hepatoblastoma (HB), a tumor type that shares many of the molecular features of HCC. Abdominal distention from mass effect was grossly visible after 20 days, and tumors grew rapidly. Without intervention, mice died within 60 days after birth. Given the speed and lethality of this model, there are limited opportunities for successful therapy.

Figures 14A, 14B, 14C:
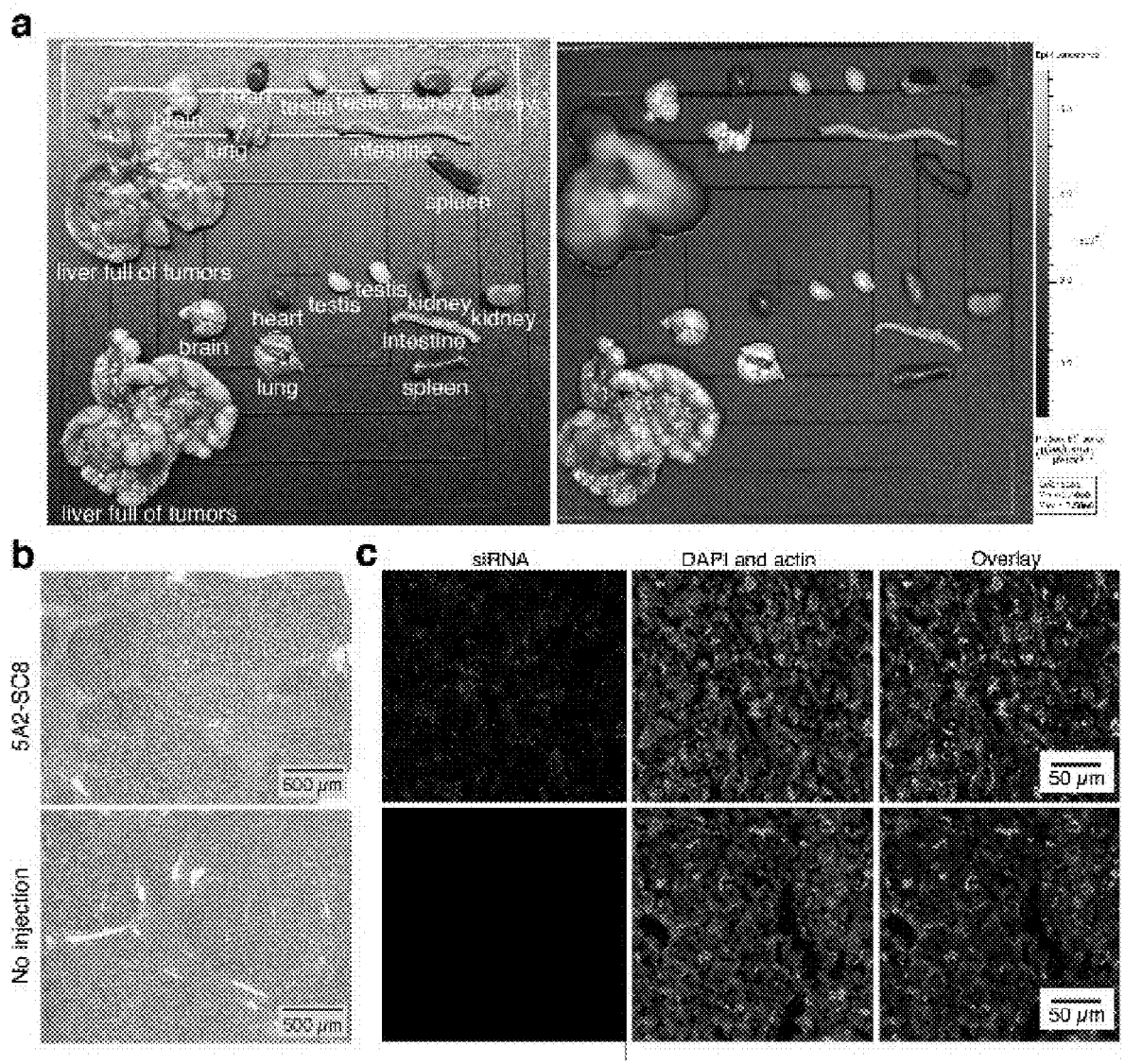
FIGS. 14A-14C show fluorescence imaging confirms delivery of siRNA into the tumor cells inside of the liver.
Figures 15A, 15B:
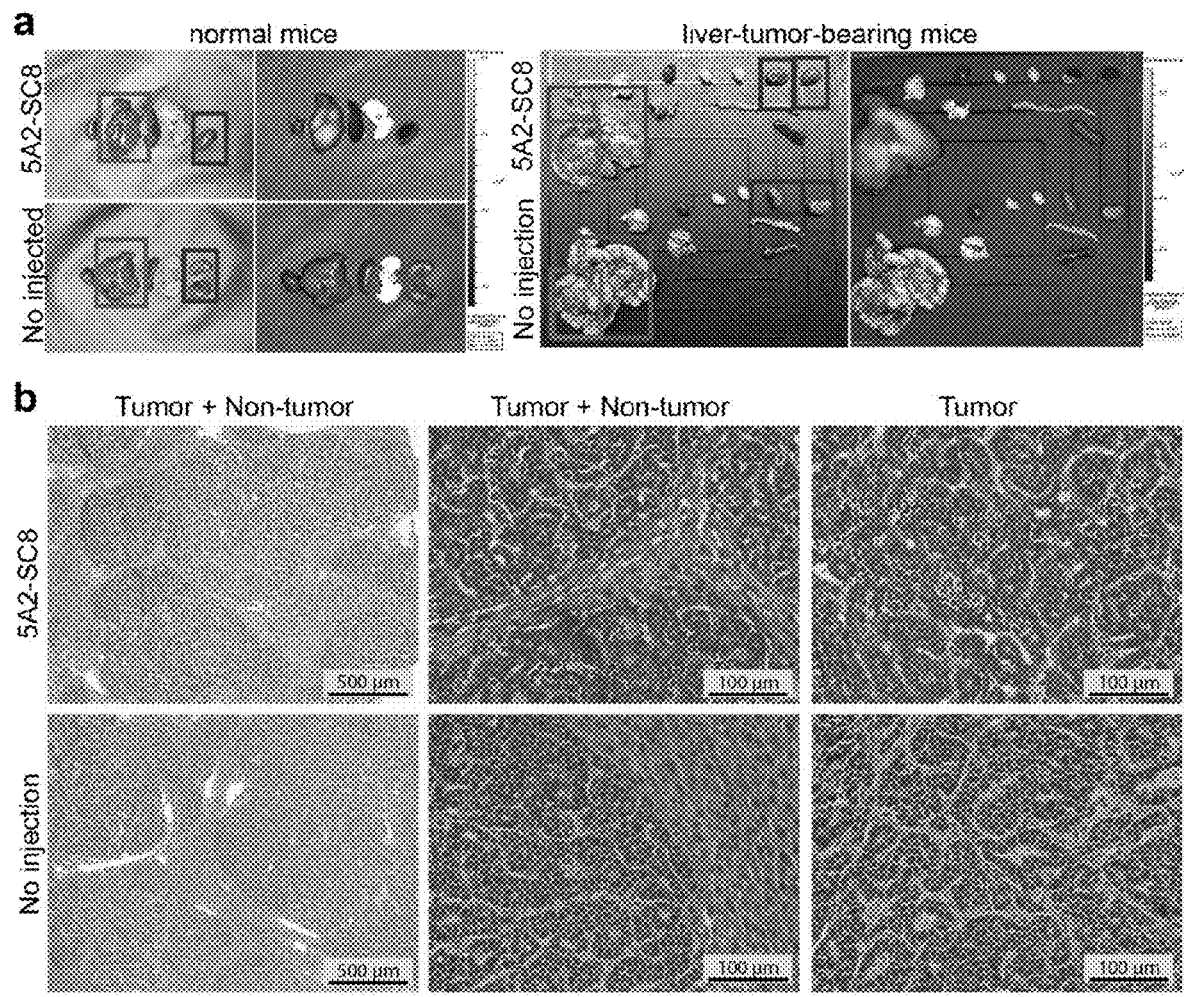
FIGS. 15A & 15B show in (FIG. 15A) the biodistribution in normal, wild type mice and liver tumor-bearing mice of 5A2-SC8 NPs formulated with Cy5.5-labeled siRNA and (FIG. 15B) H&E staining images of livers from tumor-bearing mice. 5A2-SC8 NPs mediate Cy5.5-labeled siRNA accumulation in the whole liver of both normal mice and liver tumor-bearing mice 24 hours after i.v. injection of 1 mg siRNA/kg. H&E staining images shows that the livers of tumor-bearing mice are full of tumors and that the slide used for confocal imaging contains tumor cells. Note that the size of the liver increases as the tumors grow (see proportionally equal boxes in FIG. 15A).

Since 5A2-SC8 balances low in vivo toxicity and effectiveness for silencing the hepatocellular target FVII, first, whether 5A2-SC8 NPs could deliver siRNA into tumor cells was examined. At the age of 41 days (p41), the livers of these transgenic mice are full of tumors (FIG. 14A). On p40, mice were injected intravenously with 5A2-SC8 NPs with Cy5.5-labeled siRNA at a dosage of 1 mg siRNA/kg. 24 hours post-injection, fluorescence imaging showed 5A2-SC8 mediated siRNA accumulation in the cancerous liver, with only minor accumulation in the spleen and kidneys (FIGS. 14A-14B). 5A2-SC8 NPs delivered siRNAs into normal and transgenic livers even if the cancerous livers are larger than normal ones (FIG. 15A).

To further confirm whether 5A2-SC8 NPs can deliver siRNA in vivo into tumor cells, tumor tissues of the liver were collected and imaged 24 hours after intravenous injection. H&E staining showed the tumor tissues are densely full of cellular nuclei and exhibit a cancerous phenotype (FIG. 15B). Confocal imaging confirmed that 5A2-SC8 NPs were able to effectively deliver labeled siRNA into tumor cells (FIG. 14C).

The therapeutic benefit of 5A2-SC8-mediated small RNA delivery in these chronically ill transgenic mice was then evaluated. One of the most important miRNAs is Let-7, a tumor suppressor family downregulated in many tumor types (Boyerinas et al., 2010; Roush and Slack, 2008). Because endogenous Let-7g is known to be downregulated in liver HB (Nguyen et al., 2014), tests were conducted to determine if delivery of a Let-7g mimic in this aggressive, genetically engineered mouse model could inhibit the development of liver cancer.

The 5A2-SC8 NPs were verified to be able to enable siRNA delivery in this model. Delivery of a single dose of siFVII i.v. showed potent silencing of FVII protein using a blood assay (FIG. 16A) and by qPCR in harvested liver tissues (FIG. 16B). This silencing was achieved on p26, which is after tumor development has initiated. Next, 1 mg/kg Let-7g was delivered in 5A2-SC8 NPs i.v. to tumor-bearing mice (p26). Let-7g expression was increased 7-fold in liver tissues 48 hours post-injection (FIG. 16C).

Figure 16D:
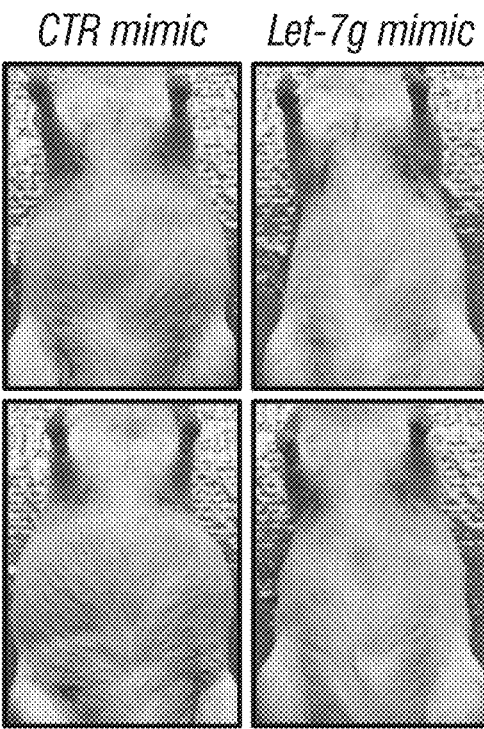
Figure 16E:
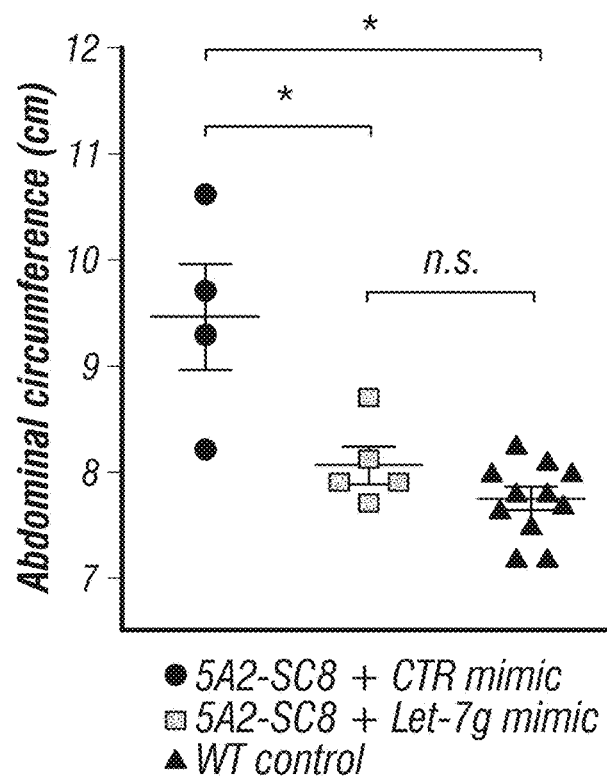
Figure 16F:
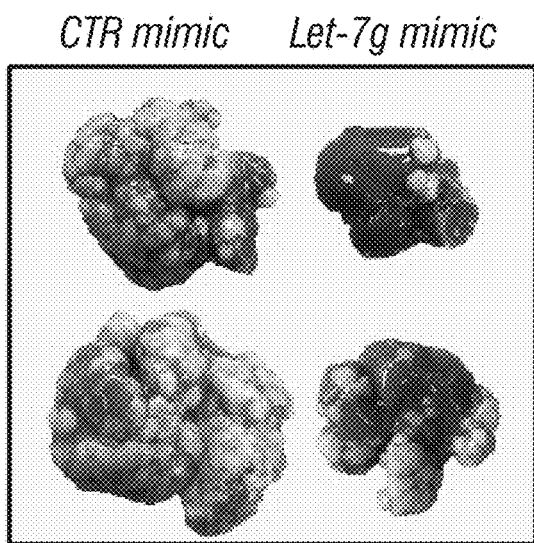
Figure 16G:
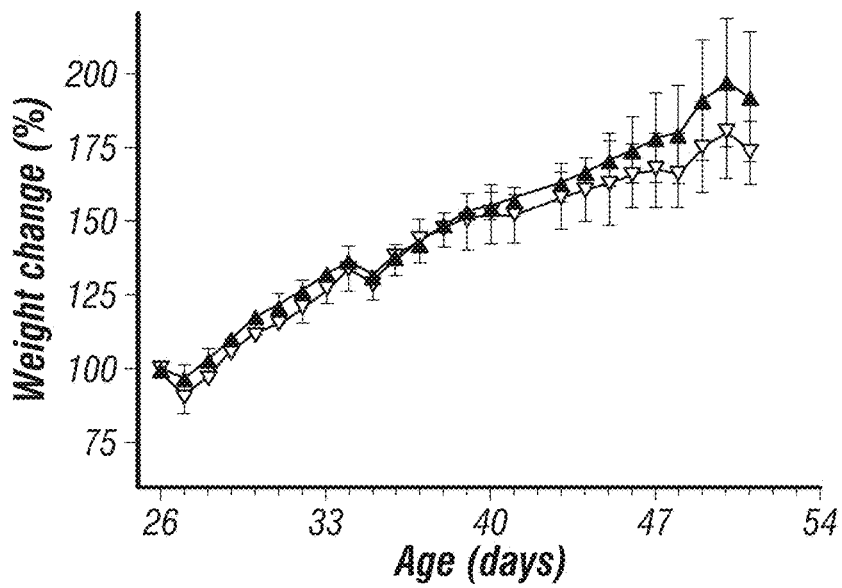
Figure 16H:
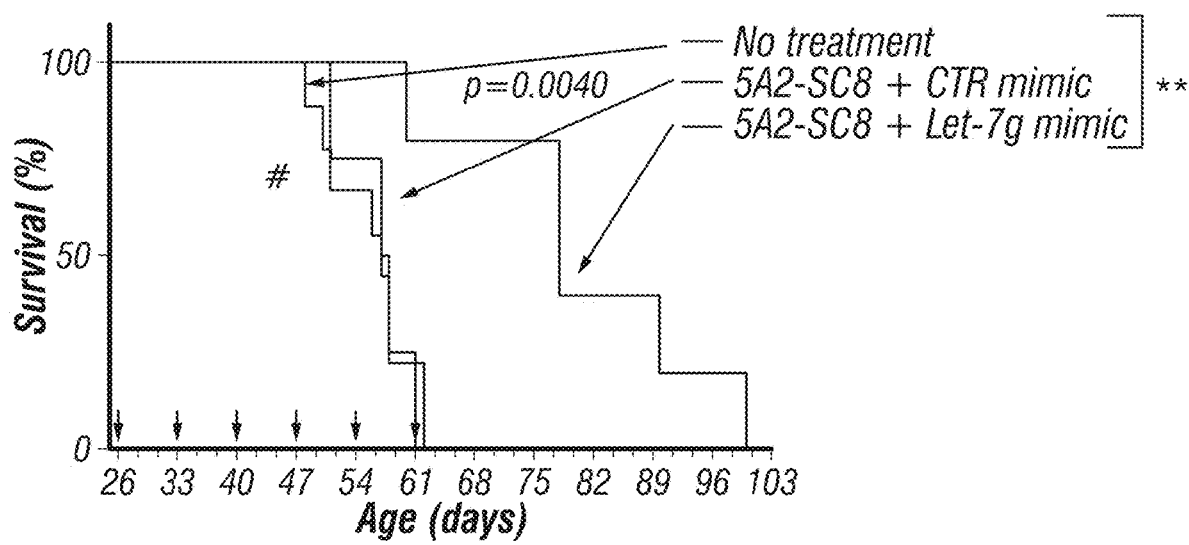

Then, a therapeutic regimen from p26 by weekly administration of 5A2-SC8 NPs containing Let-7g mimic or Control mimic at 1 mg/kg was started. At p50, the mice that received the Let-7g mimic had grossly smaller abdomens and reduced tumor burden (FIGS. 16D-16F). Let-7g caused reduction of abdominal circumference, quantitative of tumor growth (FIG. 16E). The effect on tumor growth was confirmed by ex vivo liver imaging (FIG. 16F). Most importantly, delivery of Let-7g weekly from 26 to 61 days did not affect weight gain (FIG. 16G) and significantly extended survival (FIG. 16H). All control mice receiving no treatment and mice receiving 5A2-SC8 NPs with CTR-mimic died around 60 days of age. C12-200 LNPs (Let-7g or control mimic) induced premature death, and required halting of the experiment. Delivery of Let-7g inside of 5A2-SC8 NPs provided a dramatic survival benefit, with one mouse living to 100 days. These results showed that 5A2-SC8 can balance high delivery efficacy with low toxicity to provide a significant therapeutic benefit to chronically ill transgenic mice by effective inhibition of liver tumor growth.

Example 8: Evaluation of Different Lipid Compositions for siRNA Delivery

Figure 17A:
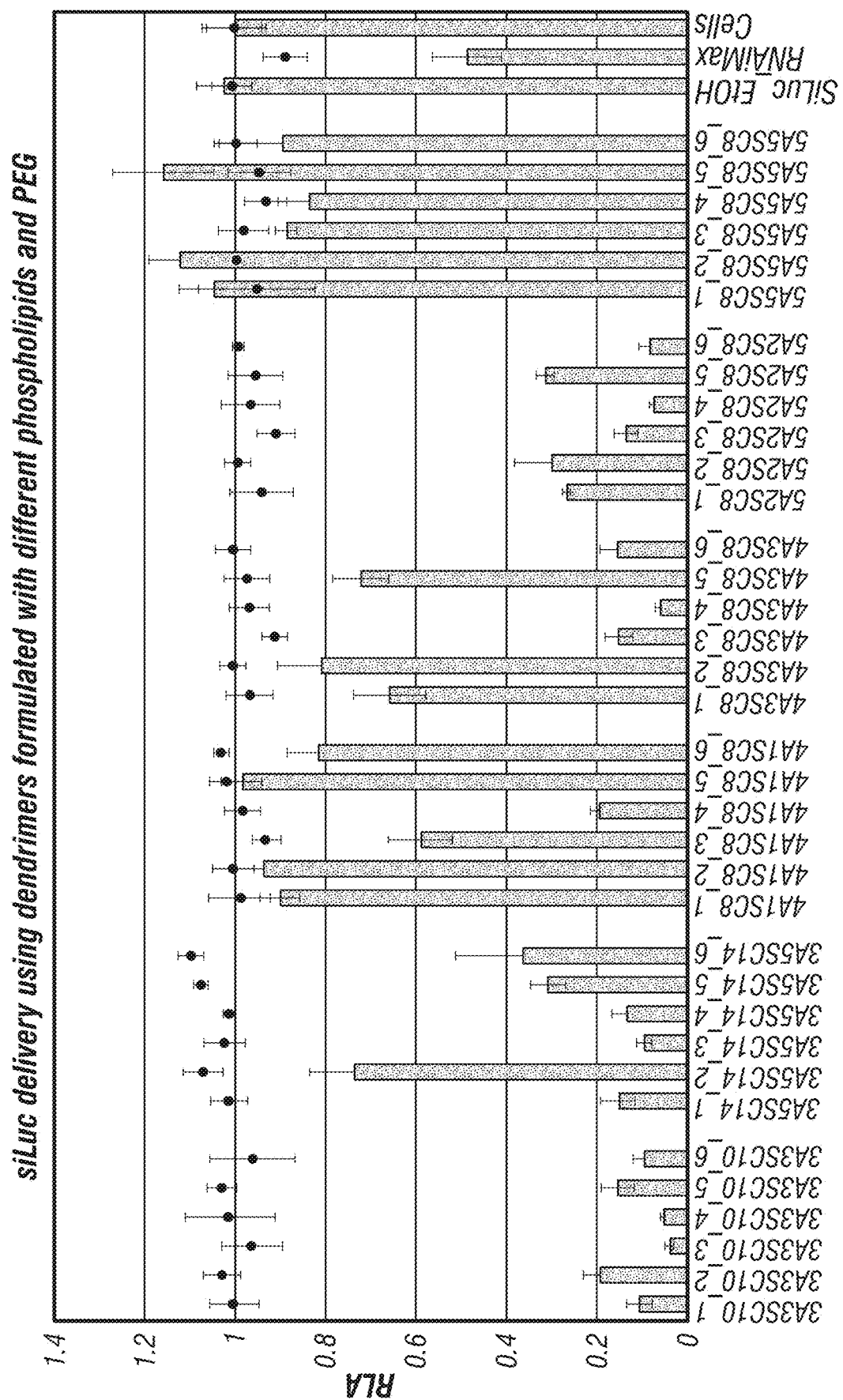
FIGS. 17A-17C show the delivery of siLuc delivery using dendrimer nanoparticles formulated with different combinations of cholesterol, phospholipids, and PEG lipids in HeLa-Luc (FIG. 17A), A549-Luc (FIG. 17B), and MDA-MB231-Luc (FIG. 17C).
Figure 17B:
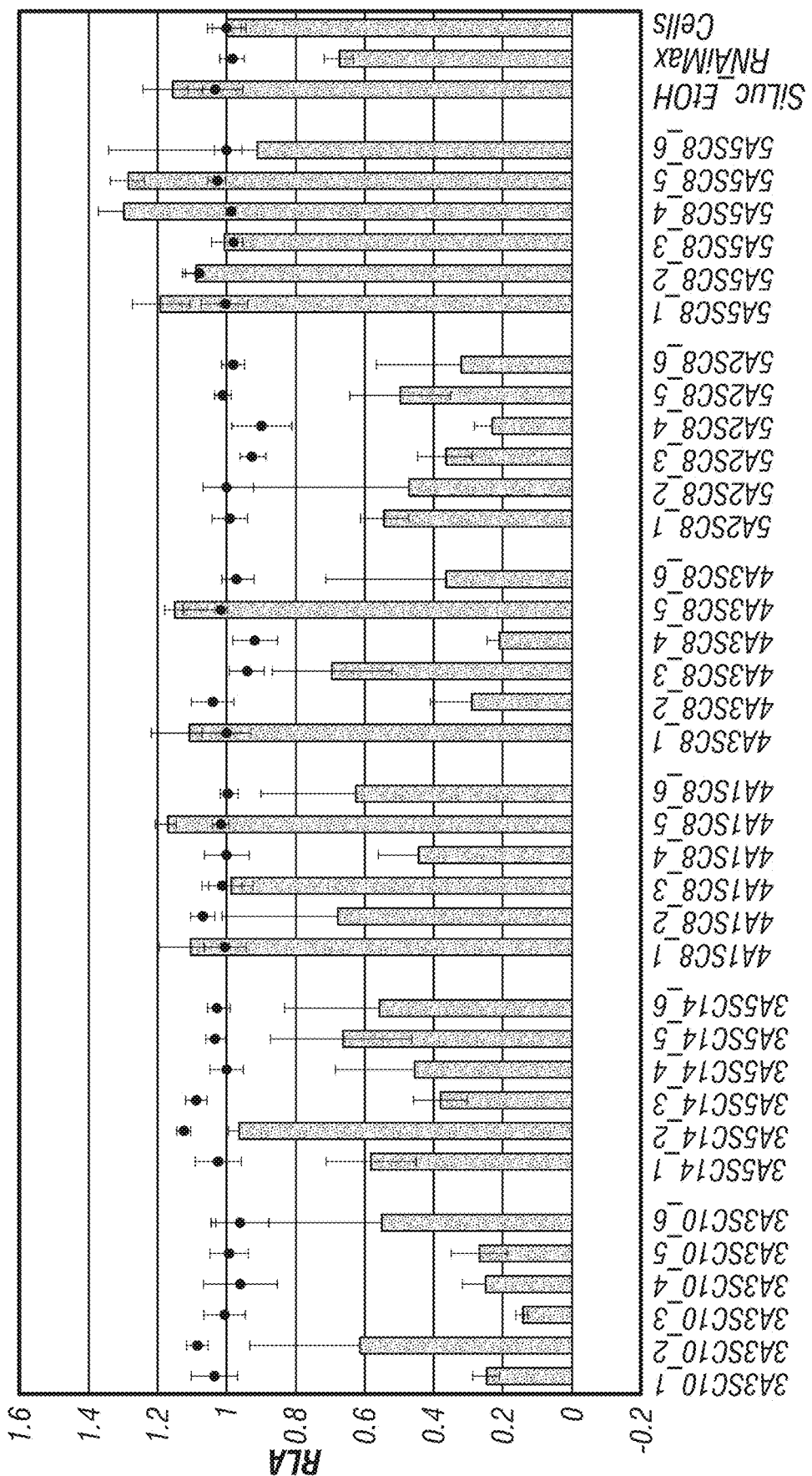
Figure 17C:
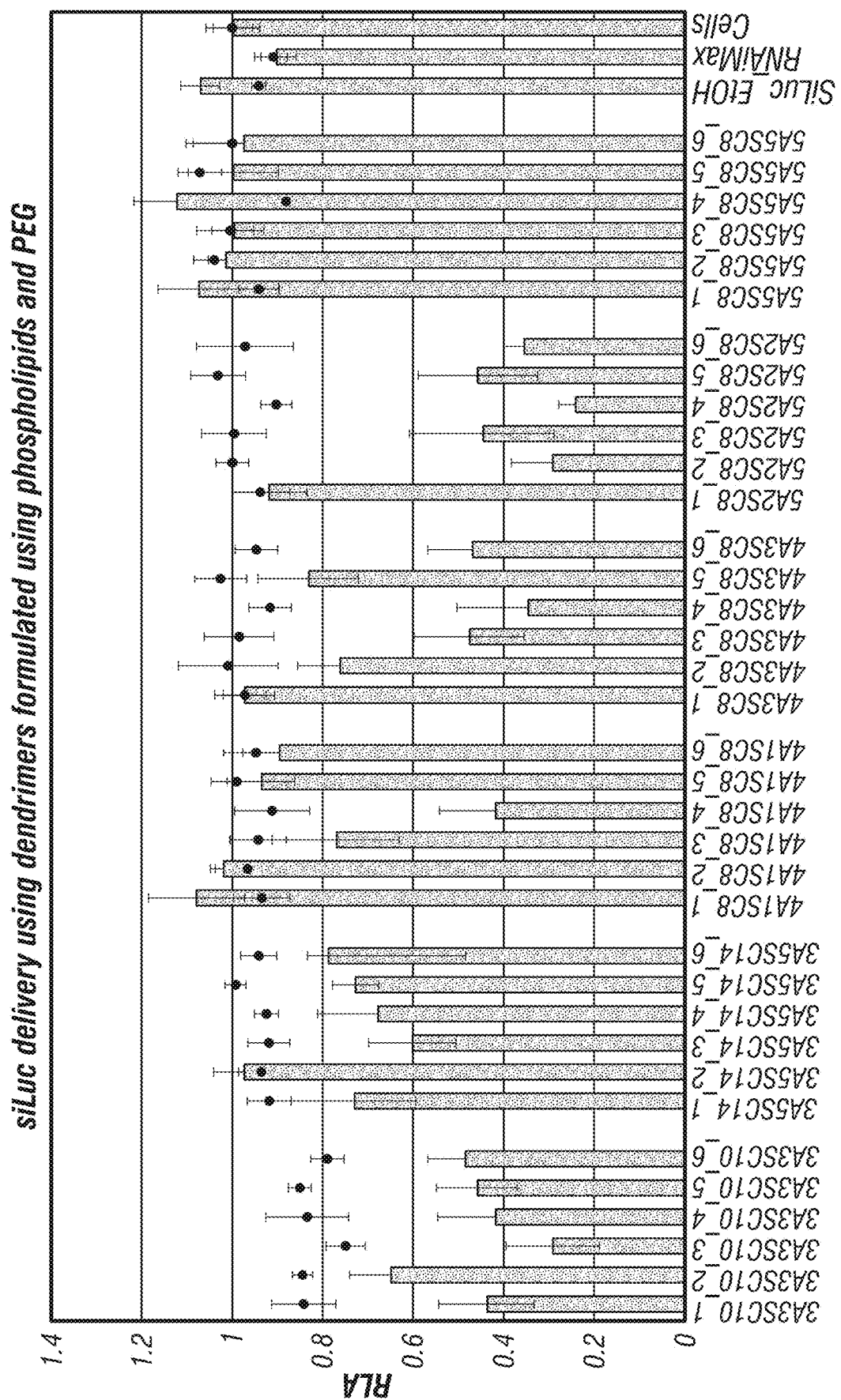

To evaluate which lipid composition within the dendrimer nanoparticles lead to improved siRNA delivery, the identity and concentration of different phospholipids and PEG-lipids were varied. Three different cell lines (HeLa-Luc, A549-Luc, and MDA-MB231-Luc) were used. The cells were present at 10K cells per well and a 24 hour incubation. The readout was determined 24 hours post transfection. In the nanoparticles, DSPC and DOPE were used as phospholipids and PEG-DSPE, PEG-DMG, and PEG-DHD were used as PEG-lipids. The compositions contain a lipid or dendrimer:cholesterol:phospholipid:PEG-lipid mole ratio of 50:38:10:2. The mole ratio of lipid/dendrimer to siRNA was 100:1 with 100 ng dose being used. The RiboGreen, Cell-titer Fluor, and OneGlo assays were used to determine the effectiveness of these compositions. Results show the relative luciferase activity in HeLa-Luc cells (FIG. 17A), A549-Luc (FIG. 17B), and MDA-MB231-Luc (FIG. 17C). The six formulations used in the studies include: dendrimer (lipid)+cholesterol+DSPC+PEG-DSPE (formulation 1), dendrimer (lipid)+cholesterol+DOPE+PEG-DSPE (formulation 2), dendrimer (lipid)+cholesterol+DSPC+PEG-DMG (formulation 3), dendrimer (lipid)+cholesterol+DOPE+PEG-DMG (formulation 4), dendrimer (lipid)+cholesterol+DSPC+PEG-DSPE (formulation 5), and dendrimer (lipid)+cholesterol+DOPE+PEG-DHD (formulation 6).

Figure 18A:
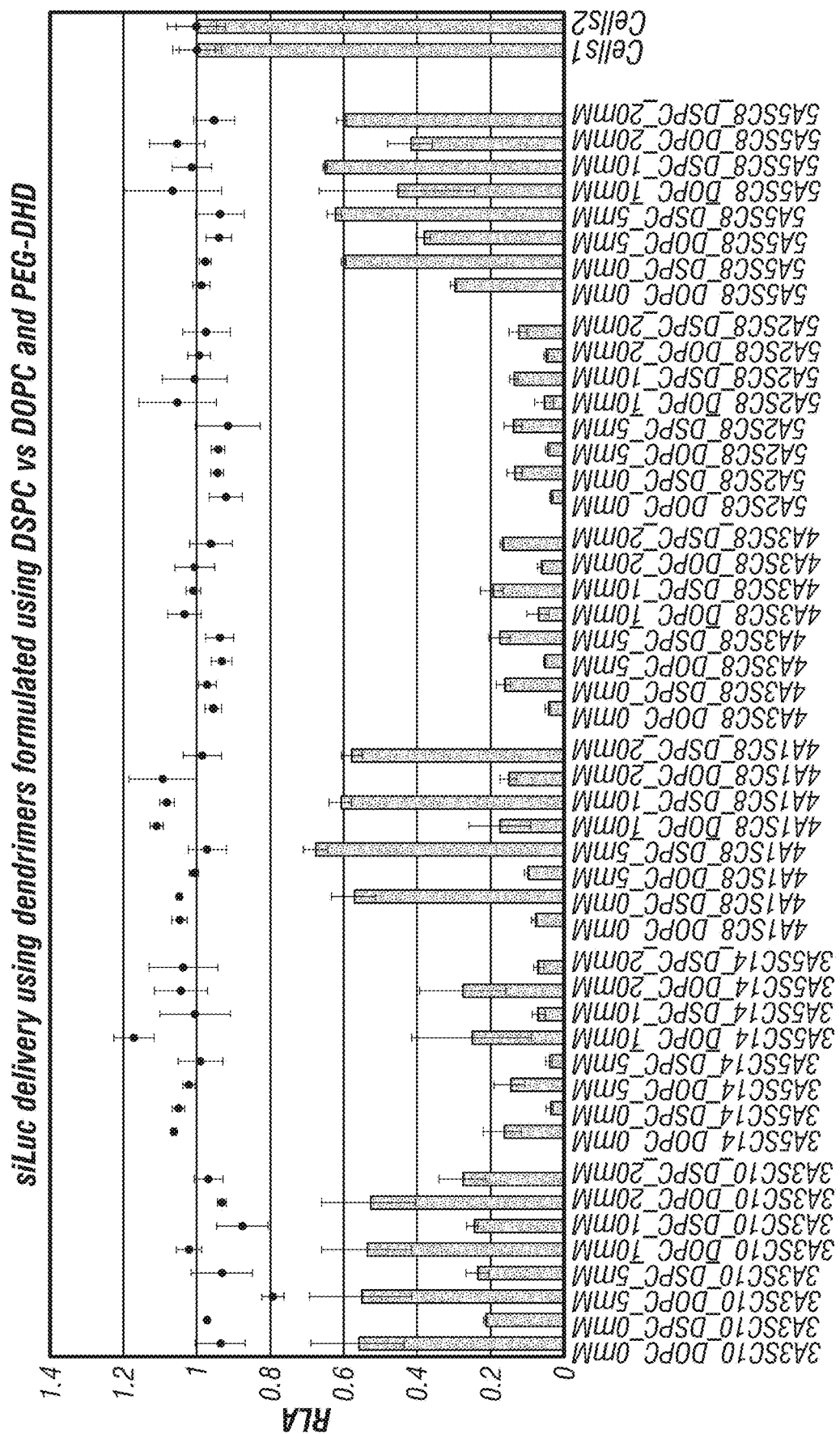
FIGS. 18A & 18B show (FIG. 18A) the comparison of different composition formulation with DSPC lipids vs. DOPE lipids with PEG-DMG in delivering siLuc to HeLa-Luc.
Figure 18B:
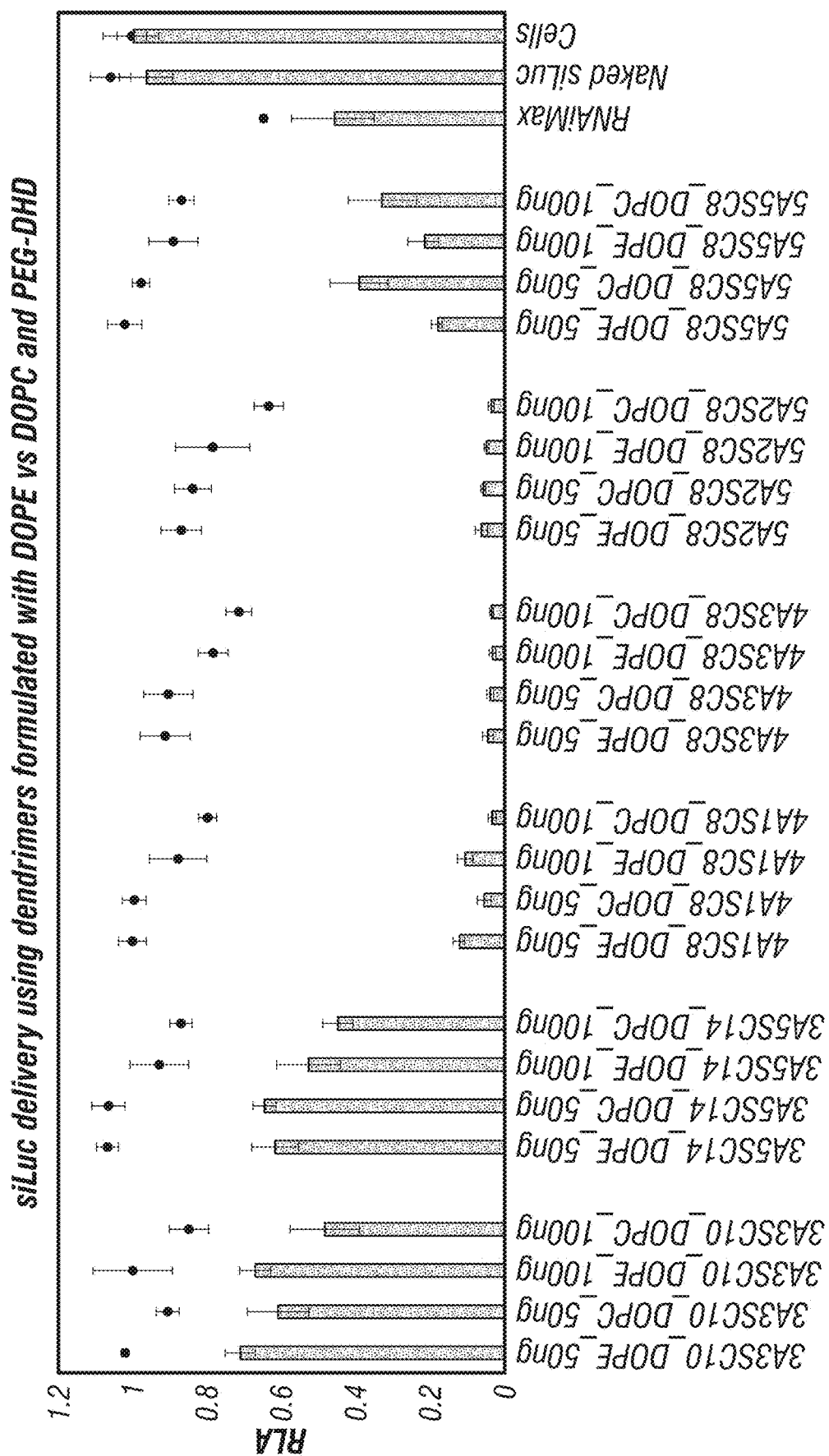

Further experiments were run to determine which phospholipids showed the increased delivery of siRNA molecules. A HeLa-Luc cell line was used with 10K cells per well, 24 hour incubation, and readout 24 hours post transfections. The compositions contained either DOPE or DOPC as the phospholipid with PEG-DHD as the PEG-lipid. The ratio of lipid (or dendrimer):cholesterol:phospholipid:PEG-lipid was 50:38:10:2 in a mole ratio with the mole ratio of dendrimer (or lipid) to siRNA of 200:1. These compositions was tested at a 50 ng dose using the Cell-titer Fluor and OneGlo assays. These results are shown in FIGS. 18A & 18B.

Figure 19:
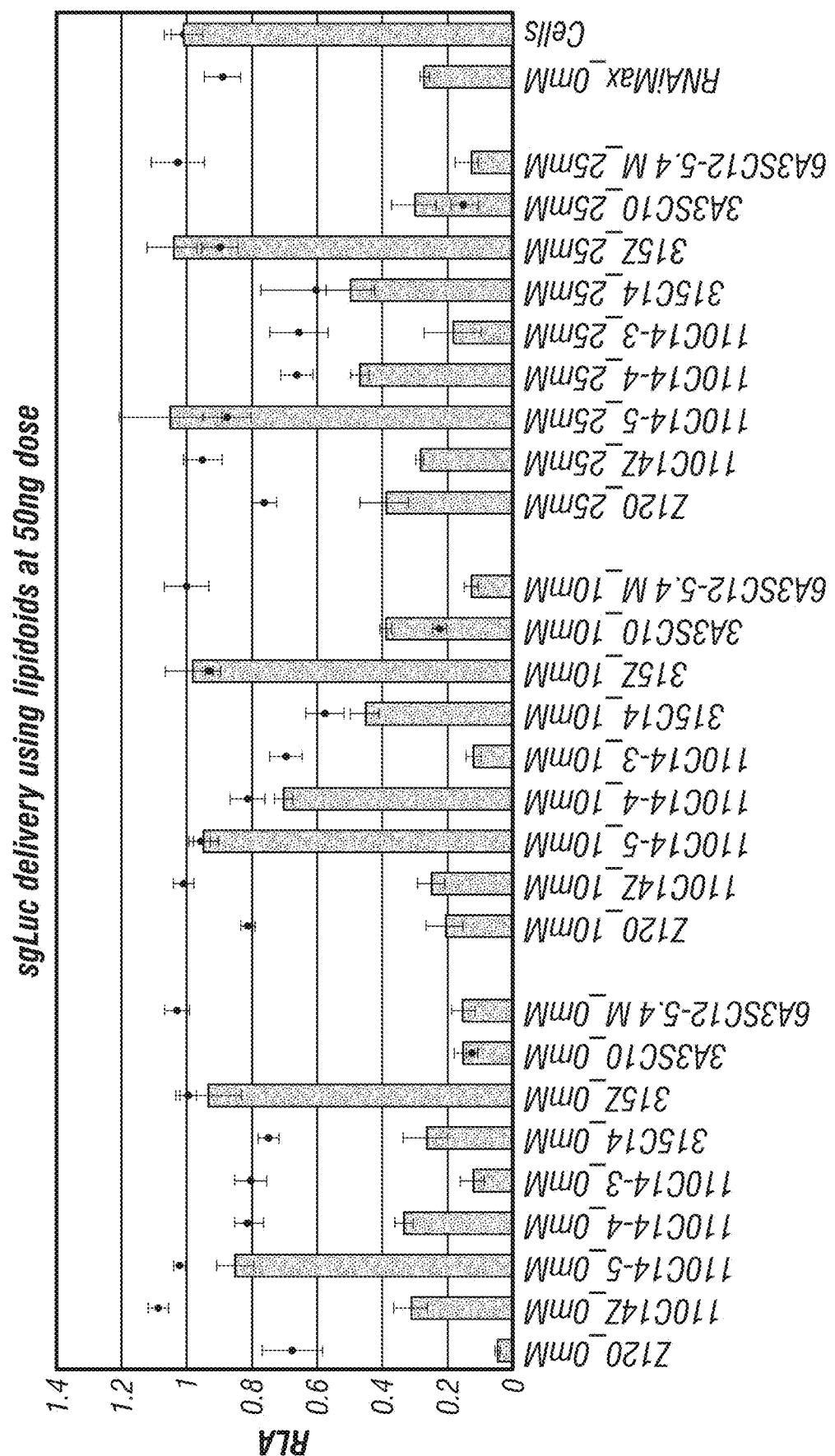
FIG. 19 shows delivery of a sgRNA delivery using a nanoparticle composition containing a dendrimer or Z120 and with and without phospholipid DSPC in the nanoparticle formulation.
Figure 20A:
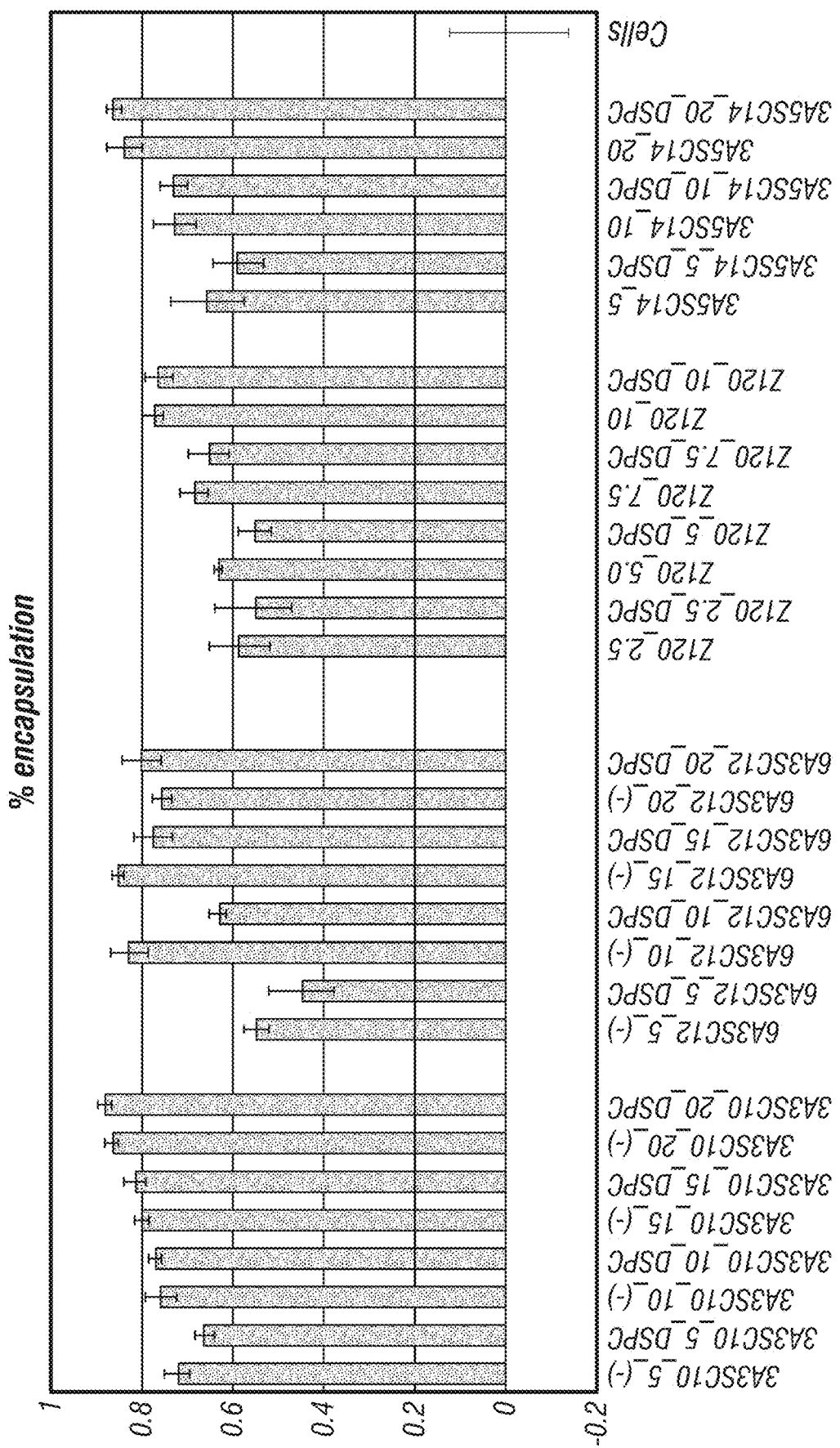
FIGS. 20A & 20B show percentage encapsulation of the sgRNA (FIG. 20A) and delivery in HeLa-Luc-Cas9 cells (FIG. 20B).
Figure 20B:
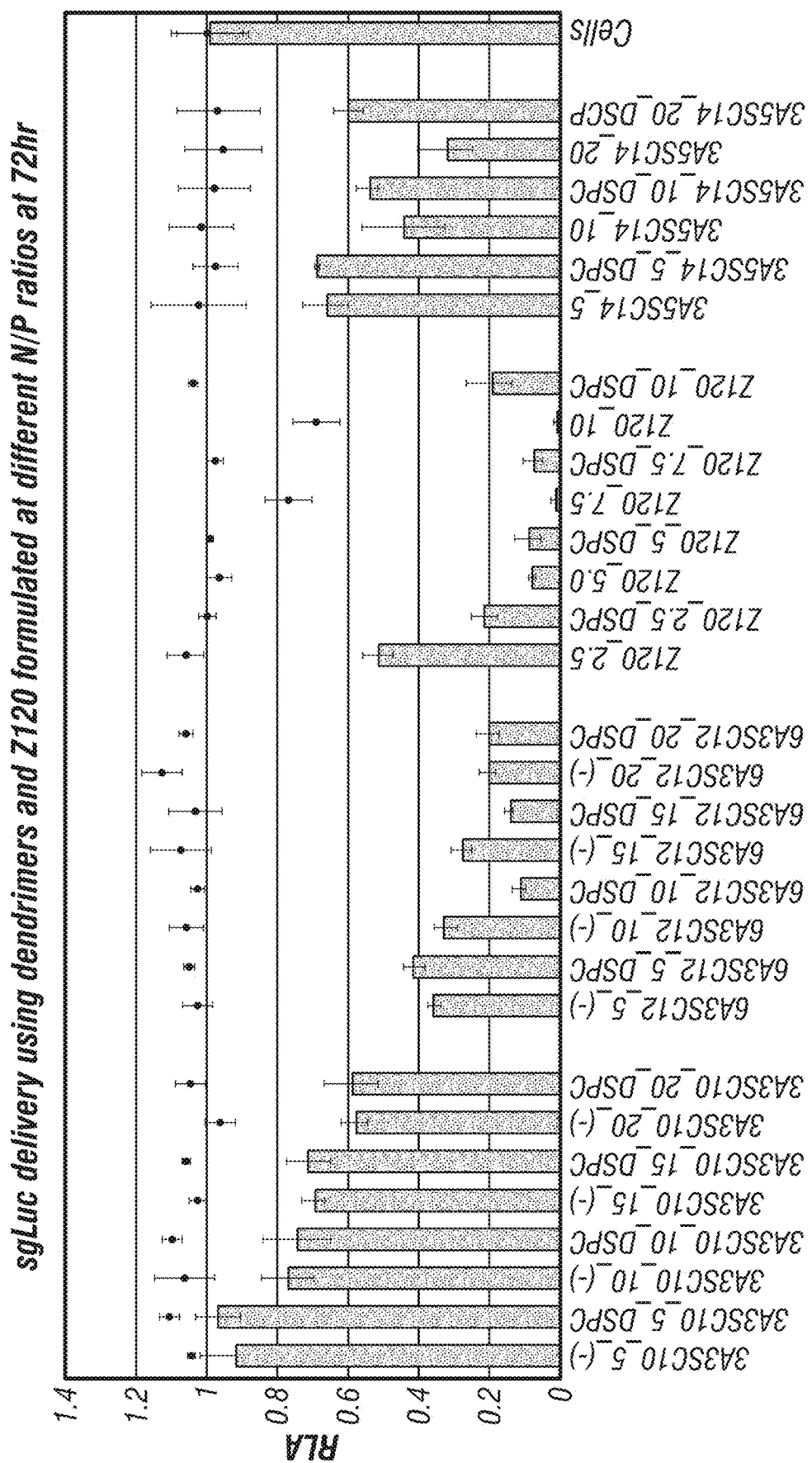

Example 9: Evaluation of Dendrimer Nanoparticles for Delivery of sgRNA and Other CRISPR Nucleic Acids To evaluate the compositions to delivery nucleic acids for CRISPR/Cas gene editing, the delivery of sgRNA and mRNA was tested. Cell lines were created that could allow for rapid screening of dendrimer NPs and Z120 for sgRNA delivery. For example, HeLa (cervical cancer) and A549 (lung cancer) cells were established to co-express luciferase and Cas9. Selection and quality control was verified. Guide RNAs were designed according to previously reported methods targeting the first exon of the desired target gene. Targets possessing the highest score indicating cleavage activity and sequence specificity were carried forward for sgRNA preparation using established protocols. DNA oligonucleotides were synthesized commercially, annealed, cloned by BsbI digestion and ligated into a plasmid backbone containing Cas9. In vitro transcription enabled the isolation of sgRNA, which could then be packaged into dendrimer NPs for delivery. A series of 5 different guides were designed for Luciferase. These guides were validated by sgLuc-Cas9 pDNA transfection using commercial reagents to select the best sgRNA sequence. Next, we packaged sgLuc into dendrimer NPs and evaluated delivery in HeLa-Luc-Cas9 cells for delivery of sgRNA. Following a determined number of hours of exposure, luciferase and viability were measured compared to untreated cells using One Glo+Tox (Promega). In a typical experiment, 10K cells were plated per well, followed by 24 hour incubation, addition of dendrimer nanoparticles containing sgLuc, and readout at 24-48 hours post transfection. These compositions contained combinations of dendrimers, DSPC or DOPE, cholesterol, and PEG-lipid. Additionally, the compositions contained various concentrations of $MgCl_2$. Molar ratios of lipid (or dendrimer):cholesterol:PEG-lipid were 50:38.5:0.5 with a mole ratio of lipid to nucleic acid (sgRNA) of 200:1 and a 50 ng dose. Again, the Cell-titer Fluor and OneGlo assays were used to obtain the results. Results without a phospholipid are shown in FIG. 19. Similar studies were carried out with phospholipid present. In these compositions, the phospholipid DSPC was used in the formulations. Using the same ratio as above for compositions which did not contain a phospholipid, the phospholipid containing compositions had a mole ratio of 50:38.5:10:0.5 (lipid/dendrimer:cholesterol:phospholipid: PEG-lipid) using the same dosing amount. These compositions were tested using RiboGreen, Cell-titer Fluor, and OneGlo at two time periods, 24 hours and 72 hours. Data obtained at 24 hours is shown in FIG. 20A and 72 hours is shown in FIG. 20B.

Example 10: Evaluation of Dendrimer Nanoparticles for Delivery of mRNA

Figure 21A:
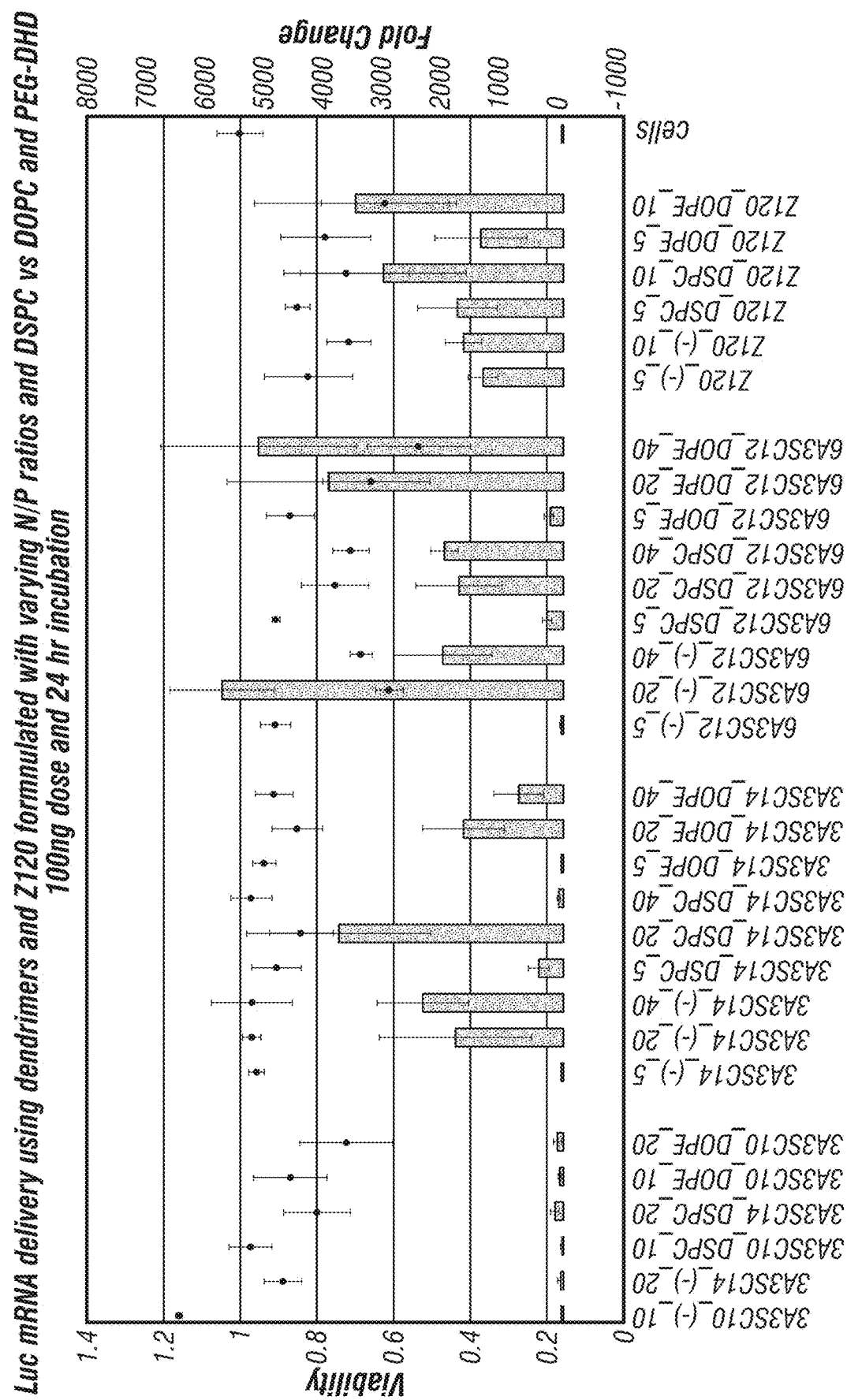
FIGS. 21A & 21B show the viability of IGROV cells to which Luc mRNA has been delivery after 24 hour incubation (FIG. 21A) and 48 hour incubation (FIG. 21B).
Figure 21B:
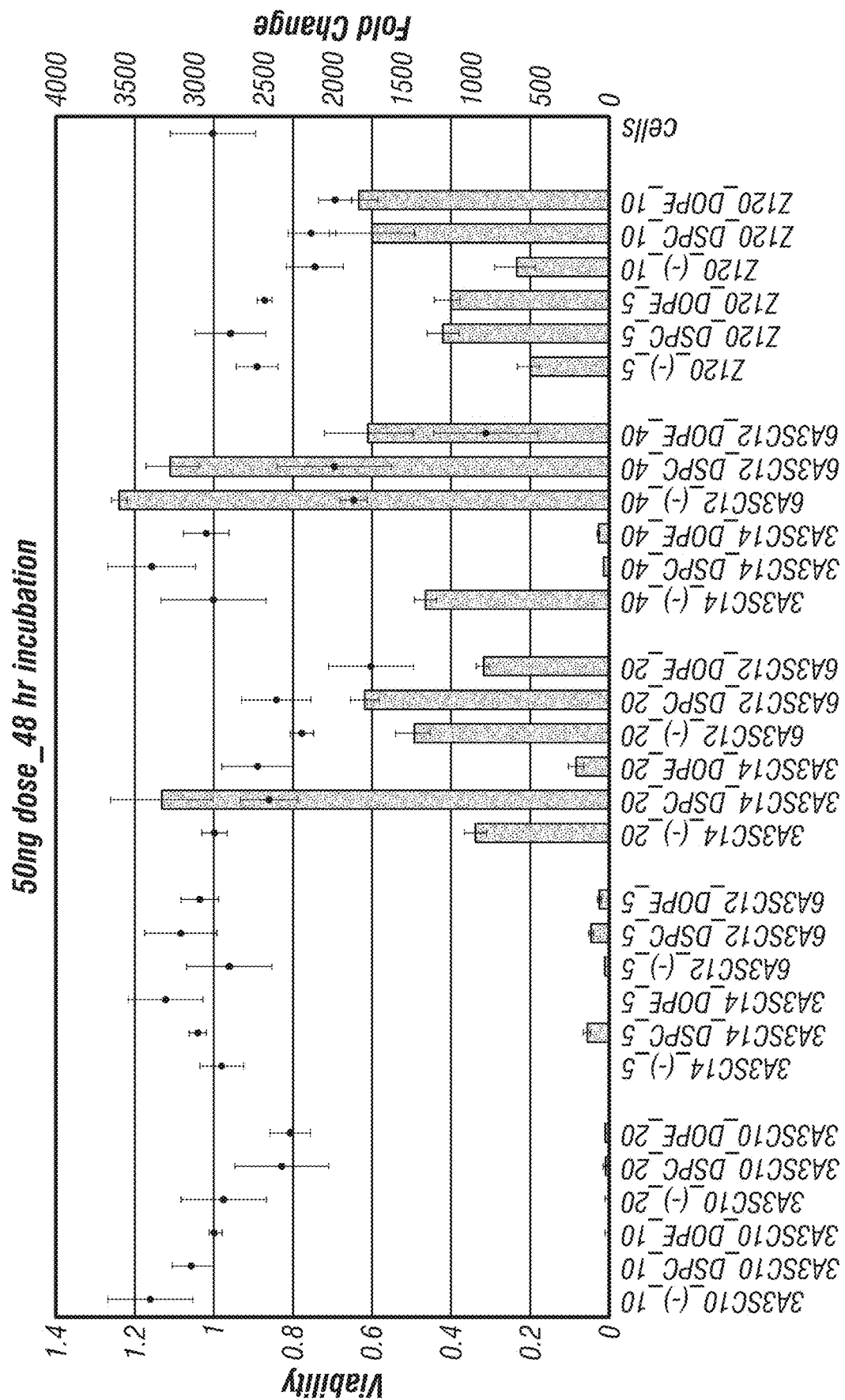
Figure 22:
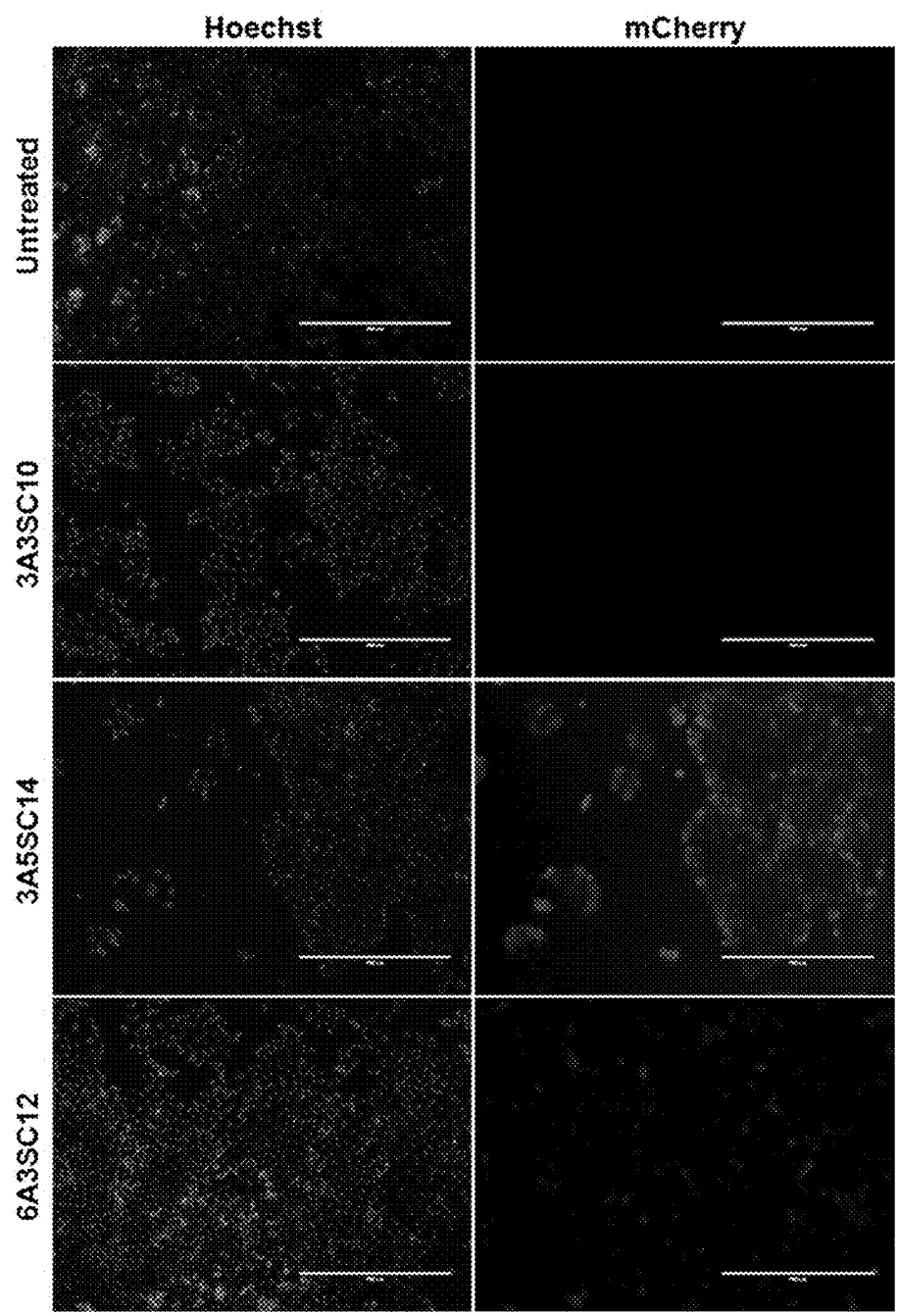
FIG. 22 shows the fluorescence microscopy of cells after treatment with mCherry mRNA showing the delivery of the mRNA to those cells.

Similar, to the studies carried out with siRNA, the delivery of mRNA molecules were tested with the dendrimers described herein and Z120. A IGROV1 cell line was used at a concentration of 4K cells per well, 24 hour incubation, and readout at 24 hours and 48 hours post transfection. These compositions contained either DSPC, DOPE, or no phospholipid and PEG-DHD as the PEG-lipid. Molar ratios of lipid (or dendrimer):cholesterol:phospholipid:PEG-lipid were 50:38.5:0(10):2 with a weight ratio of dendrimer to nucleic acid (mRNA) of 5, 10, 20, 30, or 40 to 1 and two different doses: a 50 ng dose and a 100 ng dose. The Cell-titer Fluor and OneGlo assays were used to obtain the results. These results were shown are shown in FIG. 21A (24 hours) and FIG. 21B (48 hours). Additionally, the delivery of mCherry mRNA into was visualized in FIG. 22 using a nanoparticle composition with 20:1 ratio N/P and DSPC as the phospholipid and PEG-DHD as the PEG-lipid.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,687,808
U.S. Pat. No. 4,587,044
U.S. Pat. No. 4,605,735
U.S. Pat. No. 4,667,025
U.S. Pat. No. 4,762,779
U.S. Pat. No. 4,789,737
U.S. Pat. No. 4,824,941
U.S. Pat. No. 4,828,979
U.S. Pat. No. 4,835,263
U.S. Pat. No. 4,845,205
U.S. Pat. No. 4,876,335
U.S. Pat. No. 4,904,582
U.S. Pat. No. 4,948,882
U.S. Pat. No. 4,958,013
U.S. Pat. No. 5,082,830
U.S. Pat. No. 5,109,124
U.S. Pat. No. 5,112,963
U.S. Pat. No. 5,118,802
U.S. Pat. No. 5,130,302
U.S. Pat. No. 5,134,066
U.S. Pat. No. 5,138,045
U.S. Pat. No. 5,175,273
U.S. Pat. No. 5,214,136
U.S. Pat. No. 5,218,105
U.S. Pat. No. 5,245,022
U.S. Pat. No. 5,254,469
U.S. Pat. No. 5,258,506
U.S. Pat. No. 5,262,536
U.S. Pat. No. 5,272,250

U.S. Pat. No. 5,292,873
U.S. Pat. No. 5,317,098
U.S. Pat. No. 5,367,066
U.S. Pat. No. 5,371,241
U.S. Pat. No. 5,391,723
U.S. Pat. No. 5,414,077
U.S. Pat. No. 5,416,203
U.S. Pat. No. 5,432,272
U.S. Pat. No. 5,451,463
U.S. Pat. No. 5,457,187
U.S. Pat. No. 5,459,255
U.S. Pat. No. 5,484,908
U.S. Pat. No. 5,486,603
U.S. Pat. No. 5,502,177
U.S. Pat. No. 5,510,475
U.S. Pat. No. 5,512,439
U.S. Pat. No. 5,512,667
U.S. Pat. No. 5,514,785
U.S. Pat. No. 5,525,465
U.S. Pat. No. 5,525,711
U.S. Pat. No. 5,541,313
U.S. Pat. No. 5,545,730
U.S. Pat. No. 5,552,538
U.S. Pat. No. 5,552,540
U.S. Pat. No. 5,565,552
U.S. Pat. No. 5,567,810
U.S. Pat. No. 5,574,142
U.S. Pat. No. 5,578,717
U.S. Pat. No. 5,578,718
U.S. Pat. No. 5,580,731
U.S. Pat. No. 5,585,481
U.S. Pat. No. 5,587,371
U.S. Pat. No. 5,587,469
U.S. Pat. No. 5,591,584
U.S. Pat. No. 5,594,121
U.S. Pat. No. 5,595,726
U.S. Pat. No. 5,596,091
U.S. Pat. No. 5,597,696
U.S. Pat. No. 5,599,923
U.S. Pat. No. 5,599,928
U.S. Pat. No. 5,608,046
U.S. Pat. No. 5,614,617
U.S. Pat. No. 5,645,985
U.S. Pat. No. 5,681,941
U.S. Pat. No. 5,688,941,
U.S. Pat. No. 5,750,692
U.S. Pat. No. 5,763,588
U.S. Pat. No. 5,820,873
U.S. Pat. No. 5,830,653
U.S. Pat. No. 6,005,096
U.S. Pat. No. 6,268,490
U.S. Pat. No. 6,506,559
U.S. Pat. No. 6,525,191
U.S. Pat. No. 6,573,099
U.S. Pat. No. 6,670,461
U.S. Pat. No. 6,673,611
U.S. Pat. No. 6,770,748
U.S. Pat. No. 6,794,499
U.S. Pat. No. 7,034,133
U.S. Pat. No. 7,053,207
U.S. Pat. No. 7,399,845
U.S. Pat. No. 8,450,298
U.S. patent application Ser. No. 12/129,154
U.S. Patent Application No. 60/989,574
U.S. Patent Application No. 61/026,995
U.S. Patent Application No. 61/026,998
U.S. Patent Application No. 61/056,564
U.S. Patent Application No. 61/086,231
U.S. Patent Application No. 61/097,787
U.S. Patent Application No. 61/099,844
U.S. Patent Publication No. 2004/0171570
U.S. Patent Publication No. 2002/0168707
U.S. Patent Publication No. 2003/0051263
U.S. Patent Publication No. 2003/0055020
U.S. Patent Publication No. 2003/0159161
U.S. Patent Publication No. 2004/0019001
U.S. Patent Publication No. 2004/0064842
U.S. Patent Publication No. 2004/0171570
U.S. Patent Publication No. 2004/0265839
U.S. Patent Publication No. 2005/0130923
U.S. Patent Publication No. 2007/0287831
U.S. Patent Publication No. 2008/0039618
PCT Application No. PCT/US2008/064591
PCT Application No. PCT/US2008/066154
PCT Application No. PCT/US2008/068922
PCT Publication No. WO 1994/14226
PCT Publication No. WO 2004/106356
PCT Publication No. WO 2005/021570
PCT Publication No. WO 2007/134181
PCT Publication No. WO 2008/101157
PCT Publication No. WO 2008/154401
PCT Publication No. WO 2009/006478
PCT Publication No. WO 2010/141069
Akinc et al., A combinatorial library of lipid-like materials for delivery of RNAi therapeutics. Nat. Biotechnol. 26, 561-569, 2008.
Albaek et al., J. Org. Chem., 2006, 71, 7731-7740.
Albertsson and Varma, Adv Polym Sci: 157, 1, 2002.
Ausubel et al., 1994.
Bikard et al., 2013
Bosman et al., About dendrimers: Structure, physical properties, and applications. Chem. Rev. 99, 1665-1688 (1999).
Boyerinas et al., The role of let-7 in cell differentiation and cancer. Endocr.-Relat. Cancer 17, F19-F36 (2010).
Braasch et al., Chem. Biol., 2001, 8, 1-7
Carlmark et al., New methodologies in the construction of dendritic materials. Chem. Soc. Rev. 38, 352-362, 2009.
Chattopadhyaya et al., J. Org. Chem., 2009, 74, 118-134.
Cheng et al., MicroRNA silencing for cancer therapy targeted to the tumour microenvironment. Nature 518, 107-110 (2015).
Cho et al., 2013
Coelho et al., New Engl J Med: 369, 819, 2013.
Crooke et al., J. Pharmacol. Exp. Ther., 277, 923, 1996.
Dahlman et al., Nat Nanotechnol 2014.
Daige et al., Systemic delivery of a miR34a mimic as a potential therapeutic for liver cancer. Mol. Cancer Ther. 13, 2352-2360 (2014).
Davis et al., Evidence of RNAi in humans from systemically administered siRNA via targeted nanoparticles. Nature 464, 1067-1070 (2010).
Davis et al., Nature (London, U. K.): 464, 1067, 2010.
Duncan and Izzo, Dendrimer biocompatibility and toxicity. Adv. Drug Deliv. Rev. 57, 2215-2237 (2005).
Elayadi et al., Curr. Opinion Invens. Drugs, 2001, 2, 5561
Englisch et al., Angewandte Chemie, International Edition, 30, 613, 1991.
Franc and Kakkar, "Click" methodologies: efficient, simple and greener routes to design dendrimers. Chem. Soc. Rev. 39, 1536-1544, 2010.
Fréchet and Tomalia (eds.) Dendrimers and other dendritic polymers. (John Wiley & Sons, Ltd, New York, USA; 2002).

Freier et al., Nucleic Acids Research, 1997, 25(22), 4429-4443.
Frieden et al., Nucleic Acids Research, 2003, 21, 6365-6372
Gillies and Frechet, Designing macromolecules for therapeutic applications: Polyester dendrimer-poly(ethylene oxide) "bow-tie" hybrids with tunable molecular weight and architecture. J. Am. Chem. Soc. 124, 14137-14146 (2002).
Grayson and Fréchet, Convergent dendrons and dendrimers: From synthesis to applications. Chem. Rev. 101, 3819-3868 (2001).
Green et al., ACCOUNTS CHEM RES: 41, 749, 2008.
Handbook of Pharmaceutical Salts: Properties, and Use, Stahl and Wermuth Eds.), Verlag Helvetica Chimica Acta, 2002.
Hao et al., Current Organic Chemistry: 17, 930-942, 2013.
Hsu et al., 2013
Jayaraman et al., Maximizing the potency of siRNA lipid nanoparticles for hepatic gene silencing in vivo. Angew. Chem. Int. Ed. 51, 8529-8533, 2012.
Jerome and Lecomte, Advanced Drug Delivery Reviews: 60, 1056, 2008.
Ji et al., MicroRNA expression, survival, and response to interferon in liver cancer. New Engl. J. Med. 361, 1437-1447 (2009).
Jinek et al.
Kabanov et al., FEBS Lett., 259, 327, 1990.
Kanasty et al., Delivery materials for siRNA therapeutics. Nat. Mater. 12, 967-977, 2013.
Kang et al., Tat-conjugated PAMAM dendrimers as delivery agents for antisense and siRNA oligonucleotides. Pharm. Res. 22, 2099-2106 (2005).
Kasinski and Slack, MicroRNAs en route to the clinic: progress in validating and targeting microRNAs for cancer therapy. Nat. Rev. Cancer 11, 849-864 (2011).
Khan et al., Ionizable amphiphilic dendrimer-based nanomaterials with alkyl-chain-substituted amines for tunable siRNA delivery to the liver endothelium in vivo. Angew. Chem. Int. Ed. 53, 14397-14401 (2014).
Killops et al., Robust, efficient, and orthogonal synthesis of dendrimers via thiol-ene "click" chemistry. J. Am. Chem. Soc. 130, 5062-5064, 2008.
Kim et al., ACS Macro Letters: 1, 845, 2012.
Koshkin et al., Tetrahedron, 1998, 54, 3607-3630.
Kota et al., Therapeutic microRNA delivery suppresses tumorigenesis in a murine liver cancer model. Cell 137, 1005-1017 (2009).
Kroschwitz, J. I., Ed., The Concise Encyclopedia Of Polymer Science And Engineering, John Wiley & Sons, 858-859, 1990.
Kumar et al., Bioorg. Med. Chem. Lett., 8, 2219-2222, 1998.
Ladeiro et al., MicroRNA profiling in hepatocellular tumors is associated with clinical features and oncogene/tumor suppressor gene mutations. Hepatology 47, 1955-1963 (2008).
Lee et al., Designing dendrimers for biological applications. Nat. Biotechnol. 23, 1517-1526 (2005).
Lee et al., Journal of Controlled Release: 152, 152, 2011.
Letsinger et al., Proc. Natl. Acad. Sci. USA, 86, 6553, 1989.
Leumann, C J. Bioorg. & Med. Chem. (2002) 10:841-854.
Leung et al., Lipid nanoparticles containing siRNA synthesized by microfluidic mixing exhibit an electron-dense nanostructured core. J. Phys. Chem. C 116, 22104-22104, 2012.
Ling et al., MicroRNAs and other non-coding RNAs as targets for anticancer drug development. Nat. Rev. Drug Discov. 12, 847-865 (2013).
Love et al., Lipid-like materials for low-dose, in vivo gene silencing. Proc. Natl. Acad. Sci. U.S.A. 107, 1864-1869, 2010.
Lynn and Langer, R. Journal of the American Chemical Society: 122, 10761, 2000.
Ma et al., Facile synthesis of polyester dendrimers from sequential click coupling of asymmetrical monomers. J. Am. Chem. Soc. 131, 14795-14803, 2009.
Mali et al., 2013a.
Mali et al., 2013a, b.
Manoharan et al., Ann. N.Y. Acad. Sci., 660, 306, 1992.
Manoharan et al., Bioorg. Med. Chem. Let., 3, 2765, 1993.
Manoharan et al., Bioorg. Med. Chem. Lett., 4, 1053, 1994.
Manoharan et al., Nucleosides & Nucleotides, 14, 969, 1995.
Manoharan et al., Tetrahedron Lett., 36, 3651, 1995,
March's Advanced Organic Chemistry: Reactions, Mechanisms, and Structure, 2007.
Meade et al., Efficient delivery of RNAi prodrugs containing reversible charge-neutralizing phosphotriester backbone modifications. Nat. Biotechnol. 32, 1256-1261 (2014).
Mishra et al., Biochim. Biophys. Acta, 1264, 229, 1995.
Murat and Grest, Molecular dynamics study of dendrimer molecules in solvents of varying quality. Macromolecules 29, 1278-1285 (1996).
Nelson et al., C. L. ACS Nano: 7, 8870, 2013.
Nguyen et al., Lin28b is sufficient to drive liver cancer and necessary for its maintenance in murine models. Cancer Cell 26, 248-261, 2014.
Oberhauser et al., Nucl. Acids Res., 20, 533, 1992.
Orum et al., Curr. Opinion Mol. Ther., 2001, 3, 239-243
Parmar et al., Bioconjugate Chem: 25, 896, 2014.
Percec et al., Self-assembly of Janus dendrimers into uniform dendrimersomes and other complex architectures. Science 328, 1009-1014 (2010).
Petar and. Tomalia, Chem. in Britain, 641-645, August 1994.
Philipp et al., Bioconjugate Chem: 20, 2055, 2009.
Pounder and Dove, A. Polym Chem-Uk: 1, 260, 2010.
Roberts, L. R. Sorafenib in liver cancer Just the beginning. New Engl. J. Med. 359, 420-422 (2008).
Rossi et al., New hope for a microRNA therapy for liver cancer. Cell 137, 990-992 (2009).
Roush and Slack, The let-7 family of microRNAs. Trends Cell Biol 18, 505-516, 2008.
Sahay et al., Efficiency of siRNA delivery by lipid nanoparticles is limited by endocytic recycling. Nat. Biotechnol. 31, 653-U119, 2013.
Saison-Behmoaras et al., EMBO J., 10, 111, 1991.
Sambrook et al., 1989.
Sanghvi, Y. S., Chapter 15, Antisense Research and Applications, Crooke, S. T. and Lebleu, B., Eds., CRC Press, 273-288, 1993.
Schaffert et al., Solid-phase synthesis of sequence-defined T-, i-, and U-shape polymers for pDNA and siRNA delivery. Angew. Chem. Int. Ed. 50, 8986-8989, 2011.
Scholz and Wagner, E. Journal of Controlled Release: 161, 554, 2012.
Schroeder et al., Journal of Controlled Release: 160, 172, 2012.
Scudellari, M. Drug development: Try and try again. Nature 516, S4-S6 (2014).
Semple et al., Rational design of cationic lipids for siRNA delivery. Nat. Biotechnol. 28, 172-176, 2010.
Shachaf et al., MYC inactivation uncovers pluripotent differentiation and tumour dormancy in hepatocellular cancer. Nature 431, 1112-1117 (2004).
Shea et al., Nucl. Acids Res., 18, 3777, 1990.

Siegwart et al., Combinatorial synthesis of chemically diverse core-shell nanoparticles for intracellular delivery. Proc. Natl. Acad. Sci. U.S.A. 108, 12996-13001, 2011.
Silvers et al., Polym Sci Pol Chem; 50, 3517, 2012.
Singh et al., Chem. Commun., 1998, 4, 455-456.
Singh et al., J. Org. Chem., 1998, 63, 10035-10039 Soutschek et al., 2004.
Srivastava et al., J. Am. Chem. Soc., 129(26) 8362-8379, Jul. 4, 2007.
Stiriba et al., Dendritic polymers in biomedical applications: From potential to clinical use in diagnostics and therapy. Angew. Chem. Int. Ed. 41, 1329-1334 (2002).
Svinarchuk et al., Biochimie, 75, 49, 1993.
Tan et al., Small: 7, 841, 2011.
Taratula et al., Surface-engineered targeted PPI dendrimer for efficient intracellular and intratumoral siRNA delivery. J. Control. Release 140, 284-293 (2009).
Tempelaar et al., Macromolecules, 44, 2084, 2011.
Tian et al., Prog Polym Sci: 37, 237, 2012.
Ventura and Jacks, MicroRNAs and cancer: Short RNAs go a long way. Cell 136, 586-591 (2009).
Wadhwa et al., 2004.
Wahlestedt et al., Proc. Natl. Acad. Sci. U.S.A., 2000, 97, 5633-5638.
Whitehead et al., Knocking down barriers: Advances in siRNA delivery. Nat. Rev. Drug Discov. 8, 129-138 (2009).
Whitehead et al., D. NAT REV DRUG DISCOV: 8, 129, 2009.
Whitehead et al., Degradable lipid nanoparticles with predictable in vivo siRNA delivery activity. Nat. Commun. 5, 4277, 2014.
Wu et al., Dendrimers in medicine: Therapeutic concepts and pharmaceutical challenges. Bioconjugate Chem., ASAP (2015).
Wu et al., Efficiency and fidelity in a click-chemistry route to triazole dendrimers by the copper(I)-catalyzed ligation of azides and alkynes. Angew. Chem. Int. Ed. 43, 3928-3932, 2004.
Zimmermann et al., Nature: 441, 111, 2006.
Zugates et al., Journal of the American Chemical Society: 128, 12726, 2006.

What is claimed is:

1. A method for delivering a nucleic acid to a cell of a subject, the method comprising administering to said subject said nucleic acid, wherein said nucleic acid is formulated with a nanoparticle comprising a compound having the structure of Formula (I):

Core-Repeating Unit-Terminating Group, or a pharmaceutically acceptable salt thereof,
wherein:
the core is linked to two to six repeating units, and each repeating unit is linked to a nitrogen of the core; wherein:
the core corresponds to the structure of Formula (II):

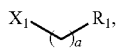
(II)

wherein, in Formula (II):
$X_1$ is optionally substituted dialkylamino$_{(C \leq 12)}$, optionally substituted heterocycloalkyl$_{(C \leq 12)}$, or optionally substituted heteroaryl$_{(C \leq 12)}$;
$R_1$ is amino, hydroxy, mercapto, optionally substituted alkylamino$_{(C \leq 12)}$, or optionally substituted dialkylamino$_{(C \leq 12)}$; and
a is 1, 2, 3, 4, 5, or 6; or
alternatively, the core corresponds to the structure of Formula (III):

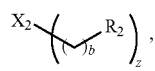
(III)

wherein, in Formula (III):
$X_2$ is $N(R_5)_y$, wherein:
$R_5$ is hydrogen or optionally substituted alkyl$_{(C \leq 18)}$; and
y is 0, 1, or 2, provided that the sum of y and z is 3;
$R_2$ is amino, hydroxy, mercapto, optionally substituted alkylamino$_{(C \leq 12)}$, or optionally substituted dialkylamino$_{(C \leq 12)}$;
b is 1, 2, 3, 4, 5, or 6; and
z is 1, 2, 3; provided that the sum of z and y is 3; or
alternatively, the core corresponds to the structure of Formula (IV):

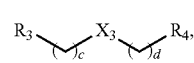
(IV)

wherein, in Formula (IV):
$X_3$ is selected from —NR$_6$—, —O—, optionally substituted alkylaminodiyl$_{(C \leq 8)}$, optionally substituted alkoxydiyl$_{(C \leq 8)}$, optionally substituted arenediyl$_{(C \leq 8)}$, optionally substituted heteroarenediyl$_{(C \leq 8)}$, and optionally substituted heterocycloalkanediyl$_{(C \leq 8)}$,
wherein $R_6$ is hydrogen or optionally substituted alkyl$_{(C \leq 8)}$;
$R_3$ and $R_4$ are each independently amino, hydroxy, mercapto, optionally substituted alkylamino$_{(C \leq 12)}$, optionally substituted dialkylamino$_{(C \leq 12)}$, or a group of the formula:

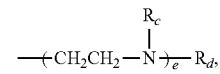

wherein:
e is 1, 2, or 3; and
$R_c$ and $R_d$ are each independently hydrogen, or optionally substituted alkyl$_{(C \leq 6)}$;
and
c and d are each independently 1, 2, 3, 4, 5, or 6;
each repeating unit
is a degradable diacyl group of Formula (VII):

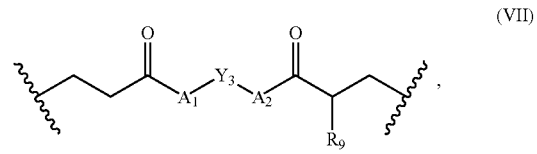
(VII)

wherein, in Formula (VII):

$A_1$ and $A_2$ are each independently —O—; and $Y_3$ is optionally substituted alkanediyl$_{(C \leq 12)}$, optionally substituted alkenediyl$_{(C \leq 12)}$, or optionally substituted arenediyl$_{(C \leq 12)}$;

$R_9$ is optionally substituted alkyl$_{(C \leq 8)}$; wherein the core contains at least one nitrogen atom and each terminating group has the structure of Formula (VIII):

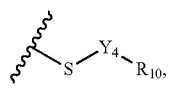
(VIII)

wherein, in Formula (VIII):

$Y_4$ is alkanediyl$_{(C \leq 18)}$ optionally substituted with one or more substituents each independently selected from the group consisting of —OH, —F, —Cl, —Br, —I, —SH, —OCH$_3$, —OCH$_2$CH$_3$, —SCH$_3$, and —OC(O)CH$_3$; and $R_{10}$ is hydrogen, wherein a protein expressed by said nucleic acid is detected in a cell of the subject following said administration of said nucleic acid formulated with said nanoparticle.

2. The method according to claim 1, wherein said nanoparticle further comprises a steroid or steroid derivative, a PEG-lipid, a phospholipid, or a combination thereof.

3. The method according to claim 2, wherein the molar ratio of said steroid or steroid derivative to the compound of Formula (I) or the pharmaceutically acceptable salt thereof is in said nanoparticle is from about 10:1 to about 1:20.

4. The method according to claim 2, wherein the molar ratio of said PEG lipid to the compound of Formula (I) or the pharmaceutically acceptable salt thereof in said nanoparticle is from about 1:1 to about 1:250.

5. The method according to claim 2, wherein the molar ratio of said phospholipid to the compound of Formula (I) or the pharmaceutically acceptable salt thereof in said nanoparticle is from about 10:1 to about 1:20.

6. The method according to claim 1, wherein the core of the compound of Formula (I), or the pharmaceutically acceptable salt thereof, corresponds to the structure of Formula (II):

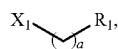
(II)

wherein, in Formula (II):

$X_1$ is optionally substituted alkylamino$_{(C \leq 12)}$, optionally substituted dialkylamino$_{(C \leq 12)}$, optionally substituted heterocycloalkyl$_{(C \leq 12)}$, or optionally substituted heteroaryl$_{(C \leq 12)}$;

$R_1$ is amino; and a is 1, 2, 3, 4, 5, or 6.

7. The method according to claim 1, wherein the core of the compound of Formula (I), or the pharmaceutically acceptable salt thereof, corresponds to the structure of Formula (III):

(III)

wherein, in Formula (III):

$X_2$ is $N(R_5)_y$, wherein:

$R_5$ is hydrogen or optionally substituted alkyl$_{(C \leq 8)}$; and y is 0 or 1 provided that the sum of y and z is 3;

$R_2$ is amino, optionally substituted alkylamino$_{(C \leq 12)}$, or optionally substituted dialkylamino$_{(C \leq 12)}$;

b is 1, 2, 3, 4, 5, or 6; and z is 2 or 3; provided that the sum of z and y is 3.

8. The method according to claim 7, wherein, in Formula (III):

$X_2$ is $N(R_5)_y$, wherein:

$R_5$ is hydrogen or alkyl$_{(C \leq 8)}$; and y is 1;

$R_2$ is amino or optionally substituted alkylamino$_{(C \leq 12)}$;

b is 1, 2, 3, 4, 5, or 6; and z is 2.

9. The method according to claim 1, wherein the core of the compound of Formula (I), or the pharmaceutically acceptable salt thereof, corresponds to the structure of Formula (IV):

$$R_3 \underbrace{\phantom{XXX}}_{c} X_3 \underbrace{\phantom{XXX}}_{d} R_4, \quad (IV)$$

wherein, in Formula (IV):

$X_3$ is —NR$_6$— wherein:

$R_6$ is hydrogen or alkyl$_{(C \leq 8)}$; and $R_3$ and $R_4$ are each independently amino, optionally substituted alkylamino$_{(C \leq 12)}$, or optionally substituted dialkylamino$_{(C \leq 12)}$; and c and d are each independently 2, 3, or 4.

10. The method according to claim 1, wherein the core of the compound of Formula (I), or the pharmaceutically acceptable salt thereof, corresponds to a structure selected from the group consisting of:

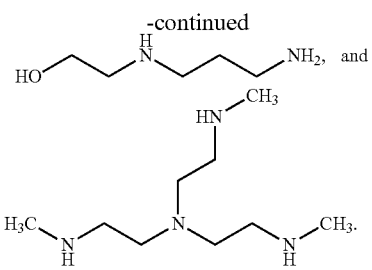

11. The method according to claim 1, wherein, in the diacyl group of Formula (VII):
$A_1$ and $A_2$ are each independently —O—;
$Y_3$ is unsubstituted alkanediyl$_{(C \leq 12)}$; and
$R_9$ is alkyl$_{(C \leq 8)}$.

12. The method according to claim 1, wherein the terminating group of Formula (VIII):
$Y_4$ is unsubstituted alkanediyl$_{(C \leq 18)}$; and
$R_{10}$ is hydrogen.

13. The method according to claim 1, wherein, in the compound of Formula (I), or the pharmaceutically acceptable salt thereof, the terminating group is each independently selected from the group consisting of:

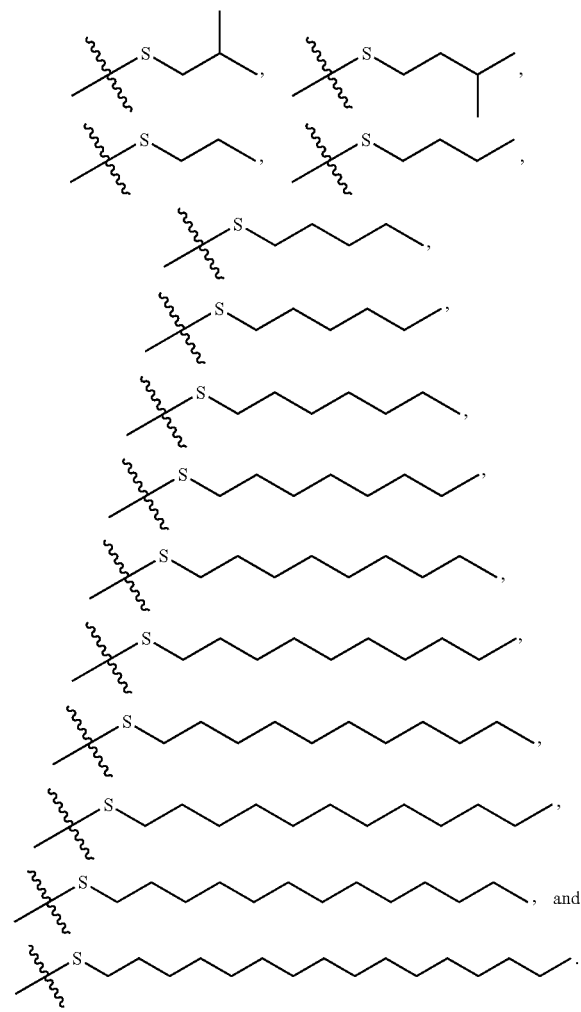

14. The method according to claim 1, wherein, in the compound of Formula (I), or the pharmaceutically acceptable salt thereof:

the core corresponds to the structure of Formula (IV):

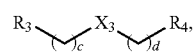

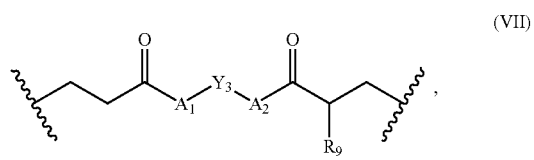

wherein, in Formula (IV):
$X_3$ is —NR$_6$—, wherein:
$R_6$ is hydrogen or alkyl$_{(C \leq 8)}$; and
$R_3$ and $R_4$ are each independently amino, optionally substituted alkylamino$_{(C \leq 12)}$, or optionally substituted dialkylamino$_{(C \leq 12)}$;
the degradable diacyl group has the structure of Formula (VII):

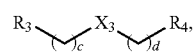

wherein, in Formula (VII):
$A_1$ and $A_2$ are —O—;
$Y_3$ is alkanediyl$_{(C \leq 12)}$; and
$R_9$ is alkyl$_{(C \leq 8)}$; and
the terminating group is each independently selected from the group consisting of:

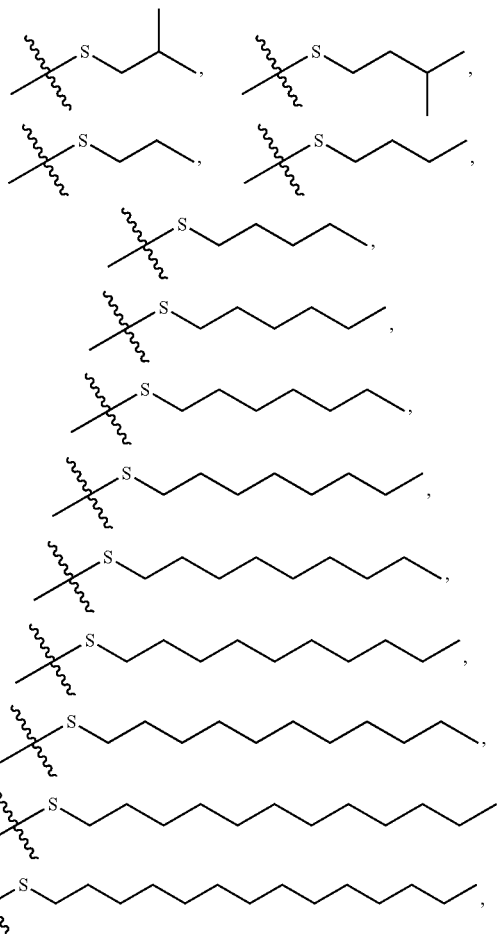

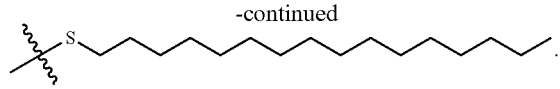

15. The method according to claim 1, wherein, in the compound of Formula (I), or the pharmaceutically acceptable salt thereof:

the core corresponds to a structure selected from the group consisting of:

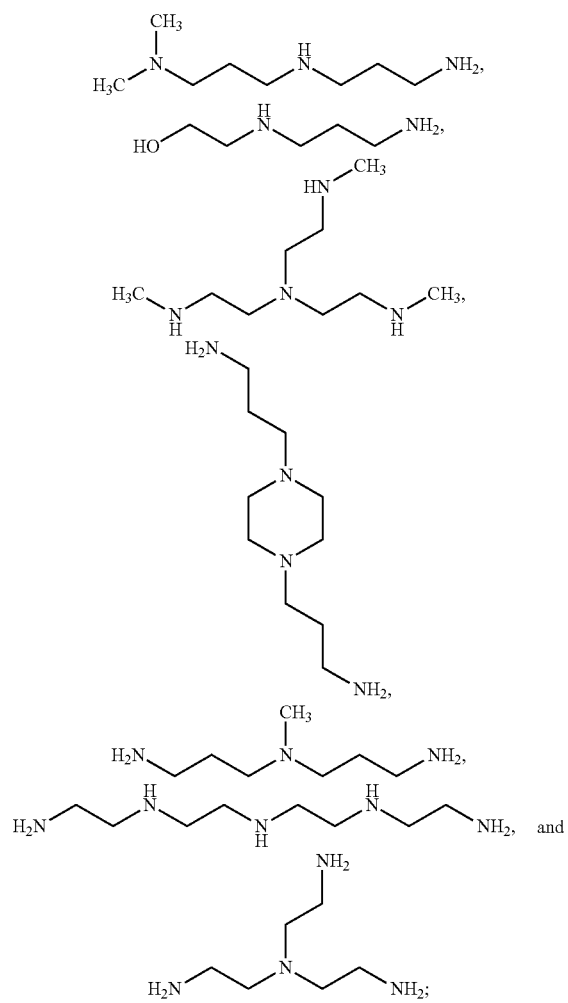

the degradable diacyl group has the structure of Formula (VII):

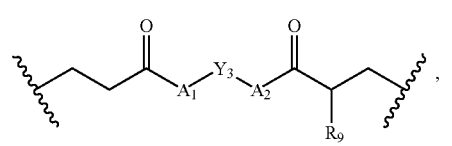

wherein, in Formula (VII):
$A_1$ and $A_2$ are —O—;
$Y_3$ is alkanediyl$_{(C \leq 12)}$; and
$R_9$ is alkyl$_{(C \leq 8)}$; and
the terminating group is each independently selected from the group consisting of:

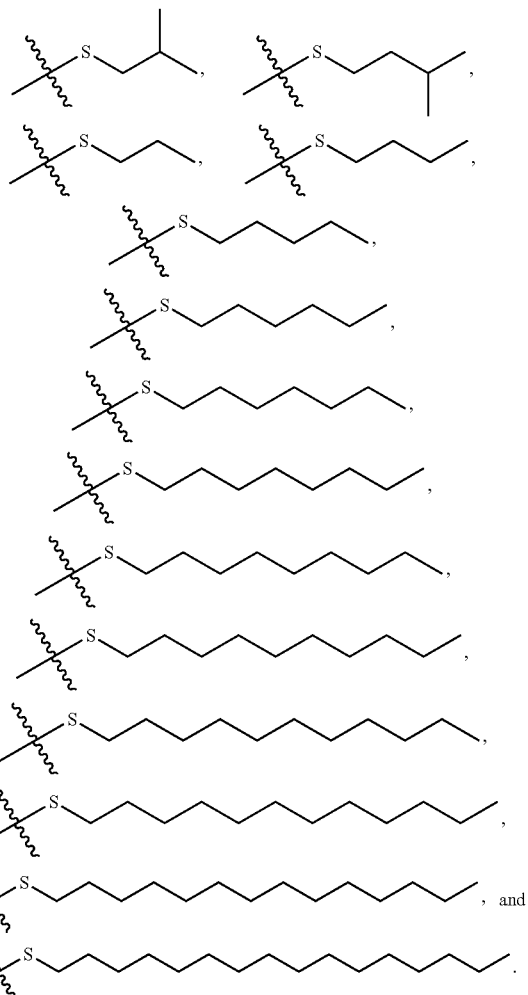

16. The method according to claim 1, wherein, in the compound of Formula (I), or the pharmaceutically acceptable salt thereof:

the core corresponds to

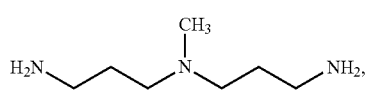

wherein the core is linked to three or four repeating units; and
the terminating group is each independently selected from the group consisting of:

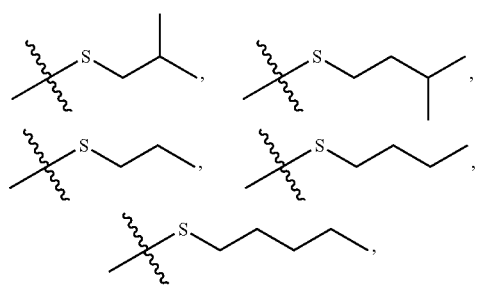

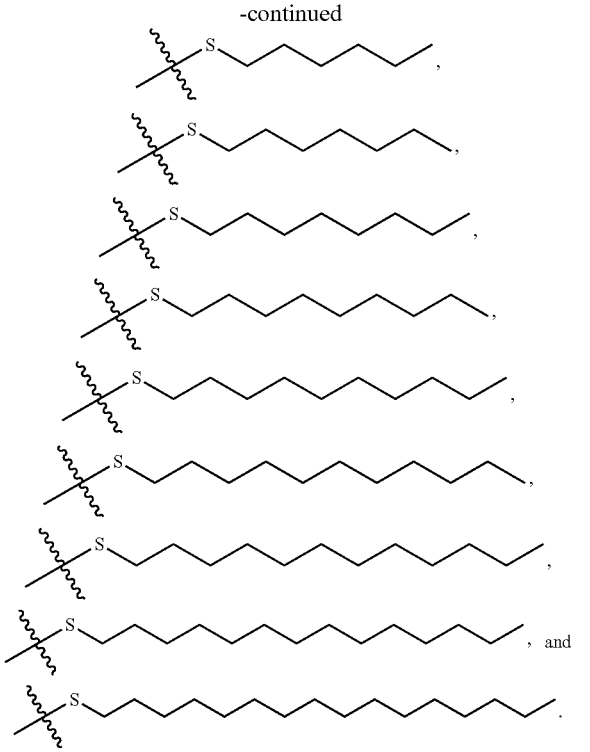

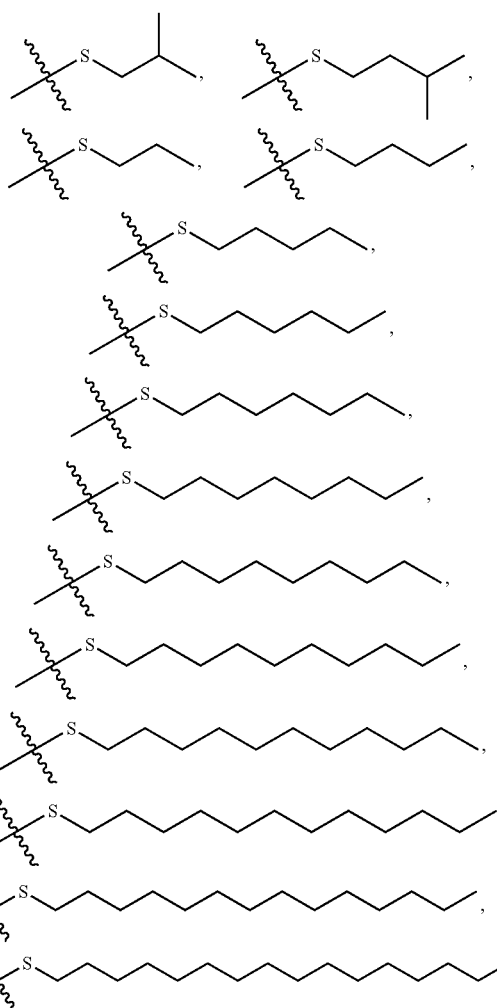

17. The method according to claim 1, wherein, in the compound of Formula (I), or the pharmaceutically acceptable salt thereof:
the core corresponds to

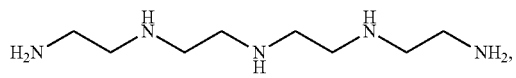 [SMILES: NCCNCCNCCNCCN]

wherein the core is linked to five or six repeating units; and
the terminating group is each independently selected from the group consisting of:

18. The method according to claim 1, wherein the compound of Formula (I), or the pharmaceutically acceptable salt thereof, is selected from the group consisting

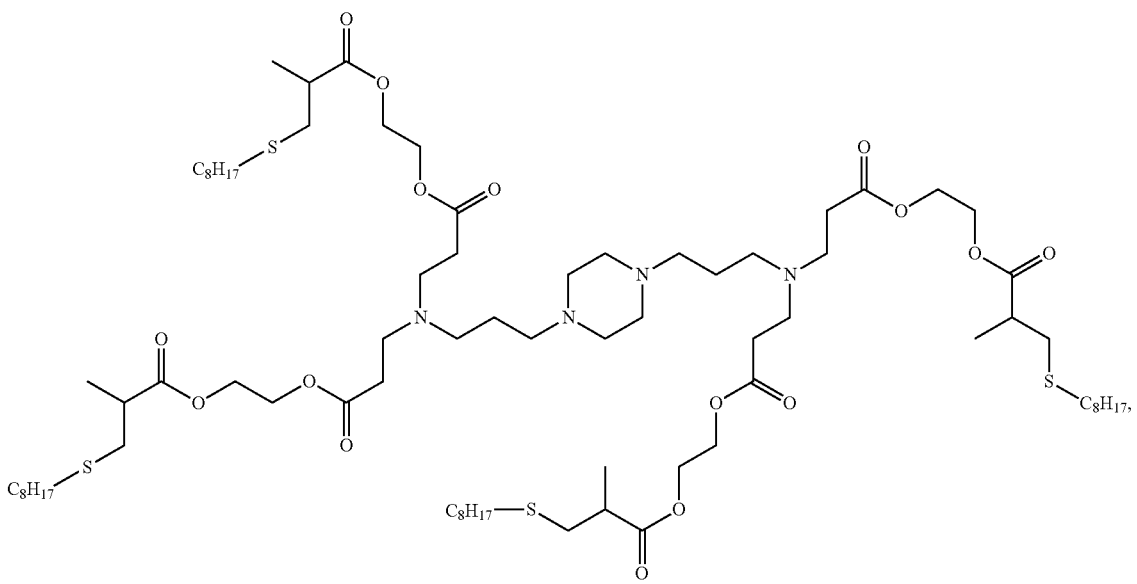

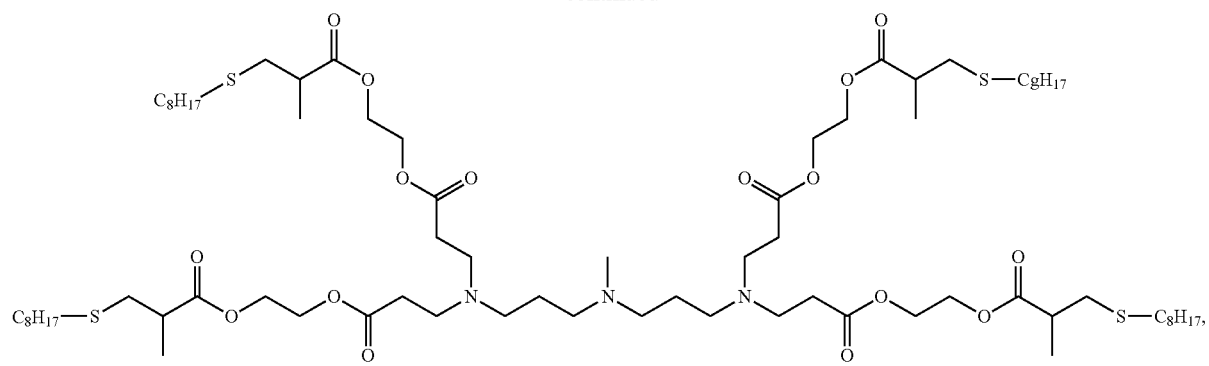
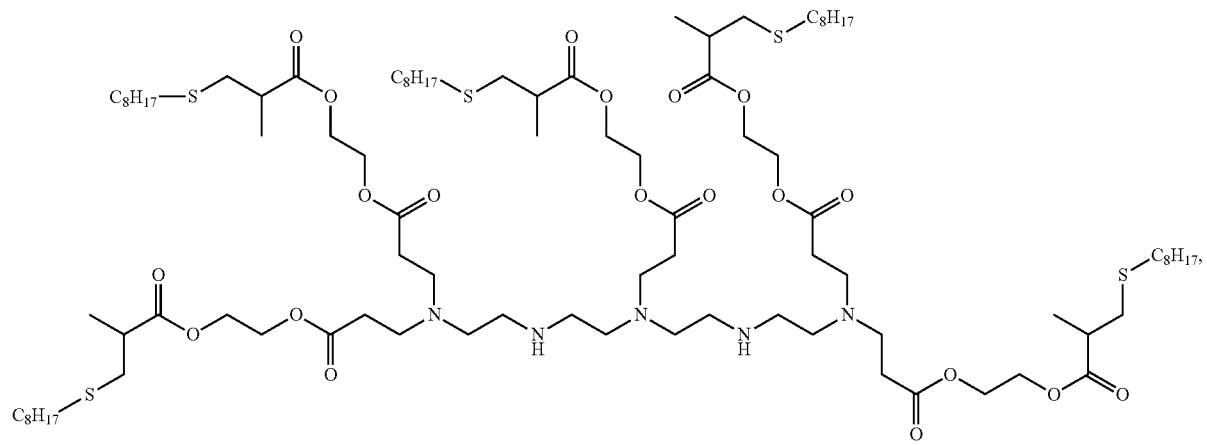
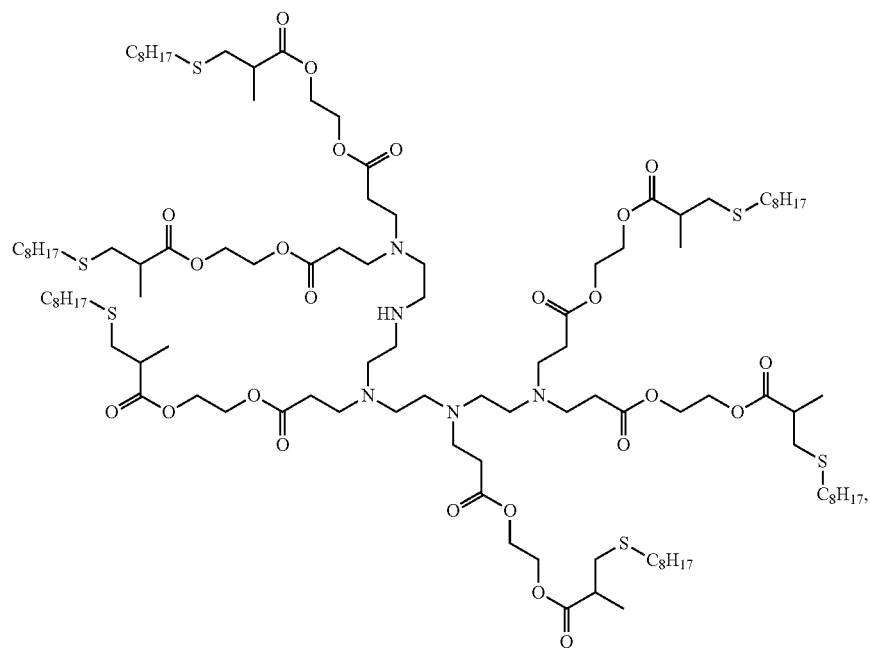

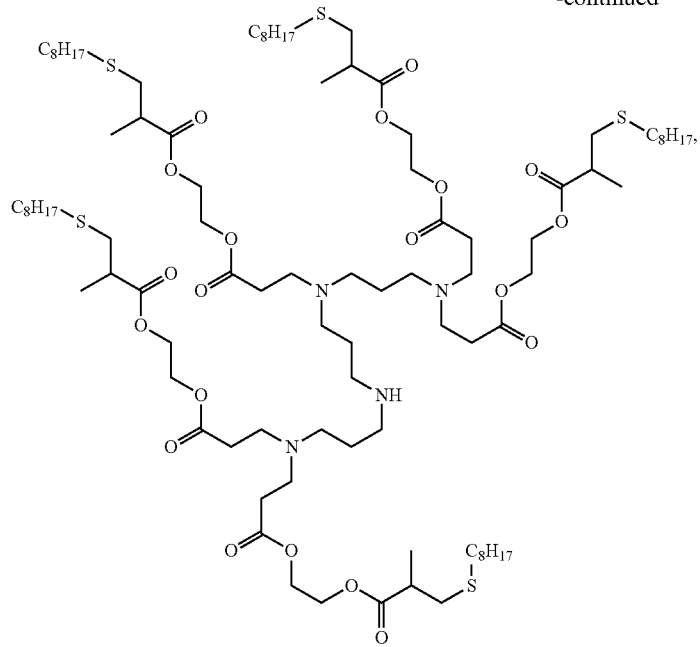
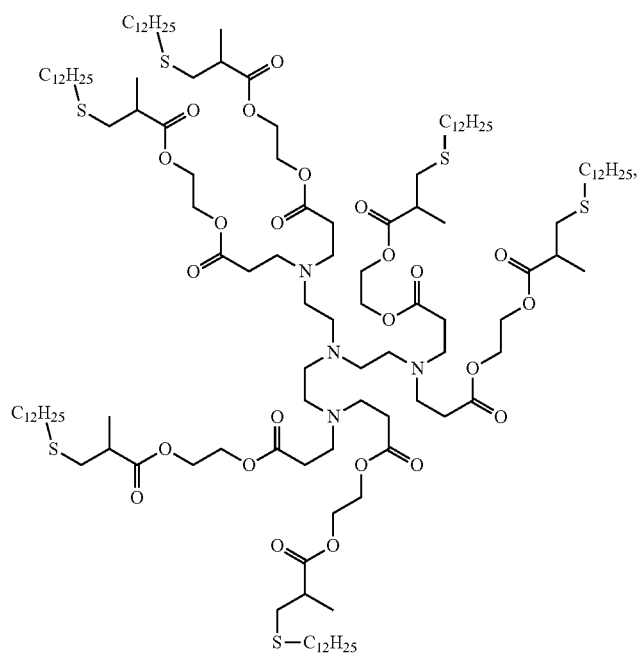

-continued
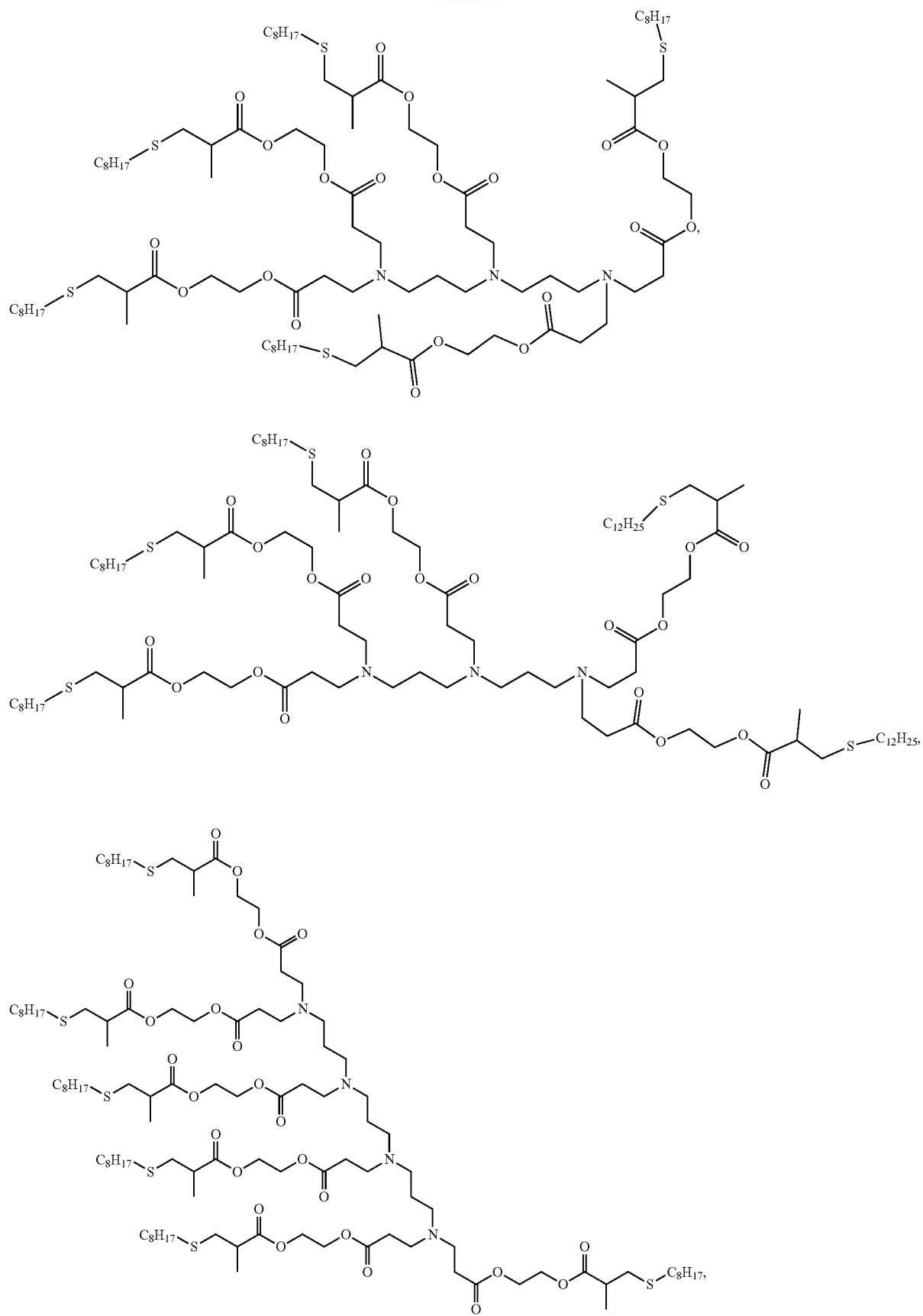

-continued

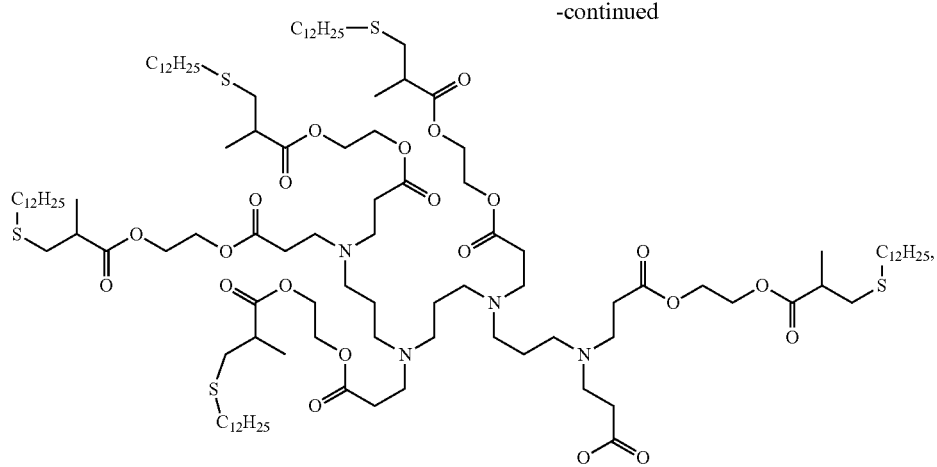

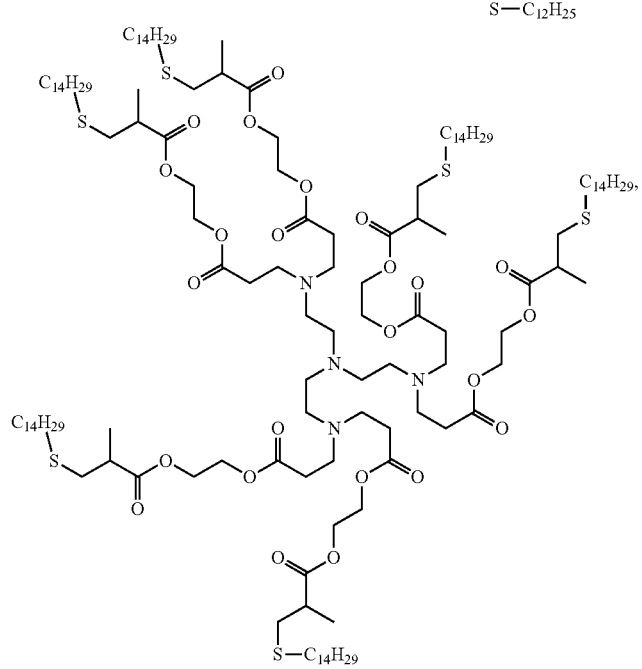

and a pharmaceutically acceptable salt of any of the foregoing.

19. The method according to claim 1, wherein said administering comprises systemically administering said nanoparticle to said subject.

20. The method according to claim 1, wherein said administering comprises locally administering said nanoparticle to said subject.

21. The method according to claim 1, wherein said administering comprises administering said nanoparticle to said subject via inhalation.

22. The method according to claim 1, wherein the protein is detected by a method comprising fluorescence imaging.

23. The method according to claim 1, wherein the protein is detected by a method comprising confocal imaging.

24. The method according to claim 2, wherein said steroid or steroid derivative is cholesterol.

25. The method according to claim 2, wherein said phospholipid is 1,2-distearoyl-sn-glycero-3-phosphocholine (DSPC) or 1,2-dioleoyl-sn-glycero-3-phosphoethanolamine (DOPE).

26. The method according to claim 2, wherein said PEG-lipid is a PEG modified dimyristoyl-sn-glycerol.

27. A method for delivering a nucleic acid to a cell of a subject, the method comprising administering to said subject said nucleic acid, wherein said nucleic acid is formulated with a nanoparticle comprising a compound having the structure of Formula (I):

Core-Repeating Unit-Terminating Group (I), wherein the core is linked to four repeating units and each repeating unit is linked to a nitrogen of the core, wherein the core has the following structure:

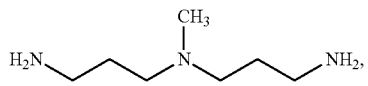

wherein the repeating unit is a degradable diacyl, having the formula:

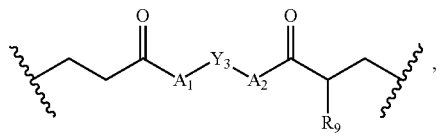
(VII)

wherein in Formula (VII),
A₁ and A₂ are each —O—;
Y₃ is —CH₂CH₂—;
R₉ is —CH₃; and
the terminating group is selected from the group consisting of:

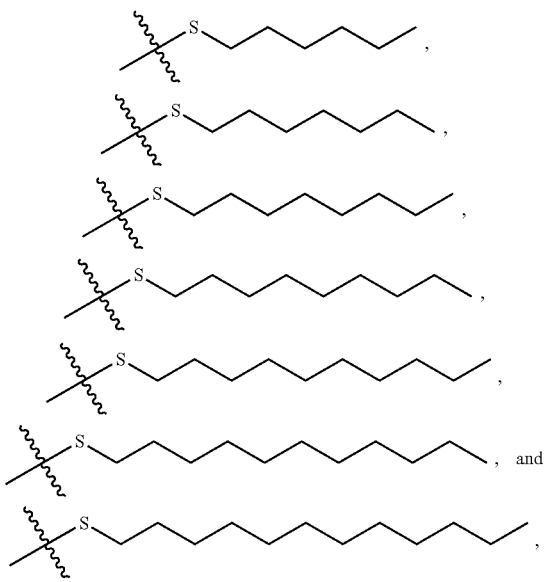
, and wherein a protein expressed by said nucleic acid is detected in a cell of the subject following said administration of said nucleic acid formulated with said nanoparticle.

28. The method according to claim 27, wherein in the compound of Formula (I) the terminating group is:

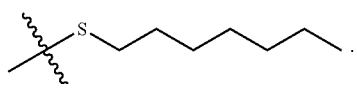 [SMILES: *SCCCCCCC ; "."]
.

29. The method according to claim 27, wherein in the compound of Formula (I) the terminating group is:

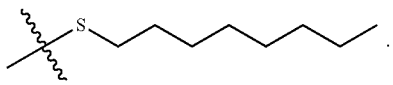 [SMILES: *SCCCCCCCC ; "."]
.

30. A method for delivering a nucleic acid to a cell of a subject, the method comprising administering to said subject said nucleic acid, wherein said nucleic acid is formulated with a nanoparticle comprising a compound having the structure of Formula (I):

Core-Repeating Unit-Terminating Group (I), wherein the core is linked to four or five repeating units and each repeating unit is linked to a nitrogen of the core, wherein the core has the following structure:

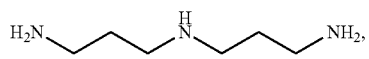

wherein the repeating unit is a degradable diacyl, having the formula:

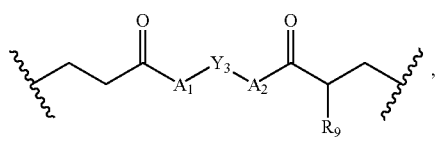
(VII)

wherein in Formula (VII),
A₁ and A₂ are each —O—;
Y₃ is —CH₂CH₂—;
R₉ is —CH₃; and
the terminating group is selected from the group consisting of:

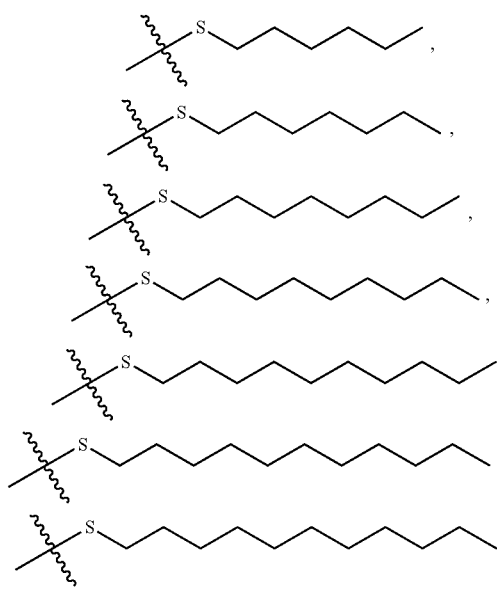
, and wherein a protein expressed by said nucleic acid is detected in a cell of the subject following said administration of said nucleic acid formulated with said nanoparticle.

31. The method according to claim 30, wherein in the compound of Formula (I) the core is linked to five repeating units and
the terminating group is:

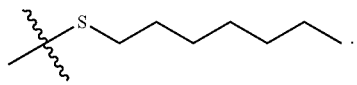 [SMILES: *SCCCCCCC ; "."]

32. The method according to claim 30, wherein in the compound of Formula (I) the core is linked to five repeating units and the terminating group is:

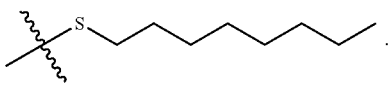

33. A method for delivering a nucleic acid to a cell of a subject, the method comprising administering to said subject said nucleic acid, wherein said nucleic acid is formulated with a nanoparticle comprising a compound having the structure of Formula (I):

Core-Repeating Unit-Terminating Group    (I), wherein the core is linked to four to six repeating units and each repeating unit is linked to a nitrogen of the core, wherein the core has the following structure:

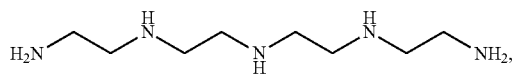

wherein the repeating unit is a degradable diacyl, having the formula:

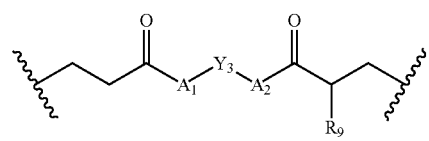    (VII)

wherein in Formula (VII),
$A_1$ and $A_2$ are each —O—;
$Y_3$ is —CH$_2$CH$_2$—;
$R_9$ is —CH$_3$; and
the terminating group is selected from the group consisting of:

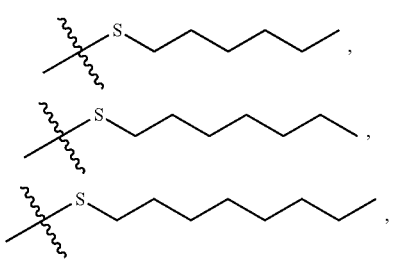

-continued

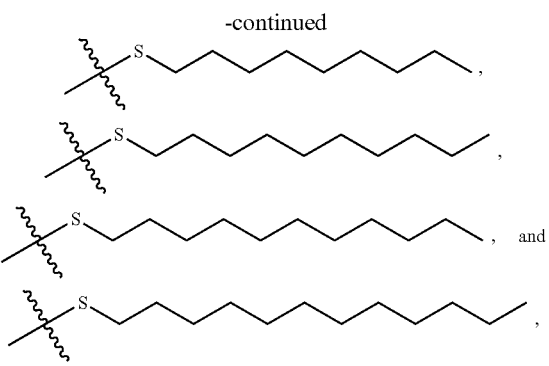
, and wherein a protein expressed by said nucleic acid is detected in a cell of the subject following said administration of said nucleic acid formulated with said nanoparticle.

34. The method according to claim 33, wherein in the compound of Formula (I):
the core is linked to six repeating units and the terminating group is:

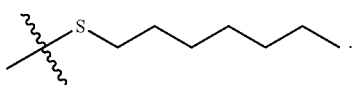

35. The method according to claim 33, wherein in the compound of Formula (I) the core is linked to six repeating units and the terminating group is:

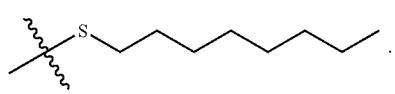

36. The method of claim 1, wherein the nucleic acid comprises a messenger RNA.
37. The method of claim 36, wherein the nanoparticle further comprises a guide RNA.
38. The method of claim 27, wherein the nucleic acid comprises a messenger RNA.
39. The method of claim 38, wherein the nanoparticle further comprises a guide RNA.
40. The method of claim 30, wherein the nucleic acid comprises a messenger RNA.
41. The method of claim 40, wherein the nanoparticle further comprises a guide RNA.
42. The method of claim 33, wherein the nucleic acid comprises a messenger RNA.
43. The method of claim 42, wherein the nanoparticle further comprises a guide RNA.
44. A method for delivering a nucleic acid to a cell of a subject, the method comprising administering to said subject said nucleic acid, wherein said nucleic acid is formulated with a nanoparticle comprising a compound having the structure of Formula (I):

Core-Repeating Unit-Terminating Group, or a pharmaceutically acceptable salt thereof, wherein:
the core is linked to two to six repeating units, and each repeating unit is linked to a nitrogen of the core, wherein:

the core corresponds to the structure of Formula (II):

(II)

wherein, in Formula (II):
$X_1$ is optionally substituted dialkylamino$_{(C \le 12)}$, optionally substituted heterocycloalkyl$_{(C \le 12)}$, or optionally substituted heteroaryl$_{(C \le 12)}$;
$R_1$ is amino, hydroxy, mercapto, optionally substituted alkylamino$_{(C \le 12)}$, or optionally substituted dialkylamino$_{(C \le 12)}$; and
a is 1, 2, 3, 4, 5, or 6; or
alternatively, the core corresponds to the structure of Formula (III):

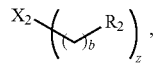
(III)

wherein, in Formula (III):
$X_2$ is $N(R_5)_y$, wherein:
$R_5$ is hydrogen or optionally substituted alkyl$_{(C \le 18)}$; and
y is 0, 1, or 2, provided that the sum of y and z is 3;
$R_2$ is amino, hydroxy, mercapto, optionally substituted alkylamino$_{(C \le 12)}$, or optionally substituted dialkylamino$_{(C \le 12)}$;
b is 1, 2, 3, 4, 5, or 6; and
z is 1, 2, 3; provided that the sum of z and y is 3; or
alternatively, the core corresponds to the structure of Formula (IV):

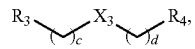
(IV)

wherein, in Formula (IV):
$X_3$ is selected from —NR$_6$—, —O—, optionally substituted alkylaminodiyl$_{(C \le 8)}$, optionally substituted alkoxydiyl$_{(C \le 8)}$, optionally substituted arenediyl$_{(C \le 8)}$, optionally substituted heteroarenediyl$_{(C \le 8)}$, and optionally substituted heterocycloalkanediyl$_{(C \le 8)}$,
wherein $R_6$ is hydrogen or optionally substituted alkyl$_{(C \le 8)}$;
$R_3$ and $R_4$ are each independently amino, hydroxy, mercapto, optionally substituted alkylamino$_{(C \le 12)}$, optionally substituted dialkylamino$_{(C \le 12)}$, or a group of the formula:

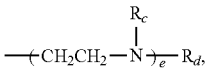

wherein:
e is 1, 2, or 3; and
$R_c$ and $R_d$ are each independently hydrogen, or optionally substituted alkyl$_{(C \le 6)}$; and
c and d are each independently 1, 2, 3, 4, 5, or 6;
each repeating unit
is a degradable diacyl group of Formula (VII):

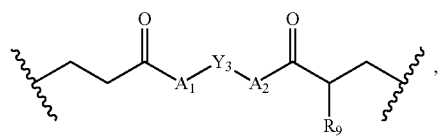
(VII)

wherein, in Formula (VII):
$A_1$ and $A_2$ are each independently —O—; and
$Y_3$ is optionally substituted alkanediyl$_{(C \le 12)}$, optionally substituted alkenediyl$_{(C \le 12)}$, or optionally substituted arenediyl$_{(C \le 12)}$; and
$R_9$ is optionally substituted alkyl$_{(C \le 8)}$; wherein the core contains at least one nitrogen atom and
each terminating group has the structure of Formula (VIII):

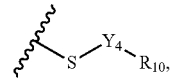
(VIII)

wherein, in Formula (VIII):
$Y_4$ is alkanediyl$_{(C \le 18)}$ optionally substituted with one or more substituents each independently selected from the group consisting of —OH, —F, —Cl, —Br, —I, —SH, —OCH$_3$, —OCH$_2$CH$_3$, —SCH$_3$, and —OC(O)CH$_3$; and
$R_{10}$ is hydrogen,
wherein a protein expressed by said nucleic acid is present in a cell of the subject following said administration of said nucleic acid formulated with said nanoparticle.

* * * * *

SEQUENCE LISTING

<160> NUMBER OF SEQ ID NOS: 6

<210> SEQ ID NO 1
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 1
ggaucaucuc aagucuuac                                                  19

<210> SEQ ID NO 2
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 2
ccuaguagag uucagaaug                                                  19

<210> SEQ ID NO 3
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 3
gauuaugucc gguuaugua                                                  19

<210> SEQ ID NO 4
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 4
cuaauacagg ccaauacau                                                  19

```
<210> SEQ ID NO 5
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 5
gcgcgauagc gcgaauaua                                                  19

<210> SEQ ID NO 6
<211> LENGTH: 19
<212> TYPE: RNA
<213> ORGANISM: Artificial sequence
<220> FEATURE:
<223> OTHER INFORMATION: Synthetic nucleic acid

<400> SEQUENCE: 6
cgcgcuaucg cgcuuauau                                                  19
```